US011149289B2

(12) United States Patent
Kühn

(10) Patent No.: US 11,149,289 B2
(45) Date of Patent: *Oct. 19, 2021

(54) PROTEIN HAVING NUCLEASE ACTIVITY, FUSION PROTEINS AND USES THEREOF

(71) Applicant: Helmholtz Zentrum München—Deutsches Forschungszentrum für Gesundheit und Umwelt (GmbH), Neuherberg (DE)

(72) Inventor: Ralf Kühn, Berlin (DE)

(73) Assignee: Helmholtz Zentrum München—Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,364

(22) Filed: Apr. 23, 2018

(65) Prior Publication Data

US 2018/0237802 A1 Aug. 23, 2018

Related U.S. Application Data

(60) Continuation of application No. 15/198,967, filed on Jun. 30, 2016, now abandoned, which is a division of application No. 14/124,117, filed as application No. PCT/EP2012/060711 on Jun. 6, 2012, now Pat. No. 9,410,134.

(30) Foreign Application Priority Data

Jun. 7, 2011 (EP) .................................... 11004635

(51) Int. Cl.

| | |
|---|---|
| ***C12N 15/90*** | (2006.01) |
| ***A01K 67/027*** | (2006.01) |
| ***C12N 15/62*** | (2006.01) |
| ***C12N 15/85*** | (2006.01) |
| ***C12N 9/22*** | (2006.01) |
| ***C12N 5/075*** | (2010.01) |
| ***C12N 9/16*** | (2006.01) |
| ***C07K 14/195*** | (2006.01) |

(52) U.S. Cl.

CPC ........ *C12N 15/907* (2013.01); *A01K 67/0275* (2013.01); *C07K 14/195* (2013.01); *C12N 5/0609* (2013.01); *C12N 9/16* (2013.01); *C12N 9/22* (2013.01); *C12N 15/62* (2013.01); *C12N 15/8509* (2013.01); *C12Y 301/21004* (2013.01); *A01K 2207/05* (2013.01); *A01K 2217/07* (2013.01); *A01K 2217/075* (2013.01); *A01K 2227/105* (2013.01); *A01K 2267/03* (2013.01); *C07K 2319/80* (2013.01); *C12N 2800/80* (2013.01); *C12N 2999/007* (2013.01)

(58) Field of Classification Search

CPC ...... C12N 15/907; C12N 5/0609; C12N 9/16; C12N 9/22; C12N 15/62; C12N 15/8509; C12N 2999/007; C12N 2800/80; C07K 14/195; C07K 2319/80; C12Y 301/21004; A01K 67/0275; A01K 2217/07; A01K 2207/05; A01K 2217/075; A01K 2227/105; A01K 2267/03

USPC ............ 435/196, 199, 455, 69.7, 320.1, 325

See application file for complete search history.

(56) References Cited

U.S. PATENT DOCUMENTS 9,410,134 B2 * 8/2016 Kuhn ................ A01K 67/0275

OTHER PUBLICATIONS

Ward et al. (200) sequence report submitted to EMBL/Gene Bank, Feb. 2009.*

Brown et al. (1994) Mol. Microbiol., vol. 14,411-426.*

Guo et al. (2010) J. Mol. Biol., vol. 400(1) 96-107.*

Brown et al. Mole Microbiol 1994;14:411-26.

Cermak et al., "Efficient design and assembly of custom TALEN and other TAL effector-based constructs for DNA targeting," Nucleic Acids Research, vol. 39, No. 12, Apr. 14, 2011, pp. 1-11.

Christian et al., "Targeting DNA Double-Strand Breaks with TAL Effector Nucleases," Genetics, vol. 186, No. 2, Oct. 1, 2010, pp. 757-761.

(Continued)

*Primary Examiner* — Anne Marie S Wehbe

(74) *Attorney, Agent, or Firm* — Cooley LLP

(57) ABSTRACT

The present invention relates to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease. Also, the present invention relates to a vector comprising the nucleic acid molecule and a protein encoded by said nucleic acid molecule. Further, the invention relates to a method of modifying the genome of a eukaryotic cell and a method of producing a non-human vertebrate or mammal.

11 Claims, 16 Drawing Sheets

Figure 1:
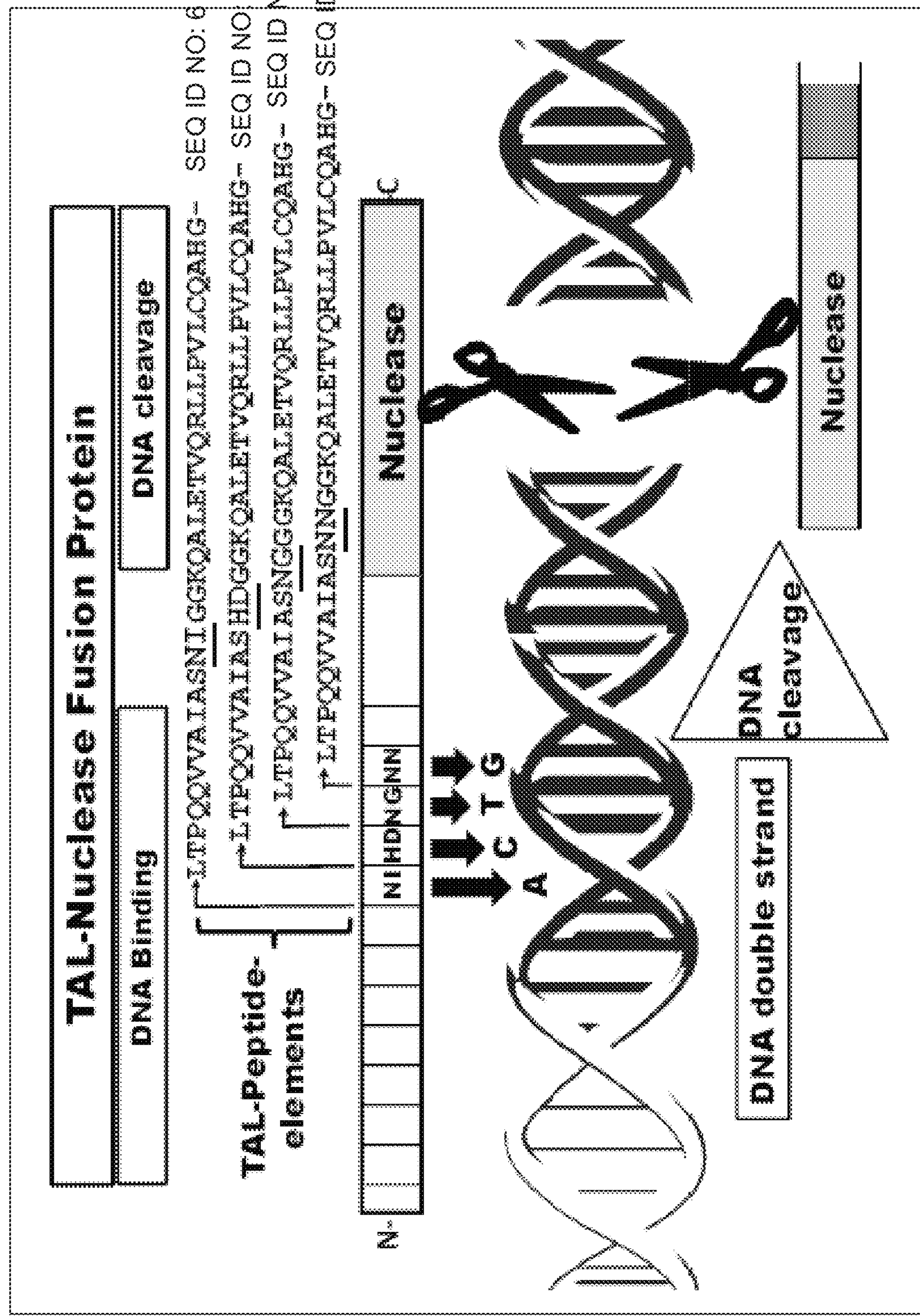

Specification includes a Sequence Listing.

(56) References Cited

OTHER PUBLICATIONS

Database UniProt [Online]. May 26, 2009, retrieved from accession No. Uniprot:C11815, 1 page.
Geurts et al., "Knockout Rats via Embryo Microinjection of Zinc-Finger Nucleases," Science, vol. 325, No. 5939, Jul. 24, 2009, p. 433.
Geurts et al., "Supporting Online Material for Knockout Rats via Embryo Microinjection of Zinc-Finger Nucleases", vol. 325, No. 5939, Jul. 24, 2009, pp. 1-15.
Li et al., TAL nucleases (TALNs): hybrid proteins composed of TAL effectors and Fokl DNA-cleavage domain, : Neucleic Acids Research, vol. 39, No. 1, Jan. 2011, pp. 1-14.
Mahfouz et al., "De novo-engineered transcription activator-like effector (TALE) hybrid nuclease with novel DNA binding specificity creates double-strand breaks," Proceedings of the National Academy of Sciences, vol. 108, No. 6, Feb. 8, 2011, pp. 2623-2628.
Moehle et al. "Targeted gene addition into a specified location in the human genome using designed zinc finger nucleases," Proceedings of the National Academy of Sciences, vol. 104, No. 9, Feb. 1, 2007, pp. 3055-3060.
Ward et al. Direct submission to EMBL/GeneBank/DDBJ databases Feb. 2009, sequence search result.

* cited by examiner

A
Wildtype cell Culture
Targeting-Vector
+ TAL-Nuclease
Modified cell culture
B
Zygote isolation
Wildtype Mouse
DSB
Tal-N
Tal-N
Vector
x
x
HR
KO/KI Allele
Zygote injection (Tal-N & Vector)
Embryo transfer
Knockout/Knock-in Mouse

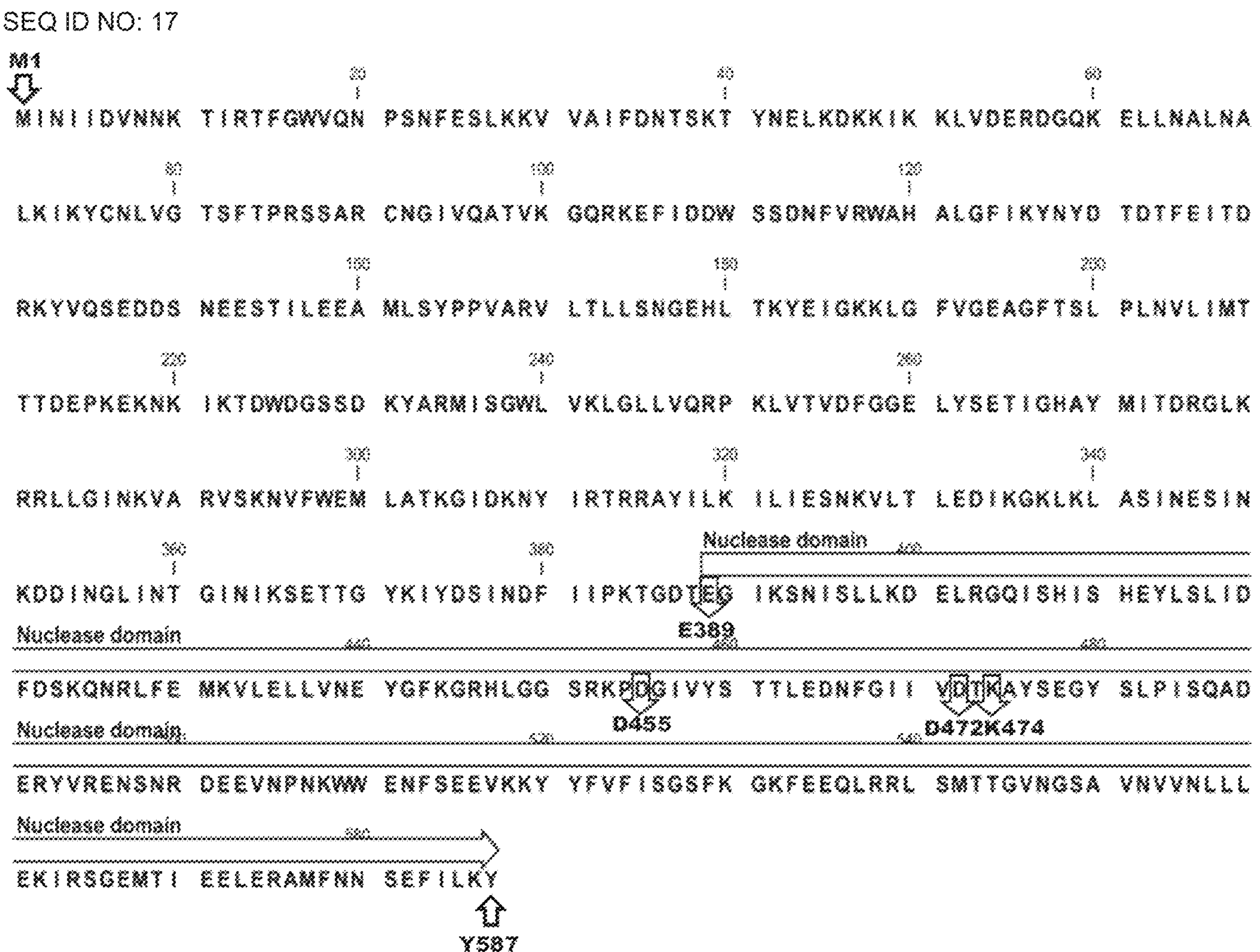

Figure 5
SEQ ID NO: 17
M1
MINIIDVNNK TIRTFGWVQN PSNFESLKKV VAIFDNTSKT YNELKDKKIK KLVDERDGQK ELLNALNA
LKIKYCNLVG TSFTPRSSAR CNGIVQATVK GQRKEFIDDW SSDNFVRWAH ALGFIKYNYD TDTFEITD
RKYVQSEDDS NEESTILEEA MLSYPPVARV LTLLSNGEHL TKYEIGKKLG FVGEAGFTSL PLNVLIMT
TTDEPKEKNK IKTDWDGSSD KYARMISGWL VKLGLLVQRP KLVTVDFGGE LYSETIGHAY MITDRGLK
RRLLGINKVA RVSKNVFWEM LATKGIDKNY IRTRRAYILK ILIESNKVLT LEDIKGKLKL ASINESIN
Nuclease domain
KDDINGLINT GINIKSETTG YKIYDSINDF IIPKTGDTEG IKSNISLLKD ELRGQISHIS HEYLSLID
E389
Nuclease domain
FDSKQNRLFE MKVLELLVNE YGFKGRHLGG SRKPDGIVYS TTLEDNFGII VDTKAYSEGY SLPISQAD
D455
D472K474
Nuclease domain
ERYVRENSNR DEEVNPNKWW ENFSEEVKKY YFVFISGSFK GKFEEQLRRL SMTTGVNGSA VNVVNLLL
Nuclease domain
EKIRSGEMTI EELERAMFNN SEFILKY
Y587

SEQ ID NO: 1
EGIKSNISLL KDELRGQISH ISHEYLSLID LAFDSKQNRL FEMKVLELLV
NEYGFKGRHL GGSRKPDGIV YSTTLEDNFG IIVDTKAYSE GYSLPISQAD
EMERYVRENS NRDEEVNPNK WWENFSEEVK KYYFVFISGS FKGKFEEQLR
RLSMTTGVNG SAVNVVNLLL GAEKIRSGEM TIEELERAMF NNSEFILKY
S423
R446
20
40
60
80
100
120
140
150
160

Figure 14
A
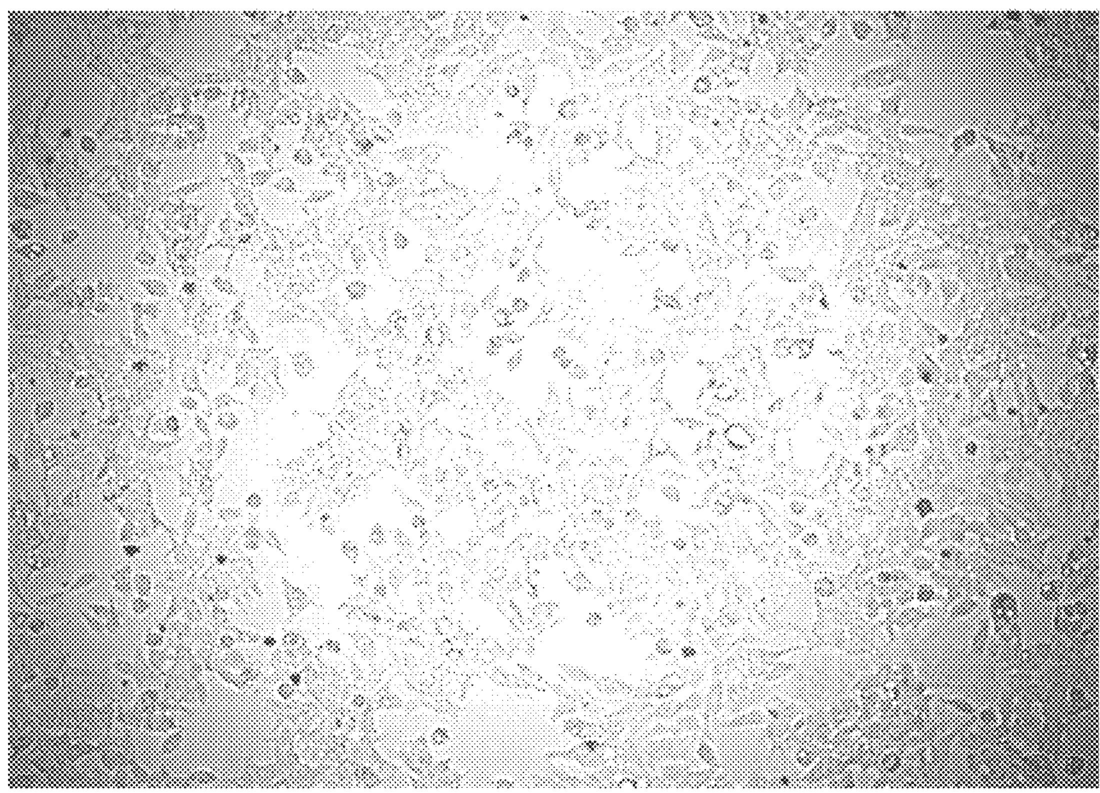
B
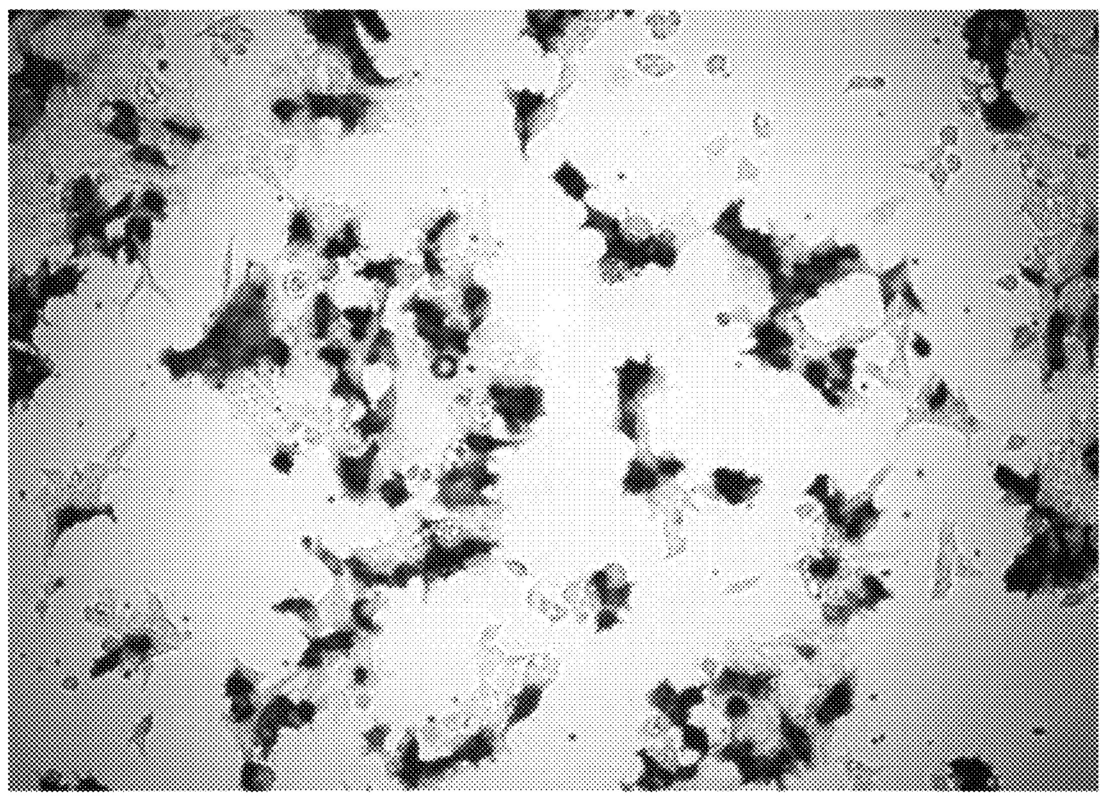

PROTEIN HAVING NUCLEASE ACTIVITY, FUSION PROTEINS AND USES THEREOF

RELATED APPLICATIONS

This application is a continuation Application of U.S. application Ser. No. 15/198,967 filed on Jun. 30, 2016, which is a divisional of Application of U.S. patent application Ser. No. 14/124,117, filed on Dec. 5, 2013, now U.S. Pat. No. 9,410,134 issued on Aug. 9, 2016, which is a U.S. National Stage Application under 35 U.S.C. § 371 of International Application Number PCT/EP2012/060711, filed on Jun. 6, 2012, which claims priority to European Patent Application No. 11004635.6, filed on Jun. 7, 2011, the contents of which applications are incorporated by reference herein in their entirety.

SEQUENCE LISTING

The text file entitled "POTH-010_CO1US_SequenceListing_ST25" created on Apr. 20, 2018, having 396 kilobytes of data, and filed concurrently herewith, is hereby incorporated by reference in its entirety in this application.

DESCRIPTION

The present invention relates to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease. Also, the present invention relates to a vector comprising the nucleic acid molecule and a protein encoded by said nucleic acid molecule. Further, the invention relates to a method of modifying the genome of a eukaryotic cell and a method of producing a non-human vertebrate or mammal.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Nucleases remain to be one of the most important tools of molecular biologists since their discovery in the late 1960s. Nucleases are enzymes capable of cleaving the phosphodiester bonds between the nucleotide subunits of nucleic acids. Enzymes catalyzing DNA and RNA cleavage are integral parts of major DNA metabolic processes such as DNA replication, DNA recombination, DNA repair, site-specific recombination and RNA splicing. In addition, nuclease activities are essential in RNA processing, maturation, RNA interference and are components of microbial defense mechanisms.

RNA and DNA present only two types of phosphodiester bonds for cleavage, 5'- or 3'- of a scissile phosphate and the fundamental chemistry is bimolecular nucleophilic substitution. Nonetheless, structures and catalytic mechanisms of RNA and DNA nucleases are greatly varied and complex. Nucleases may be endo- or exonucleases, DNA or RNA specific, topoisomerases, recombinases, ribozymes, or RNA splicing enzymes. Their reaction can be divided into the three stages of nucleophilic attack, the formation of a negatively charged penta-covalent intermediate and the breakage of the scissile bond. Nucleases utilize a variety of nucleophiles to cleave a scissile phosphate bond. The most common nucleophiles are water molecules deprotonated by a general base for direct hydrolysis. For DNA cleavage, the side chains of Ser, Tyr and His serve as nucleophiles to form a covalent DNA phosphoryl-protein intermediate, which is subsequently resolved either by phosphoryl transfer reaction back to DNA during recombination and topoisomerization or by hydrolysis in two-step cleavage reactions. To enable the controlled degradation or processing of cellular DNA or RNA, nuclease activities are strictly regulated by stringent substrate specificity, confined localization, or by potent inhibitors.

For convenience nucleases can be classified according to their catalytic mechanism into three major classes based on their metal-ion dependence (Yang, W. (2011). Q. Rev. Biophys. 44(1): 1-93). These classes of two-metal-ion-dependent, one-metal-ion-dependent and metal-independent nucleases are further divided into families or superfamilies according to sequence and structure conservation and functional diversity.

Restriction Endonucleases

Various families of restriction endonucleases are found among all three catalytic classes. The type I, III and IV restriction enzymes are multisubunit and complex molecular machines that combine multiple activities including restriction, methylation and DNA translocation, require additional cofactors (AdoMet, ATP or GTP), bind more than one target site, and cleave outside the recognition sequence, often at a random distance. Type II restriction endonucleases are enzymes that recognize short DNA sequences (usually 4-8-bp long) and cleave the target in both strands at, or in close proximity to the recognition site. Orthodox type II restriction enzymes are homodimeric, cleave within palindromic sequences, require $Mg2^+$ ions and can act on single copies of their targets. Because of their remarkably high specificity in recognizing and cleaving their target sequences, they are of high interest as the most frequently used tools for recombinant DNA technology (Pingoud, A., M. Fuxreiter, et al. (2005). Cell Mol Life Sci 62(6): 685-707; Orlowski, J. and J. M. Bujnicki (2008). Nucleic Acids Res 36(11): 3552-69). In nature, type II REases (restriction endonucleases) are found in prokaryotic organisms, where they form restriction-modification systems with DNA methyltransferases of the same or very similar substrate specificity. DNA methyltransferases use S-adenosylmethionine (AdoMet) as a methyl group donor to modify specific bases in the target sequence, thereby rendering it resistant to cleavage by the restriction enzyme. While the Restriction-Modification system's own DNA is protected against self-degradation by the nuclease, any foreign DNA (e.g. from phages) that invades the host cell and lacks methylation, can be efficiently destroyed. In order to distinguish the components of restriction-modification systems the names of methylases and nucleases are preceded with 'M'. and 'R.' prefixes (e.g. M. FokI and R. FokI).

Many commonly used type-II restriction endonucleases share the conserved motif PD-(D/E)XK. Said motif is generally found in proteins that interact with nucleic acid molecules such as DNA and is not limited to the presence in nucleases. The three catalytic residues are located close to each other on an uneven n-hairpin. The first D is located at the beginning of the first and shorter strand, and the E and K, separated by a hydrophobic residue x, are located in the middle of the second and longer strand. The first D is most conserved and coordinates both metal ions, whereas the second E can be replaced by Q, D, N, H or S, and the third K can be replaced E, Q, D, S, N or T. By varying dimeric interfaces and thus the relative positions of the two catalytic centers, dimeric endonucleases can cleave DNA to generate blunt ends or staggered ends with various 5'- or 3'-overhangs. The catalytic module invariably approaches DNA from the minor groove side, and the sequence-specific binding is conducted by a separate module/subdomain in the major groove. The first two carboxylates of the DEK motif coordinate the metal ions. The third, which usually is hydrogen bonded with both the nucleophilic water and the DNA-binding module in the major groove, couples DNA sequence recognition with the cleavage reaction. Members of this superfamily have a very diverse primary sequence and thus different structures surrounding the catalytic core. Database searches with restriction enzyme sequences typically reveal either no significant similarity to any protein, or very high similarity (>90% identity) to a few isoschizomers, and no similarity to other proteins. This strongly biased distribution of similarities and dissimilarities made comparative sequence analysis of all restriction enzymes difficult and raised a question whether the diversity of amino acid sequences of restriction endonucleases indicates polyphyletic evolution (convergence) or extreme divergence from a common ancestor.

While ~70% of restriction endonucleases belong to the PD-(D/E)XK superfamily, other superfamily members can be monomeric or tetrameric and be involved in other processes such as DNA repair and homologous recombination. In addition to endonucleases, members in this superfamily can also be 5'- or 3'-exonucleases. The most comprehensive source of information on restriction enzymes is the REBASE database (rebase.neb.com) that lists several thousand functionally characterized enzymes and several thousand putative enzymes, inferred from sequence comparisons or genomic analyses. Therefore, a large disproportion exists between the number of known or predicted sequences and the small number of ~50 experimentally characterized proteins with known three-dimensional structures. Presently, a large fraction of putative enzymes remains without any predictions or experimental data.

Type II REases are further subdivided into several types according to their recognition site symmetry, structural organization or cofactor requirement. Most of the restriction enzymes used for recombinant DNA work belong to type IIP (P-palindromic). Type IIA enzymes recognize asymmetric sequences, like Bpu10I, a dimer of non-identical subunits, each of which is responsible for cleavage of one strand of the DNA. Type IIB enzymes cleave DNA at both sides of the recognition sequence, an example being BplI that cleaves the topstrand 8 nucleotides before and 13 nucleotides after the recognition sequence, while the bottom strand is cleaved 13 nucleotides before and 8 nucleotides after the recognition sequence. Type IIC enzymes have both cleavage and modification domains within one polypeptide. Type IIE enzymes need to interact with two copies of their recognition sequence for efficient cleavage, one copy being the target for cleavage, the other serving as an allosteric effector. Type IIE enzymes like NaeI recognize palindromic nucleotide sequences in a manner similar to the type IIP enzymes and cleave DNA within the boundaries of their recognition sites; however, they possess a separate DNA binding domain to perform allosteric function. Type IIF enzymes are typically homotetrameric restriction endonucleases that also interact with two copies of their recognition site, but cleave both of them in a concerted manner. Type IIG enzymes, essentially a subgroup of Type IIC enzymes, have both cleavage and modification domains within one polypeptide. They are in general stimulated by AdoMet, but otherwise behave as typical Type II enzymes. Type IIH enzymes behave like type II enzymes, but their genetic organization resembles Type I Restriction-Modification systems. Type IIM enzymes recognize a specific methylated sequence and cleave the DNA at a fixed site. The best known representative is DpnI which cleaves Gm6ATC, Gm6ATm4C and Gm6ATm5C, yet not GATC, GATm4C, GATm5C or hemimethylated sites. Many other restriction enzymes are more or less tolerant to methylation, but for Type IIM enzymes the methyl group is an essential recognition element. Orthodox Type IIP enzymes like EcoRI recognize symmetric nucleotide sequences and cleave within their recognition sites. They share both a common structural core comprising the five stranded mixed β-sheet flanked by α-helices. The DNA binding sites of Type IIP enzymes, however, are highly diverse and usually form a patch on the protein surface composed of amino acid residues located on the different structural elements (α-helices, β-strands, loops). Orthodox Type IIP enzymes interact with DNA as homodimers, and each subunit contributes to the recognition of half of the palindromic sequence. Type IIS enzymes cleave at least one strand of the target DNA outside of the recognition sequence. The best-known type IIS enzyme is FokI, which like many other type IIS enzymes interacts with two recognition sites before cleaving DNA. Type IIS enzymes are active as homodimers and are composed of two domains, one responsible for target recognition and the other for catalysis (also serving as the dimerization domain). This is apparent from the crystal structure and biochemical studies of FokI (Bitinaite, J., D. A. Wah, et al. (1998). Proc Natl Acad Sci USA 95(18): 10570-5; Wah, D. A., J. Bitinaite, et al. (1998). Proc Natl Acad Sci USA 95(18): 10564-9). Crystal structure analysis of FokI reveals that it is composed of a specific DNA binding module fused to the cleavage domain that possesses a conserved endonuclease catalytic core but cuts DNA in a nonspecific manner. Modular architecture is also characteristic for the type IIS enzyme BfiI, which is composed of two DNA binding domains fused to the dimeric catalytic core similar to the nonspecific nuclease belonging to the phospholipase D family. The presence of a separate nuclease domain has been also reported from the crystal structure of the Type IIP enzyme SdaI (Tamulaitiene, G., A. Jakubauskas, et al. (2006). Structure 14(9): 1389-400)

Modified Restriction Enzymes and Chimaeric Nucleases as Tools for Qenome Editing Nucleases that cleave nucleic acid molecules at specific sites rather than randomly are of increasing importance in emerging technologies such as, e.g., in genetic engineering and gene targeting. Gene targeting is a process in which a DNA molecule introduced into a cell replaces the corresponding chromosomal segment by homologous recombination, and thus presents a precise way to manipulate the genome (Capecchi, M. R. (2005). Nat Rev Genet 6(6): 507-12). In the past, the application of gene targeting to mammalian cells has been limited by its low efficiency. Experiments in model systems have demonstrated that the frequency of homologous recombination of a gene targeting vector is strongly increased if a double-strand break is induced within its chromosomal target sequence. Using the yeast homing endonuclease I-SceI, that cuts DNA at an 18 base pair-long recognition site, it was initially shown that homologous recombination and gene targeting are stimulated over 1000-fold in mammalian cells when a recognition site is inserted into a target gene and I-SceI is expressed in these cells (Rouet, P., Smih, F., Jasin, M.; Mol Cell Biol 1994; 14: 8096-8106; Rouet, P., Smih, F. Jasin, M; Proc Natl Acad Sci USA 1994; 91: 6064-6068). In the absence of a gene targeting vector for homology directed repair, the cells frequently close the double-strand break by non-homologous end-joining (NHEJ). Since this mechanism is error-prone it frequently leads to the deletion or insertion of multiple nucleotides at the cleavage site. If the cleavage site is located within the coding region of a gene it is thereby possible to identify and select mutants that exhibit reading frameshift mutations from a mutagenised population and that represent non-functional knockout alleles of the targeted gene.

Therefore, sequence specific nucleases represent an important tool for biotechnology to modify the genome of model organisms or cell lines. In order to construct nucleases that specifically recognise new target sequences within genes, two approaches have been pursued that rely on the modification of natural homing endonucleases or on the fusion of a natural or engineered DNA binding domain to a nuclease domain. Such modified restriction enzymes or chimaeric nucleases can target large DNA sites (up to 36 bp) and can be engineered to bind to desired DNA sequences.

Homing endonucleases, such as I-SceI of yeast, are natural genetic elements that catalyze their own duplication into recipient alleles by creating site-specific DSBs that initiate their own genetic transfer by homologous recombination. A key feature of these enzymes is that they create double-strand breaks at recognition sites that are 14- to 40-bp long. The major limitation to the use of homing endonucleases in gene targeting is that each enzyme recognises exclusively its natural target sequence. By protein engineering it has been attempted to modify homing endonucleases in order to recognize new target sites. In this work, modifications could be made that alter the natural target site within some nucleotides, but it is yet not possible to design enzymes specific for entirely new target regions.

Due to the difficulty of manipulating the sequence recognition of homing enonucleases, zinc-finger nucleases (ZFN) are presently the most commonly used artificial nucleases for genetic engineering (Urnov, F. D., E. J. Rebar, et al. Nat Rev Genet 11(9): 636-46). Zinc-finger nucleases were developed by fusing the nonsequence-specific cleavage domain of the FokI type IIS restriction endonuclease (Fn domain) to a new DNA binding domain. The advantage of zinc-finger nucleases is that the zinc-finger DNA binding domain can be modified to recognize novel target sequences, including those in endogenous genes. The protein modules known as zinc-fingers are found in the DNA-binding domain of the most abundant family of transcription factors in most eukaryotic genomes. Each finger is composed of 30 aminoacids, coordinates one $Zn2+$-ion using two cysteines and two histidine residues, and contacts primarily three basepairs of DNA. Two critical features of the structure are that each finger binds its 3-bp target site independently and that each nucleotide seemed to be contacted by a single amino acid side chain projecting from one end of the α-helix into the major groove of the DNA. Individual fingers have been designed to recognize many of the 64 different target triplets, but the greatest success has been in designing zinc fingers to recognize 5'-GNN-3' triplets. Although zinc-finger recognition codes have been proposed, no code currently exists that consistently results in zinc-fingers with high affinity binding. Improving the specificity of zinc-finger binding, such as by increasing the number of fingers or by constructing multi-finger proteins using two-finger units, remains an active area of research.

Using zinc-finger nucleases in the absence of a gene targeting vector for homology directed repair, knockout alleles were generated in mammalian cell lines and knockout zebra fish and rats were obtained upon the expression of ZFN mRNA in one cell embryos (Santiago Y, Chan E, Liu P Q, Orlando S, Zhang L, Urnov F D, Holmes M C, Guschin D, Waite A, Miller J C, Rebar E J, Gregory P D, Klug A, Collingwood T N.; Proc Natl Acad Sci USA 2008; 105: 5809-5814; Doyon Y, McCammon J M, Miller J C, Faraji F, Ngo C, Katibah G E, Amora R, Hocking T D, Zhang L, Rebar E J, Gregory P D, Urnov F D, Amacher S L.; Nat Biotechnol 2008; 26:702-708; Geurts A M, Cost G J, Freyvert Y, Zeitler B, Miller J C, Choi V M, Jenkins S S, Wood A, Cui X, Meng X, Vincent A, Lam S, Michalkiewicz M, Schilling R, Foeckler J, Kalloway S, Weiler H, Menoret S, Anegon I, Davis G D, Zhang L, Rebar E J, Gregory P D, Urnov F D, Jacob H J, Buelow R.; Science 2009; 325:433). Furthermore, zinc-finger nucleases were used in the presence of exogeneous gene targeting vectors that contain homology regions to the target gene for homology driven repair of the double strand break through gene conversion. This methodology has been applied to gene engineering in mammalian cell lines and gene correction in primary human cells (Urnov F D, Miller J C, Lee Y L, Beausejour C M, Rock J M, Augustus S, Jamieson A C, Porteus M H, Gregory P D, Holmes M C.; Nature 2005; 435:646-651; Porteus M H, Baltimore D. 2003. Science 300:763; Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, Jaenisch R.; Nat Biotechnol 2009; 27:851-857).

Although the use of zinc-finger nucleases results in a higher frequency of homologous recombination, considerable efforts and time are required to design zinc-finger proteins that bind a new DNA target sequence at high efficiency and that act as sequence specific nuclease. In addition, it has been long ignored that the nature of the nuclease domain of zinc-finger and other chimaeric nucleases may represent an equally important success factor for the overall activity of the fusion protein. The reason for this neglection is based on the fact that up to date only a single nuclease domain has been found that retains nuclease activity within a separate protein folding domain and that can be combined with DNA binding domains, in order to generate a sequence specific nuclease fusion proteins. This nuclease domain is derived from the type IIS FokI restriction enzyme that has been characterised in detail and is known to act as an obligate dimer (Bitinaite, J., D. A. Wah, et al. (1998). Proc Natl Acad Sci USA 95(18): 10570-5; Wah, D. A., J. Bitinaite, et al. (1998). Proc Natl Acad Sci USA 95(18): 10564-9). In most other restriction enzymes DNA recognition and cleavage are combined into a single protein domain and can not be separated. An exception is the SdaI enzyme that has been structurally characterised to possess a separate nuclease domain (Tamulaitiene, G., A. Jakubauskas, et al.

(2006). Structure 14(9): 1389-400). In addition, it has not been possible to isolate mutants that loose DNA recognition but retain DNA cleavage activity.

Therefore, due to the lack other comparable functional nuclease domains, it was for a long time essentially unknown whether the enzymatic properties of the FokI Fn domain may constitute a limiting factor for the nuclease activity of Fn domain fusion proteins. For example, the intrinsic structure of the Fn domain may restrict its enzymatic processivity or the small dimerisation interface of two Fn domains may lead to a suboptimal interaction and a low cleavage rate of the DNA substrate.

By site-directed mutagenesis the FokI Fn domain has been engineered into the KK and EL variants that preferentially act as heterodimers (Miller, J. C., M. C. Holmes, et al. (2007). Nat Biotechnol 25(7): 778-85). The use of these variants provides the improved target sequence specificity of zinc-finger nucleases and reduces toxicity in mammalian cells since less genomic off-target sequences are recognised and processed. However, the overall nuclease activity of the KK and EL variants is at most comparable to that of the Fn wildtype domain.

Only very recently it has been found that the wildtype FokI Fn domain indeed exhibits only a suboptimal enzymatic nuclease activity that limits the use of zinc-finger nucleases for genome engineering. In a study of directed protein evolution the Fn domain has been randomly mutagenised and subjected to an *E. coli* based nuclease assay able to select mutants that exhibit increased enzymatic activity (Guo, J., T. Gaj, et al. (2010), J Mol Biol 400(1): 96-107). By this procedure it has been possible to isolate mutants that exhibit >10-fold higher nuclease activity as compared to the wildtype Fn domain. Upon coupling of these mutants to zinc-finger domains such fusion proteins showed a three to sixfold improved substrate processing in mammalian cells. However, it remains unknown at present whether the activity of the Fn domain can be further enhanced or whether the intrinsic protein architecture of the Fn domain may restrict any further improvements.

Besides zinc-finger DNA-binding domains fused to nuclease domains, very recently also TAL effector protein DNA-binding domains have been identified. As compared to zinc-finger motifs, TAL repeat elements within TAL effector proteins provide a new type of DNA binding domain that may be combined with a nuclease domain into sequence specific nucleases. A key feature of the TAL peptide elements is provided by their modulatory nature. Thereby, new sequence specific DNA-binding proteins can be generated through the combination of just four basic TAL elements that are each specific for the A, C, G or T nucleotide. Currently, only the nuclease domain of FokI is successfully used in fusion with TAL effector protein DNA-binding domains (Miller et al. (2010). Nat. Biotechnol. 29, 143-148).

In summary, there is an ongoing need for nucleases that can be used in various experimental settings including their fusion to other proteins and modification of the nuclease domain.

The technical problem underlying the present invention was to identify alternative and/or improved means and methods for cleaving nucleic acid molecules.

The solution to this technical problem is achieved by providing the embodiments characterized in the claims.

Accordingly, the present invention relates in a first embodiment to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease.

In accordance with the present invention the term "nucleic acid molecule" defines a linear molecular chain consisting of at least (for each) 2, 5, 10, 25, 50, 75, 100, 250, 500, such as at least 750, 1000, or at least 2500 or more nucleotides. The group of molecules designated herein as "nucleic acid molecules" also comprises complete genes. The term "nucleic acid molecule" is interchangeably used herein with the term "polynucleotide".

The term "nucleic acid molecule" in accordance with the present invention includes DNA, such as cDNA or double or single stranded genomic DNA and RNA. In this regard, "DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases that are linked together on a ribose sugar backbone. RNA typically has one strand of nucleotide bases. Included are also single- and double-stranded hybrid molecules, i.e., DNA-RNA. The nucleic acid molecule may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphorarnidate linkage. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. Also included are nucleic acids containing modified bases, for example thiouracil, thio-guanine and fluoro-uracil. A nucleic acid molecule typically carries genetic information, including the information used by cellular machinery to make proteins and/or polypeptides. The nucleic acid molecule of the invention may additionally comprise promoters, enhancers, response elements, signal sequences, polyadenylation sequences, introns, 5'- and 3'-non-coding regions, and the like.

The term "polypeptide" as used herein interchangeably with the term "protein" describes linear molecular chains of amino acids, including single chain proteins, containing more than 30 amino acids, whereas the term "peptide" describes linear molecular chains of amino acids, including single chain proteins, containing less than and up to 30 amino acids. Polypeptides may further form oligomers consisting of at least two identical or different molecules. The corresponding higher order structures of such multimers are, correspondingly, termed homo- or heterodimers, homo- or heterotrimers etc. The polypeptides of the invention may form heteromultimers or homomultimers, such as heterodimers or homodimers. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide" and "protein" also refer to naturally modified polypeptides and proteins where the modification is effected e.g. by glycosylation, acetylation, phosphorylation, ubiqitinylation and similar modifications which are well known in the art.

The term "a polypeptide having the activity of an endonuclease" as used herein means a polypeptide which is capable of cleaving the phosphodiester bonds between nucleotides subunits of nucleic acids within a polynucleotide chain.

According to the invention, the endonuclease enzymatic activity is considered as stable when, in the respective conditions, the enzyme is capable of lasting long enough to obtain the desired effect, namely the cleavage of its substrate. In this regard it is noted that endonuclease activity can be assayed as described in the examples of the specification or by methods well known in the art. For example, a nucleic acid molecule can be exposed to a protein whose endonuclease activity is to be assessed under conditions that are suitable for endonuclease enzymatic activity. After incubation, the composition comprising the nucleic acid molecule (with or without said protein to be assessed) may be subjected to an assay for assessing the length of a nucleic acid molecule such as, e.g., gel-electrophoresis, to determine whether the nucleic acid molecule has been cleaved.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 95% identity) may be determined, when the (sub)sequences are compared and aligned for maximum correspondence over a window of comparison, or over a designated region as measured using a sequence comparison algorithm as known in the art, or when manually aligned and visually inspected. This definition also applies to the complement of any sequence to be aligned. Amino acid sequence analysis and alignment in connection with the present invention was carried out using the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) and the CLC main workbench software (version 5.7.1; CLC bio, Aarhus, Denmark) which are preferably employed in accordance with this invention. Preferably, the published standard parameters are used (Altschul et al. loc cit.). The skilled person is aware of additional suitable programs to align nucleic acid sequences. A preferred program for nucleic acid sequence alignment in accordance with the invention is the CLC main workbench software using the standard alignment parameters of the software program (version 5.7.1; CLC bio, Aarhus, Denmark).

As defined in the embodiments herein above, certain amino acid sequence identities are envisaged by the invention. Also envisaged are—with increasing preference—amino acid sequence identities of at least 75%, at least 80%, at least 85%, at least 90%, at least 95%, at least 97.5%, at least 98%, at least 98.5%, at least 99%, at least 99.5%, at least 99.8%, and 100% identity to the respective amino acid sequence in accordance with the invention.

As defined in the embodiments herein above, certain nucleotide sequence identities are envisaged by the invention. Also envisaged are—with increasing preference—nucleotide sequence identities of at least 55%, at least 60%, at least 65%, at least 70%, at least 75%, at least 80%, at least 85%, at least 90%, at least 95%, at least 97.5%, at least 98%, at least 98.5%, at least 99%, at least 99.5%, at least 99.8%, and 100% identity to the respective nucleic acid sequence in accordance with the invention.

It will be readily appreciated by the skilled person that more than one nucleic acid molecule may encode the same polypeptide due to the degeneracy of the genetic code. Degeneracy results because a triplet code designates 20 amino acids and a stop codon. Because four bases exist which are utilized to encode genetic information, triplet codons are required to produce at least 21 different codes. The possible $4^3$ possibilities for bases in triplets give 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having different sequences, but still encoding the same polypeptide are envisaged and can be employed in accordance with the method of present invention.

Fragments according to the present invention are polypeptides having the activity of an endonuclease as defined herein above and comprise at least 90 amino acids. In this regard, it is preferred—with increasing preference—that the fragments according the present invention are polypeptides of at least 100, at least 125, at least 150, at least 200 amino acids, at least 300 amino acids, at least 400 amino acids. Fragments of the polypeptide of the invention, which substantially retain endonuclease activity, include N-terminal truncations, C-terminal truncations, amino acid substitutions, internal deletions and addition of amino acids (either internally or at either terminus of the protein). For example, conservative amino acid substitutions are known in the art and may be introduced into the endonuclease of the invention without substantially affecting endonuclease activity, i.e. reducing said activity.

As is evident from the examples, the inventor was able to identify and isolate a novel nuclease, in particular the endonuclease domain, derived from a *Clostridium* strain as detailed below. Specifically, the inventor could establish the utility of the gene product of a putative bacterial gene without known functional connotation as a sequence unspecific nuclease. The novel nuclease can be employed in various experimental settings just as any other nuclease. For example, it may be used to randomly cleave nucleic acid molecules or, e.g., in fusion with DNA-binding domains, for site-specific cleavage of nucleic acid molecules. Importantly, and as outlined below and specifically in the examples, the novel endonuclease can be used in combination with TAL effector protein DNA-binding domains as part of a fusion protein for sequence-specific nucleic acid cleavage. In this respect, the novel nuclease shows its superiority over state of the art endonucleases other than FokI which could so far not be shown to be active in corresponding fusion proteins. Briefly, the inventors tested the gene product of said uncharacterised, hypothetical microbial gene which they designated as "Clo051" (SEQ ID NO: 17) and which is derived from the genome of *Clostridium* spec. 7_2_43FAA (NCBI Reference Sequence: ZP_05132802.1; publication/database release date: Jun. 9, 2010), more specifically its putative nuclease domain (see FIGS. 5 and 6), for its endonuclease activity in combination with the DNA-binding domain of a TAL effector protein. Also various known endonuclease proteins were tested in combination with TAL effector protein DNA binding domains as well as two more hypothetical microbial genes. Surprisingly, only the nuclease domain from Clo051 could be shown to be active, whereas the other fusion proteins did not show activity (see Example 1 for details). The comparative experiments emphasized the significance of the finding of the present invention in that a novel nuclease has been identified that also exhibits activity when fused to the DNA-binding domains of TAL effector proteins. TAL effector proteins are expressed by plant pathogens of the genus *Xanthomonas* and reprogram host cells by mimicking eukaryotic transcription factors. TAL effector proteins are characterized by a central domain of tandem repeats of 32 to 34 amino acid that constitute a DNA-binding domain. The number and order of repeats in a TAL effector protein determines its specific DNA binding activity. (Boch, J., et al. 2009 Science 326: 1509-12). The amino acid sequences of the repeats are conserved, except for two adjacent highly variable residues (at positions 12 and 13) that determine specificity towards the DNA base A, G, C or T. Binding to DNA is mediated by contacting a nucleotide of the DNA double helix with the variable residues at position 12 and 13 within the Tal effector motif resulting into a one-to-one correspondence between sequential repeats in the Tal effector proteins and sequential nucleotides in the target DNA. Binding to longer DNA sequences is achieved by linking several of these Tal effector motifs in tandem to form a "DNA-binding domain of a Tal effector protein". The use of such DNA-binding domains of Tal effector proteins for the creation of Tal effector motif—nuclease fusion proteins that recognize and cleave a specific target sequence depends on the reliable creation of DNA-binding domains of Tal effector proteins that can specifically recognize said particular target. The advantage of the TAL repeat elements, as compared to e.g. zinc-finger elements, is provided by their truly modular nature. Thereby, new sequence specific DNA binding proteins can be generated through the combination of the four basic TAL elements that are specific for the A, C, G or T nucleotide.

It is important to note that in the present invention the Clo051 nuclease domain fused to DNA-binding domains of TAL effector proteins has been tested and found to be active in mammalian, specifically human cultured cells. Therefore, the utility of Clo051 nuclease domain fusion proteins for DNA and gene manipulation, specifically but without limitation in mammalian cells has been directly proven in the biological system that provides important applications for this technology. This finding is of particular importance since studies on protein function that are performed in lower eucaryotic organims, like e.g. yeast, do not allow a definite conclusion on the utility of the protein under study in mammalian cells. For example, a specific protein may function optimal at 30° Celsius, the growth temperature of yeast, but becomes unstable or inactive at 37° Celsius as the typical body temperature of mammals. In addition, the intracellular milieu of e.g. yeast cells, like ion and protein concentration, protein diversity and protein degradation mechanisms, are distinguished from the intracellular milieu of mammalian cells.

While the examples only describe the use of the nuclease domain of Clo051 (SEQ ID NO: 1), e.g. in combination with DNA-binding domains, the skilled person will appreciate that one may also employ the entire sequence of Clo051 as set forth in SEQ ID NO: 17 or shorter fragments thereof having endonuclease activity and comprising the amino acid sequence of SEQ ID NO: 1. The amino acid sequence of SEQ ID NO: 1 starts at E389 and ends at Y587 of the amino acid of SEQ ID NO: 17 as also exemplified in FIG. 5.

In a preferred embodiment of the nucleic acid molecule of the invention, in (I)(c) in said amino acid sequence having at least 70% sequence identity to SEQ ID NO: 1 the amino acid residues P66, D67, D84 and/or K86 of SEQ ID NO: 1 are not modified.

The nuclease domain of Clo051, like many type-II restriction endonucleases and e.g. the DNA repair protein MutH, share the conserved sequence motif PD-(D/E)XK within the core of their catalytic domain. The core serves as a scaffold for a weakly conserved active site, typically comprising two or three acidic residues (Asp or Glu) and one Lys residue, which together form the hallmark bipartite catalytic motif [(P)D. Xn. (D/E)XK] (where X is any amino acid). This motif has led to naming this superfamily of proteins as 'PD-(D/E)XK'. Work on restriction enzymes and DNA repair proteins has shown that the three catalytic residues are located close to each other on an uneven β-hairpin. The first D is located at the beginning of the first and shorter strand, and the E and K, separated by a hydrophobic residue x, are located in the middle of the second and longer strand. The catalytic module invariably approaches DNA from the minor groove side, and the sequence-specific binding is conducted by a separate module/subdomain in the major groove. The first two carboxylates of the DEK motif coordinate the metal ions. The first D is most conserved and coordinates both metal ions, whereas the second E can be replaced by Q, D, N, H or S, and the third K can be replaced E, Q, D, S, N or T. The Lysine residue in the conserved DEK motif coordinates the nucleophilic water in conjunction with the phosphate 3' to the scissile bond; the same Lysine is also hydrogen bonded with a carbonyl oxygen in the DNA binding module. This Lysine, which is conserved in many restriction endonucleases and is replaced by Glu or Gln in BamHI and BglII, has been proposed as a sensor for DNA binding and a hub that couples base recognition and DNA cleavage (Lee et al. (2005). Molecular Cell 20, 155-166; Orlowski, J. and J. M. Bujnicki (2008). Nucleic Acids Res 36(11): 3552-69).

Figure 13:
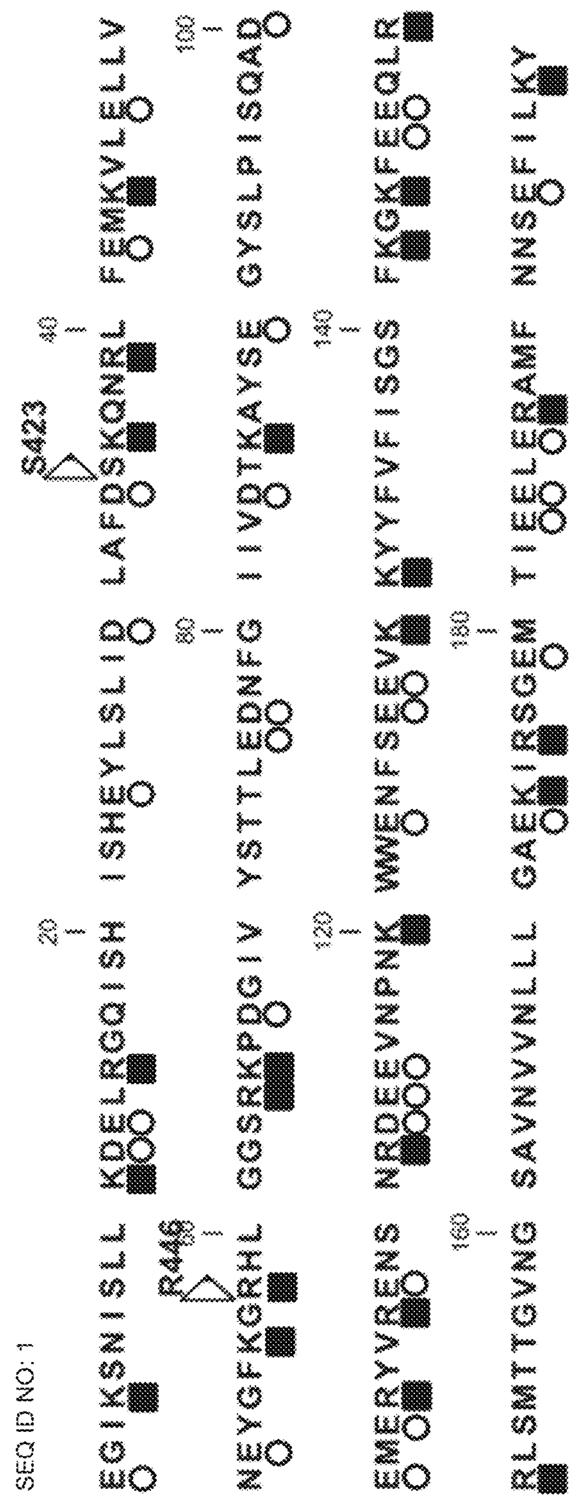

The primary sequence of the Clo051 nuclease domain between the positions E389 and Y587 of the sequence of SEQ ID NO: 17, i.e. the sequence of SEQ ID NO: 1, exhibits a unique distribution of the positively charged arginine (R)

and lysine (K) residues and of negatively charged glutamate (E) and aspartate (D) residues (FIG. 13). These residues constitute a three-dimensional landscape of charges within the Clo051 domain that determines the unique tertiary structure of this nuclease, as shown in the structural model in FIG. 6. Certain replacements of polar versus non-polar residues or of non-polar residues against polar residues, e.g. at the positions S35 and/or R58 of SEQ ID NO:1 (or S423 and R446 of SEQ ID NO: 17), alter the three-dimensional structure of the protein chain and may result into an increase of the nuclease activity. Such amino acid replacements may be made by trial and error or may follow specific hypotheses on the structural and functional impact on the Clo051 nuclease domain. Alternatively, a large number of randomly mutagenised variants of the Clo051 nuclease domain coding region can be assembled in a library by mutagenic, error prone PCR. This library of mutant molecules can be tested for the presence of hyperactive nuclease variants by a phenotypic screening assay in *E. coli*, yeast or mammalian cells that is coupled to a functional nuclease readout, e.g. as described for the improvement of the FLP recombinase (Buchholz et al., Nat. Biotechnol. 16, 657-62, 1998). Such a functional screen for improved nuclease variants can result into the replacement of single or multiple residues that lead to increased nuclease activity as compared to the Clo051 wildtype form.

Also envisaged are embodiments where more than the amino acid residues P66, D67, D84 and/or K86 of SEQ ID NO: 1 are not modified such as, e.g., amino acid stretches as, e.g. from at least P66 to at least K86, at least R64 to at least Y88, at least G62 to at least E90, as well as L60 to at least Y92 of SEQ ID NO: 1.

In a preferred embodiment of the invention, the nucleic acid molecule further encodes a DNA-binding domain.

In this embodiment the nucleic acid molecule of the invention encodes a fusion protein having the activity of an endonuclease and comprises a DNA-binding domain and a cleavage domain comprising or consisting of the novel endonuclease domain. The term "fusion protein" is well-known in the art and has the same meaning herein. Namely, it refers to a protein generated by joining two or more target nucleic acid sequences, e.g. genes, which originally code for separate proteins to create a fusion construct. Translation of said fusion construct results in a single protein with the functional properties derived from said separate proteins. The two proteins giving rise to the fusion protein may be connected by a linker, such as, e.g., a peptide linker. In other words, the DNA-binding domain and the cleavage domain of the nucleases may be directly fused to one another or may be fused via a linker.

The term "linker" as used in accordance with the present invention relates to a sequel of amino acids (i.e. peptide linkers) as well as to non-peptide linkers.

Peptide linkers as envisaged by the present invention are peptide or polypeptide linkers of at least 1 amino acid in length. Preferably, the linkers are 1 to 100 amino acids in length. More preferably, the linkers are 5 to 50 amino acids in length and even more preferably, the linkers are 10 to 20 amino acids in length. It is well known to the skilled person that the nature, i.e. the length and/or amino acid sequence of the linker may modify or enhance the stability and/or solubility of the molecule. Thus, the length and sequence of a linker depends on the composition of the respective portions of the fusion protein.

The skilled person is aware of methods to test the suitability of different linkers. For example, the properties of the molecule can easily be tested by testing the nuclease activity as well as the DNA-binding specificity of the respective portions of the fusion protein to be used in the method of the invention.

It will be appreciated by the skilled person that when the fusion protein is provided as a nucleic acid molecule encoding the fusion protein in expressible form, the linker is a peptide linker also encoded by said nucleic acid molecule.

The term "non-peptide linker", as used in accordance with the present invention, refers to linkage groups having two or more reactive groups but excluding peptide linkers as defined above. For example, the non-peptide linker may be a polymer having reactive groups at both ends, which individually bind to reactive groups of the individual portions of the fusion protein, for example, an amino terminus, a lysine residue, a histidine residue or a cysteine residue. The reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end. Preferably, the linker is a peptide linker. More preferably, the peptide linker consists of seven glycine residues.

Also the fusion protein may be flanked N- or C-terminally by additional sequences unrelated to said proteins in the fusion protein. In accordance with the present invention, a fusion protein of the invention comprises a DNA-binding domain. The term "DNA-binding domain" has the same meaning as known in the art and relates to a sequence motif/conformation within a protein that binds to DNA motifs. Protein domains that can specifically bind to a nucleic acid sequence include, e.g., zinc finger repeats, the helix-turn-helix (HTH) motif of homeodomains, and the ribbon-helix-helix (RHH) motif. Specific binding refers to the sequence specific binding and is specific, when a DNA-binding domain statistically only binds to a particular sequence and does not or essentially not bind to an unrelated sequence. The skilled person is well-aware of sequences encoding DNA-binding domains (Rohs et al. (2010). Annu. Rev. Biochem. 79, 233-269; Maeder et al. (2009). Nat. Protocols 10, 1471-1501).

In a more preferred embodiment of the nucleic acid molecule of the invention, the DNA-binding domain is a TAL effector motif of a TAL effector protein.

This embodiment relates to a nucleic acid molecule also encoding a TAL nuclease. The term "TAL nuclease" as used herein, is well known in the art and refers to a fusion protein comprising a DNA-binding domain, wherein the DNA-binding domain comprises or consists of Tal effector motifs of a TAL effector protein and the non-specific cleavage domain of a restriction nuclease. The fusion protein of the invention that is also employed in the method of the invention below retains or essentially retains the enzymatic activity of the endonuclease of the invention. In accordance with the present invention, said endonuclease activity (also referred to as function) is essentially retained if at least 60% of the biological activity of the endonuclease activity are retained. Preferably, at least 75% or at least 80% of the endonuclease activity are retained. More preferred is that at least 90% such as at least 95%, even more preferred at least 98% such as at least 99% of the biological activity of the endonuclease are retained. Most preferred is that the biological activity is fully, i.e. to 100%, retained. Also in accordance with the invention, fusion proteins having an increased biological activity compared to the endonuclease when not fused to a DNA-binding domain, i.e. more than 100% activity, are envisaged. Methods of assessing biological activity of (restriction) endonucleases are well known to the person skilled in the art and include, without being limiting, the incubation of an endonuclease with recombinant DNA and the analysis of the reaction products by gel electrophoresis (Bloch K D.; Curr Protoc Mol Biol 2001; Chapter 3:Unit 3.2).

The term "Tal effector protein", as used herein, refers to proteins belonging to the TAL (transcription activator-like) family of proteins. These proteins are expressed by bacterial plant pathogens of the genus *Xanthomonas*. Members of the large TAL effector family are key virulence factors of *Xanthomonas* and reprogram host cells by mimicking eukaryotic transcription factors. The pathogenicity of many bacteria depends on the injection of effector proteins via type III secretion into eukaryotic cells in order to manipulate cellular processes. TAL effector proteins from plant pathogenic *Xanthomonas* are important virulence factors that act as transcriptional activators in the plant cell nucleus. PthXo1, a TAL effector protein of a *Xanthomonas* rice pathogen, activates expression of the rice gene Os8N3, allowing *Xanthomonas* to colonize rice plants. TAL effector proteins are characterized by a central domain of tandem repeats, i.e. a DNA-binding domain as well as nuclear localization signals (NLSs) and an acidic transcriptional activation domain. Members of this effector family are highly conserved and differ mainly in the amino acid sequence of their repeats and in the number of repeats. The number and order of repeats in a TAL effector protein determine its specific activity. These repeats are referred to herein as "TAL effector motifs". One exemplary member of this effector family, AvrBs3 from *Xanthomonas campestris* pv. *vesicatoria*, contains 17.5 repeats and induces expression of UPA (up-regulated by AvrBs3) genes, including the Bs3 resistance gene in pepper plants (Kay, et al. 2005 Mol Plant Microbe Interact 18(8): 838-48; Kay, S. and U. Bonas 2009 Curr Opin Microbiol 12(1): 37-43). The repeats of AvrBs3 are essential for DNA binding of AvrBs3 and represent a distinct type of DNA binding domain. The mechanism of sequence specific DNA recognition has been elucidated by recent studies on the AvrBs3, Hax2, Hax3 and Hax4 proteins that revealed the TAL effectors' DNA recognition code (Boch, J., et al. 2009 Science 326: 1509-12).

Tal effector motifs or repeats are 32 to 34 amino acid protein sequence motifs. The amino acid sequences of the repeats are conserved, except for two adjacent highly variable residues (at positions 12 and 13) that determine specificity towards the DNA base A, G, C or T. In other words, binding to DNA is mediated by contacting a nucleotide of the DNA double helix with the variable residues at position 12 and 13 within the Tal effector motif of a particular Tal effector protein (Boch, J., et al. 2009 Science 326: 1509-12). Therefore, a one-to-one correspondence between sequential amino acid repeats in the Tal effector proteins and sequential nucleotides in the target DNA was found. Each Tal effector motif primarily recognizes a single nucleotide within the DNA substrate. For example, the combination of histidine at position 12 and aspartic acid at position 13 specifically binds cytosine; the combination of asparagine at both position 12 and position 13 specifically binds guanosine; the combination of asparagine at position 12 and isoleucine at position 13 specifically binds adenosine and the combination of asparagine at position 12 and glycine at position 13 specifically binds thymidine. Binding to longer DNA sequences is achieved by linking several of these Tal effector motifs in tandem to form a "DNA-binding domain of a Tal effector protein". Thus, a DNA-binding domain of a Tal effector protein relates to DNA-binding domains found in naturally occurring Tal effector proteins as well as to DNA-binding domains designed to bind to a specific target nucleotide sequence as described in the examples below. The use of such DNA-binding domains of Tal effector proteins for the generation of Tal effector motif—nuclease fusion proteins that recognize and cleave a specific target sequence depends on the reliable generation of DNA-binding domains of Tal effector proteins that can specifically recognize said particular target. Methods for the generation of DNA-binding domains of Tal effector proteins are well-known in the art (Zhang et al. (2011). Nat Biotechol. 29, 149-153; Cermak et al. (2011). Nucleic Acis Res. April 14, PubMed identifier 21493687).

Preferably, the DNA-binding domain is derived from the Tal effector motifs found in naturally occurring Tal effector proteins, such as for example Tal effector proteins selected from the group consisting of AvrBs3, Hax2, Hax3 or Hax4 (Bonas et al. 1989. Mol Gen Genet 218(1): 127-36; Kay et al. 2005 Mol Plant Microbe Interact 18(8): 838-48).

Envisaged in accordance with the present invention are fusion proteins that are provided as a DNA-binding domain of a Tal effector protein coupled with a single nuclease domain. These monomeric proteins can be combined to act as a functional dimer in order to develop nuclease activity through the cooperation of two nuclease domains, each being part of one fusion protein.

Preferably, the TAL nuclease in accordance with the present invention comprises more than one, i.e. several Tal effector motifs, such as at least 12 Tal effector motifs, such as for example at least 14 or at least 16 Tal effector motifs. More preferably, the TAL nuclease comprises at least 18 Tal effector motifs. In other words, the DNA-binding domain of a Tal effector protein within said fusion protein is comprised of at least 18 Tal effector motifs. In the case of fusion proteins consisting of dimers as described above this means that each fusion protein monomer comprises at least nine Tal effector motifs. Methods for testing the DNA-binding specificity of a fusion protein in accordance with the present invention are known to the skilled person and include, without being limiting, transcriptional reporter gene assays and electrophoretic mobility shift assays (EMSA).

Preferably, the binding site of the fusion protein is up to 500 nucleotides, such as up to 250 nucleotides, up to 100 nucleotides, up to 50 nucleotides, up to 25 nucleotides, up to 10 nucleotides such as up to 5 nucleotides upstream (i.e. 5') or downstream (i.e. 3') of the nucleotide(s) that is/are modified in accordance with the method of the present invention as detailed below.

In another embodiment, the invention relates to a vector encoding the nucleic acid molecule of the invention.

The term "vector" in accordance with the invention preferably means a plasmid, cosmid, virus, bacteriophage or another vector used e.g. conventionally in genetic engineering which carries the nucleic acid molecule of the invention either encoding the peptide or the fusion protein of the invention. Accordingly, the nucleic acid molecule of the invention may be inserted into several commercially available vectors. Non-limiting examples include prokaryotic plasmid vectors, such as of the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen).

The nucleic acid molecule of the present invention referred to above may also be inserted into vectors such that a (further) translational fusion with another nucleic acid molecule is generated. To this aim, overlap extension PCR can be applied (e.g. Wurch, T., Lestienne, F., and Pauwels, P. J., A modified overlap extension PCR method to create chimeric genes in the absence of restriction enzymes, Biotechn. Techn. 12, 9, Sep. 1998, 653-657). The products arising therefrom are termed fusion proteins and will be described further below. The other nucleic acid molecules may encode a protein which may e.g. increase the solubility and/or facilitate the purification of the protein encoded by the nucleic acid molecule of the invention. Non-limiting examples include pET32, pET41, pET43. The vectors may also contain an additional expressible nucleic acid coding for one or more chaperones to facilitate correct protein folding. Suitable bacterial expression hosts comprise e.g. strains derived from BL21 (such as BL21(DE3), BL21 (DE3)PlysS, BL21(DE3)RIL, BL21(DE3)PRARE) or Rosetta®.

Particularly preferred plasmids which can be used to introduce the nucleic acid encoding the polypeptide of the invention having the activity of an endonuclease into the host cell are: pUC18/19 (Roche Biochemicals), pBluescript II (Alting-Mees, et al. (1992). Meth. Enzymol., 216, 483-495), pKK-177-3H (Roche Biochemicals), pBTac2 (Roche Biochemicals), pKK223-3 (Amersham Pharmacia Biotech), pKK-233-3 (Stratagene) and pET (Novagen).

For vector modification techniques, see Sambrook and Russel, 2001. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, transcriptional termination sequences, promoters, enhancers, and/or insulators), internal ribosomal entry sites (IRES) and optionally poly-A signals ensuring termination of transcription and stabilization of the transcript. Additional regulatory elements may include transcriptional as well as translational enhancers, and/or naturally-associated or heterologous promoter regions. The regulatory elements may heterologous regulatory elements. Preferably, the nucleic acid molecule of the invention is operably linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically designed vectors allow the shuttling of DNA between different hosts, such as bacteria-fungal cells or bacteria-animal cells.

The co-transfection with a selectable marker such as kanamycin or ampicillin resistance genes for culturing in *E. coli* and other bacteria allows the identification and isolation of the transfected cells. Selectable markers for mammalian cell culture are the dhfr, gpt, neomycin, hygromycin resistance genes. The transfected nucleic acid can also be amplified to express large amounts of the encoded polypeptide. The DHFR (dihydrofolate reductase) marker is useful to develop cell lines that carry several hundred or even several thousand copies of the gene of interest. Another useful selection marker is the enzyme glutamine synthase (GS) (Fisher et al., Infect Immun. 1991 October; 59(10):3562-5; Bebbington et al., Biotechnology (NY). 1992 February; 10(2):169-75).

Using such markers, the cells are grown in selective medium and the cells with the highest resistance are selected.

In another embodiment the invention relates to a host cell comprising, e.g., as a result of transformation, transduction, microinjection or transfection, the nucleic acid molecule or the vector of the invention.

A variety of host-expression systems may be conceived to express the endonuclease coding sequence in a host cell using a suitable vector.

The "host cell" in accordance with the invention may be produced by introducing the nucleic acid molecule or vector(s) of the invention into the host cell which upon its/their presence preferably mediates the expression of the nucleic acid molecule of the invention encoding the endonuclease of the invention. The host from which the host cell is derived may be any prokaryote or eukaryotic cell.

A suitable eukaryotic host cell may be a vertebrate cell, an amphibian cell, a fish cell, an insect cell, a fungal/yeast cell, a nematode cell or a plant cell. The insect cell may be a *Spodoptera frugiperda* cell, a *Drosophila* S2 cell or a *Spodoptera* Sf9 cell, the fungal/yeast cell may a *Saccharomyces cerevisiae* cell, *Pichia pastoris* cell or an *Aspergillus* cell. It is preferred that the vertebrate cell is a mammalian cell such as a human cell, CHO, COS, 293 or Bowes melanoma cell. The plant cell is preferably selected independently from a cell of *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna* and *Zea*. The cell may be a part of a cell line. The cell from plant may, e.g., be derived from root, leave, bark, needle, bole or caulis.

Suitable prokaryotes (bacteria) useful as hosts for the invention are those generally used for cloning and/or expression like *E. coli* (e.g., *E. coli* strains BL21, HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis, Streptomyces* or *Bacillus subtilis*. Appropriate culture mediums and conditions for the above described host cells are known in the art.

Preferred examples for host cell to be genetically engineered with the nucleic acid molecule or the vector(s) of the invention is a cell of yeast, *E. coli* and/or a species of the genus *Bacillus* (e.g., *B. subtilis*). The most preferred host cell is *Bacillus* spec.

In a further embodiment the invention relates to a method of producing a protein or fusion having the activity of an endonuclease as defined herein above comprising the steps: (a) culturing the host cell of the invention and (b) isolating the produced protein or fusion protein having the activity of said endonuclease.

Suitable conditions for culturing a prokaryotic or eukaryotic host are well known to the person skilled in the art. Suitable conditions for culturing *E. coli* DH18BΔkat E (Invitrogen), *Pichia pastoris* or *Aspergillus niger* are, for example provided in the examples of the invention. In general, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, *Aspergillus* sp. may be grown on Sabouraud dextrose agar, or potato dextrose agar at about to 10° C. to about 40° C., and preferably at about 25° C. Suitable conditions for yeast cultures are known, for example from Guthrie and Fink, "Guide to Yeast Genetics and Molecular Cell Biology" (2002); Academic Pr Inc. The skilled person is also aware of all these conditions and may further adapt these conditions to the needs of a particular host species and the requirements of the polypeptide expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycin. The cells can be kept at 37° C. in a 5% CO2, water saturated atmosphere.

Suitable expression protocols for eukaryotic cells are well known to the skilled person and can be retrieved e.g. from in Sambrook, 2001.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

The step of protein isolation is preferably a step of protein purification. Protein purification in accordance with the invention specifies a process or a series of processes intended to further isolate the polypeptide of the invention from a complex mixture preferably to homogeneity. Purification steps, for example, exploit differences in protein size, physico-chemical properties and binding affinity. For example, proteins may be purified according to their isoelectric points by running them through a pH graded gel or an ion exchange column. Further, proteins may be separated according to their size or molecular weight via size exclusion chromatography or by SDS-PAGE (sodium dodecyl sulfate-polyacrylamide gel electrophoresis) analysis. In the art, proteins are often purified by using 2D-PAGE and are then further analysed by peptide mass fingerprinting to establish the protein identity. This is very useful for scientific purposes and the detection limits for protein are very low and nanogram amounts of protein are sufficient for their analysis. Proteins may also be separated by polarity/hydrophobicity via high performance liquid chromatography or reversed-phase chromatography. Thus, methods for protein purification are well known to the skilled person.

Furthermore, the invention relates in one embodiment to a protein or fusion protein having the activity of an endonuclease encoded by the nucleic acid molecule or vector of the invention.

The definitions for proteins or fusion proteins having the activity of an endonuclease encoded by the nucleic acid molecule or vector of the invention already given in the above embodiments pertaining to the nucleic acid molecule or vector of the invention apply explicitly also to this embodiment.

As a consequence of its endonuclease activity, another embodiment of the invention relates to the use of the protein or fusion protein of the invention to cleave a nucleic acid molecule, e.g. in one of the methods of the invention described below.

Furthermore, the present invention also relates to a kit comprising the nucleic acid molecule, the protein and/or the fusion protein of the invention. The various components of the kit may be packaged in one or more containers such as one or more vials. The vials may, in addition to the components, comprise preservatives or buffers for storage. In addition, the kit may contain instructions for use.

In another embodiment, the invention relates to a method of modifying a target sequence in the genome of a eukaryotic cell, the method comprising the step: (a) introducing into said cell the nucleic acid molecule, the vector or the protein or fusion protein of the invention.

The term "modifying" as used in accordance with the present invention refers to random and site-specific genomic manipulations resulting in changes in the nucleotide sequence of the genome of the eukaryotic host. When the fusion protein of the invention is introduced, site-specific modification of said "target sequence" in the genome is achieved via the DNA-binding domain. When only the protein of the invention is introduced, the "target sequence" is no specific sequence, because the novel endonuclease is not site-specific. Thus, the protein of the invention may be used to introduce random mutations into a genome, i.e. the "target sequence" occurs multiple times with in the genome and does not depend on a specific sequence motif. The genetic material comprising these changes in its nucleotide sequence is also referred to herein as the "modified target sequence" when modification is site-specific as, e.g. in the case of using the fusion protein of the invention. The term "modifying" includes, but is not limited to, substitution, insertion and deletion of one or more nucleotides within the target sequence. In the process of homologous recombination, the end product may reflect a deletion of sequences. As is understood by the skilled person, a homologous recombination, on the other hand, always also includes the incorporation of genetic material from the donor DNA sequence, which in this embodiment, however, leads to an overall deletion. It is understood by the skilled person that by simply introducing double-strand breaks into the genome of a cell modifications can be introduced that are the result of homologous recombination (in the presence and absence of exogenous donor sequences) or an endogenous DNA-repair mechanism such as, e.g., the non-homologous end joining (NHEJ) DNA repair that is prone to introducing small deletions at the site of the double-strand break in the course of ligating the broken ends.

The term “substitution”, as used herein, refers to the replacement of nucleotides with other nucleotides. The term includes for example the replacement of single nucleotides resulting in point mutations. Said point mutations can lead to an amino acid exchange in the resulting protein product but may also not be reflected on the amino acid level. Also encompassed by the term “substitution” are mutations resulting in the replacement of multiple nucleotides, such as for example parts of genes, such as parts of exons or introns as well as replacement of entire genes.

The term “insertion” in accordance with the present invention refers to the incorporation of one or more nucleotides into a nucleic acid molecule. Insertion of parts of genes, such as parts of exons or introns as well as insertion of entire genes is also encompassed by the term “insertion”. When the number of inserted nucleotides is not dividable by three, the insertion can result in a frameshift mutation within a coding sequence of a gene. Such frameshift mutations will alter the amino acids encoded by a gene following the mutation. In some cases, such a mutation will cause the active translation of the gene to encounter a premature stop codon, resulting in an end to translation and the production of a truncated protein. When the number of inserted nucleotides is instead dividable by three, the resulting insertion is an “in-frame insertion”. In this case, the reading frame remains intact after the insertion and translation will most likely run to completion if the inserted nucleotides do not code for a stop codon. However, because of the inserted nucleotides, the resulting protein will contain, depending on the size of the insertion, one or multiple new amino acids that may effect the function of the protein.

The term “deletion” as used in accordance with the present invention refers to the loss of nucleotides or part of genes, such as exons or introns as well as entire genes. As defined with regard to the term “insertion”, the deletion of a number of nucleotides that is not evenly dividable by three will lead to a frameshift mutation, causing all of the codons occurring after the deletion to be read incorrectly during translation, potentially producing a severely altered and most likely non-functional protein. If a deletion does not result in a frameshift mutation, i.e. because the number of nucleotides deleted is dividable by three, the resulting protein is nonetheless altered as the it will lack, depending on the size of the deletion, several amino acids that may affect or effect the function of the protein.

The above defined modifications are not restricted to coding regions in the genome, but can also occur in non-coding regions of the target genome, for example in regulatory regions such as promoter or enhancer elements or in introns.

Examples of modifications of the target genome include, without being limiting, the introduction of mutations into a wild type gene in order to analyse its effect on gene function; the replacement of an entire gene with a mutated gene or, alternatively, if the target sequence comprises mutation(s), the alteration of these mutations to identify which mutation is causative of a particular effect; the removal of entire genes or proteins or the removal of regulatory elements from genes or proteins as well as the introduction of fusion-partners, such as for example purification tags such as the his-tag or the tap-tag etc. In the latter case, the term “addition” may also be used instead of “insertion” so as to describe the preferable addition of a tag to a terminus of a polypeptide rather than within the sequence of a polypeptide The term “eukaryotic cell” as used herein, refers to any cell of a unicellular or multi-cellular eukaryotic organism, including cells from animals like vertebrates and from fungi and plants. Preferably, but without limitation, the cell is a mammalian cell. The term “mammalian cell” as used herein, is well known in the art and refers to any cell belonging to an animal that is grouped into the class of mammalia. The term “cell” as used in connection with the present invention can refer to a single and/or isolated cell or to a cell that is part of a multicellular entity such as a tissue, an organism or a cell culture another. In other words the method can be performed in vivo, ex vivo or in vitro. Depending on the particular goal to be achieved through modifying the genome of a mammalian cell, cells of different mammalian subclasses such as prototheria or theria may be used. For example, within the subclass of theria, preferably cells of animals of the infraclass eutheria, more preferably of the order primates, artiodactyla, perissodactyla, rodentia and lagomorpha are used in the method of the invention as detailed below. Furthermore, within a species one may choose a cell to be used in the method of the invention based on the tissue type and/or capacity to differentiate equally depending on the goal to be achieved by modifying the genome. Three basic categories of cells make up the mammalian body: germ cells, somatic cells and stem cells. A germ cell is a cell that gives rise to gametes and thus is continuous through the generations. Stem cells can divide and differentiate into diverse specialized cell types as well as self renew to produce more stem cells. In mammals there are two main types of stem cells: embryonic stem cells and adult stem cells. Somatic cells include all cells that are not a gametes, gametocytes or undifferentiated stem cells. The cells of a mammal can also be grouped by their ability to differentiate. A totipotent (also known as omnipotent) cell is a cell that is able to differentiate into all cell types of an adult organism including placental tissue such as a zygote (fertilized oocyte) and subsequent blastomeres, whereas pluripotent cells, such as embryonic stem cells, cannot contribute to extraembryonic tissue such as the placenta, but have the potential to differentiate into any of the three germ layers endoderm, mesoderm and ectoderm. Multipotent progenitor cells have the potential to give rise to cells from multiple, but limited number of cell lineages. Further, there are oligopotent cells that can develop into only a few cell types and unipotent cells (also sometimes termed a precursor cell) that can develop into only one cell type. There are four basic types of tissues: muscle tissue, nervous tissue, connective tissue and epithelial tissue that a cell to be used in the method of the invention can be derived from, such as for example hematopoietic stem cells or neuronal stem cells. To the extent human cells are envisaged for use in the method of the invention, it is preferred that such human cell is not obtained from a human embryo, in particular not via methods entailing destruction of a human embryo. On the other hand, human embryonic stem cells are at the skilled person's disposal such as taken from existent embryonic stem cell lines commercially available. Accordingly, the present invention may be worked with human embryonic stem cells without any need to use or destroy a human embryo. Alternatively, or instead of human embryonic stem cells, pluripotent cells that resemble embryonic stem cells such induced pluripotent stem (iPS) cells may be used, the generation of which is state of the art (Hargus G et al., Proc Natl Acad Sci USA 107:15921-15926; Jaenisch R. and Young R., 2008, Cell 132:567-582; Saha K, and Jaenisch R., 2009, Cell Stem Cell 5:584-595).

The term "nucleic acid molecules encoding said protein or fusion protein in expressible form" refers to a nucleic acid molecule which, upon expression in a cell or a cell-free system, results in a functional protein or fusion protein of the invention. Preferably, but without limitation, said nucleic acid is mRNA. Alternatively, DNA having appropriate transcription signals to enable expression or cDNA may be used.

Introduction of the protein, fusion protein or of the nucleic acid molecule encoding said protein, fusion protein in expressible form into a cell can be achieved by methods known in the art and depends on the nature of said proteins or nucleic acid molecules. For example, and in the case of introducing nucleic acid molecules, said introducing can be achieved by chemical based methods (calcium phosphate, liposomes, DEAE-dextrane, polyethylenimine, nucleofection), non chemical methods (electroporation, sonoporation, optical transfection, gene electrotransfer, hydrodynamic delivery), particle-based methods (gene gun, magnetofection, impalefection) and viral methods. Preferably, the nucleic acid molecules are to be introduced into the nucleus by methods such as, e.g., microinjection or nucleofection. Methods for carrying out microinjection are well known in the art and are described for example in Nagy et al. (Nagy A, Gertsenstein M, Vintersten K, Behringer R., 2003. Manipulating the Mouse Embryo. Cold Spring Harbour, New York: Cold Spring Harbour Laboratory Press) as well as in the examples herein below. It is understood by the skilled person that depending on the method of introduction it may be advantageous to adapt DNA molecules. For example, a linear DNA molecule may be more efficient in homologous recombination events when using electroporation as method to introduce said DNA molecule into a, e.g., mammalian cell, whereas a circular DNA molecule may be more advantageous when injecting cells.

All the definitions and preferred embodiments defined above with regard to the nucleic acid molecule, protein or fusion protein of the invention also apply mutatis mutandis in the context of the method of the invention.

In accordance with the present invention, the term "target sequence in the genome" refers to the genomic location that is to be modified by the method of the invention. The "target sequence in the genome" comprises but is not restricted to the nucleotide(s) subject to the particular modification. Furthermore, and preferably with regard to the fusion protein of the invention the term "target sequence in the genome" also comprises regions for binding of homologous sequences of a second nucleic acid molecule. In other words, the term "target sequence in the genome" also comprises the sequence flanking/surrounding the relevant nucleotide(s) to be modified. In some instances, the term "target sequence" may also refer to the entire gene to be modified.

Specific binding has been defined herein above and ensures that double-strand breaks are only introduced within said target sequence.

In a more preferred embodiment of the method of the invention, the modification of said target sequence is by homologous recombination with a donor nucleic acid sequence, further comprising the step: (b) introducing a nucleic acid molecule into said cell, wherein said nucleic acid molecule comprises said donor nucleic acid sequence, wherein said donor DNA sequence is flanked upstream by a first flanking element and downstream by a second flanking element, wherein said first and second flanking element are different and wherein each of said first and second flanking element are homologous to a continuous DNA sequence on either side of the double-strand break introduced in (a) of the method of the invention within said target sequence in the genome of said eukaryotic cell.

The term "homologous recombination", is used according to the definitions provided in the art. Thus, it refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular for the repair of double strand breaks. The mechanism of homologous recombination is well known to the skilled person and has been described, for example by Paques and Haber (Paques F, Haber J E.; Microbiol Mol Biol Rev 1999; 63:349-404). In the method of the present invention, homologous recombination of the donor sequence is enabled by the presence of said first and said second flanking element being placed upstream (5') and downstream (3'), respectively, of said donor DNA sequence each of which being homologous to a continuous DNA sequence within said target sequence.

In accordance with the present invention, the term "donor DNA sequence" refers to a DNA sequence that serves as a template in the process of homologous recombination and that carries the modification that is to be introduced into the target sequence. By using this donor DNA sequence as a template, the genetic information, including the modifications, is copied into the target sequence within the genome of the cell by way of homologous recombination. In non-limiting examples, the donor nucleic acid sequence can be essentially identical to the part of the target sequence to be replaced, with the exception of one nucleotide which differs and results in the introduction of a point mutation upon homologous recombination or it can consist of an additional gene previously not present in the target sequence. Conceivably, the nature, i.e. its length, base composition, similarity with the target sequence, of the donor DNA sequence depends on how the target sequence is to be modified as well as the particular goal to be achieved by the modification of the target sequence. It is understood by those skilled in the art that said donor DNA sequence is flanked by sequences that are homologous to sequences within the target sequence to enable homologous recombination to take place leading to the incorporation of the donor DNA sequence into the genome of said cell. In addition to being homologous to a continuous DNA sequence within the genomic DNA, the first and the second flanking element are different to allow targeted homologous recombination to take place.

The term "homologous to a continuous DNA sequence on either side of the double-strand break introduced in (a) of the method of the invention within said target sequence", in accordance with the present invention, refers to regions having sufficient sequence identity to ensure specific binding to the target sequences that lie upstream and downstream of the location of the double-strand break. The term "homologous" as used herein can be interchanged with the term "identical" as outlined herein elsewhere with regard to varying levels of sequence identity. Methods to evaluate the identity level between two nucleic acid sequences are well known in the art and have been described herein above. These methods involving programs, in addition to providing a pairwise sequence alignment, also report the sequence identity level (usually in percent identity) and the probability for the occurrence of the alignment by chance (P-value) and can further be used to predict the occurrence of specific binding.

Preferably, said first and second flanking element being "homologous to a continuous DNA sequence within said target sequence" (also referred to as "homology arms" in the art) have a sequence identity with the corresponding part of the target sequence of at least 95%, more preferred at least 97%, more preferred at least 98%, more preferred at least 99%, even more preferred at least 99.9% and most preferred 100%. The above defined sequence identities are defined only with respect to those parts of the target sequence which serve as binding sites for the homology arms, i.e. said first and said second flanking element. Thus, the overall sequence identity between the entire target sequence and the homologous regions of the nucleic acid molecule of step (b) of the method of modifying a target sequence of the present invention can differ from the above defined sequence identities, due to the presence of the part of the target sequence which is to be replaced by the donor DNA sequence.

The flanking elements homologous to the target sequence comprised in the DNA molecule have a length of at least 170 bp each. Preferably, the elements each have a length of at least 250 nucleotides, at least 300 nucleotides, at least 400 nucleotides, at least 500 nucleotides, such as at least 600 nucleotides, at least 750 bp nucleotides, more preferably at least 1000 nucleotides, such as at least 1500 nucleotides, even more preferably at least 2000 nucleotides and most preferably at least 2500 nucleotides. The maximum length of the elements homologous to the target sequence comprised in the nucleic acid molecule depends on the type of cloning vector used and can be up to a length 20.000 nucleotides each in *E. coli* high copy plasmids using the col EI replication origin (e.g. pBluescript) or up to a length of 300.000 nucleotides each in plasmids using the F-factor origin (e.g. in BAC vectors such as for example pTARBAC1).

The DNA molecules comprising the donor DNA sequence and the flanking elements are—necessarily if the site-specific nuclease (fusion protein) binding site is contained undisrupted within one of the flanking elements and preferably if the site-specific nuclease (fusion protein) binding site is disrupted by the donor sequence, i.e. one part on each of the flanking elements—modified so that the fusion protein not introduce a double-strand break into the sequence of the donor DNA as part of a DNA molecule. When the fusion protein is a TAL or zinc-finger nuclease, this can be achieved, e.g., by modifying either the binding or cleavage motif (see Example 2, FIG. 12).

It will be appreciated by one of skill in the art that said DNA molecule to be introduced into the cell in item (b) of the method of the invention may comprise all a nucleic acid molecule (sequence) encoding said fusion protein in expressible form and the nucleic acid molecule comprising the donor nucleic acid sequence and the flanking elements homologous to the target sequence. Alternatively, the nucleic acid molecule of item (b) may be a distinct nucleic acid molecule, to be introduced in addition to the nucleic acid molecules encoding said fusion protein in expressible form of item (a).

Also envisaged in a preferred embodiment of the method of the invention is that said cell is analysed for successful modification of said target sequence in the genome.

Methods for analysing for the presence or absence of a modification are well known in the art and include, without being limiting, assays based on physical separation of nucleic acid molecules, sequencing assays as well as cleavage and digestion assays and DNA analysis by the polymerase chain reaction (PCR).

Examples for assays based on physical separation of nucleic acid molecules include without limitation MALDI-TOF, denaturating gradient gel electrophoresis and other such methods known in the art, see for example Petersen et al., Hum. Mutat. 20 (2002) 253-259; Hsia et al., Theor. Appl. Genet. 111 (2005) 218-225; Tost and Gut, Clin. Biochem. 35 (2005) 335-350; Palais et al., Anal. Biochem. 346 (2005) 167-175.

Examples for sequencing assays comprise without limitation approaches of sequence analysis by direct sequencing, fluorescent SSCP in an automated DNA sequencer and pyrosequencing. These procedures are common in the art, see e.g. Adams et al. (Ed.), "Automated DNA Sequencing and Analysis", Academic Press, 1994; Alphey, "DNA Sequencing: From Experimental Methods to Bioinformatics", Springer Verlag Publishing, 1997; Ramon et al., J. Transl. Med. 1 (2003) 9; Meng et al., J. Clin. Endocrinol. Metab. 90 (2005) 3419-3422.

Examples for cleavage and digestion assays include without limitation restriction digestion assays such as restriction fragments length polymorphism assays (RFLP assays), RNase protection assays, assays based on chemical cleavage methods and enzyme mismatch cleavage assays, see e.g. Youil et al., Proc. Natl. Acad. Sci. U.S.A. 92 (1995) 87-91; Todd et al., J. Oral Maxil. Surg. 59 (2001) 660-667; Amar et al., J. Clin. Microbiol. 40 (2002) 446-452.

Alternatively, instead of analysing the cells for the presence or absence of the desired modification, in particular in the case of sequence-specific modification, successfully modified cells may be selected by incorporation of appropriate selection markers. Selection markers include positive and negative selection markers, which are well known in the art and routinely employed by the skilled person. Non-limiting examples of selection markers include dhfr, gpt, neomycin, hygromycin, dihydrofolate reductase, G418 or glutamine synthase (GS) (Murphy et al., Biochem J. 1991, 227:277; Bebbington et al., Bio/Technology 1992, 10:169). Using these markers, the cells are grown in selective medium and the cells with the highest resistance are selected. Also envisaged are combined positive-negative selection markers, which may be incorporated into the target genome by homologous recombination or random integration. After positive selection, the first cassette comprising the positive selection marker flanked by recombinase recognition sites is exchanged by recombinase mediated cassette exchange against a second, marker-less cassette. Clones containing the desired exchange cassette are then obtained by negative selection.

In a preferred embodiment of the method of the invention, the cell is selected from the group consisting of a mammalian or vertebrate cell, a plant cell or a fungal cell.

In another preferred embodiment of the method of the invention, the cell is an oocyte.

As used herein the term "oocyte" refers to the female germ cell involved in reproduction, i.e. the ovum or egg cell. In accordance with the present invention, the term "oocyte" comprises both oocytes before fertilisation as well as fertilised oocytes, which are also called zygotes. Thus, the oocyte before fertilisation comprises only maternal chromosomes, whereas an oocyte after fertilisation comprises both maternal and paternal chromosomes. After fertilisation, the oocyte remains in a double-haploid status for several hours, in mice for example for up to 18 hours after fertilisation. In accordance with the invention, the oocyte may be non-human.

In a more preferred embodiment of the method of the invention, the oocyte is a fertilised oocyte. The term "fertilised oocyte", as used herein, refers to an oocyte after fusion with the fertilizing sperm. For a period of many hours (such as up to 18 hours in mice) after fertilisation, the oocyte is in a double-haploid state, comprising one maternal haploid pronucleus and one paternal haploid pronucleus. After migration of the two pronuclei together, their membranes break down, and the two genomes condense into chromosomes, thereby reconstituting a diploid organism. Preferably, the mammalian or avian oocyte used in the method of the present invention is a fertilised mammalian or avian oocyte in the double-haploid state.

In the case of oocytes to be used as cells in the method of the invention the protein, fusion protein or the nucleic acid molecule encoding said protein or fusion protein is introduced into the oocyte by microinjection. Microinjection into the oocyte can be carried out by injection into the nucleus (before fertilisation), the pronucleus (after fertilisation) and/or by injection into the cytoplasm (both before and after fertilisation). When a fertilised oocyte is employed, injection into the pronucleus is carried out either for one pronucleus or for both pronuclei. Injection of the Tal-finger nuclease or of a DNA encoding the Tal-finger nuclease of step (a) of the method of modifying a target sequence of the present invention is preferably into the nucleus/pronucleus, while injection of an mRNA encoding the Tal-finger nuclease of step (a) is preferably into the cytoplasm. Injection of the nucleic acid molecule of step (b) is preferably into the nucleus/pronucleus. However, injection of the nucleic acid molecule of step (b) can also be carried out into the cytoplasm when said nucleic acid molecule is provided as a nucleic acid sequence having a nuclear localisation signal to ensure delivery into the nucleus/pronucleus. Preferably, the microinjection is carried out by injection into both the nucleus/pronucleus and the cytoplasm. For example, the needle can be introduced into the nucleus/pronucleus and a first amount of the Tal-finger nuclease and/or nucleic acid molecule are injected into the nucleus/pronucleus. While removing the needle from the oocyte, a second amount of the Tal-finger nuclease and/or nucleic acid molecule is injected into the cytoplasm.

Methods for carrying out microinjection are well known in the art and are described for example in Nagy et al. (Nagy A, Gertsenstein M, Vintersten K, Behringer R., 2003. Manipulating the Mouse Embryo. Cold Spring Harbour, New York: Cold Spring Harbour Laboratory Press) as well as in the examples herein below.

Also preferred is that the nucleic acid molecule of step (b) of the method of the invention is (also) introduced into the cell by microinjection.

In another embodiment, the invention relates to method of producing a non-human vertebrate or mammal carrying a modified target sequence in its genome, the method comprising transferring a cell produced by the method of the invention into a pseudo pregnant female host.

In accordance with the present invention, the term "transferring a cell produced by the method of the invention into a pseudopregnant female host" includes the transfer of a fertilised oocyte but also the transfer of pre-implantation embryos of for example the 2-cell, 4-cell, 8-cell, 16-cell and blastocyst (70- to 100-cell) stage. Said pre-implantation embryos can be obtained by culturing the cell under appropriate conditions for it to develop into a pre-implantation embryo. Furthermore, injection or fusion of the cell with a blastocyst are appropriate methods of obtaining a pre-implantation embryo. Where the cell produced by the method of the invention is a somatic cell, derivation of induced pluripotent stem cells is required prior to transferring the cell into a female host such as for example prior to culturing the cell or injection or fusion of the cell with a pre-implantation embryo. Methods for transferring an oocyte or pre-implantation embryo to a pseudo pregnant female host are well known in the art and are, for example, described in Nagy et al., (Nagy A, Gertsenstein M, Vintersten K, Behringer R., 2003. Manipulating the Mouse Embryo. Cold Spring Harbour, New York: Cold Spring Harbour Laboratory Press).

It is further envisaged in accordance with the method of producing a non-human vertebrate or mammal carrying a modified target sequence in its genome that a step of analysis of successful genomic modification is carried out before transplantation into the female host. As a non-limiting example, the oocyte can be cultured to the 2-cell, 4-cell or 8-cell stage and one cell can be removed without destroying or altering the resulting embryo. Analysis for the genomic constitution, e.g. the presence or absence of the genomic modification, can then be carried out using for example PCR or southern blotting techniques or any of the methods described herein above. Such methods of analysis of successful genotyping prior to transplantation are known in the art and are described, for example in Peippo et al. (Peippo J, Viitala S, Virta J, Raty M, Tammiranta N, Lamminen T, Aro J, Myllymaki H, Vilkki J.; Mol Reprod Dev 2007; 74:1373-1378).

Where the cell is an oocyte, the method of producing a non-human vertebrate or mammal carrying a modified target sequence in its genome comprises (a) modifying the target sequence in the genome of a vertebrate or mammalian oocyte in accordance with the method of the invention; (b) transferring the oocyte obtained in (a) to a pseudopregnant female host; and, optionally, (c) analysing the offspring delivered by the female host for the presence of the modification.

For this method of producing a non-human vertebrate or mammal, fertilisation of the oocyte is required. Said fertilisation can occur before the modification of the target sequence in step (a) in accordance with the method of producing a non-human vertebrate or mammal of the invention, i.e. a fertilised oocyte can be used for the method of modifying a target sequence in accordance with the invention. The fertilisation can also be carried out after the modification of the target sequence in step (a), i.e. a non-fertilised oocyte can be used for the method of modifying a target sequence in accordance with the invention, wherein the oocyte is subsequently fertilised before transfer into the pseudopregnant female host.

The step of analysing for the presence of the modification in the offspring delivered by the female host provides the necessary information whether or not the produced non-human vertebrate or mammal carries the modified target sequence in its genome. Thus, the presence of the modification is indicative of said offspring carrying a modified target sequence in its genome whereas the absence of the modification is indicative of said offspring not carrying the modified target sequence in its genome. Methods for analysing for the presence or absence of a modification have been detailed above.

The non-human vertebrate or mammal produced by the method of the invention is, inter alia, useful to study the function of genes of interest and the phenotypic expression/ outcome of modifications of the genome in such animals. It is furthermore envisaged, that the non-human mammals of the invention can be employed as disease models and for testing therapeutic agents/compositions. Furthermore, the non-human vertebrate or mammal of the invention can also be used for livestock breeding.

In a preferred embodiment, the method of producing a non-human vertebrate or mammal further comprises culturing the cell to form a pre-implantation embryo or introducing the cell into a blastocyst prior to transferring it into the pseudo pregnant female host. Methods for culturing the cell to form a pre-implantation embryo or introducing the cell into a blastocyst are well known in the art and are, for example, described in Nagy et al., loc. cit.

The term "introducing the cell into a blastocyst" as used herein encompasses injection of the cell into a blastocyst as well as fusion of a cell with a blastocyst. Methods of introducing a cell into a blastocyst are described in the art, for example in Nagy et al., loc. cit.

The present invention further relates to a non-human vertebrate or mammalian animal obtainable by the above described method of the invention.

In a preferred embodiment of the methods of the invention, the cell is from a mammal selected from the group consisting of rodents, dogs, felides, primates, rabbits, pigs, or cows or the cell is from an avian selected from the group consisting of chickens, turkeys, pheasants, ducks, geese, quails and ratites including ostriches, emus and cassowaries or the cell is from a fish such as for example a zebrafish, salmon, trout, common carp or coi carp.

All of the mammals, avians and fish described herein are well known to the skilled person and are taxonomically defined in accordance with the prior art and the common general knowledge of the skilled person.

Non-limiting examples of "rodents" are mice, rats, squirrels, chipmunks, gophers, porcupines, beavers, hamsters, gerbils, guinea pigs, degus, chinchillas, prairie dogs, and groundhogs.

Non-limiting examples of "dogs" include members of the subspecies canis lupus familiaris as well as wolves, foxes, jackals, and coyotes.

Non-limiting examples of "felides" include members of the two subfamilies: the pantherinae, including lions, tigers, jaguars and leopards and the felinae, including cougars, cheetahs, servals, lynxes, caracals, ocelots and domestic cats.

The term "primates", as used herein, refers to all monkey including for example cercopithecoid (old world monkey) or platyrrhine (new world monkey) as well as lemurs, tarsiers, apes and marmosets (*Callithrix jacchus*).

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: TAL-Nuclease Expression Vectors.

The figure shows the structure and function of TAL-Nuclease fusion proteins, consisting of a sequence-specific DNA-binding domain and a nonspecific DNA cleavage (nuclease) domain. The DNA-binding domain can be assembled from the four types of 34 amino acid TAL peptide elements that exhibit binding specificity against one of the DNA nucleotides through the amino acid positions 12 and 13 (NI-A; HD-C; NG-T; NN-G). Upon binding of the TAL element domain to the selected target DNA sequence, the nuclease domain of the fusion protein comes into close contact to the DNA double-strand but does not cleave the DNA as a nuclease monomer. Only upon the binding of a second TAL-Nuclease fusion protein to a second DNA target sequence located downstream of the binding site of the first fusion protein, the DNA double strand is cleaved through cooperation of the two nuclease domains that are in close contact.

Figure 2:
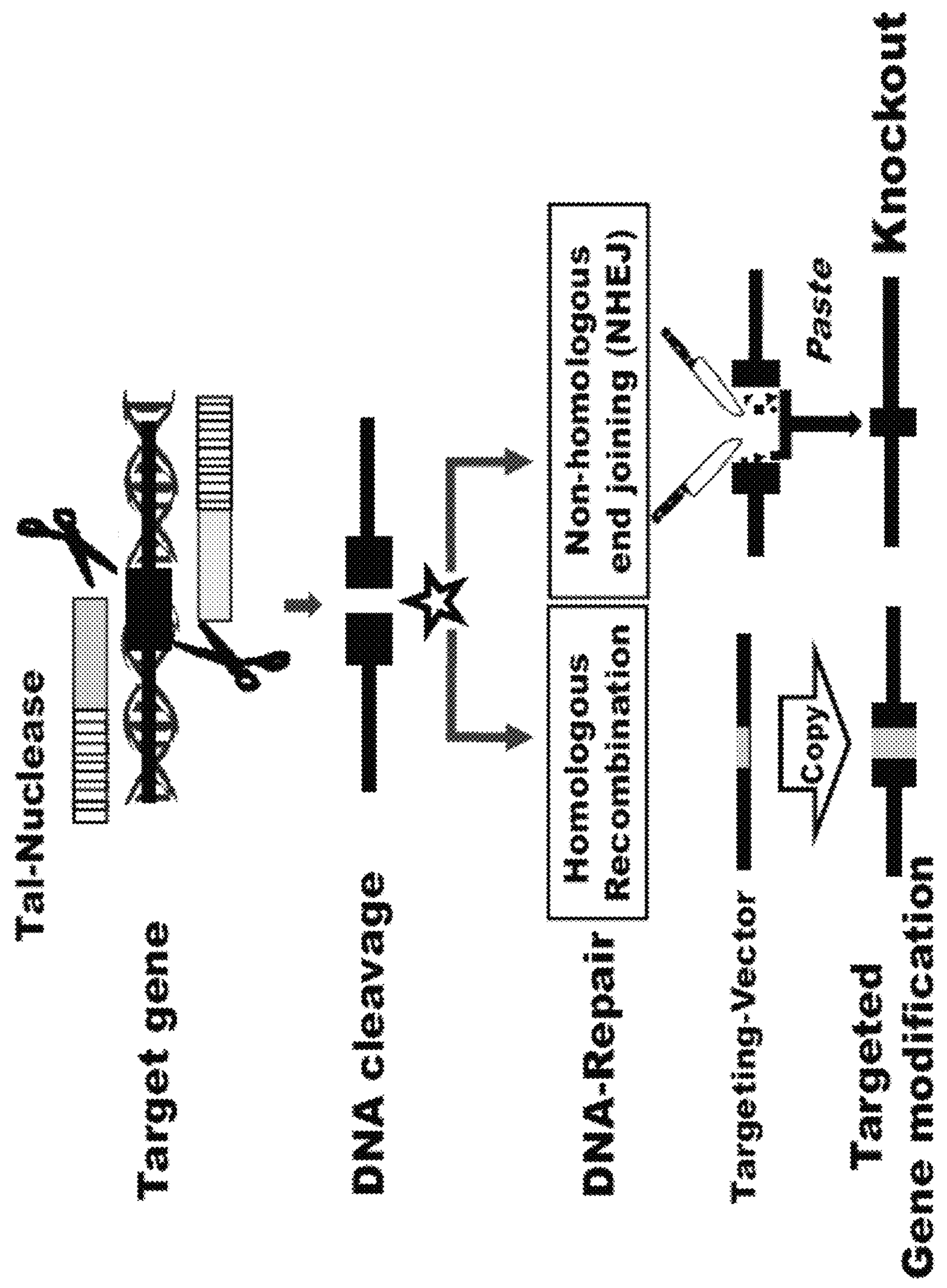

FIG. 2: TAL-Nuclease Induced Modification of Genomic Sequences.

The figure shows a pair of TAL-nuclease fusion proteins that bind up- and downstream of a selected target site within a genomic target gene. Upon the creation of a DNA double-strand break within the target site two competing DNA repair mechanisms are strongly activated in cells: i) by homologous recombination, in the presence of an externally introduced gene targeting vector that comprises two homology regions to the target gene and a predesigned genetic modification/mutation, the preplanned modification is copied from the targeting vector into the genome; by this route any targeted gene modification (e.g. knock-out, knock-in) can be placed into the genome, ii) by the non-homologous end joining repair pathway (NHEJ) the free DNA ends are closed by ligation without a repair template; by this route a variable number of nucleotides is frequently lost (knife symbol) before end ligation and results frequently into a knockout allele of the target gene.

Figure 3:
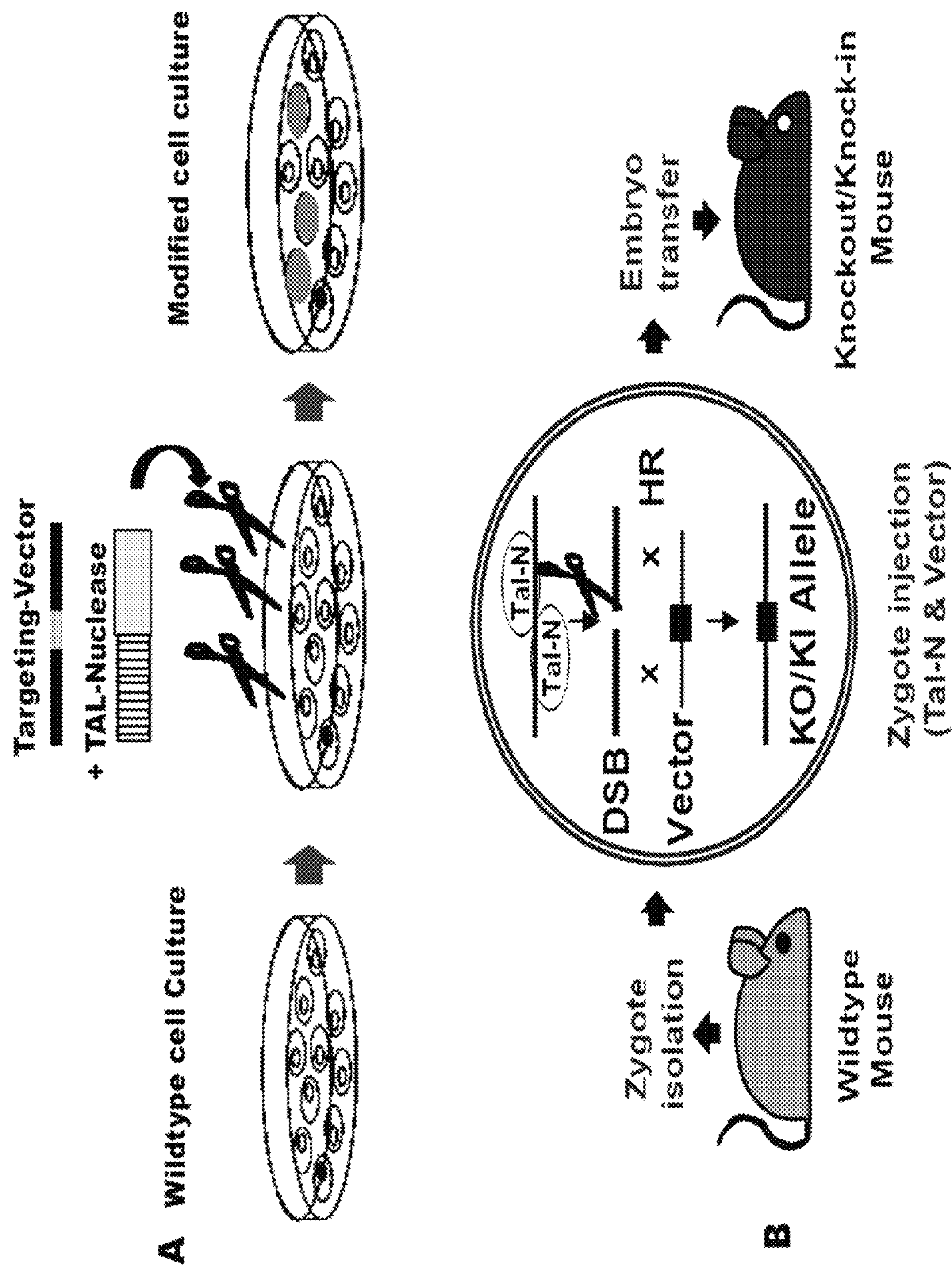

FIG. 3: Use of TAL-Nucleases for Gene Targeting in Mammalian Cell Lines and Zygotes.

A: For the generation of genetic modifications in mammalian cell lines TAL-nuclease expression vectors can be transfected, together with or without a specific gene targeting vector, into cultured cells. Upon nuclease expression and DNA repair a fraction of the treated cells contains the desired genetic alteration. These cells can be isolated and further cultured as a pure genetically modified cell line. B: Upon the microinjection of TAL-nuclease mRNA, together with or without a specific gene targeting vector, into fertilized mammalian oocytes (zygotes, isolated from wildtype female e.g. mice) a knockout (KO) or Knockin (KI) allele can be directly introduced into the genome of the one-cell embryo. Pseudopregnant females deliver live offspring from microinjected oocytes. The offspring is genotyped for the presence of the induced genetic modification. Positive animals are selected for further breeding to establish a gene targeted strain.

Figure 4:
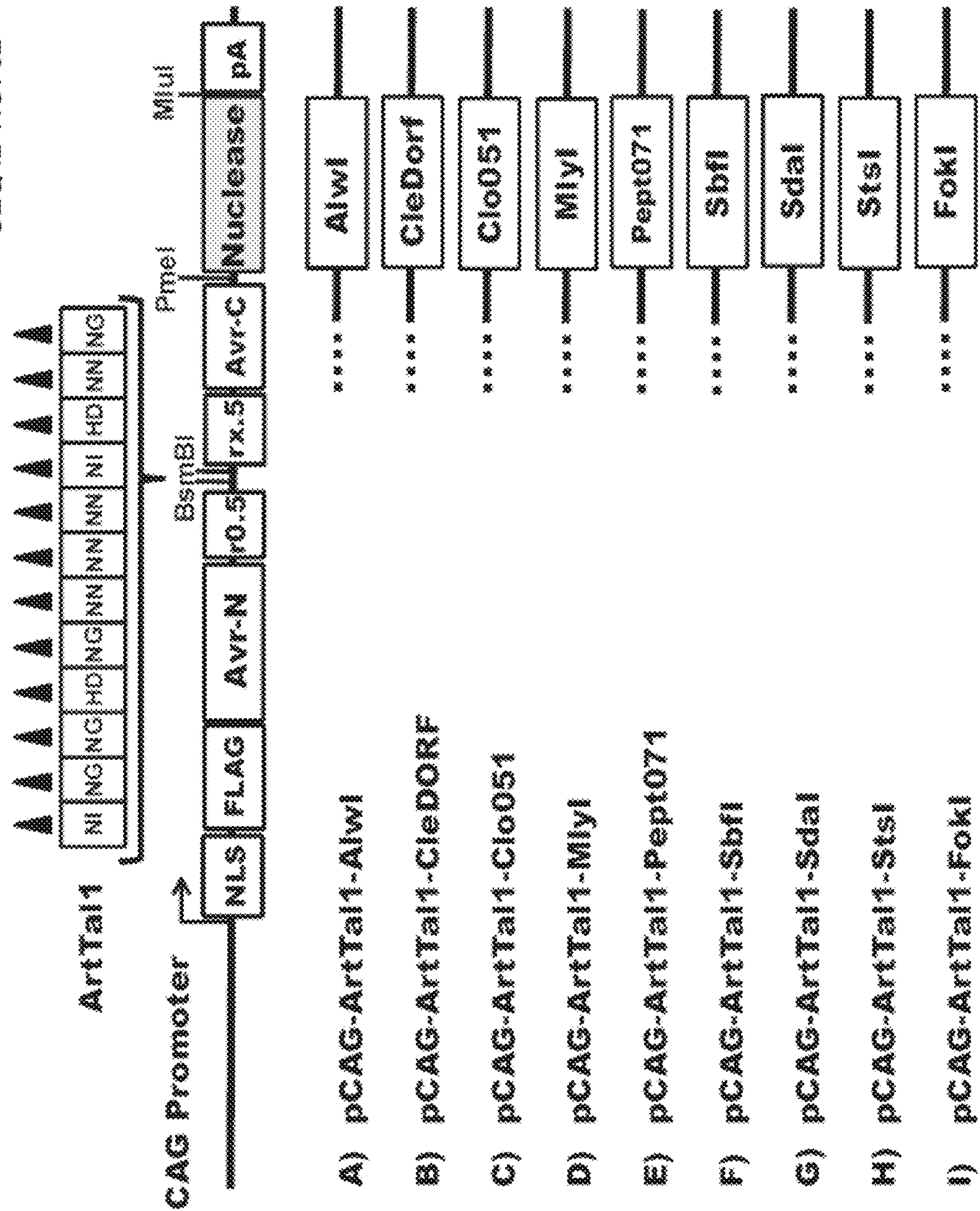

FIG. 4: TAL-Nuclease Expression Vectors.

The Tal nuclease expression vector pCAG-Tal-nuclease contains a CAG promoter region and a transcriptional unit comprising, upstream of a central pair of BsmBI restriction sites, an ATG start codon (arrow), a nuclear localisation sequence (NLS), a FLAG Tag sequence (FLAG), a linker sequence, a segment coding for 110 amino acids of the Tal protein AvrBs3 (AvrN) and its invariable N-terminal Tal repeat (r0.5). Downstream of the BsmBI sites the transcriptional unit contains an invariable C-terminal Tal repeat (rx.5), a segment coding for 44 amino acids derived from the Tal protein AvrBs3, a PmeI and MluI restriction site for the insertion of nuclease coding regions and a polyadenylation signal sequence (pA). DNA segments coding for TAL repeat elements can be inserted into the BsmBI sites of pCAG-Tal-nuclease for the expression of variable TAL-nuclease fusion proteins. To create ArtTal1-nuclease expression vectors the ArtTal1 array of TAL repeat elements, recognizing the specified 12 bp target sequence, was inserted into the BsmBI sites of pCAG-TAL-nuclease. Each 34 amino acid Tal repeat is drawn as a square indicating the repeat's amino acid code at positions 12/13 that confers binding to one of the DNA nucleotides of the target sequence (NI>A, NG>T, HD>C, NN>G) shown above. Next, synthetic nuclease domain coding regions were inserted into the PmeI and MluI sites of pCAG-ArtTal1-nuclease to obtain the expression vectors: A: pCAG-ArtTal1-Alw including the nuclease domain of the AlwI restriction endonuclease, B: pCAG-ArtTal1-CleDORF including the nuclease domain of the CleDORF gene, C: pCAG-ArtTal1-Clo051 including the nuclease domain of the Clo051 gene, D: pCAG-ArtTal1-Mly including the nuclease domain of the MlyI restriction endonuclease, E: pCAG-ArtTal1-Pept071 including the nuclease domain of the Pept071 gene, F: pCAG-ArtTal1-Sbf including the nuclease domain of the SbfI restriction endonuclease, G: pCAG-ArtTal1-SdaI including the nuclease domain of the SdaI restriction endonuclease, H: pCAG-ArtTal1-Sst including the nuclease domain of the StsI restriction endonuclease, and I: pCAG-ArtTal1-Fok including the nuclease domain of the FokI restriction endonuclease FIG. 5: Amino Acid Sequence of the Clo051 Protein Sequence of the 587 amino acid Clo051 protein in the single letter code. Indicated are the methionine at position 1 (M1), the tyrosine at position 587 (Y587) and the 199 residue nuclease domain between position E389 and Y587. Further highlighted are the positions D455, D472 and K474 that are characteristic for the conserved active site of the 'PD-(D/E)XK' superfamily of enzymes interacting with DNA.

Figure 6:
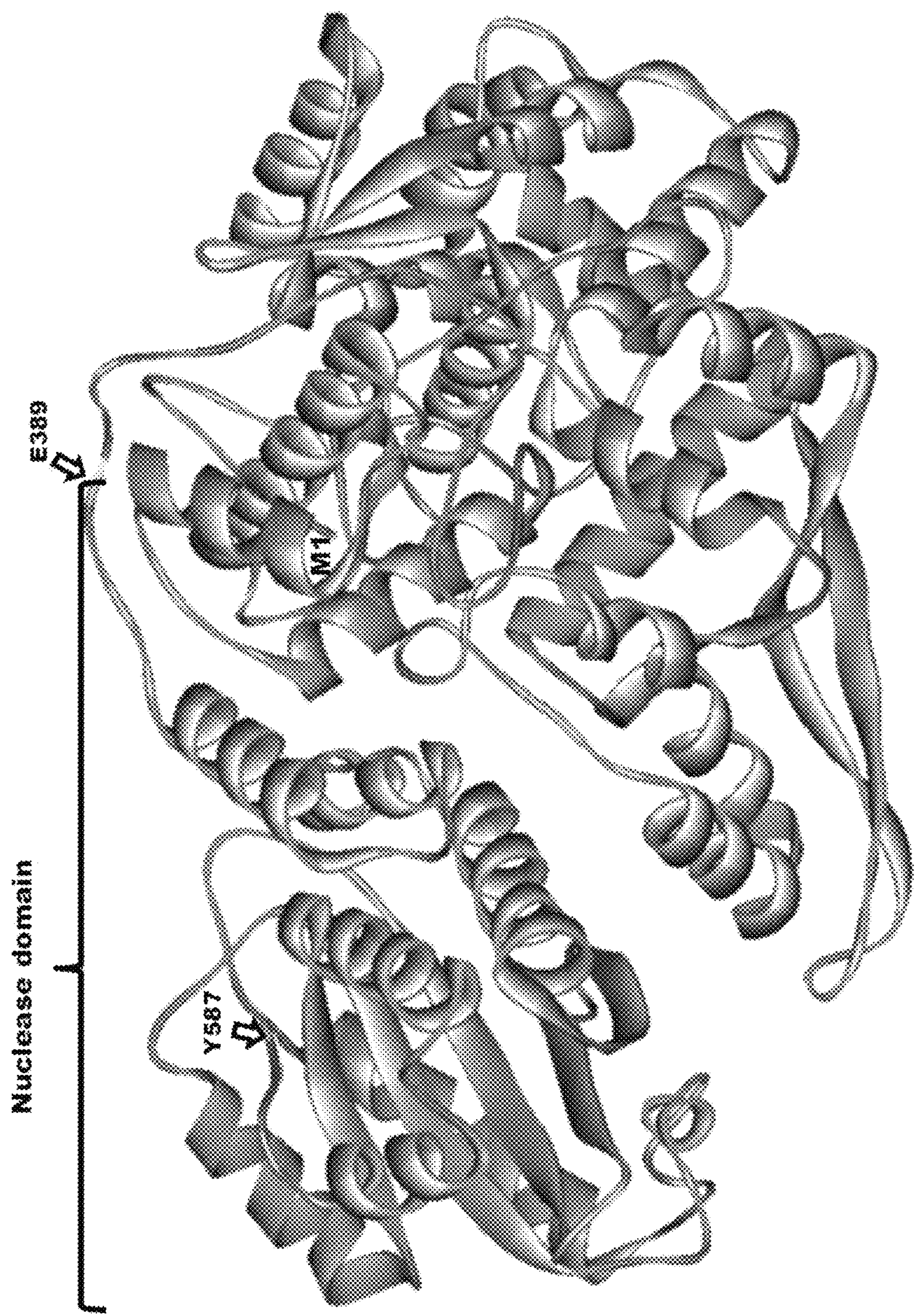

FIG. 6: Predicted Structure of the Clo051 Protein and its Nuclease Domain.

The tertiary structure of the Clo051 protein was predicted from its amino acid sequence (FIG. 5) using the I-TASSER software. The secondary structures are shown as alpha-helical and beta-stranded regions. Highlighted are the methionine at position 1 (M1), the glutamate residue 389 (E389) and tyrosine 587 (Y587). The protein chain between E389 and Y587 forms a separate folding domain that acts as a nuclease.

Figure 7:
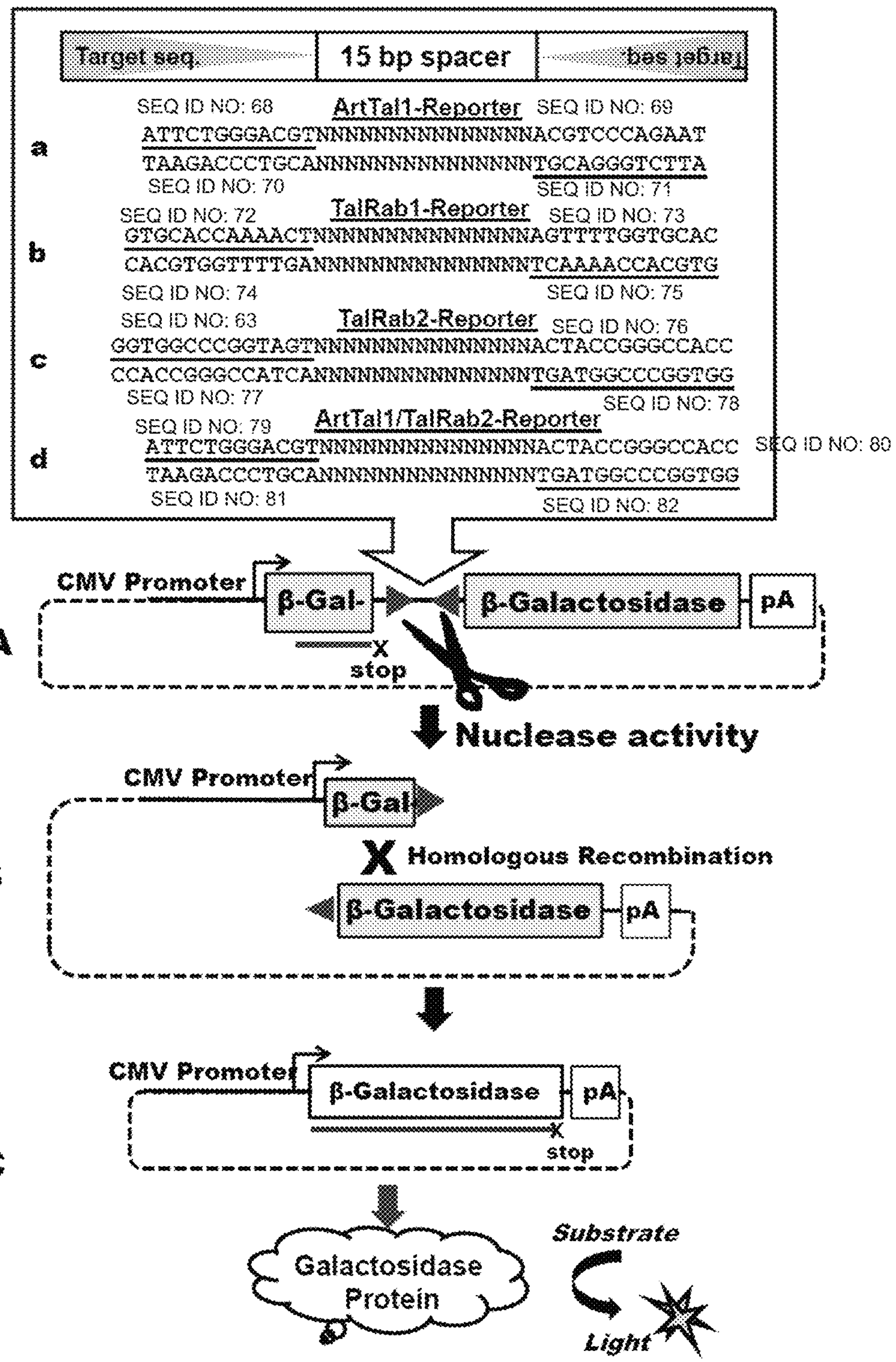

FIG. 7: TAL-Nuclease Reporter Plasmids and Nuclease Reporter Assay.

A: TAL-nuclease reporter plasmids contain a CMV promoter region, a 400 bp sequence coding for the N-terminal segment of β-galactosidase and a stop codon. This unit is followed by a TAL binding target region consisting of two inverse oriented recognition sequences (underlined), separated by a 15 bp spacer region (NNN . . . ), for the ArtTal1 array (a), the TalRab1 array (b), the TalRab2 array (c), or a hybrid binding region composed of one ArtTal1 and one TalRab2 recognition sequence (d). The TAL-nuclease target region is followed by the complete coding region for β-galactosidase and a polyadenylation signal (pA). To test for nuclease activity against the target sequence a TAL-nuclease expression vector (FIG. 4) is transiently cotransfected with its corresponding reporter plasmid into HEK 293 cells. Upon expression of the TAL-nuclease protein the reporter plasmid is opened by a nuclease-induced double-strand break within the TAL-nuclease target sequence (scissor symbol). B: The DNA regions adjacent to the double-strand break are identical over 400 bp and can be aligned and recombined (X) by homologous recombination DNA repair. C: Homologous recombination of an opened reporter plasmid results into a functional β-galactosidase expression vector that produces the β-galactosidase enzyme. After two days the transfected cells are lysed and the enzyme activity in the lysate is determined with a chemiluminescent reporter assay. The levels of the reporter catalysed light emission are measured and indicate TAL-nuclease activity in comparison to samples that were transfected with the reporter plasmid alone.

Figure 8:
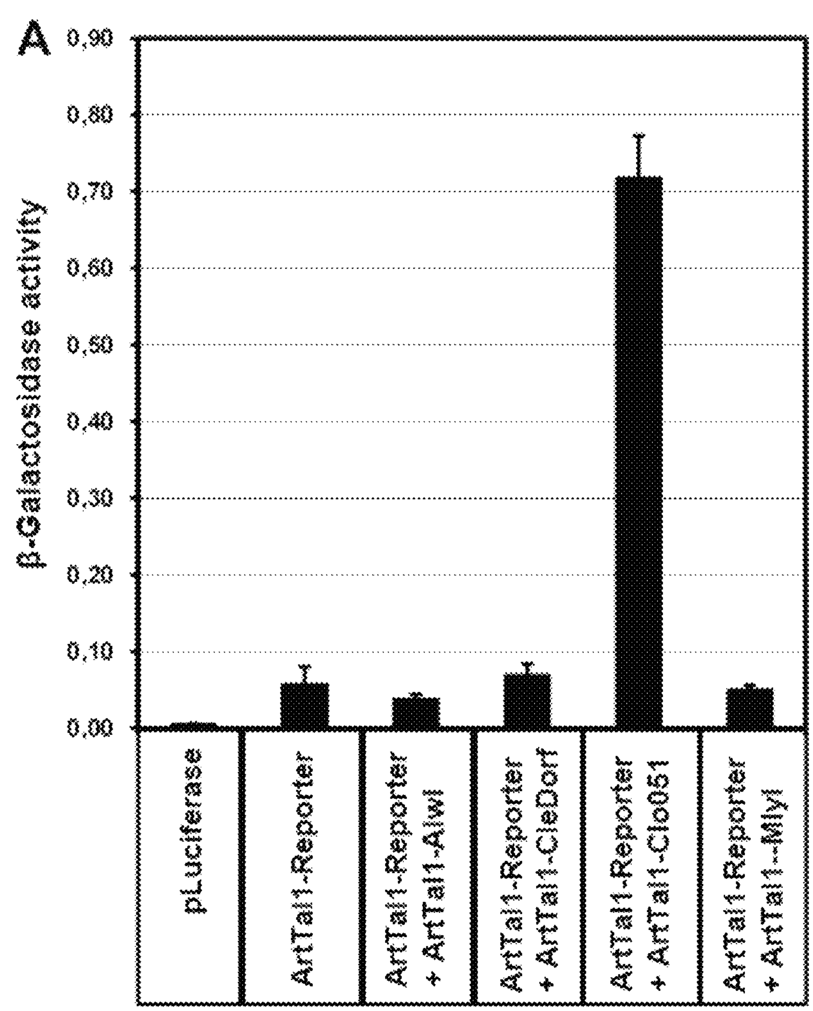
Figure 8:
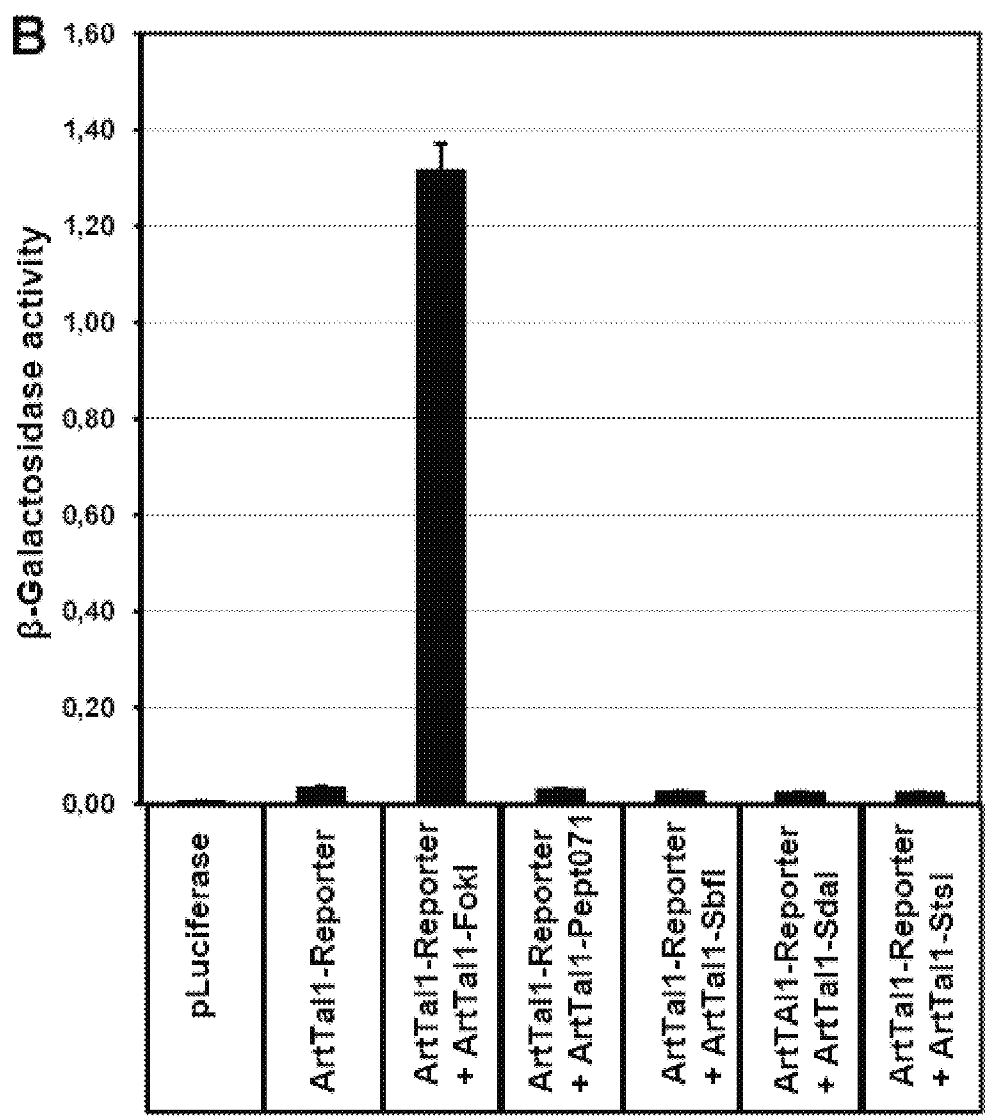

FIG. 8: Activity of Tal Nuclease Fusion Proteins in HEK 293 Cells.

To test for the nuclease activity of TAL-nuclease domain fusion proteins, expression vectors for the ArtTal1-AlwI, -CleDORF, -Clo051, -MlyI, -FokI, -Pept071, -SbfI, -SdaI, and -StsI proteins (FIG. 4) were transfected together with the ArtTal1 reporter plasmid (FIG. 7) into HEK 293 cells. Specific nuclease activity against the reporter plasmid's target sequence leads to homologous recombination and the expression of β-galactosidase. Two days after transfection the cell populations were lysed and the□ β-galactosidase activity determined with a chemiluminescent reporter assay. The levels of light emission were normalised in relation to the activity of a cotransfected Luciferase expression plasmid (pLuciferase) and are shown in comparison to the activity of a positive control β-galactosidase expression vector. The bar for each transfected sample represents the mean value and SD derived from three culture wells transfected side by side. A: The transfection of the ArtTal1 reporter plasmid without nuclease expression vector results in a low background level of β-galactosidase. The cotransfection of pCAG-ArtTal1-AlwI, -CleDORF, and -MlyI with the ArtTal1 reporter plasmid did not lead to a significant increase of reporter expression, indicating that the ArtTal1-AlwI, -CleDORF, and -MlyI fusion proteins do not exhibit nuclease activity. In contrast, the cotransfection of the ArtTal1 reporter and the pCAG-ArtTal1-Clo051 plasmids resulted in a strong increase of reporter expression, indicating that the ArtTal1-Clo051 fusion protein exhibits target specific nuclease activity in 293 cells. B: In an independent transfection experiment the cotransfection of pCAG-ArtTal1-Pept071, -SbfI, -SdaI and -Sst with the ArtTal1 reporter plasmid did not lead to a significant increase of reporter expression, as compared to the ArtTal1 reporter plasmid alone, indicating that the ArtTal1-Pept071, -SbfI, -SdaI, and -StsI fusion proteins do not exhibit nuclease activity. In contrast, the cotransfection of the ArtTal1 reporter and the pCAG-ArtTal1-FokI plasmids resulted in the increase of reporter expression, indicating the nuclease activity of the ArtTal1-FokI fusion protein in 293 cells.

Figure 9:
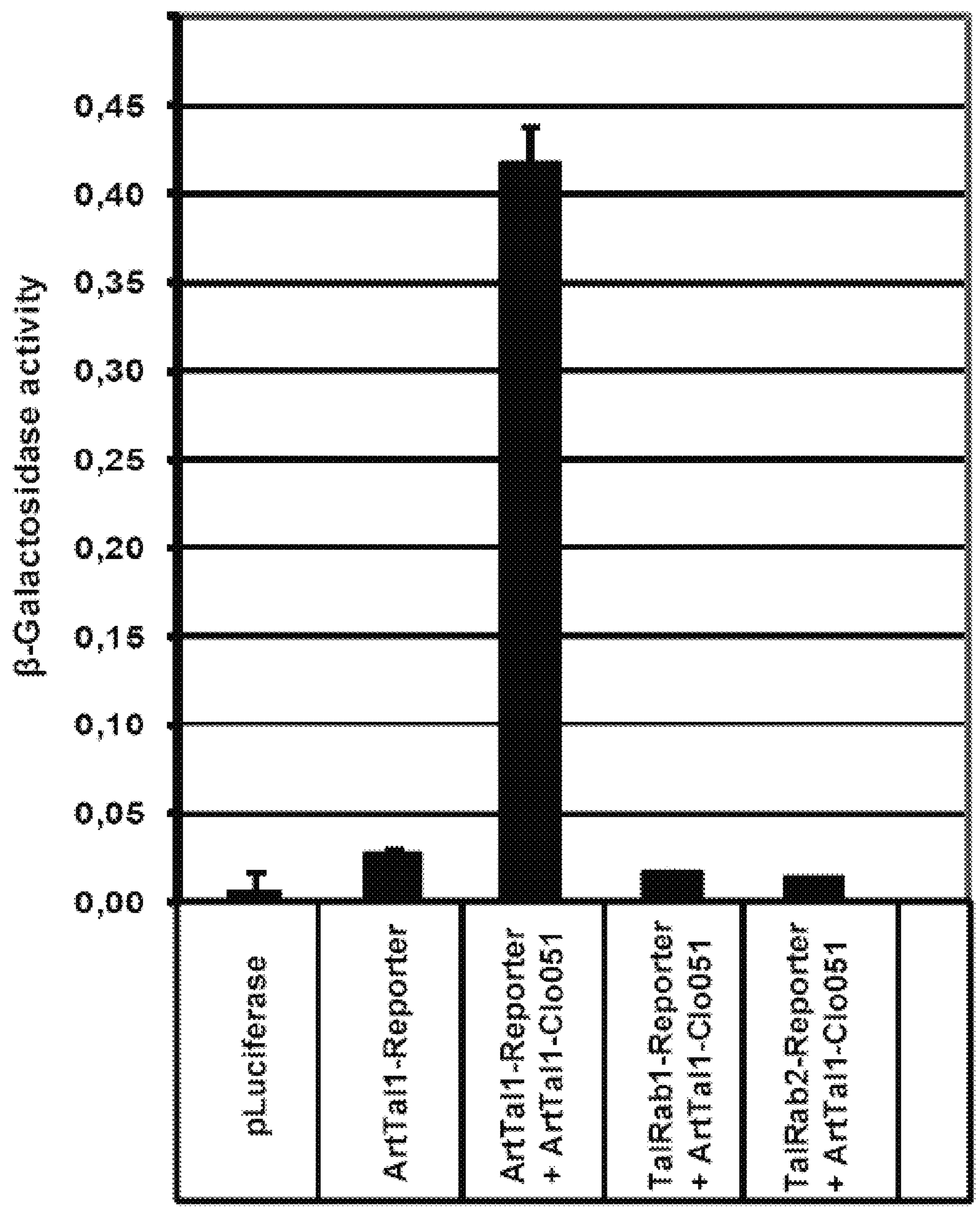

FIG. 9: Target Sequence Specificity of the ArtTal1-Clo051 Nuclease.

To test for the specificity of the ArtTal1-Clo051 nuclease against the predesigned target sequence in comparison to unrelated DNA sequences, the pCAG-ArtTal1-Clo051 expression vector was cotransfected with the corresponding ArtTal1-reporter plasmid or with the TalRab1 or TalRab2 reporter plasmids (FIG. 7), which contain unrelated target sequences, into HEK 293 cells. Strong nuclease activity developed only in the specific combination of the ArtTal1-Clo051 expression vector together with the ArtTal1-reporter plasmid, indicating that the ArtTal1-Clo051 nuclease acts specifically against the predesigned target sequence.

Figure 10:
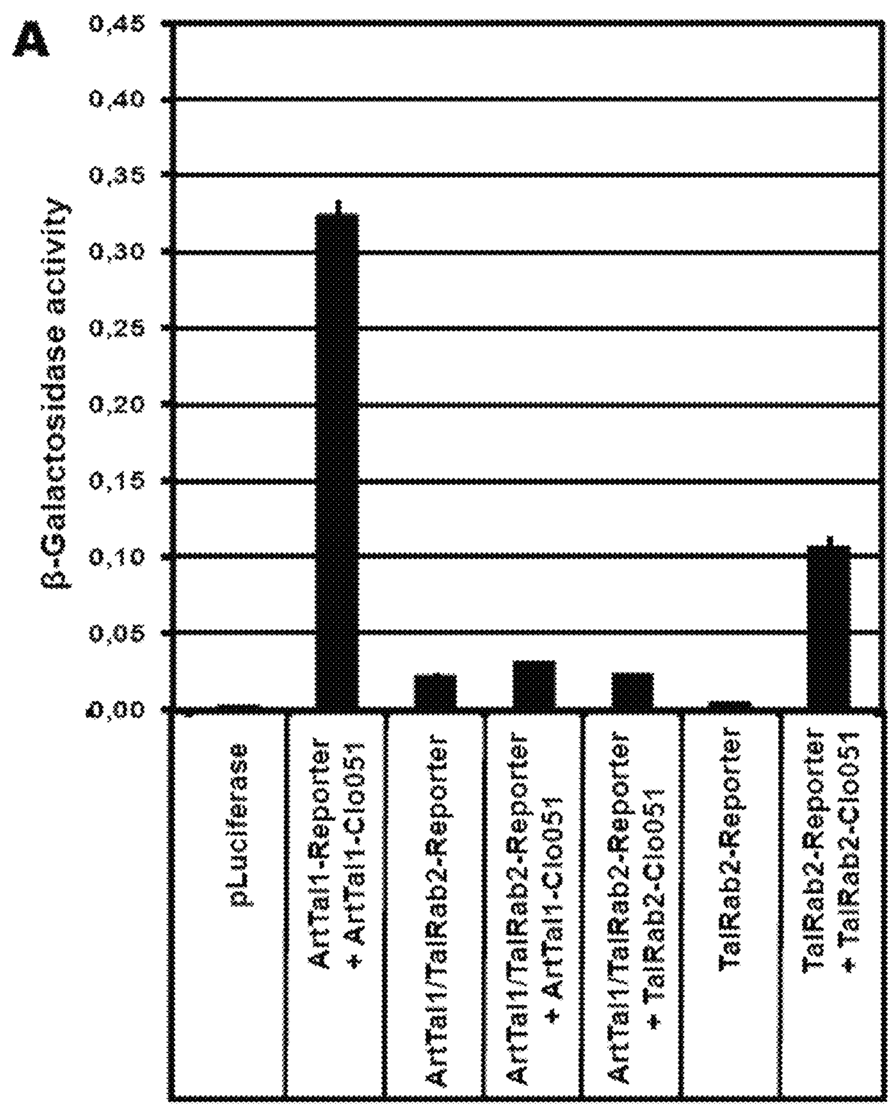
Figure 10:
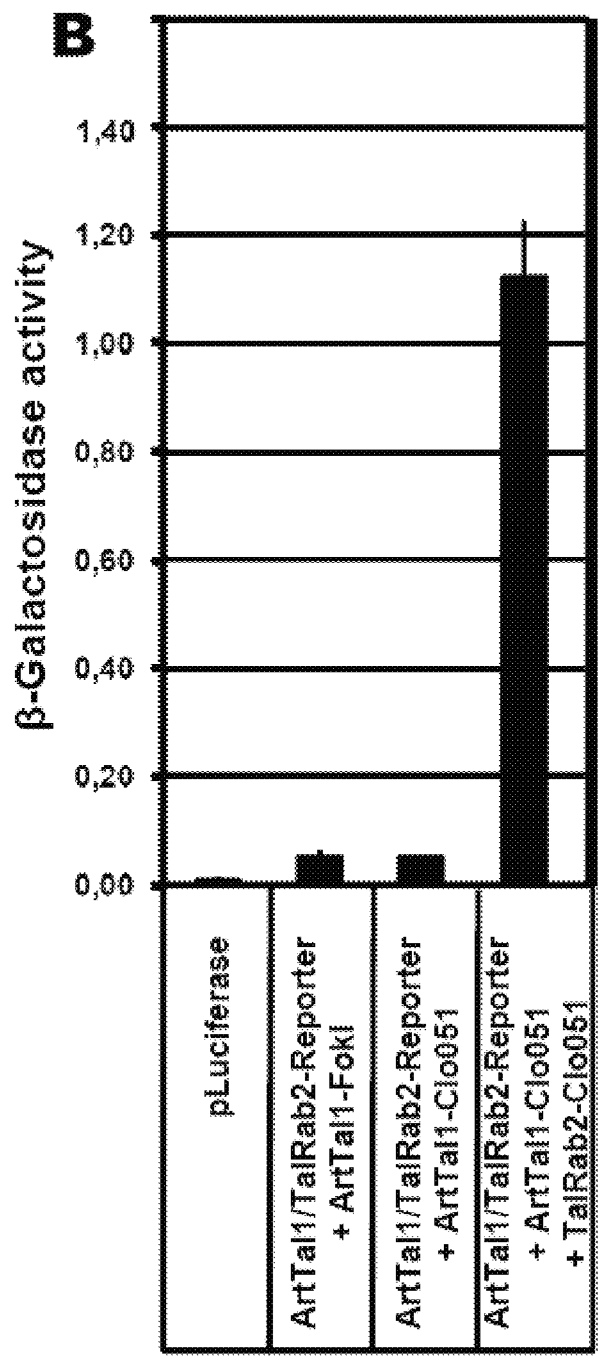

FIG. 10: Characterisation of the Cooperativity of TAL-Clo051 Nuclease Fusion Proteins A: To test for the cooperativity of the Clo051 nuclease domains of a pair of TAL-Clo051 fusion proteins, expression vectors for the ArtTal1-Clo051 or TalRab2-Clo051 fusion proteins were cotransfected with the corresponding ArtTal1- or TalRab2-reporter plasmid (FIG. 7) and compared to the cotransfection with the ArtTal1/TalRab2-reporter plasmid, that contains a hybrid target region (FIG. 7). Significant nuclease activity developed only in the combination of TAL-nuclease expression vectors with reporter plasmids that contain two identical, inverse copies of the corresponding TAL array target sequence, but not with the ArtTal1/TalRab2-reporter plasmid that contains only a single binding sequence of the ArtTal1-Clo051 and TalRab2-Clo051 fusion proteins. This result indicates that two Clo051 nuclease domains must cooperate to induce a DNA double-strand break, whereas a single Clo051 nuclease domain does not act as a nuclease. B: The cotransfection of the ArtTal1/TalRab2-reporter plasmid with both expression vectors for ArtTal1-Clo051 and TalRab2-Clo051, but not with ArtTal1-Clo051 or -Fok alone, results into strong nuclease activity, as compared to the transfection of the ArtTal1/TalRab2 reporter plasmid. This result indicates that nuclease activity and the induction of double-strand breaks in the target region occurs only upon the binding of two TAL-Clo051 fusion proteins and the interaction of a pair of Clo051 nuclease domains.

Figure 11:
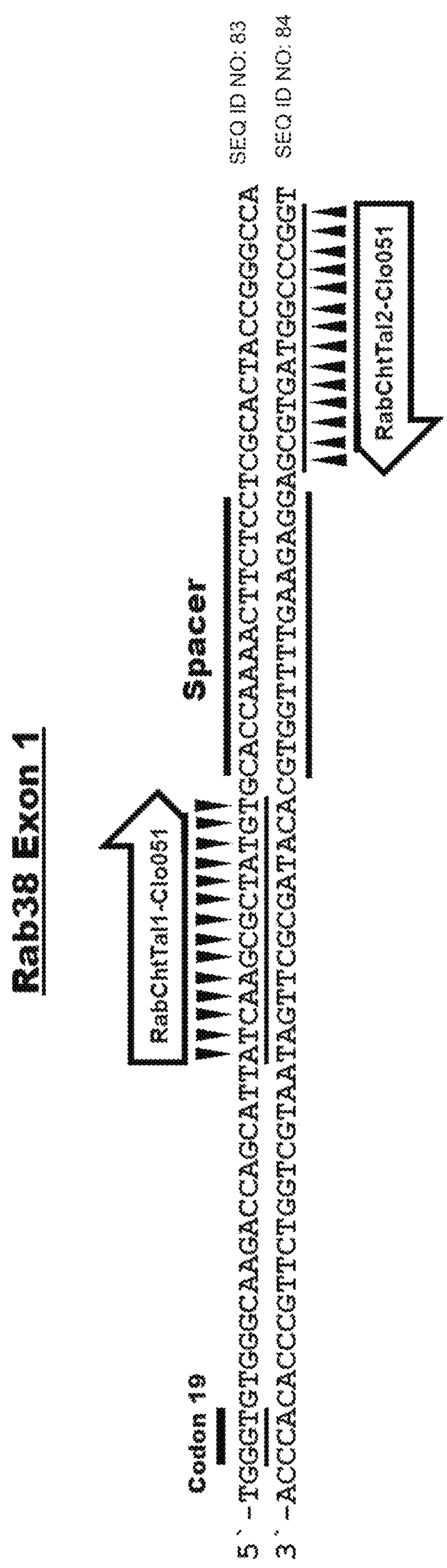

FIG. 11: Design of a TAL-Clo051 Fusion Protein Pair in Accordance with the Present Invention, Recognizing the Mouse Rab38 Gene.

TAL nucleases recognizing a target sequence within exon 1 of the mouse Rab38 gene. The trinucleotide representing codon 19 is underlined. Indicated is each of a 14 nucleotide sequence that is recognised by one the indicated TAL-Clo051 fusion proteins RabChtTal1- and RabChtTal2-Clo051. The two 14 bp target sequences are flanking a central 15 bp spacer sequence that is cleaved by the Clo051 nuclease domains.

Figure 12:
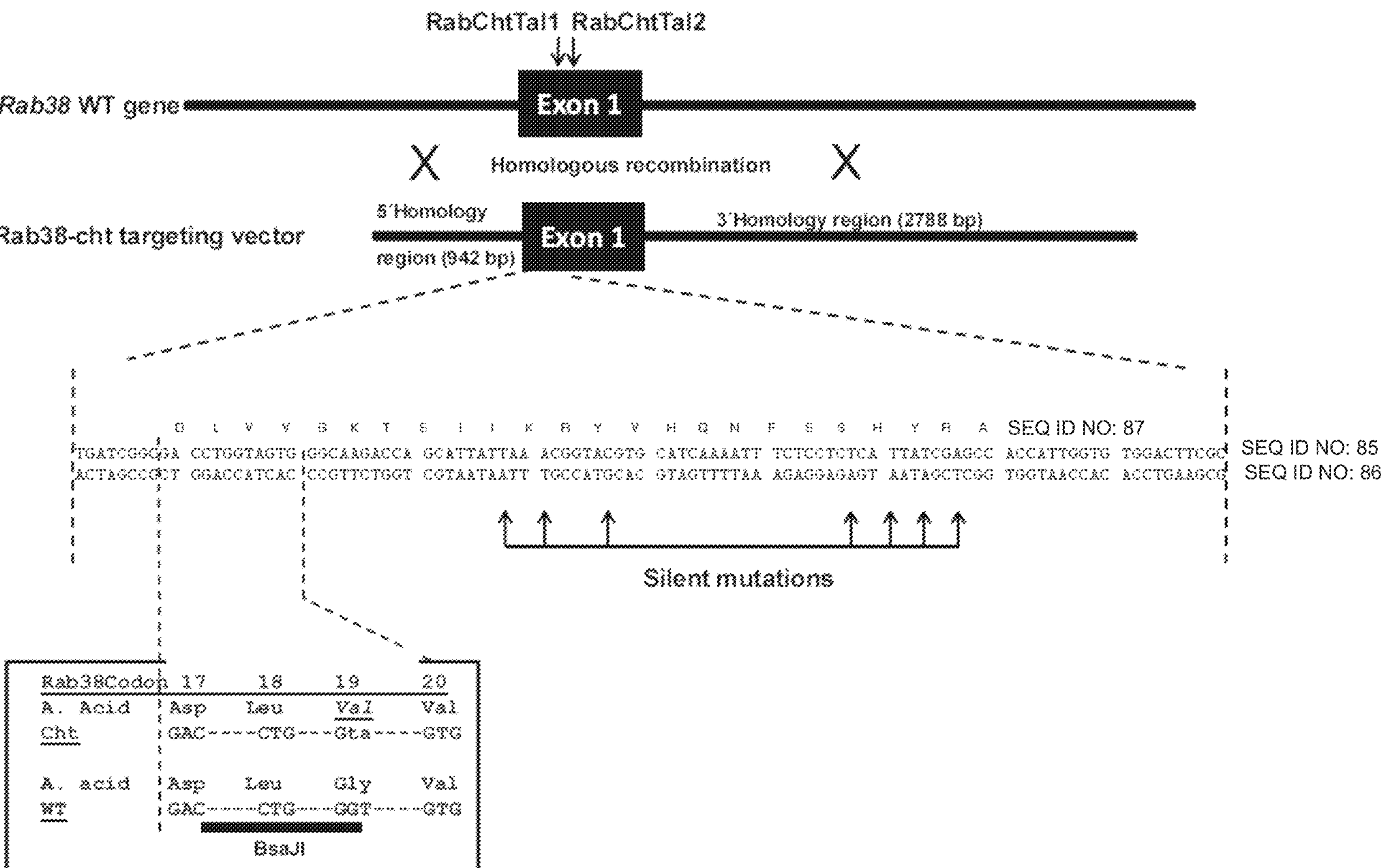

FIG. 12: Strategy for the Modification of the Mouse Rab38 Gene in ES Cells and Zygotes Using TAL-Clo051 Fusion Proteins.

Within exon 1 of the wildtype Rab38 gene (Rab38 WT) the position of the binding sites for the TAL nuclease pair RabChtTal1- and RabChtTal2-Clo051 are indicated. The Rab38-cht targeting vector contains a 942 bp 5'-homology region and a 2788 bp 3'-homology region flanking the Rab38 TAL recognition sites. Within exon1 two nucleotide changes within codon 19 (Gta) of Rab38 create a chocolate (cht) missense mutation coding for valine (Val) instead of the wildtype (WT) glycine (Gly), and remove a BsaJI restriction site. In each of the adjacent Rab38 TAL recognition sites several silent mutations were introduced to prevent the binding of Rab38 TAL proteins to the targeting vector. The induction of a double-strand break within the wildtype Rab38 gene by the RabChtTal protein pair stimulates homologous recombination with the Rab38-cht targeting vector and integrates the chocolate missense and the silent mutations into the genome.

FIG. 13: Isolation of Hyperactive Clo051 Nuclease Mutants.

The figure shows the primary sequence of the Clo051 nuclease domain between the positions E389 and Y587. Indicated is the distribution of the positively charged arginine (R) and lysine (K) residues (filled squares) and of negatively charged glutamate (E) and aspartate (D) residues (open circles). Triangles indicate the positions S423 and R446. These residues constitute a three-dimensional framework of charges within the Clo051 domain that determines the unique tertiary structure of this nuclease, as modelled in the structure of FIG. 6. Certain replacements of polar versus non-polar residues or of non-polar residues against polar residues, e.g. at the positions 423 and 446, changes the three-dimensional structure of the protein chain and results into a more efficiently working nuclease activity.

FIG. 14: Activity of ArtTal1-Clo051 Nuclease on a Genomic Reporter in HEK 293 Cells HEK293 cells harboring genomic integrated copies of the pCMV-Rab-Reporter(hygro) reporter construct were transfected with pBluescript or pCAG.ArtTal1-Clo051. Specific nuclease activity against the reporter's target sequence leads to homologous recombination and the expression of β-galactosidase. Two days after transfection the cell populations were fixed and the fraction of β-galactosidase expressing cells was determined by histochemical X-Gal staining. A: X-Gal stained reporter cell culture upon transfection with pBluescript. B: X-Gal stained reporter cell culture upon transfection with pCAG-ArtTal1-Clo051 nuclease expression vector.

The examples illustrate the invention:

EXAMPLE 1

Construction of Expression and Reporter Vectors for Tal Nucleases and Detection of Specific Nuclease Activity Construction of TAL-Nuclease Expression Vectors For the expression of TAL-nucleases in mammalian cells we designed the generic expression vector pCAG-TAL-nuclease (SEQ ID NO: 3) (FIG. 4), that contains a CAG hybrid promoter region and a transcriptional unit comprising a sequence coding for a N-terminal peptide of 176 amino acids (SEQ ID NO: 4) of TAL nuclease fusion proteins, located upstream of a pair of BsmBI restriction sites. This N-terminal regions includes an ATG start codon, a nuclear localisation sequence, a FLAG Tag sequence, a glycine rich linker sequence, a segment coding for 110 amino acids of the Tal protein AvrBs3 and the invariable N-terminal Tal repeat of the Hax3 TAL effector. Downstream of the central BsmBI sites, the transcriptional unit contains 78 codons (SEQ ID NO: 5) including an invariable C-terminal TAL repeat (34 amino acids) and 44 residues derived from the TAL protein AvrBs3, followed by a PmeI and MluI restriction site for the insertion of a nuclease coding region and by a polyadenylation signal sequence (pA). DNA segments coding for arrays of TAL repeats, designed to bind a TAL nuclease target sequence can be inserted into the BsmBI sites of pCAG-Tal-nuclease in frame with the up- and downstream coding regions for the expression of predesigned TAL-nuclease proteins.

To generate TAL-nuclease vectors for expression in mammalian cells we inserted a synthetic DNA segment with the coding region of an array of 12 Tal repeats, designated ArtTal1 (SEQ ID NO: 6), into the BsmBI sites of pCAG-TAL-nuclease, to derive the plasmid pCAG-ArtTal1-nuclease (SEQ ID NO: 7). The TAL element array ArtTal1 recognises the artificial DNA target sequence 5'-ATTCTGGGACGT-3' (SEQ ID NO: 62) (FIG. 4), In another example we inserted a synthetic DNA segment with the coding region of an array of 14 Tal repeats, designated TalRab2 (SEQ ID NO: 8), into the BsmBI sites of pCAG-TAL-nuclease, to derive the plasmid pCAG-TalRab2-nuclease (SEQ ID NO: 9). The TAL element array TalRab2 recognises the DNA target sequence 5'-GGTGGCCCGGTAGT-3' (SEQ ID NO: 63) (FIG. 7) that occurs within the mouse Rab38 gene. The TAL target sequences were selected such that the binding regions of the TAL proteins are preceded by a T nucleotide. Following the sequence downstream of the initial T in the 5'>3' direction, specific TAL DNA-binding domains were combined together into arrays of 12 (ArtTal1) (FIG. 4), or 14 (TalRab2) TAL elements. Each TAL element motif consists of 34 amino acids, the position 12 and 13 of which determines the specificity towards recognition of A, G, C or T within the target sequence. To derive TAL element DNA-binding domains we used the TAL effector motif (repeat) #11 of the *Xanthomonas* Hax3 protein (GenBank accession No. AY993938.1 (LTPEQVVAIASNIGGKQALETVQRLLPVLCQAHG) (SEQ ID NO: 64) with amino acids N12 and I13 to recognize A, the TAL effector motif (repeat) #5 (LTPQQVVAIASHDGGKQALETVQRLLPVLCQAHG) (SEQ ID NO: 65) derived from the Hax3 protein with amino acids H12 and D13 to recognize C, and the TAL effector motif (repeat) #4 (LTPQQVVAIASNGGGKQALETVQRLLPVLCQAHG) (SEQ ID NO: 66) from the *Xanthomonas* Hax4 protein (Genbank accession No.: AY993939.1) with amino acids N12 and G13 to recognize T. To recognize a target G nucleotide we used the TAL effector motif (repeat) #4 from the Hax4 protein with replacement of the amino acids 12 into N and 13 into N (LTPQQVVAIASNNGGKQALETVQRLLPVLCQAHG) (SEQ ID NO: 67).

Next, we constructed fusion proteins of the ArtTal1 DNA binding domain with protein domains derived from known or putative nucleases and tested whether these TAL-nuclease fusion proteins are able to induce a double-strand break next to the DNA bound by the TAL recognition region. For this purpose we inserted synthetic DNA segments comprising the coding regions of eight putative nuclease domains and the known nuclease domain of FokI (SEQ ID NO: 10), into the PmeI and MluI sites of the pCAG-ArtTal1-nuclease plasmid. Among the eight putative nuclease domains we selected domains from the five known restriction enzymes AlwI (SEQ ID NO: 11), MlyI (SEQ ID NO: 12), SbfI (SEQ ID NO: 13), SdaI (SEQ ID NO: 14) and StsI (SEQ ID NO: 15). In addition, we selected putative nuclease domains of three yet uncharacterised, hypothetical microbial genes, designated here as 'CleDORF' (SEQ ID NO: 16) (NCBI Reference Sequence: ZP_02080987.1, derived from the genome of *Clostridium leptum* DSM753), 'Clo051' (SEQ ID NO: 17) (NCBI Reference Sequence: ZP_05132802.1, derived from the genome of *Clostridium* spec.7_2_43FAA) and 'Pept071' (SEQ ID NO: 18) (NCBI Reference Sequence: ZP_07399918.1, derived from the genome of *Peptoniphilus duerdenii* ATCC BAA-1640). These proteins were selected by characteristic sequence features that are compatible with the conserved active site of the 'PD-(D/E)XK' superfamily of enzymes (Kosinski, J., et al. (2005). BMC Bioinformatics, 6,172) interacting with DNA (see FIG. 6 for the Clo051 protein).

In particular, the 587 residue Clo051 protein can be classified as a member of the PD-(D/E)XK protein family by the location of the amino acid pairs P454/D455 (PD motif) and D472/K474 (DXK motif) (FIG. 5). To elucidate whether the Clo051 protein contains a separate nuclease domain we performed a three-dimensional structural prediction from its primary amino acid sequence using the I-TASSER software (Roy, A. et al. (2010). Nat Protoc., 5(4):725-38). As shown in FIG. 6 the Clo051 protein is composed of two protein domains. The C-terminal domain of Clo051, approximately beginning with the residue E389, contains the PD-(D/E)XK family consensus motif and appears as a non specific nuclease domain.

For the expression of these protein domains in mammalian cells we used synthetic coding regions optimised according to the mammalian codon usage and inserted segments comprising the putative nuclease domains of AlwI (SEQ ID NO: 19), CleDORF (SEQ ID NO: 20), Clo051 (SEQ ID NO: 1), MlyI (SEQ ID NO: 21), Pept071 (SEQ ID NO: 22), SbfI (SEQ ID NO: 23), SdaI (SEQ ID NO: 24), StsI (SEQ ID NO: 25) and the known nuclease domain of FokI (SEQ ID NO: 26) into the PmeI and MluI sites of the pCAG-ArtTal1-nuclease plasmid, to derive the expression vectors pCAG-ArtTal1-AlwI (SEQ ID NO: 27) (FIG. 4A), pCAG-ArtTal1-CleDORF (SEQ ID NO: 28) (FIG. 4B), pCAG-ArtTal1-Clo051 (SEQ ID NO: 29) (FIG. 4C), pCAG-ArtTal1-MlyI (SEQ ID NO: 30) (FIG. 4D), pCAG-ArtTal1-Pept071 (SEQ ID NO: 31) (FIG. 4E), pCAG-ArtTal1-SbfI (SEQ ID NO: 32) (FIG. 4F), pCAG-ArtTal1-SdaI (SEQ ID NO: 33) (FIG. 4G), pCAG-ArtTal1-StsI (SEQ ID NO: 34) (FIG. 4H), and pCAG-ArtTal1-FokI (SEQ ID NO: 35) (FIG. 4I). These expression vectors code for the TAL-fusion proteins designated as ArtTal1-AlwI (SEQ ID NO: 36), ArtTal1-CleDORF (SEQ ID NO: 37), ArtTal1-Clo051 (SEQ ID NO: 38), ArtTal1-MlyI (SEQ ID NO: 39), ArtTal1-Pept071 (SEQ ID NO: 40), ArtTal1-SbfI (SEQ ID NO: 41), ArtTal1-SdaI (SEQ ID NO: 42), ArtTal1-StsI (SEQ ID NO: 43), and ArtTal1-FokI (SEQ ID NO: 44).

Construction of TAL Nuclease Reporter Plasmids

To determine the activity and specificity of TAL nuclease domain fusion proteins in mammalian cells we constructed TAL nuclease reporter plasmids that contain two copies of a TAL DNA target sequence in inverse orientation, separated by a 15 nucleotide spacer region (FIG. 7*a-d*). This configuration enables to measure the activity of a single type of TAL nuclease that interacts as a homodimer of two protein molecules that are bound to the inverse pair of target sequences of the reporter plasmid. Upon DNA binding and interaction of two nuclease domains the reporter plasmid DNA is cleaved within the 15 bp spacer region and exhibits a double-strand break.

The TAL nuclease reporter plasmids contain a CMV promoter region, a 400 bp sequence coding for the N-terminal segment of β-galactosidase and a stop codon. This unit is followed by the TAL nuclease target region (consisting of two inverse oriented recognition sequences separated by a 15 bp spacer region) for ArtTal1-fusion proteins in the plasmid ArtTal1-reporter (SEQ ID NO: 45) (FIG. 7*a*), by the unrelated target sequence TalRab1 in the TalRab1-reporter plasmid (SEQ ID NO: 46) (FIG. 7*b*), by the target region for TalRab2 fusion proteins in the TalRab2-reporter plasmid (SEQ ID NO: 47) (FIG. 8*c*), or a hybrid target region containing one copy of the ArtTal1 and the TalRab2 recognition sequence in the ArtTal1/TalRab2-reporter plasmid (SEQ ID NO: 48) (FIG. 8*d*).

Within these reporter plasmids the TAL nuclease target regions are followed by the complete coding region for β-galactosidase and a polyadenylation signal (pA). To test for nuclease activity against the specific target sequence a TAL nuclease expression vector (FIG. 4) was transiently cotransfected with its corresponding reporter plasmid into mammalian cells. Upon expression of the TAL nuclease protein the reporter plasmid is opened by a nuclease-induced double-strand break within the TAL nuclease target sequence (FIG. 7A). The DNA regions adjacent to the double-strand break are identical over 400 bp and can be aligned and recombined by homologous recombination DNA repair (FIG. 7B). Homologous recombination of an opened reporter plasmid will subsequently result into a functional β-galactosidase coding region transcribed from the CMV promoter that leads to the production of β-galactosidase protein (FIG. 7C). In lysates of transfected cells the enzymatic activity of β-galactosidase can be determined by chemiluminescense and reports the nuclease activity of the TAL fusion proteins.

Measurement of TAL-Nuclease Activity and Specificity in Human 293 Cells

To determine the activity and specificity of TAL nucleases in mammalian cells, we electroporated one million HEK 293 cells (ATCC #CRL-1573) (Graham F L, Smiley J, Russell W C, Nairn R., J. Gen. Virol. 36, 59-74, 1977) with 5 μg plasmid DNA of one of the TAL nuclease expression vectors (FIG. 4) together with 5 μg of one of the TAL nuclease reporter plasmids (FIG. 7). In addition, each sample received 5 μg of the firefly Luciferase expression plasmid pCMV-hLuc (SEQ ID NO: 49) and was adjusted to a total DNA amount of 20 μg with pBluescript (pBS) plasmid DNA (SEQ ID NO: 50). Upon transfection the cells were seeded in triplicate wells of a 6-well tissue culture plate and cultured for two days before analysis was started. For analysis the transfected cells of each well were lysed and the β-galactosidase and luciferase enzyme activities of the lysates were individually determined using chemiluminescent reporter assays following the manufacturer's instruction (Roche Applied Science, Germany) in a luminometer (Berthold Centro LB 960). As positive control we transfected 5 μg of the β-galactosidase expression plasmid pCMVβ (SEQ ID NO: 51) with 15 μg pBS, as negative control 5 μg pCMV-hLuc were transfected with 15 μg pBS or 5 μg pCMV-hLuc together with 5 μg of a TAL nuclease reporter plasmid and 10 μg pBS. The triplicate β-galactosidase values of each sample were normalised in relation to the levels of Luciferase activity and the mean value and standard deviation of β-galactosidase activity were calculated and expressed in comparison to the pCMVβ positive control. In this type of recombination assay the level of the β-galactosidase catalysed light emission reflects the cleavage and repair of the reporter plasmids and thereby indicates the activity of TAL nucleases.

As shown in FIG. 8 transfection of the ArtTal1-Reporter plasmid alone resulted in just background levels of β-galactosidase. The cotransfection of the ArtTal1-Reporter plasmid with the expression vectors pCAG-ArtTal1-AlwI, -CleDORF, -MlyI, -Pept071, -SbfI, -SdaI, and -StsI did not reveal any significant nuclease activity of the encoded TAL fusion proteins (FIG. 8), indicating that the selected nuclease domains are unable to operate in combination with TAL DNA binding elements. In contrast, the cotransfection of the ArtTal1-Reporter plasmid with the expression vectors pCAG-ArtTal1-Clo051 (FIG. 8A) and -FokI (FIG. 8*b*) resulted in significantly increased reporter activity, indicating that the selected FokI and Clo051 protein domains are able to function as nuclease in fusion with TAL DNA binding elements.

Since in repeated assays TAL fusions with the Clo051 domain appeared more active as compared to fusions with the FokI nuclease domain, we believe that the Clo051 domain is most suited for the construction of highly active TAL-nucleases.

In order to define whether the ArtTal1-Clo051 nuclease specifically recognizes its target sequence within the ArtTal1-reporter plasmid (FIG. 7*a*), pCAG-ArtTal1-Clo051 was cotransfected with the corresponding ArtTal1- or with the unrelated TalRab1- or TalRab2-reporter plasmids (FIG. 7*b, c*) into HEK 293 cells. As shown in FIG. 9 significantly increased reporter activity was detected only from the specific combination of the ArtTal-Clo051 nuclease with its corresponding promoter, whereas the cotransfection with unrelated reporter plasmids did not exhibit significant nuclease activity. These results indicate that the Clo051 nuclease domain in fusion with TAL DNA binding elements acts in a target sequence specific manner and that unrelated target sequences are not processed.

Next, we characterized whether the Clo051 nuclease domain induces recombinogenic double-strand breaks as a monomer, or whether the interaction of two nuclease domains as dimer is required. For this purpose we constructed the hybrid reporter plasmid ArtTal1/TalRab2-reporter (SEQ ID NO: 48) (FIG. 7*d*) that contains one ArtTal1 recognition sequence upstream of the spacer region and one TalRab2 recognition sequence downstream of the spacer region. The TalRab2 array (SEQ ID NO: 8) is composed of 14 TAL elements recognising the target sequence 5'-GGTGGCCCGGTAGT-3' (SEQ ID NO: 63). The Clo051 nuclease domain was cloned as synthetic coding region into the PmeI and MluI sites of plasmid pCAG-TalRab2-nuclease (SEQ ID NO: 9) to derive the expression vector pCAG-TalRab2-Clo051 (SEQ ID NO: 52) for the expression of the TalRab2-Clo051 protein (SEQ ID NO: 53). As shown in FIG. 10A the cotransfection of pCAG-ArtTal1-Clo051 together with the ArtTal1-reporter plasmid resulted in significant reporter gene expression indicating specific nuclease activity of the ArtTal1-Clo051 fusion protein. Since the ArtTal1-reporter plasmids contains two inverse ArtTal1 binding sequences, the nuclease activity of ArtTal1-Clo051 may result from the action of a single fusion protein or the combined action of two molecules. To distinguish between these possibilities pCAGArtTal1-Clo051 was cotransfected with the ArtTal1/TalRab2-reporter plasmid that contains only one ArtTal1 binding sequence. As shown in FIG. 10A the ArtTal1-Clo051 nuclease did not exhibit significant nuclease activity on the ArtTal1/TalRab2-reporter, indicating that two Clo051 nuclease domains must interact as a dimer to induce a DNA double-strand break. These results were confirmed with the TalRab2-Clo051 nuclease that acted on its corresponding TalRab2-reporter but not on the hybrid ArtTal1/TalRab2-reporter plasmid (FIG. 10A). As expected, the ArtTal1-FokI fusion protein did likewise not exhibit nuclease activity on the ArtTal1/TalRab2-reporter (FIG. 10B).

Next, we studied whether two Clo051 nuclease domains, that are fused to different arrays of TAL DNA binding elements, are also able to interact and to induce double-strand breaks. For this purpose the expression vectors pCAG-ArtTal1-Clo051 and pCAG-TalRab2-Clo051 were cotransfected together with the ArtTal1/TalRab2-reporter plasmid and the results compared to the cotransfection of pCAG-ArtTal1-Clo051 together with the ArtTal1/TalRab2-reporter. As shown in FIG. 10B, significant nuclease activity on the ArtTal1/TalRab2-reporter developed only by the coexpression of the ArtTal1- and TalRab2-Clo051 nucleases, indicating that Clo051 nuclease domains fused with different TAL arrays are able to interact and to induce a DNA double-strand break within a hybrid target region containing the recognition sequences of two distinguished TAL DNA binding arrays.

EXAMPLE 2

Targeting of the Mouse Rab38 Gene in ES Cells and Zygotes with TAL-Clo051 Nucleases Construction of Rab38 Specific TAL-Clo051 Nucleases and a Targeting Vector To demonstrate the functionality of TAL effector DNA-binding domain—nuclease fusion proteins in mammalian cells we designed a pair of fusion proteins that recognizes a DNA target sequence within the mouse Rab38 gene (FIG. 11). The two TAL effector DNA-binding domain—nuclease fusion proteins are intended to bind together to the bipartite target DNA region and to induce a double strand break in the spacer region of the target region to stimulate homologus recombination at the target locus in mammalian cells.

The mouse Rab38 gene encodes the RAB38 protein that is a member of a family of proteins known to play a crucial role in vesicular trafficking. In chocolate (cht) mutant mice a single nucleotide exchange at position 146 (G>T mutation) within the first exon of Rab38 leads to the replacement of glycine by valine at codon 19 (Loftus, S. K., et al., Proc Natl Acad Sci USA, 2002. 99(7): p. 4471-6). This amino acid replacement is located within the conserved GTP binding domain of RAB38 and impairs the sorting of the tyrosinase-related protein 1 (TYRP1) into the melanosomes of $Rab38^{cht}/Rab38^{cht}$ melanocytes. TYRP1 is a melanosomal membrane glycoprotein, which functions both as a 5,6-Dihydroxyindol-2-carbonic-acid oxidase enzyme to produce melanin and as a provider of structural stability to tyrosinase in the melanogenic enzyme complex. TYRP1 is believed to transit from the trans-Golgi network to stage II melanosomes by means of clathrin-coated vesicles. The reduced amount of correctly located TYRP1 leads to an impairment of pigment production and the change of fur color from black to a chocolate-like brown color in $Rab38^{cht}/Rab38^{cht}$ mice. Since mutations of genes needed for melanocyte function are known to cause oculocutaneous albinism (OCD), such as Hermansky-Pudlak syndrome in man, the Rab38 gene is a candidate locus in OCD patients.

We aimed to introduce a phenocopy of the chocolate mutation at codon 19 of Rab38 using a pair of TAL-nucleases (RabChtTal1- and RabChtTal2-Clo051) that each recognise a 14 bp target sequence located up- and downstream of a central 15 bp spacer sequence within exon 1 of the Rab38 gene (FIG. 11). To derive expression vectors for the RabChtTal1- and RabChtTal2-Clo051 nucleases synthetic coding regions for the DNA binding domains RabChtTal1 and RabChtTal2 composed of 14 TAL elements and the Clo051 nuclease domain were inserted into the pCAG-TAL-nuclease vector. The resulting plasmid pCAG-RabChtTal1-Clo051 (SEQ ID NO: 54) encodes the RabChtTal1-Clo051 fusion protein (SEQ ID NO: 55), and the plasmid pCAG-RabChtTal2-Clo051 (SEQ ID NO: 56) encodes the RabChtTal2-Clo051 fusion protein (SEQ ID NO: 57).

For the modification of the Rab38 gene by homologous recombination in fertilised oocytes we constructed the gene targeting vector pRab38-chtTAL (FIG. 12) (SEQ ID NO: 58), comprised of two homology regions encompassing 942 and 2788 bp of genomic sequence flanking exon1 of the mouse Rab38 gene (SEQ ID NO: 59). For this purpose the vectors 5'- and 3'-homology arms were amplified from the genomic BAC clone RPC1-421G2 (derived from the C57BL/6J genome, Imagenes GmbH, Berlin) using specific PCR primers. Within the sequence of codon 19 we introduced two nucleotide changes that modify codon 19 from the wildtype sequence GGT, coding for glycine, into GTA, coding for valine. This new chocolate mutation can be distinguished from the natural chocolate mutation, which exhibits only a single nucleotide exchange within codon 19 (GTT) coding for valine (Loftus, S. K., et al., Proc Natl Acad Sci USA, 2002. 99(7): p. 4471-6). Both chocolate mutant alleles can be further distinguished from the wildtype allele by restriction analysis since the mutations in codon 19 remove a recognition site for the restriction endonuclease BsaJI (FIG. 12). The recognition region for the TAL-nucleases is located downstream of codon 19 (FIG. 11). For the construction of the targeting vector 3'-homology region each 14 bp TAL fusion protein recognition sequence was further modified by the introduction of silent nucleotide changes that do not alter the RAB38 protein sequence (FIG. 12), in order to avoid the potential processing of the targeting vector by the Rab38 specific TAL-nucleases.

For the modification of the Rab38 gene by homologous recombination in mouse ES cells we modified the gene targeting vector pRab38-chtTAL (FIG. 12) by the insertion of a neomycin resistance gene as selection marker into spacer region of the TAL-nuclease recognition region, to derive the targeting vector pRab38-chtTAL-neo (SEQ ID NO: 60).

Targeting of the Rab38 Gene in ES Cells and Zygotes

To demonstrate the utility of the RabChtTal1- and RabChtTal2-Clo051 proteins for gene targeting in mammalian cells (FIG. 3) we introduced the expression vectors or protein coding mRNA together with the pRab38-chtTAL-neo targeting vector into mouse ES cells or with the pRab38-chtTAL vector into fertilised mouse oocytes.

For targeting in ES cells we transfected IDG3.2 ES cells (Hitz, C. et al. Nucleic Acids Res. 35, e90, 2007) with linearised pRab38-chtTAL-neo targeting vector together with or without the TAL-nuclease expression plasmids pCAG-RabChtTal1- and pCAG-RabChtTal2-Clo051. The transfection, selection, expansion and genotyping of neomycin resistant ES cell clones was performed according to standard gene targeting procedures as described ((Nagy A, Gertsenstein M, Vintersten K, Behringer R., 2003. Manipulating the Mouse Embryo. Cold Spring Harbour, New York: Cold Spring Harbour Laboratory Press). The analysis of resistant ES cell clones revealed that the expression of the TAL-nucleases lead to a significantly increased rate of homologous recombination at the Rab38 gene in ES cells.

For microinjection into fertilised mouse oocytes the circular pRab38-chtTAL vector DNA was mixed with in vitro transcribed mRNA coding for RabChtTal1- and RabChtTal2-Clo051 proteins in injection buffer as described (Meyer, M., et al., Proc Natl Acad Sci USA. 107(34): p. 15022-6). TAL-nuclease mRNA is prepared from the linearised expression plasmids pCAG-RabChtTAl1- and pCAG-RabChtTal2-Clo051 by in vitro transcription from the T7 promoter using the mMessage mMachine kit (Ambion) according to the manufacturers instructions. The mRNA is further modified by the addition of a poly-A tail using the Poly(A) tailing kit and purified with MegaClear columns from Ambion. Finally the mRNA is precipitated and resolved in injection buffer.

To isolate fertilised oocytes, males of the C57BL/6 strain are mated to super-ovulated females of the FVB strain. For super-ovulation three-week old FVB females are treated with 2.5 IU pregnant mares serum (PMS) 2 days before mating and with 2.5 IU Human chorionic gonadotropin (hCG) at the day of mating. Fertilised oocytes are isolated from the oviducts of plug positive females and microinjected in M2 medium (Sigma-Aldrich Inc Cat. No. M7167) with the TAL-nuclease mRNA and pRab38-chtTAL targeting vector preparation into one pronucleus and the cytoplasm following standard procedures (Nagy A, Gertsenstein M, Vintersten K, Behringer R., 2003. Manipulating the Mouse Embryo. Cold Spring Harbour, New York: Cold Spring Harbour Laboratory Press).

Upon microinjection the TAL-nuclease mRNAs are translated into proteins that induce a double-strand break at one or both Rab38 alleles in one or more cells of the developing embryo. This event stimulates the recombination of the pRab38-chtTAL targeting vector with a Rab38 allele via the homology regions present in the vector and leads to the site-specific insertion of the mutant codon 19 into the genome, resulting into a Rab38$^{cht}$ allele bearing the chocolate mutation (FIG. 12). The microinjected zygotes were transferred into pseudopregnant females to allow their further development into live mice (Nagy A, Gertsenstein M, Vintersten K, Behringer R., 2003. Manipulating the Mouse Embryo. Cold Spring Harbour, New York: Cold Spring Harbour Laboratory Press). From the resulting offspring genomic DNA was extracted from tail tips to analyse for the presence of the desired homologous recombination event at the Rab38 locus by PCR. This analysis was performed by the PCR amplification of the genomic region encompassing exon1. The presence of a Rab38$^{cht}$ allele can be recognised upon digestion of the PCR products with BsaJI, since the Rab38$^{cht}$ mutation at codon 19 leads to the removal of a BsaJI restriction site that is present in the wildtype sequence.

In one such experiment, mice derived from microinjected zygotes were analysed by a Rab38 PCR assay. Among this group most mice exhibited two alleles of the normal Rab38 wildtype genotype, whereas some individuals harboured one allele of the preplanned Rab38 chocolate mutation, as indicated by the absence of the BsaJI restriction site in exon 1

Taken together, it was possible to introduce a preplanned modification into the coding region of the Rab38 gene by TAL-Clo051 nuclease-assisted homologous recombination in mouse ES cells and fertilised oocytes.

EXAMPLE 3

Isolation of Hyperactive Clo051 Nuclease Mutants

As shown in FIG. 13 the primary sequence of the Clo051 nuclease domain between the positions E389 and Y587 exhibits a unique distribution of the positively charged arginine (R) and lysine (K) residues and of negatively charged glutamate (E) and aspartate (D) residues. These residues constitute a three-dimensional landscape of charges within the Clo051 domain that determines the unique tertiary structure of this nuclease, as shown in the structural model in FIG. 6. Certain replacements of polar versus non-polar residues or of non-polar residues against polar residues, e.g. at the positions 423 and 446, alter the three-dimensional structure of the protein chain and can result into an increase of the nuclease activity.

Such amino acid replacements may be made by trial and error or may follow specific hypotheses on the structural and functional impact on the Clo051 nuclease domain. Alternatively, a large number of randomly mutagenised variants of the Clo051 nuclease domain coding region can be assembled in a library by mutagenic PCR. This library of mutant molecules can be tested for the presence of hyperactive nuclease variants by a phenotypic screening assay in yeast, mammalian or *E. coli* cells that is coupled to a functional nuclease readout, e.g. as described for the improvement of the FLP recombinase (Buchholz et al., Nat. Biotechnol. 16, 657-62, 1998).

Such a functional screen for improved nuclease variants can result into the replacement of e.g. the residue 423 from a serine to a proline and of the residue 446 from an arginine to a glutamate. Such variant molecules can prove a superior nuclease activity as compared to the Clo051 wildtype form.

EXAMPLE 4

Clo051 Nuclease Induced Recombination of Genomic Substrates in Human Cells

The action of Clo051 nuclease was further tested in human HEK293 cells on a genomic integrated reporter construct. For this purpose the ArtTal1 reporter plasmid (FIG. 7) was modified by the insertion of a hygromycin resistance gene into the plasmid backbone. In addition the β-galactosidase reading frame was fused with the coding region of the neomycin resistance gene, resulting in the reporter plasmid pCMV-Rab-Reporter(hygro) (SEQ ID NO: 61). To generate a cell line harboring the reporter construct in its genome, linearized reporter plasmid DNA was electroporated into human HEK 293 cells (ATCC #CRL-1573) (Graham F L, Smiley J, Russell W C, Nairn R., J. Gen. Virol. 36, 59-74, 1977) and hygromycin resistant clones were selected and isolated. One of the resistant clones, that showed no background activity of the reporter gene, 293ArtTal-Rep#2, was chosen for further work.

Next, one million reporter cells were transfected with 5 μg plasmid DNA of the Tal nuclease expression vector pCAG-ArtTal1-Clo051 (FIG. 4) or with 5 μg of the unrelated cloning vector pBluescript as negative control. Upon transfection the cells were seeded in duplicate wells of a 6-well tissue culture plate and cultured for two days before analysis was started. For analysis the transfected cells of each well were fixed for 10 minutes with 4% formaldehyde and incubated for 4 hours with X-Gal staining solution (5 mM K3(Felll(CN)6), 5 mM K4(Fell(CN)6), 2 mM MgCl2, 1 mg/ml X-Gal (5-bromo-chloro-3-indoyl-β-D-galactopyranosid). Recombined cells that express the reporter gene are visualized by an intracellular blue staining and were quantified on photographic images using the ImageJ software's cell counter function (available at the website with the address http://imagej.nih.gov/ij). As shown in FIG. 14A, transfection with the pBluescript control plasmid did not result in positive reporter cells (>0.1%, 0 positive cells of 1076 counted cells). In contrast, the transfection of pCAG-ArtTal-1 resulted into a substantial fraction of cells that recombined the reporter construct and express β-galactosidase (FIG. 14B). As quantified from photographic images, 42.7% of the reporter cells (227 positive cells of 531 counted cells) showed successful recombination as indicated by expression of the reporter gene. In conclusion, this result indicates that ArtTal1-Clo051 nuclease protein can efficiently process a target sequence located within mammalian genomic DNA.

The invention claimed is:

1. A nucleic acid molecule encoding a fusion protein comprising a DNA-binding domain and an endonuclease, wherein the nucleic acid molecule:

(I) encodes a polypeptide having the activity of an endonuclease, wherein the polypeptide is an endonuclease comprising an amino acid sequence comprising the amino acid sequence of SEQ ID NO: 1, wherein the amino acid residues S35 and/or R58 are replaced with a non-polar amino acid; or (II) is a nucleic acid molecule corresponding to the nucleic acid molecule of (I) wherein T is replaced by U.

2. The nucleic acid molecule of claim 1, wherein the DNA-binding domain is a TAL effector motif of a TAL effector protein.

3. A vector comprising the nucleic acid molecule of claim 1.

4. An isolated host cell comprising the nucleic acid molecule of claim 1.

5. A method of modifying a target sequence in the genome of a eukaryotic cell, the method comprising the step of:

(a) introducing into said cell the nucleic acid molecule of claim 1, or a vector of claim 3.

6. The method of claim 5, wherein the modification of said target sequence is by homologous recombination with a donor nucleic acid sequence, further comprising the step:

(b) introducing a nucleic acid molecule into said cell, wherein said nucleic acid molecule comprises said donor nucleic acid sequence, wherein said donor DNA sequence is flanked upstream by a first flanking element and downstream by a second flanking element, wherein said first and second flanking element are different and wherein each of said first and second flanking element are homologous to a continuous DNA sequence on either side of the double-strand break introduced in (a) of claim 5 within said target sequence in the genome of said eukaryotic cell.

7. The method of claim 5, wherein said cell is analysed for successful modification of said target sequence in the genome.

8. The method of claim 5, wherein the cell is selected from the group consisting of a mammalian or vertebrate cell, a plant cell or a fungal cell.

9. The method of claim 5, wherein the cell is an oocyte.

10. The method of claim 5, wherein the cell is selected from the group consisting of rodents, dogs, felides, primates, rabbits, pigs, cows, chickens, turkeys, pheasants, ducks, geese, quails, ostriches, emus, cassowaries and zebrafish.

11. An isolated host cell comprising the vector of claim 3.

* * * * *

SEQUENCE LISTING

<160> NUMBER OF SEQ ID NOS: 87

<210> SEQ ID NO 1
<211> LENGTH: 199
<212> TYPE: PRT
<213> ORGANISM: Clostridium spec. 7_2_43 FAA

<400> SEQUENCE: 1

```
Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
            20                  25                  30

Phe Asp Ser Lys Gln Asn Arg Leu Phe Glu Met Lys Val Leu Glu Leu
        35                  40                  45

Leu Val Asn Glu Tyr Gly Phe Lys Gly Arg His Leu Gly Gly Ser Arg
    50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
        115                 120                 125

Val Lys Lys Tyr Tyr Phe Val Phe Ile Ser Gly Ser Phe Lys Gly Lys
    130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Glu Leu Glu Arg Ala Met Phe Asn Asn
            180                 185                 190

Ser Glu Phe Ile Leu Lys Tyr
        195
```

<210> SEQ ID NO 2
<211> LENGTH: 597
<212> TYPE: DNA
<213> ORGANISM: Clostridium spec. 7_2_43 FAA

<400> SEQUENCE: 2

```
gaaggcatca aaagcaacat ctccctcctg aaagacgaac tccgggggca gattagccac      60

attagtcacg aatacctctc cctcatcgac ctggctttcg atagcaagca gaacaggctc     120

tttgagatga aagtgctgga actgctcgtc aatgagtacg ggttcaaggg tcgacacctc     180

ggcggatcta ggaaaccaga cggcatcgtg tatagtacca cactggaaga caactttggg     240

atcattgtgg ataccaaggc atactctgag ggttatagtc tgcccatttc acaggccgac     300

gagatggaac ggtacgtgcg cgagaactca aatagagatg aggaagtcaa ccctaacaag     360

tggtgggaga acttctctga ggaagtgaag aaatactact tcgtctttat cagcgggtcc     420

ttcaagggta aatttgagga acagctcagg agactgagca tgactaccgg cgtgaatggc     480

agcgccgtca acgtggtcaa tctgctcctg ggcgctgaaa agattcggag cggagagatg     540

accatcgaag agctggagag ggcaatgttt aataatagcg agtttatcct gaaatac        597
```

<210> SEQ ID NO 3

<211> LENGTH: 5866
<212> TYPE: DNA
<213> ORGANISM: Artificial sequence
<220> FEATURE:
<223> OTHER INFORMATION: pCAG-TAL-nuclease

<400> SEQUENCE: 3
ggcgcgccgg attcgacatt gattattgac tagttattaa tagtaatcaa ttacggggtc 60
attagttcat agcccatata tggagttccg cgttacataa cttacggtaa atggcccgcc 120
tggctgaccg cccaacgacc cccgcccatt gacgtcaata atgacgtatg ttcccatagt 180
aacgccaata gggactttcc attgacgtca atgggtggag tatttacggt aaactgccca 240
cttggcagta catcaagtgt atcatatgcc aagtacgccc cctattgacg tcaatgacgg 300
taaatggccc gcctggcatt atgcccagta catgacctta tgggactttc ctacttggca 360
gtacatctac gtattagtca tcgctattac catggtcgag gtgagcccca cgttctgctt 420
cactctcccc atctcccccc cctccccacc cccaattttg tatttattta tttttaatt 480 attttgtgca gcgatggggg cggggggggg ggggggggcgc gcgccaggcg gggcggggcg 540
gggcgagggg cggggcgggg cgaggcggag aggtgcggcg gcagccaatc agagcggcgc 600
gctccgaaag tttcctttta tggcgaggcg gcggcggcgg cggccctata aaaagcgaag 660
cgcgcggcgg gcgggagtcg ctgcgcgctg ccttcgcccc gtgccccgct ccgccgccgc 720
ctcgcgccgc ccgccccggc tctgactgac cgcgttactc ccacaggtga gcgggcggga 780
cggcccttct cctccgggct gtaattagcg cttggtttaa tgacggcttg tttcttttct 840
gtggctgcgt gaaagccttg aggggctccg ggagggccct ttgtgcgggg gggagcggct 900 cgggggggtgc gtgcgtgtgt gtgtgcgtgg ggagcgccgc gtgcggctcc gcgctgcccg 960
gcggctgtga gcgctgcggg cgcggcgcgg ggctttgtgc gctccgcagt gtgcgcgagg 1020
ggagcgcggc cgggggcggt gccccgcggt gcgggggggg ctgcgagggg aacaaaggct 1080
gcgtgcgggg tgtgtgcgtg ggggggtgag cagggggtgt gggcgcgtcg gtcgggctgc 1140 aacccccccct gcacccccct ccccgagttg ctgagcacgg cccggcttcg ggtgcggggc 1200
tccgtacggg gcgtggcgcg gggctcgccg tgccgggcgg ggggtggcgg caggtggggg 1260
tgccgggcgg ggcggggccg cctcgggccg gggagggctc gggggagggg cgcggcggcc 1320
cccggagcgc cggcggctgt cgaggcgcgg cgagccgcag ccattgcctt ttatggtaat 1380
cgtgcgagag ggcgcaggga cttcctttgt cccaaatctg tgcggagccg aaatctggga 1440
ggcgccgccg caccccctct agcgggcgcg ggcgaagcg gtgcggcgcc ggcaggaagg 1500
aaatgggcgg ggagggcctt cgtgcgtcgc cgcgccgccg tccccttctc cctctccagc 1560
ctcggggctg tccgcggggg gacggctgcc ttcgggggggg acggggcagg gcggggttcg 1620
gcttctggcg tgtgaccggc ggctctagag cctctgctaa ccatgttcat gccttcttct 1680
ttttcctaca gatccttaat taataatacg actcactata ggggccgcca ccatgggacc 1740
taagaaaaag aggaaggtgg cggccgctga ctacaaggat gacgacgata aaccaggtgg 1800
cggaggtagt ggcggaggtg ggtacccgc cagtccagca gcccaggtgg atctgagaac 1860
cctcggctac agccagcagc agcaggagaa gatcaaacca aaggtgcggt ccaccgtcgc 1920
tcagcaccat gaagcactgg tggggcacgg tttcacacac gcccatattg tggctctgtc 1980
tcagcatccc gctgcactcg ggactgtggc cgtcaaatat caggacatga tcgccgctct 2040
gcctgaggca acccacgaag ccattgtggg cgtcggaaag cagtggagcg gtgccagagc 2100
actcgaagca ctcctcaccg tcgccgggga actgcggggt ccaccactcc agtccggact 2160

```
ggacactgga cagctgctga agatcgctaa acgcggcgga gtgacagctg tggaagctgt   2220
gcacgcttgg aggaatgctc tgacaggagc ccccactgaat cttatgagac gacgtctcac   2280
ggcctgaccc cacagcaggt cgtcgctatt gcttctaatg gcggagggcg gcctgctctg   2340
gagagcattg tggctcagct gtccaggccc gatcctgccc tggctagatc cgcactcact   2400
aacgatcatc tggtcgctct cgcttgcctc ggtggacggc ccgctctgga cgcagtcaaa   2460
aagggtctcc cccatgctcc cgcactgatc aagagaacca acaggagaat tcctgaggga   2520
tccgatcgtt taaacgatca cgcgtaaatg attgcagatc cactagttct agaattccag   2580
ctgagcgccg gtcgctacca ttaccagttg gtctggtgtc aaaaataata ataaccgggc   2640
agggggggatc tgcatggatc tttgtgaagg aaccttactt ctgtggtgtg acataattgg   2700
acaaactacc tacagagatt taaagctcta aggtaaatat aaaattttta agtgtataat   2760
gtgttaaact actgattcta attgtttgtg tattttagat tccaacctat ggaactgatg   2820
aatgggagca gtggtggaat gccagatcca gacatgataa gatacattga tgagtttgga   2880
caaaccacaa ctagaatgca gtgaaaaaaa tgctttattt gtgaaatttg tgatgctatt   2940
gctttatttg taaccattat aagctgcaat aaacaagtta acaacaacaa ttgcattcat   3000
tttatgtttc aggttcaggg ggaggtgtgg gaggtttttt aaagcaagta aaacctctac   3060
aaatgtggta tggctgatta tgatctgcgg ccgccactgg ccgtcgtttt acaacgtcgt   3120
gactgggaaa accctggcgt tacccaactt aatcgccttg cagcacatcc ccctttcgcc   3180
agctggcgta atagcgaaga ggcccgcacc gatcgccctt cccaacagtt gcgcagcctg   3240
aatggcgaat ggaacgcgcc ctgtagcggc gcattaagcg cggcgggtgt ggtggttacg   3300
cgcagcgtga ccgctacact tgccagcgcc ctagcgcccg ctcctttcgc tttcttccct   3360
tcctttctcg ccacgttcgc cggctttccc cgtcaagctc taaatcgggg gctcccttta   3420
gggttccgat ttagtgcttt acggcacctc gaccccaaaa aacttgatta gggtgatggt   3480
tcacgtagtg ggccatcgcc ctgatagacg gtttttcgcc ctttgacgtt ggagtccacg   3540
ttctttaata gtggactctt gttccaaact ggaacaacac tcaaccctat ctcggtctat   3600
tcttttgatt tataagggat tttgccgatt tcggcctatt ggttaaaaaa tgagctgatt   3660
taacaaaaat ttaacgcgaa ttttaacaaa atattaacgc ttacaattta ggtggcactt   3720
ttcggggaaa tgtgcgcgga acccctattt gtttattttt ctaaatacat tcaaatatgt   3780
atccgctcat gagacaataa ccctgataaa tgcttcaata atattgaaaa aggaagagta   3840
tgagtattca acatttccgt gtcgccctta ttcccttttt tgcggcattt tgccttcctg   3900
tttttgctca cccagaaacg ctggtgaaag taaaagatgc tgaagatcag ttgggtgcac   3960
gagtgggtta catcgaactg gatctcaaca gcggtaagat ccttgagagt tttcgccccg   4020
aagaacgttt tccaatgatg agcactttta aagttctgct atgtggcgcg gtattatccc   4080
gtattgacgc cgggcaagag caactcggtc gccgcataca ctattctcag aatgacttgg   4140
ttgagtactc accagtcaca gaaaagcatc ttacggatgg catgacagta agagaattat   4200
gcagtgctgc cataaccatg agtgataaca ctgcggccaa cttacttctg acaacgatcg   4260
gaggaccgaa ggagctaacc gcttttttgc acaacatggg ggatcatgta actcgccttg   4320
atcgttggga accggagctg aatgaagcca taccaaacga cgagcgtgac accacgatgc   4380
ctgtagcaat ggcaacaacg ttgcgcaaac tattaactgg cgaactactt actctagctt   4440
cccggcaaca attaatagac tggatggagg cggataaagt tgcaggacca cttctgcgct   4500
```

```
cggcccttcc ggctggctgg tttattgctg ataaatctgg agccggtgag cgtgggtctc   4560

gcggtatcat tgcagcactg gggccagatg gtaagccctc ccgtatcgta gttatctaca   4620

cgacggggag tcaggcaact atggatgaac gaaatagaca gatcgctgag ataggtgcct   4680

cactgattaa gcattggtaa ctgtcagacc aagtttactc atatatactt tagattgatt   4740

taaaacttca tttttaattt aaaaggatct aggtgaagat cctttttgat aatctcatga   4800

ccaaaatccc ttaacgtgag ttttcgttcc actgagcgtc agaccccgta gaaaagatca   4860

aaggatcttc ttgagatcct ttttttctgc gcgtaatctg ctgcttgcaa acaaaaaaac   4920

caccgctacc agcggtggtt tgtttgccgg atcaagagct accaactctt tttccgaagg   4980

taactggctt cagcagagcg cagataccaa atactgtcct tctagtgtag ccgtagttag   5040

gccaccactt caagaactct gtagcaccgc ctacatacct cgctctgcta atcctgttac   5100

cagtggctgc tgccagtggc gataagtcgt gtcttaccgg gttggactca agacgatagt   5160

taccggataa ggcgcagcgg tcgggctgaa cggggggttc gtgcacacag cccagcttgg   5220

agcgaacgac ctacaccgaa ctgagatacc tacagcgtga gctatgagaa agcgccacgc   5280

ttcccgaagg gagaaaggcg gacaggtatc cggtaagcgg cagggtcgga acaggagagc   5340

gcacgaggga gcttccaggg ggaaacgcct ggtatcttta tagtcctgtc gggtttcgcc   5400

acctctgact tgagcgtcga tttttgtgat gctcgtcagg ggggcggagc ctatggaaaa   5460

acgccagcaa cgcggccttt ttacggttcc tggccttttg ctggcctttt gctcacatgt   5520

tctttcctgc gttatcccct gattctgtgg ataaccgtat taccgccttt gagtgagctg   5580

ataccgctcg ccgcagccga acgaccgagc gcagcgagtc agtgagcgag gaagcggaag   5640

agcgcccaat acgcaaaccg cctctccccg cgcgttggcc gattcattaa tgcagctggc   5700

acgacaggtt tcccgactgg aaagcgggca gtgagcgcaa cgcaattaat gtgagttagc   5760

tcactcatta ggcaccccag gctttacact ttatgcttcc ggctcgtatg ttgtgtggaa   5820

ttgtgagcgg ataacaattt cacacaggaa acagctatga ccatga                 5866
```

```
<210> SEQ ID NO 4
<211> LENGTH: 176
<212> TYPE: PRT
<213> ORGANISM: Artificial sequence
<220> FEATURE:
<223> OTHER INFORMATION: N-terminal peptide

<400> SEQUENCE: 4

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125
```

```
Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175


<210> SEQ ID NO 5
<211> LENGTH: 78
<212> TYPE: PRT
<213> ORGANISM: Artificial sequence
<220> FEATURE:
<223> OTHER INFORMATION: C-terminal peptide

<400> SEQUENCE: 5

Leu Thr Pro Gln Gln Val Val Ala Ile Ala Ser Asn Gly Gly Gly Arg
1               5                   10                  15

Pro Ala Leu Glu Ser Ile Val Ala Gln Leu Ser Arg Pro Asp Pro Ala
            20                  25                  30

Leu Ala Arg Ser Ala Leu Thr Asn Asp His Leu Val Ala Leu Ala Cys
        35                  40                  45

Leu Gly Gly Arg Pro Ala Leu Asp Ala Val Lys Lys Gly Leu Pro His
    50                  55                  60

Ala Pro Ala Leu Ile Lys Arg Thr Asn Arg Arg Ile Pro Glu
65                  70                  75


<210> SEQ ID NO 6
<211> LENGTH: 408
<212> TYPE: PRT
<213> ORGANISM: Artificial sequence
<220> FEATURE:
<223> OTHER INFORMATION: ArtTal1

<400> SEQUENCE: 6

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
```

```
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly
                405
```

<210> SEQ ID NO 7
<211> LENGTH: 7067
<212> TYPE: DNA
<213> ORGANISM: Artificial sequence
<220> FEATURE:
<223> OTHER INFORMATION: pCAG-ArtTal1-nuclease

<400> SEQUENCE: 7

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

ccccccccctc cccaccccca attttgtatt tatttatttt ttaattattt tgtgcagcga    480

tgggggcggg gggggggggg gggcgcgcgc caggcggggc ggggcggggc gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

gagtcgctgc gcgctgcctt cgccccgtgc cccgctccgc cgccgcctcg cgccgcccgc    720

cccggctctg actgaccgcg ttactcccac aggtgagcgg gcgggacggc ccttctcctc    780
```

```
cgggctgtaa ttagcgcttg gtttaatgac ggcttgtttc ttttctgtgg ctgcgtgaaa    840
gccttgaggg gctccgggag ggccctttgt gcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct ttgtgcgctc cgcagtgtgc gcgaggggag cgcggccggg   1020
ggcggtgccc cgcggtgcgg ggggggctgc gaggggaaca aaggctgcgt gcggggtgtg   1080
tgcgtggggg ggtgagcagg gggtgtgggc gcgtcggtcg ggctgcaacc ccccctgcac   1140
cccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cgggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
```

```
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acgatcacgc gtaaatgatt gcagatccac tagttctaga attccagctg agcgccggtc   3780
gctaccatta ccagttggtc tggtgtcaaa aataataata accgggcagg ggggatctgc   3840
atggatcttt gtgaaggaac cttacttctg tggtgtgaca taattggaca aactacctac   3900
agagatttaa agctctaagg taaatataaa atttttaagt gtataatgtg ttaaactact   3960
gattctaatt gtttgtgtat tttagattcc aacctatgga actgatgaat gggagcagtg   4020
gtggaatgcc agatccagac atgataagat acattgatga gtttggacaa accacaacta   4080
gaatgcagtg aaaaaaatgc tttatttgtg aaatttgtga tgctattgct ttatttgtaa   4140
ccattataag ctgcaataaa caagttaaca acaacaattg cattcatttt atgtttcagg   4200
ttcaggggga ggtgtgggag gttttttaaa gcaagtaaaa cctctacaaa tgtggtatgg   4260
ctgattatga tctgcggccg ccactggccg tcgttttaca acgtcgtgac tgggaaaacc   4320
ctggcgttac ccaacttaat cgccttgcag cacatccccc tttcgccagc tggcgtaata   4380
gcgaagaggc ccgcaccgat cgcccttccc aacagttgcg cagcctgaat ggcgaatgga   4440
acgcgccctg tagcggcgca ttaagcgcgg cgggtgtggt ggttacgcgc agcgtgaccg   4500
ctacacttgc cagcgcccta gcgcccgctc ctttcgcttt cttcccttcc tttctcgcca   4560
cgttcgccgg ctttccccgt caagctctaa atcgggggct ccctttaggg ttccgattta   4620
gtgctttacg gcacctcgac cccaaaaaac ttgattaggg tgatggttca cgtagtgggc   4680
catcgccctg atagacggtt tttcgccctt tgacgttgga gtccacgttc tttaatagtg   4740
gactcttgtt ccaaactgga acaacactca accctatctc ggtctattct tttgatttat   4800
aagggatttt gccgatttcg gcctattggt taaaaaatga gctgatttaa caaaaattta   4860
acgcgaattt taacaaaata ttaacgctta caatttaggt ggcacttttc ggggaaatgt   4920
gcgcggaacc cctatttgtt tatttttcta aatacattca aatatgtatc cgctcatgag   4980
acaataaccc tgataaatgc ttcaataata ttgaaaaagg aagagtatga gtattcaaca   5040
tttccgtgtc gcccttattc ccttttttgc ggcattttgc cttcctgttt ttgctcaccc   5100
agaaacgctg gtgaaagtaa aagatgctga agatcagttg ggtgcacgag tgggttacat   5160
cgaactggat ctcaacagcg gtaagatcct tgagagtttt cgccccgaag aacgttttcc   5220
aatgatgagc acttttaaag ttctgctatg tggcgcggta ttatcccgta ttgacgccgg   5280
gcaagagcaa ctcggtcgcc gcatacacta ttctcagaat gacttggttg agtactcacc   5340
agtcacagaa aagcatctta cggatggcat gacagtaaga gaattatgca gtgctgccat   5400
aaccatgagt gataacactg cggccaactt acttctgaca acgatcggag gaccgaagga   5460
gctaaccgct tttttgcaca acatggggga tcatgtaact cgccttgatc gttgggaacc   5520
```

```
ggagctgaat gaagccatac caaacgacga gcgtgacacc acgatgcctg tagcaatggc   5580

aacaacgttg cgcaaactat taactggcga actacttact ctagcttccc ggcaacaatt   5640

aatagactgg atggaggcgg ataaagttgc aggaccactt ctgcgctcgg cccttccggc   5700

tggctggttt attgctgata aatctggagc cggtgagcgt gggtctcgcg gtatcattgc   5760

agcactgggg ccagatggta agccctcccg tatcgtagtt atctacacga cggggagtca   5820

ggcaactatg gatgaacgaa atagacagat cgctgagata ggtgcctcac tgattaagca   5880

ttggtaactg tcagaccaag tttactcata tatactttag attgatttaa aacttcattt   5940

ttaatttaaa aggatctagg tgaagatcct ttttgataat ctcatgacca aaatccctta   6000

acgtgagttt tcgttccact gagcgtcaga ccccgtagaa aagatcaaag gatcttcttg   6060

agatcctttt tttctgcgcg taatctgctg cttgcaaaca aaaaaaccac cgctaccagc   6120

ggtggtttgt ttgccggatc aagagctacc aactcttttt ccgaaggtaa ctggcttcag   6180

cagagcgcag ataccaaata ctgtccttct agtgtagccg tagttaggcc accacttcaa   6240

gaactctgta gcaccgccta catacctcgc tctgctaatc ctgttaccag tggctgctgc   6300

cagtggcgat aagtcgtgtc ttaccgggtt ggactcaaga cgatagttac cggataaggc   6360

gcagcggtcg ggctgaacgg ggggttcgtg cacacagccc agcttggagc gaacgaccta   6420

caccgaactg agatacctac agcgtgagct atgagaaagc gccacgcttc ccgaagggag   6480

aaaggcggac aggtatccgg taagcggcag ggtcggaaca ggagagcgca cgagggagct   6540

tccaggggga aacgcctggt atctttatag tcctgtcggg tttcgccacc tctgacttga   6600

gcgtcgattt ttgtgatgct cgtcaggggg gcggagccta tggaaaaacg ccagcaacgc   6660

ggccttttta cggttcctgg ccttttgctg gccttttgct cacatgttct ttcctgcgtt   6720

atcccctgat tctgtggata accgtattac cgcctttgag tgagctgata ccgctcgccg   6780

cagccgaacg accgagcgca gcgagtcagt gagcgaggaa gcggaagagc gcccaatacg   6840

caaaccgcct ctccccgcgc gttggccgat tcattaatgc agctggcacg acaggtttcc   6900

cgactggaaa gcgggcagtg agcgcaacgc aattaatgtg agttagctca ctcattaggc   6960

accccaggct ttacacttta tgcttccggc tcgtatgttg tgtggaattg tgagcggata   7020

acaatttcac acaggaaaca gctatgacca tgaggcgcgc cggattc                 7067


<210> SEQ ID NO 8
<211> LENGTH: 476
<212> TYPE: PRT
<213> ORGANISM: Artificial sequence
<220> FEATURE:
<223> OTHER INFORMATION: TalRab2

<400> SEQUENCE: 8

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
```

```
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly
465                 470                 475
```

<210> SEQ ID NO 9
<211> LENGTH: 7271
<212> TYPE: DNA
<213> ORGANISM: Artificial sequence
<220> FEATURE:
<223> OTHER INFORMATION: pCAG-TalRab2-nuclease

<400> SEQUENCE: 9

```
ggcgcgccgg attcgacatt gattattgac tagttattaa tagtaatcaa ttacggggtc      60
attagttcat agcccatata tggagttccg cgttacataa cttacggtaa atggcccgcc     120
tggctgaccg cccaacgacc cccgcccatt gacgtcaata atgacgtatg ttcccatagt     180
aacgccaata gggactttcc attgacgtca atgggtggag tatttacggt aaactgccca     240
cttggcagta catcaagtgt atcatatgcc aagtacgccc cctattgacg tcaatgacgg     300
taaatggccc gcctggcatt atgcccagta catgacctta tgggactttc ctacttggca     360
gtacatctac gtattagtca tcgctattac catggtcgag gtgagcccca cgttctgctt     420
cactctcccc atctcccccc cctccccacc cccaattttg tatttattta tttttttaatt     480
attttgtgca gcgatggggg cggggggggg ggggggggcgc gcgccaggcg gggcggggcg     540
gggcgagggg cggggcgggg cgaggcggag aggtgcggcg gcagccaatc agagcggcgc     600
gctccgaaag tttcctttta tggcgaggcg gcggcggcgg cggccctata aaaagcgaag     660
cgcgcggcgg gcgggagtcg ctgcgcgctg ccttcgcccc gtgccccgct ccgccgccgc     720
ctcgcgccgc ccgccccggc tctgactgac cgcgttactc ccacaggtga gcgggcggga     780
cggcccttct cctccgggct gtaattagcg cttggtttaa tgacggcttg tttcttttct     840
gtggctgcgt gaaagccttg aggggctccg ggagggccct ttgtgcgggg gggagcggct     900
cgggggggtgc gtgcgtgtgt gtgtgcgtgg ggagcgccgc gtgcggctcc gcgctgcccg     960
gcggctgtga gcgctgcggg cgcggcgcgg ggctttgtgc gctccgcagt gtgcgcgagg    1020
ggagcgcggc cgggggcggt gccccgcggt gcgggggggg ctgcgagggg aacaaaggct    1080
gcgtgcgggg tgtgtgcgtg ggggggtgag cagggggtgt gggcgcgtcg gtcgggctgc    1140
aacccccccct gcacccccct ccccgagttg ctgagcacgg cccggcttcg ggtgcggggc    1200
tccgtacggg gcgtggcgcg gggctcgccg tgccgggcgg ggggtggcgg caggtggggg    1260
tgccgggcgg ggcggggccg cctcgggccg gggagggctc gggggagggg cgcggcggcc    1320
cccggagcgc cggcggctgt cgaggcgcgg cgagccgcag ccattgcctt ttatggtaat    1380
cgtgcgagag ggcgcaggga cttcctttgt cccaaatctg tgcggagccg aaatctggga    1440
ggcgccgccg caccccctct agcgggcgcg gggcgaagcg gtgcggcgcc ggcaggaagg    1500
aaatgggcgg ggagggcctt cgtgcgtcgc cgcgccgccg tccccttctc cctctccagc    1560
ctcggggctg tccgcggggg gacggctgcc ttcggggggg acggggcagg gcggggttcg    1620
gcttctggcg tgtgaccggc ggctctagag cctctgctaa ccatgttcat gccttcttct    1680
ttttcctaca gatccttaat taataatacg actcactata ggggccgcca ccatgggacc    1740
taagaaaaag aggaaggtgg cggccgctga ctacaaggat gacgacgata aaccaggtgg    1800
cggaggtagt ggcggaggtg ggtacccgc cagtccagca gcccaggtgg atctgagaac    1860
cctcggctac agccagcagc agcaggagaa gatcaaacca aaggtgcggt ccaccgtcgc    1920
tcagcaccat gaagcactgg tggggcacgg tttcacacac gcccatattg tggctctgtc    1980
tcagcatccc gctgcactcg ggactgtggc cgtcaaatat caggacatga tcgccgctct    2040
gcctgaggca acccacgaag ccattgtggg cgtcggaaag cagtggagcg gtgccagagc    2100
actcgaagca ctcctcaccg tcgccgggga actgcggggt ccaccactcc agtccggact    2160
ggacactgga cagctgctga agatcgctaa acgcggcgga gtgacagctg tggaagctgt    2220
```

-continued

```
gcacgcttgg aggaatgctc tgacaggagc cccactgaat ctgacacccc agcaggtggt   2280
ggccattgct agcaacaatg ggggcaagca ggctctggag acagtgcagc gcctgctgcc   2340
tgtgctgtgc caggctcacg gactgactcc acagcaggtg gtggccatcg cttccaacaa   2400
tggagggaaa caggctctgg aaacagtgca gaggctgctg cccgtgctgt gccaggctca   2460
tggactgaca cctcagcagg tcgtcgccat tgcttctaac ggcggaggga agcaggctct   2520
ggagactgtg cagagactgc tgccagtgct gtgccaggcc catggactga cccctcagca   2580
ggtcgtggct atcgctagta acaatggcgg aaaacaggct ctggaaactg tgcagcggct   2640
gctccccgtg ctgtgccagg cccacggcct cactccacag caggtcgtcg ctatcgcctc   2700
taataacggg ggcaagcagg ctctggagac agtacagcgc ctgttacccg tgctgtgcca   2760
ggcacacggc ctcacacctc agcaggtcgt ggcaatcgct tcccatgacg gagggaaaca   2820
ggctctggaa acggtccaga ggctgctccc cgtgctgtgc caagctcacg gcctcacccc   2880
tcagcaggtg gtcgctattg cttctcatga tggcggaaag caggctctgg agaccgtgca   2940
gagactgctc cctgtgctgt gccaagccca cggcctgact ccacagcagg tcgtggccat   3000
cgctagtcat gacgggggca aacaggctct ggaaacagta cagcggctgt tacccgtgct   3060
gtgccaagcc catggcctca cacctcagca agtcgtcgct atcgctagca acaatggagg   3120
gaagcaggct ctggagacgg tgcagcgcct gctcccagtg ctgtgccaag ctcatggcct   3180
cacccctcag caagtcgtcg caattgcttc caataacggc ggaaaacagg ctctggaaac   3240
cgtccagagg ctgctgcccg tgctgtgcca agcacatggc ttaactccac agcaagtggt   3300
ggccattgct tctaatgggg gcggaaagca ggccctggag acagtccaga gactgttgcc   3360
cgtgctgtgc caagcgcatg gactgacacc tgaacaggtc gtcgctatcg ctagtaatat   3420
tgggggcaaa caggccctgg aaacagtgca gcggctgctt cccgtgctgt gccaggcgca   3480
tggactcaca ccccagcagg tcgtcgcaat cgcctctaat aacggaggga agcaggccct   3540
ggaaaccgtg cagagactgt tacctgtgct gtgccaggca catggtctga caccacagca   3600
ggtggtcgca attgctagca atggcggagg gaagcaggcc ctggagactg tccagagact   3660
gctacccgtg ctgtgccaag cgcacggcct gaccccacag caggtcgtcg ctattgcttc   3720
taatggcgga gggcggcctg ctctggagag cattgtggct cagctgtcca ggcccgatcc   3780
tgccctggct agatccgcac tcactaacga tcatctggtc gctctcgctt gcctcggtgg   3840
acggcccgct ctggacgcag tcaaaaaggg tctcccccat gctcccgcac tgatcaagag   3900
aaccaacagg agaattcctg agggatccga tcgtttaaac gatcacgcgt aaatgattgc   3960
agatccacta gttctagaat tccagctgag cgccggtcgc taccattacc agttggtctg   4020
gtgtcaaaaa taataataac cgggcagggg ggatctgcat ggatctttgt gaaggaacct   4080
tacttctgtg gtgtgacata attggacaaa ctacctacag agatttaaag ctctaaggta   4140
aatataaaat ttttaagtgt ataatgtgtt aaactactga ttctaattgt ttgtgtattt   4200
tagattccaa cctatggaac tgatgaatgg gagcagtggt ggaatgccag atccagacat   4260
gataagatac attgatgagt ttggacaaac cacaactaga atgcagtgaa aaaaatgctt   4320
tatttgtgaa atttgtgatg ctattgcttt atttgtaacc attataagct gcaataaaca   4380
agttaacaac aacaattgca ttcattttat gtttcaggtt cagggggagg tgtgggaggt   4440
tttttaaagc aagtaaaacc tctacaaatg tggtatggct gattatgatc tgcggccgcc   4500
actggccgtc gttttacaac gtcgtgactg ggaaaaccct ggcgttaccc aacttaatcg   4560
ccttgcagca catccccctt tcgccagctg gcgtaatagc gaagaggccc gcaccgatcg   4620
```

```
ccctttcccaa cagttgcgca gcctgaatgg cgaatggaac gcgccctgta gcggcgcatt   4680

aagcgcggcg ggtgtggtgg ttacgcgcag cgtgaccgct acacttgcca gcgccctagc   4740

gcccgctcct ttcgctttct tcccttcctt tctcgccacg ttcgccggct ttccccgtca   4800

agctctaaat cgggggctcc ctttagggtt ccgatttagt gctttacggc acctcgaccc   4860

caaaaaactt gattagggtg atggttcacg tagtgggcca tcgccctgat agacggtttt   4920

tcgccctttg acgttggagt ccacgttctt taatagtgga ctcttgttcc aaactggaac   4980

aacactcaac cctatctcgg tctattcttt tgatttataa gggattttgc cgatttcggc   5040

ctattggtta aaaaatgagc tgatttaaca aaaatttaac gcgaatttta acaaaatatt   5100

aacgcttaca atttaggtgg cacttttcgg ggaaatgtgc gcggaacccc tatttgttta   5160

tttttctaaa tacattcaaa tatgtatccg ctcatgagac aataaccctg ataaatgctt   5220

caataatatt gaaaaaggaa gagtatgagt attcaacatt tccgtgtcgc ccttattccc   5280

ttttttgcgg cattttgcct tcctgttttt gctcacccag aaacgctggt gaaagtaaaa   5340

gatgctgaag atcagttggg tgcacgagtg ggttacatcg aactggatct caacagcggt   5400

aagatccttg agagttttcg ccccgaagaa cgttttccaa tgatgagcac ttttaaagtt   5460

ctgctatgtg gcgcggtatt atcccgtatt gacgccgggc aagagcaact cggtcgccgc   5520

atacactatt ctcagaatga cttggttgag tactcaccag tcacagaaaa gcatcttacg   5580

gatggcatga cagtaagaga attatgcagt gctgccataa ccatgagtga taacactgcg   5640

gccaacttac ttctgacaac gatcggagga ccgaaggagc taaccgcttt tttgcacaac   5700

atgggggatc atgtaactcg ccttgatcgt tgggaaccgg agctgaatga agccatacca   5760

aacgacgagc gtgacaccac gatgcctgta gcaatggcaa caacgttgcg caaactatta   5820

actggcgaac tacttactct agcttcccgg caacaattaa tagactggat ggaggcggat   5880

aaagttgcag gaccacttct gcgctcggcc cttccggctg gctggtttat tgctgataaa   5940

tctggagccg gtgagcgtgg gtctcgcggt atcattgcag cactggggcc agatggtaag   6000

ccctcccgta tcgtagttat ctacacgacg gggagtcagg caactatgga tgaacgaaat   6060

agacagatcg ctgagatagg tgcctcactg attaagcatt ggtaactgtc agaccaagtt   6120

tactcatata tactttagat tgatttaaaa cttcattttt aatttaaaag gatctaggtg   6180

aagatccttt ttgataatct catgaccaaa atcccttaac gtgagttttc gttccactga   6240

gcgtcagacc ccgtagaaaa gatcaaagga tcttcttgag atcctttttt tctgcgcgta   6300

atctgctgct tgcaaacaaa aaaaccaccg ctaccagcgg tggtttgttt gccggatcaa   6360

gagctaccaa ctctttttcc gaaggtaact ggcttcagca gagcgcagat accaaatact   6420

gtccttctag tgtagccgta gttaggccac cacttcaaga actctgtagc accgcctaca   6480

tacctcgctc tgctaatcct gttaccagtg gctgctgcca gtggcgataa gtcgtgtctt   6540

accgggttgg actcaagacg atagttaccg gataaggcgc agcggtcggg ctgaacgggg   6600

ggttcgtgca cacagcccag cttggagcga acgacctaca ccgaactgag atacctacag   6660

cgtgagctat gagaaagcgc cacgcttccc gaagggagaa aggcggacag gtatccggta   6720

agcggcaggg tcggaacagg agagcgcacg agggagcttc cagggggaaa cgcctggtat   6780

ctttatagtc ctgtcgggtt tcgccacctc tgacttgagc gtcgattttt gtgatgctcg   6840

tcaggggggc ggagcctatg gaaaaacgcc agcaacgcgg cctttttacg gttcctggcc   6900

ttttgctggc cttttgctca catgttcttt cctgcgttat cccctgattc tgtggataac   6960
```

```
cgtattaccg cctttgagtg agctgatacc gctcgccgca gccgaacgac cgagcgcagc   7020

gagtcagtga gcgaggaagc ggaagagcgc ccaatacgca aaccgcctct ccccgcgcgt   7080

tggccgattc attaatgcag ctggcacgac aggtttcccg actggaaagc gggcagtgag   7140

cgcaacgcaa ttaatgtgag ttagctcact cattaggcac cccaggcttt acactttatg   7200

cttccggctc gtatgttgtg tggaattgtg agcggataac aatttcacac aggaaacagc   7260

tatgaccatg a                                                        7271
```

```
<210> SEQ ID NO 10
<211> LENGTH: 583
<212> TYPE: PRT
<213> ORGANISM: Flavobacterium okeanokoites

<400> SEQUENCE: 10

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
        275                 280                 285

Thr Arg Val Pro Lys Arg Val Tyr Trp Glu Met Leu Ala Thr Asn Leu
    290                 295                 300

Thr Asp Lys Glu Tyr Val Arg Thr Arg Arg Ala Leu Ile Leu Glu Ile
305                 310                 315                 320
```

```
Leu Ile Lys Ala Gly Ser Leu Lys Ile Glu Gln Ile Gln Asp Asn Leu
            325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365

Tyr Gln Leu Lys Asp His Ile Leu Gln Phe Val Ile Pro Asn Arg Gly
    370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
        435                 440                 445

Gly Ser Arg Lys Pro Asp Gly Ala Ile Tyr Thr Val Gly Ser Pro Ile
    450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
        515                 520                 525

Lys Gly Asn Tyr Lys Ala Gln Leu Thr Arg Leu Asn His Ile Thr Asn
    530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580


<210> SEQ ID NO 11
<211> LENGTH: 558
<212> TYPE: PRT
<213> ORGANISM: Acinetobacter lwoffii

<400> SEQUENCE: 11

Met Ser Thr Trp Leu Leu Gly Asn Thr Thr Val Arg Ser Pro Phe Arg
1               5                   10                  15

Leu Ile Asp Gly Leu Lys Val Phe Ala Leu Thr Asn Gly Asp Ile Arg
            20                  25                  30

Gly Thr Lys Glu Lys Glu Leu Val Phe Cys Lys Ala Leu Val Glu Gly
        35                  40                  45

Gly Ile Ile Ser Ala Ser Phe Glu Ala Glu Asp Thr Ser Gly Phe Ser
    50                  55                  60

Asp Thr Thr Tyr Ser Val Gly Arg Lys Trp Arg Ser Ala Leu Glu Lys
65                  70                  75                  80

Leu Gly Phe Ile Glu Gln Phe Asn Gln Ile Tyr Ile Leu Thr Glu Asn
                85                  90                  95

Gly Arg Asn Leu Leu Asn Ser Gln Thr Leu Gln Ser Asp Gln Glu Cys
```

-continued

```
            100                 105                 110

Tyr Leu Arg Ser Leu Ile Leu Tyr Ser Tyr Lys Ala Glu Asn Ser Asp
        115                 120                 125

Asn Pro Gly Gly Phe Phe Ser Pro Leu Met Leu Thr Leu His Ile Met
    130                 135                 140

Lys Glu Leu Glu Ile Arg Thr Gly Ser Ser Arg Ile Ser Phe Gln Glu
145                 150                 155                 160

Met Ala Ala Val Ile Gln Leu Thr Phe Ser Tyr Leu Asp Ile Asn Gln
                165                 170                 175

Ser Val Asn Glu Ile Leu Thr Ile Arg Ser Asn Arg Gln Ala Ser Leu
            180                 185                 190

Ser Lys Lys Lys Phe Asp Arg Glu Leu Tyr Glu Ser Lys Ser Ser Lys
        195                 200                 205

Ala Lys Ile Lys Ala Pro Ser Ile Lys Asp Tyr Ala Asp Thr Asn Leu
    210                 215                 220

Arg Tyr Leu Lys Ser Thr Gly Leu Phe Thr Ala Ser Gly Lys Gly Ile
225                 230                 235                 240

Cys Phe Ile Asp Asp Lys Lys Ile Val Ile Asp Lys Leu Ile Ala Met
                245                 250                 255

Tyr Gly Thr Phe Asp Ile Ser Gln Ser Asp Leu Lys Ile Gln Lys Gly
            260                 265                 270

Ala Pro Leu Pro Thr Asp His Lys Glu Thr Asn Ile Leu Leu Val Glu
        275                 280                 285

Gln Leu Glu Glu Thr Leu Asn Arg Asn Arg Ile Leu Phe Glu Lys Asn
    290                 295                 300

Ser Ser Ile Ala Gln Ala Pro Ile Gly Glu Ile Lys Asn Tyr Arg Tyr
305                 310                 315                 320

His Leu Glu Glu Leu Leu Phe Glu Asn Asn Glu Lys Lys Phe Ala Glu
                325                 330                 335

Asn Gln Lys Asn Glu Trp Asp Glu Ile Leu Ala Tyr Met Asp Leu Leu
            340                 345                 350

Ile Ser Pro Lys Pro Ile Ser Ile Glu Ile Ala Asp Lys Glu Ile Ser
        355                 360                 365

Ile Pro Ser Gly Glu Arg Pro Ala Tyr Phe Glu Trp Val Leu Trp Arg
    370                 375                 380

Ala Phe Leu Ala Leu Asn His Leu Ile Ile Glu Pro Gln Gln Cys Arg
385                 390                 395                 400

Arg Phe Lys Val Asp Gln Asp Phe Lys Pro Ile His Asn Ala Pro Gly
                405                 410                 415

Gly Gly Ala Asp Val Ile Phe Glu Tyr Glu Asn Phe Lys Ile Leu Gly
            420                 425                 430

Glu Val Thr Leu Thr Ser Asn Ser Arg Gln Glu Ala Ala Glu Gly Glu
        435                 440                 445

Pro Val Arg Arg His Ile Ala Val Glu Thr Val Asn Thr Pro Asp Lys
    450                 455                 460

Asp Val Tyr Gly Leu Phe Leu Ala Leu Thr Ile Asp Thr Asn Thr Ala
465                 470                 475                 480

Glu Thr Phe Arg His Gly Ala Trp Tyr His Gln Glu Glu Leu Met Asp
                485                 490                 495

Val Lys Ile Leu Pro Leu Thr Leu Glu Ser Phe Lys Lys Tyr Leu Glu
            500                 505                 510

Ser Leu Arg Lys Lys Asn Gln Val Glu Thr Gly Ile Phe Asp Leu Lys
        515                 520                 525
```

```
Lys Met Met Asp Glu Ser Leu Lys Leu Arg Glu Thr Leu Thr Ala Pro
    530                 535                 540

Gln Trp Lys Asn Glu Ile Thr Asn Lys Phe Ala Arg Pro Ile
545                 550                 555


<210> SEQ ID NO 12
<211> LENGTH: 556
<212> TYPE: PRT
<213> ORGANISM: Micrococcus lylae

<400> SEQUENCE: 12

Met Ala Ser Leu Ser Lys Thr Lys His Leu Phe Gly Phe Thr Ser Pro
1               5                   10                  15

Arg Thr Ile Glu Lys Ile Ile Pro Glu Leu Asp Ile Leu Ser Gln Gln
            20                  25                  30

Phe Ser Gly Lys Val Trp Gly Glu Asn Gln Ile Asn Phe Phe Asp Ala
        35                  40                  45

Ile Phe Asn Ser Asp Phe Tyr Glu Gly Thr Thr Tyr Pro Gln Asp Pro
    50                  55                  60

Ala Leu Ala Ala Arg Asp Arg Ile Thr Arg Ala Pro Lys Ala Leu Gly
65                  70                  75                  80

Phe Ile Gln Leu Lys Pro Val Ile Gln Leu Thr Lys Ala Gly Asn Gln
                85                  90                  95

Leu Val Asn Gln Lys Arg Leu Pro Glu Leu Phe Thr Lys Gln Leu Leu
            100                 105                 110

Lys Phe Gln Leu Pro Ser Pro Tyr His Thr Gln Ser Pro Thr Val Asn
        115                 120                 125

Phe Asn Val Arg Pro Tyr Leu Glu Leu Leu Arg Leu Ile Asn Glu Leu
    130                 135                 140

Gly Ser Ile Ser Lys Thr Glu Ile Ala Leu Phe Phe Leu Gln Leu Val
145                 150                 155                 160

Asn Tyr Asn Lys Phe Asp Glu Ile Lys Asn Lys Ile Leu Lys Phe Arg
                165                 170                 175

Glu Thr Arg Lys Asn Asn Arg Ser Val Ser Trp Lys Thr Tyr Val Ser
            180                 185                 190

Gln Glu Phe Glu Lys Gln Ile Ser Ile Ile Phe Ala Asp Glu Val Thr
        195                 200                 205

Ala Lys Asn Phe Arg Thr Arg Glu Ser Ser Asp Glu Ser Phe Lys Lys
    210                 215                 220

Phe Val Lys Thr Lys Glu Gly Asn Met Lys Asp Tyr Ala Asp Ala Phe
225                 230                 235                 240

Phe Arg Tyr Ile Arg Gly Thr Gln Leu Val Thr Ile Asp Lys Asn Leu
                245                 250                 255

His Leu Lys Ile Ser Ser Leu Lys Gln Asp Ser Val Asp Phe Leu Leu
            260                 265                 270

Lys Asn Thr Asp Arg Asn Ala Leu Asn Leu Ser Leu Met Glu Tyr Glu
        275                 280                 285

Asn Tyr Leu Phe Asp Pro Asp Gln Leu Ile Val Leu Glu Asp Asn Ser
    290                 295                 300

Gly Leu Ile Asn Ser Lys Ile Lys Gln Leu Asp Asp Ser Ile Asn Val
305                 310                 315                 320

Glu Ser Leu Lys Ile Asp Asp Ala Lys Asp Leu Leu Asn Asp Leu Glu
                325                 330                 335

Ile Gln Arg Lys Ala Lys Thr Ile Glu Asp Thr Val Asn His Leu Lys
```

```
            340                 345                 350

Leu Arg Ser Asp Ile Glu Asp Ile Leu Asp Val Phe Ala Lys Ile Lys
        355                 360                 365

Lys Arg Asp Val Pro Asp Val Pro Leu Phe Leu Glu Trp Asn Ile Trp
    370                 375                 380

Arg Ala Phe Ala Ala Leu Asn His Thr Gln Ala Ile Glu Gly Asn Phe
385                 390                 395                 400

Ile Val Asp Leu Asp Gly Met Pro Leu Asn Thr Ala Pro Gly Lys Lys
                405                 410                 415

Pro Asp Ile Glu Ile Asn Tyr Gly Ser Phe Ser Cys Ile Val Glu Val
            420                 425                 430

Thr Met Ser Ser Gly Glu Thr Gln Phe Asn Met Glu Gly Ser Ser Val
        435                 440                 445

Pro Arg His Tyr Gly Asp Leu Val Arg Lys Val Asp His Asp Ala Tyr
    450                 455                 460

Cys Ile Phe Ile Ala Pro Lys Val Ala Pro Gly Thr Lys Ala His Phe
465                 470                 475                 480

Phe Asn Leu Asn Arg Leu Ser Thr Lys His Tyr Gly Gly Lys Thr Lys
                485                 490                 495

Ile Ile Pro Met Ser Leu Asp Asp Phe Ile Cys Phe Leu Gln Val Gly
            500                 505                 510

Ile Thr His Asn Phe Gln Asp Ile Asn Lys Leu Lys Asn Trp Leu Asp
        515                 520                 525

Asn Leu Ile Asn Phe Asn Leu Glu Ser Glu Asp Glu Glu Ile Trp Phe
    530                 535                 540

Glu Glu Ile Ile Ser Lys Ile Ser Thr Trp Ala Ile
545                 550                 555


<210> SEQ ID NO 13
<211> LENGTH: 323
<212> TYPE: PRT
<213> ORGANISM: Streptomyces spec. Bf-61

<400> SEQUENCE: 13

Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
            20                  25                  30

Val Arg Ser Ala Val Thr Leu Leu Ala Leu Ala Gly Leu Lys Pro Gly
        35                  40                  45

Asp Arg Trp Val Asp Ser Thr Thr Pro Arg Leu Gly Val Gln Lys Ile
    50                  55                  60

Met Asp Trp Ser Gly Glu His Trp Ala Lys Pro Tyr Ala Thr Gly Ser
65                  70                  75                  80

Arg Glu Asp Phe Arg Lys Lys Thr Leu Arg Gln Trp Val Asp Asn Gly
                85                  90                  95

Phe Ala Val Leu Asn Ala Asp Asn Leu Asn Ile Ala Thr Asn Ser Gln
            100                 105                 110

Leu Asn Glu Tyr Cys Leu Ser Asp Glu Ala Leu Gln Ala Leu Arg Ala
        115                 120                 125

Tyr Gly Thr Glu Gly Phe Glu Glu Ser Leu Val Val Phe Leu Asp Glu
    130                 135                 140

Ala Ser Lys Ala Val Lys Ala Arg Ala Glu Ala Leu Gln Ala Ala Met
145                 150                 155                 160
```

```
Ile Ser Val Asp Leu Pro Gly Gly Glu Glu Phe Leu Leu Ser Pro Ala
                165                 170                 175

Gly Gln Asn Pro Leu Leu Lys Lys Met Val Glu Glu Phe Val Pro Arg
            180                 185                 190

Phe Ala Pro Arg Ser Thr Val Leu Tyr Leu Gly Asp Thr Arg Gly Lys
        195                 200                 205

His Ser Leu Phe Glu Arg Glu Ile Phe Glu Glu Val Leu Gly Leu Thr
    210                 215                 220

Phe Asp Pro His Gly Arg Met Pro Asp Leu Ile Leu His Asp Glu Val
225                 230                 235                 240

Arg Gly Trp Leu Phe Leu Met Glu Ala Val Lys Ser Lys Gly Pro Phe
                245                 250                 255

Asp Glu Glu Arg His Arg Ser Leu Gln Glu Leu Phe Val Thr Pro Ser
            260                 265                 270

Ala Gly Leu Ile Phe Val Asn Cys Phe Glu Asn Arg Glu Ser Met Arg
        275                 280                 285

Gln Trp Leu Pro Glu Leu Ala Trp Glu Thr Glu Ala Trp Val Ala Glu
    290                 295                 300

Asp Pro Asp His Leu Ile His Leu Asn Gly Ser Arg Phe Leu Gly Pro
305                 310                 315                 320

Tyr Glu Arg


<210> SEQ ID NO 14
<211> LENGTH: 323
<212> TYPE: PRT
<213> ORGANISM: Streptomyces diastaticus

<400> SEQUENCE: 14

Met Thr Asn Ser Asn Asp Ile Asp Glu Thr Ala Ala Thr Ile Asp Thr
1               5                   10                  15

Ala Arg Ala Leu Leu Lys Ser Phe Gly Phe Glu Ala Gln Arg His Asn
            20                  25                  30

Val Arg Ser Ala Val Thr Leu Leu Ala Leu Ala Gly Leu Lys Pro Gly
        35                  40                  45

Asp His Trp Ala Asp Ser Thr Thr Pro Arg Leu Gly Val Gln Lys Ile
    50                  55                  60

Met Asp Trp Ser Gly Ala Tyr Trp Ala Lys Pro Tyr Ala Thr Gly Ser
65                  70                  75                  80

Arg Glu Asp Phe Arg Lys Lys Thr Leu Arg Gln Trp Val Asp Asn Gly
                85                  90                  95

Phe Ala Val Leu Asn Pro Asp Asn Leu Asn Ile Ala Thr Asn Ser Gln
            100                 105                 110

Leu Asn Glu Tyr Cys Leu Ser Asp Glu Ala Ala Gln Ala Ile Arg Ser
        115                 120                 125

Tyr Gly Thr Asp Ala Phe Glu Ser Ala Leu Val Asp Phe Leu Ser Lys
    130                 135                 140

Ala Ser Asp Thr Val Arg Ala Arg Ala Glu Ala Leu Arg Ala Ala Met
145                 150                 155                 160

Ile Ser Val Asp Leu Ala Asp Gly Asp Glu Phe Leu Leu Ser Pro Ala
                165                 170                 175

Gly Gln Asn Pro Leu Leu Lys Lys Met Val Glu Glu Phe Met Pro Arg
            180                 185                 190

Phe Ala Pro Gly Ala Lys Val Leu Tyr Ile Gly Asp Trp Arg Gly Lys
        195                 200                 205
```

```
His Thr Arg Phe Glu Lys Arg Ile Phe Glu Glu Thr Leu Gly Leu Thr
    210                 215                 220

Phe Asp Pro His Gly Arg Met Pro Asp Leu Val Leu His Asp Lys Val
225                 230                 235                 240

Arg Lys Trp Leu Phe Leu Met Glu Ala Val Lys Ser Lys Gly Pro Phe
                245                 250                 255

Asp Glu Glu Arg His Arg Thr Leu Arg Glu Leu Phe Ala Thr Pro Val
            260                 265                 270

Ala Gly Leu Val Phe Val Asn Cys Phe Glu Asn Arg Glu Ala Met Arg
        275                 280                 285

Gln Trp Leu Pro Glu Leu Ala Trp Glu Thr Glu Ala Trp Val Ala Asp
    290                 295                 300

Asp Pro Asp His Leu Ile His Leu Asn Gly Ser Arg Phe Leu Gly Pro
305                 310                 315                 320

Tyr Glu Arg


<210> SEQ ID NO 15
<211> LENGTH: 602
<212> TYPE: PRT
<213> ORGANISM: Streptococcus sanguis

<400> SEQUENCE: 15

Met Thr Ile Ser Ile Asn Glu Tyr Ser Asp Leu Asn Asn Leu Ala Phe
1               5                   10                  15

Gly Leu Gly Gln Asp Val Ser Gln Asp Leu Lys Glu Leu Val Lys Val
            20                  25                  30

Ala Ser Ile Phe Met Pro Asp Ser Lys Ile His Lys Trp Leu Ile Asp
        35                  40                  45

Thr Arg Leu Glu Glu Val Val Thr Asp Leu Asn Leu Arg Tyr Glu Leu
    50                  55                  60

Lys Ser Val Ile Thr Asn Thr Pro Ile Ser Val Thr Trp Lys Gln Leu
65                  70                  75                  80

Thr Gly Thr Arg Thr Lys Arg Glu Ala Asn Ser Leu Val Gln Ala Val
                85                  90                  95

Phe Pro Gly Gln Cys Ser Arg Leu Ala Ile Val Asp Trp Ala Ala Lys
            100                 105                 110

Asn Tyr Val Ser Val Ala Val Ala Phe Gly Leu Leu Lys Phe His Arg
        115                 120                 125

Ala Asp Lys Thr Phe Thr Ile Ser Glu Ile Gly Ile Gln Ala Val Lys
    130                 135                 140

Leu Tyr Asp Ser Glu Glu Leu Ala Glu Leu Asp Lys Phe Leu Tyr Glu
145                 150                 155                 160

Arg Leu Leu Glu Tyr Pro Tyr Ala Ala Trp Leu Ile Arg Leu Leu Gly
                165                 170                 175

Asn Gln Pro Ser Lys Gln Phe Ser Lys Phe Asp Leu Gly Glu His Phe
            180                 185                 190

Gly Phe Ile Asp Glu Leu Gly Phe Glu Thr Ala Pro Ile Glu Ile Phe
        195                 200                 205

Leu Asn Gly Leu Ala Gln Ala Glu Ile Asp Gly Asp Lys Thr Ala Ala
    210                 215                 220

Gln Lys Ile Lys Ser Asn Phe Glu Ser Thr Ser Asp Lys Tyr Met Arg
225                 230                 235                 240

Trp Leu Ala Gly Val Leu Val Thr Ala Gly Leu Ala Thr Ser Thr Thr
                245                 250                 255
```

```
Lys Lys Val Thr His Thr Tyr Lys Asn Arg Lys Phe Glu Leu Thr Leu
            260                 265                 270

Gly Thr Val Tyr Gln Ile Thr Ala Lys Gly Leu Thr Ala Leu Lys Glu
        275                 280                 285

Val Asn Gly Lys Ser Arg Tyr Pro Arg Ser Arg Lys Arg Val Met Trp
    290                 295                 300

Glu Phe Leu Ala Thr Lys Asp Lys Glu Ala Ile Ala Lys Lys Thr Ser
305                 310                 315                 320

Arg Ser Leu Met Leu Lys His Leu Thr Glu Lys Lys Asn Pro Ile Gln
                325                 330                 335

Ala Glu Val Ile Ala Thr Leu Ile Asn Thr Asp Tyr Pro Thr Leu Glu
            340                 345                 350

Ile Thr Pro Glu Glu Val Ile Asp Asp Cys Ile Gly Leu Asn Arg Ile
        355                 360                 365

Gly Ile Glu Ile Leu Ile Asp Gly Asp Lys Leu Thr Leu Asn Asp Lys
    370                 375                 380

Leu Phe Asp Phe Glu Ile Pro Val Gln Lys Asp Val Val Leu Glu Lys
385                 390                 395                 400

Ser Asp Ile Glu Lys Phe Lys Asn Gln Leu Arg Thr Glu Leu Thr Asn
                405                 410                 415

Ile Asp His Ser Tyr Leu Lys Gly Ile Asp Ile Ala Ser Lys Lys Lys
            420                 425                 430

Thr Ser Asn Val Glu Asn Thr Glu Phe Glu Ala Ile Ser Thr Lys Ile
        435                 440                 445

Phe Thr Asp Glu Leu Gly Phe Ser Gly Lys His Leu Gly Gly Ser Asn
    450                 455                 460

Lys Pro Asp Gly Leu Leu Trp Asp Asp Asp Cys Ala Ile Ile Leu Asp
465                 470                 475                 480

Ser Lys Ala Tyr Ser Glu Gly Phe Pro Leu Thr Ala Ser His Thr Asp
                485                 490                 495

Ala Met Gly Arg Tyr Leu Arg Gln Phe Thr Glu Arg Lys Glu Glu Ile
            500                 505                 510

Lys Pro Thr Trp Trp Asp Ile Ala Pro Glu His Leu Asp Asn Thr Tyr
        515                 520                 525

Phe Ala Tyr Val Ser Gly Ser Phe Ser Gly Asn Tyr Lys Glu Gln Leu
    530                 535                 540

Gln Lys Phe Arg Gln Asp Thr Asn His Leu Gly Gly Ala Leu Glu Phe
545                 550                 555                 560

Val Lys Leu Leu Leu Leu Ala Asn Asn Tyr Lys Thr Gln Lys Met Ser
                565                 570                 575

Lys Lys Glu Val Lys Lys Ser Ile Leu Asp Tyr Asn Ile Ser Tyr Glu
            580                 585                 590

Glu Tyr Ala Pro Leu Leu Ala Glu Ile Glu
        595                 600


<210> SEQ ID NO 16
<211> LENGTH: 593
<212> TYPE: PRT
<213> ORGANISM: Clostridium leptum

<400> SEQUENCE: 16

Met Ile His Leu Ile Pro Thr Glu Ala Lys Arg Phe Arg Thr Phe Gly
1               5                   10                  15

Trp Val Gln Asp Pro Ser Asp Phe Arg Ser Leu Cys Asp Val Val Ala
            20                  25                  30
```

```
Ile Phe Asp Glu Thr Ser Leu Lys His Gln Glu Leu Ala Gly Gln Val
        35                  40                  45

Ile Pro Ala Leu Val Glu Glu Arg Asp Gly Arg Gln Arg Leu Leu Asp
    50                  55                  60

Ala Leu Asn Gln Arg Pro Leu Arg Ile Ser Tyr Thr Asp Leu Val Gly
65                  70                  75                  80

Thr Ser Phe Thr Pro Arg Ser Ala Ala Arg Cys Asn Gly Ile Val Gln
                85                  90                  95

Ala Ala Val Arg Gly Gln Val Arg Pro Phe Ile Gly Asp Trp Pro Ala
            100                 105                 110

Asp Asn Phe Val Arg Trp Ala His Ala Leu Gly Phe Leu Arg Tyr Gly
        115                 120                 125

Tyr Gln Gly Asp Ala Phe Glu Leu Thr Glu Thr Gly Lys Ala Leu Ala
    130                 135                 140

Gln Ala Arg Thr Gln Gly Glu Glu Leu Asn Ser Gln Glu Lys Glu Leu
145                 150                 155                 160

Leu Thr Ser Ala Val Leu Ala Tyr Pro Pro Ala Val Arg Ile Leu Ser
                165                 170                 175

Leu Leu Gly Glu Gly Glu Gly Ala His Leu Thr Lys Phe Glu Leu Gly
            180                 185                 190

Lys Gln Leu Gly Phe Val Gly Glu Asp Gly Phe Thr Ser Leu Pro Gln
        195                 200                 205

Thr Val Leu Val Arg Ser Leu Ala Ser Ser Lys Asp Ala Lys Glu Lys
    210                 215                 220

Asn Lys Met Lys Thr Asp Trp Asp Gly Ser Ser Asp Lys Tyr Ala Arg
225                 230                 235                 240

Met Ile Ala Lys Trp Leu Glu Lys Leu Gly Leu Val Lys Gln Glu Ala
                245                 250                 255

Lys Pro Val Thr Val Thr Leu Ala Gly Arg Lys Tyr Thr Glu Ser Ile
            260                 265                 270

Gly Gln Ser Tyr Val Ile Thr Gly Leu Gly Ile Thr Ala Leu Asn Arg
        275                 280                 285

Thr Leu Gly Lys Ser Arg His Lys Arg Ile Pro Lys Asn Val Ser Phe
    290                 295                 300

Glu Met Met Ala Thr Lys Gly Asp Asp Arg Glu Tyr Leu Arg Thr Arg
305                 310                 315                 320

Arg Thr Cys Val Leu Lys Ala Val Ser Glu Gly Lys Gly Arg Val Ser
                325                 330                 335

Tyr Thr Glu Ile Gln Lys Tyr Leu Glu Ala Leu Gly Leu Gln Glu Asp
            340                 345                 350

Glu Ala Thr Ile Arg Asp Asp Val Gln Gly Leu Ile His Ile Gly Leu
        355                 360                 365

Asn Ile Ala Ala Gly Glu Arg Glu Cys Val Trp Lys Asp Glu Ile Asn
    370                 375                 380

Asp Leu Ile Leu Pro Val Pro Lys Lys Leu Ala Lys Ser Ser Gln Ser
385                 390                 395                 400

Glu Thr Lys Glu Lys Leu Arg Glu Lys Leu Arg Asn Leu Pro His Glu
                405                 410                 415

Tyr Leu Ser Leu Val Asp Leu Ala Tyr Asp Ser Lys Gln Asn Arg Leu
            420                 425                 430

Phe Glu Met Lys Val Ile Glu Leu Leu Thr Glu Glu Cys Gly Phe Gln
        435                 440                 445
```

```
Gly Leu His Leu Gly Gly Ser Arg Arg Pro Asp Gly Val Leu Tyr Thr
    450                 455                 460

Ala Gly Leu Thr Asp Asn Tyr Gly Ile Ile Leu Asp Thr Lys Ala Tyr
465                 470                 475                 480

Ser Ser Gly Tyr Ser Leu Pro Ile Ala Gln Ala Asp Glu Met Glu Arg
                485                 490                 495

Tyr Val Arg Glu Asn Gln Thr Arg Asp Glu Leu Val Asn Pro Asn Gln
            500                 505                 510

Trp Trp Glu Asn Phe Glu Asn Gly Leu Gly Thr Phe Tyr Phe Leu Phe
        515                 520                 525

Val Ala Gly His Phe Asn Gly Asn Val Gln Ala Gln Leu Glu Arg Ile
    530                 535                 540

Ser Arg Asn Thr Gly Val Leu Gly Ala Ala Ala Ser Ile Ser Gln Leu
545                 550                 555                 560

Leu Leu Leu Ala Asp Ala Ile Arg Gly Gly Arg Met Asp Arg Glu Arg
                565                 570                 575

Leu Arg His Leu Met Phe Gln Asn Glu Glu Phe Leu Leu Glu Gln Glu
            580                 585                 590

Leu


<210> SEQ ID NO 17
<211> LENGTH: 587
<212> TYPE: PRT
<213> ORGANISM: Clostridium spec. 7_2_43 FAA

<400> SEQUENCE: 17

Met Ile Asn Ile Ile Asp Val Asn Asn Lys Thr Ile Arg Thr Phe Gly
1               5                   10                  15

Trp Val Gln Asn Pro Ser Asn Phe Glu Ser Leu Lys Lys Val Val Ala
            20                  25                  30

Ile Phe Asp Asn Thr Ser Lys Thr Tyr Asn Glu Leu Lys Asp Lys Lys
        35                  40                  45

Ile Lys Lys Leu Val Asp Glu Arg Asp Gly Gln Lys Glu Leu Leu Asn
    50                  55                  60

Ala Leu Asn Ala Asn Pro Leu Lys Ile Lys Tyr Cys Asn Leu Val Gly
65                  70                  75                  80

Thr Ser Phe Thr Pro Arg Ser Ser Ala Arg Cys Asn Gly Ile Val Gln
                85                  90                  95

Ala Thr Val Lys Gly Gln Arg Lys Glu Phe Ile Asp Asp Trp Ser Ser
            100                 105                 110

Asp Asn Phe Val Arg Trp Ala His Ala Leu Gly Phe Ile Lys Tyr Asn
        115                 120                 125

Tyr Asp Thr Asp Thr Phe Glu Ile Thr Asp Val Gly Arg Lys Tyr Val
    130                 135                 140

Gln Ser Glu Asp Asp Ser Asn Glu Glu Ser Thr Ile Leu Glu Glu Ala
145                 150                 155                 160

Met Leu Ser Tyr Pro Pro Val Ala Arg Val Leu Thr Leu Leu Ser Asn
                165                 170                 175

Gly Glu His Leu Thr Lys Tyr Glu Ile Gly Lys Lys Leu Gly Phe Val
            180                 185                 190

Gly Glu Ala Gly Phe Thr Ser Leu Pro Leu Asn Val Leu Ile Met Thr
        195                 200                 205

Leu Ala Thr Thr Asp Glu Pro Lys Glu Lys Asn Lys Ile Lys Thr Asp
    210                 215                 220
```

```
Trp Asp Gly Ser Ser Asp Lys Tyr Ala Arg Met Ile Ser Gly Trp Leu
225                 230                 235                 240

Val Lys Leu Gly Leu Leu Val Gln Arg Pro Lys Leu Val Thr Val Asp
                245                 250                 255

Phe Gly Gly Glu Leu Tyr Ser Glu Thr Ile Gly His Ala Tyr Met Ile
            260                 265                 270

Thr Asp Arg Gly Leu Lys Ala Val Arg Arg Leu Leu Gly Ile Asn Lys
        275                 280                 285

Val Ala Arg Val Ser Lys Asn Val Phe Trp Glu Met Leu Ala Thr Lys
    290                 295                 300

Gly Ile Asp Lys Asn Tyr Ile Arg Thr Arg Arg Ala Tyr Ile Leu Lys
305                 310                 315                 320

Ile Leu Ile Glu Ser Asn Lys Val Leu Thr Leu Glu Asp Ile Lys Gly
                325                 330                 335

Lys Leu Lys Leu Ala Ser Ile Asn Glu Ser Ile Asn Thr Ile Lys Asp
            340                 345                 350

Asp Ile Asn Gly Leu Ile Asn Thr Gly Ile Asn Ile Lys Ser Glu Thr
        355                 360                 365

Thr Gly Tyr Lys Ile Tyr Asp Ser Ile Asn Asp Phe Ile Ile Pro Lys
    370                 375                 380

Thr Gly Asp Thr Glu Gly Ile Lys Ser Asn Ile Ser Leu Leu Lys Asp
385                 390                 395                 400

Glu Leu Arg Gly Gln Ile Ser His Ile Ser His Glu Tyr Leu Ser Leu
                405                 410                 415

Ile Asp Leu Ala Phe Asp Ser Lys Gln Asn Arg Leu Phe Glu Met Lys
            420                 425                 430

Val Leu Glu Leu Leu Val Asn Glu Tyr Gly Phe Lys Gly Arg His Leu
        435                 440                 445

Gly Gly Ser Arg Lys Pro Asp Gly Ile Val Tyr Ser Thr Thr Leu Glu
    450                 455                 460

Asp Asn Phe Gly Ile Ile Val Asp Thr Lys Ala Tyr Ser Glu Gly Tyr
465                 470                 475                 480

Ser Leu Pro Ile Ser Gln Ala Asp Glu Met Glu Arg Tyr Val Arg Glu
                485                 490                 495

Asn Ser Asn Arg Asp Glu Glu Val Asn Pro Asn Lys Trp Trp Glu Asn
            500                 505                 510

Phe Ser Glu Glu Val Lys Lys Tyr Tyr Phe Val Phe Ile Ser Gly Ser
        515                 520                 525

Phe Lys Gly Lys Phe Glu Glu Gln Leu Arg Arg Leu Ser Met Thr Thr
    530                 535                 540

Gly Val Asn Gly Ser Ala Val Asn Val Val Asn Leu Leu Leu Gly Ala
545                 550                 555                 560

Glu Lys Ile Arg Ser Gly Glu Met Thr Ile Glu Glu Leu Glu Arg Ala
                565                 570                 575

Met Phe Asn Asn Ser Glu Phe Ile Leu Lys Tyr
            580                 585
```

<210> SEQ ID NO 18
<211> LENGTH: 589
<212> TYPE: PRT
<213> ORGANISM: Peptoniphilus duerdenii

<400> SEQUENCE: 18

```
Met Ala Glu Arg Thr Leu Gly Trp Ile Gln Asn Pro Ser Ser Phe Glu
1               5                   10                  15
```

-continued

```
Asn Leu Lys Asn Val Val Ser Val Phe Asp Lys Asn Ser Asp Ile Tyr
            20                  25                  30

Lys Glu Ile Leu Asn Thr Lys Leu Pro Lys Leu Val Lys Asp Leu Asp
        35                  40                  45

Leu Gln Asn Lys Leu Ile Ser Glu Leu Glu Lys Asp Pro Leu Glu Met
    50                  55                  60

Asp Tyr Val Leu Leu Lys Gly His Gly Ile Lys Ser Gly Gln Lys Arg
65                  70                  75                  80

Ala Asp Ala Glu Cys Ser Gly Ile Val Gln Ala Ala Ile Thr Thr Gln
                85                  90                  95

Gly Gly Arg Ala Tyr Thr Asp Asp Trp Thr Ala Asp Gly Phe Leu Arg
            100                 105                 110

Trp Gly Ile Ser Ile Gly Leu Leu Asp Tyr Asp Thr Glu Lys Asp Thr
        115                 120                 125

Val Ser Ile Thr Lys Leu Gly Glu Lys Phe Val Lys Ser Asn Ser Glu
    130                 135                 140

Asp Ser Asp Lys Glu Ile Leu Ile Ser Ala Phe Leu Ser Tyr Pro Pro
145                 150                 155                 160

Ala Val Arg Ile Leu Thr Leu Leu Glu Asn Gly Asp His Leu Thr Lys
                165                 170                 175

Phe Glu Leu Gly Lys Gln Leu Gly Gly Leu Gly Glu Ala Gly Phe Thr
            180                 185                 190

Ser Ile Pro Gln Asp Leu Tyr Ile Gln Ala Ile Glu Leu Ala Ala Asp
        195                 200                 205

Lys Asp Lys Ala Ser Ile Arg Ser Asn Thr Glu Gly Ser Ala Asp Lys
    210                 215                 220

Tyr Ala Arg Met Ile Ser Gly Trp Leu Ser Lys Val Gly Leu Ile Gln
225                 230                 235                 240

Arg Ile Gly Lys Glu Val Ser Thr Lys Ile Gly Asp Val Glu Tyr Lys
                245                 250                 255

Val Asn Ile Gly His Ser Phe Arg Ile Thr Leu Asn Gly Ile Lys Glu
            260                 265                 270

Leu Lys Arg Ala Met Gly Leu Ser Ser Tyr Pro Lys Thr Asp Lys Ile
        275                 280                 285

Val Tyr Trp Gln Met Leu Ala Thr Lys Gly Lys Asp Arg Asp Tyr Ile
    290                 295                 300

Arg Asn Arg Arg Gly Tyr Ile Ile Lys Ala Ile Asn Asn Arg Glu Arg
305                 310                 315                 320

Asn Leu Glu Asp Ile Lys Ala Tyr Leu Leu Glu Asn Asn Ile Asp Glu
                325                 330                 335

Ser Ile Thr Thr Ile Glu Asp Glu Leu Lys Val Ile Glu Ala Met Gly
            340                 345                 350

Leu Ser Phe Lys His Ser Arg Asn Gly Tyr Val Ile Asp Asp Asn Ile
        355                 360                 365

Ile Lys Leu Glu Ile Pro Arg Thr Lys Ile Ser Lys Thr Asn Val Leu
    370                 375                 380

Glu Leu Lys Asp Lys Val Arg Asp Lys Leu Lys Tyr Val Asp His Arg
385                 390                 395                 400

Tyr Leu Ala Leu Ile Asp Leu Ala Tyr Asp Gly Thr Ala Asn Arg Asp
                405                 410                 415

Phe Glu Ile Gln Thr Ile Asp Leu Leu Ile Asn Glu Leu Lys Phe Lys
            420                 425                 430
```

```
Gly Val Arg Leu Gly Glu Ser Arg Lys Pro Asp Gly Ile Ile Ser Tyr
        435                 440                 445

Asn Ile Asn Gly Val Ile Ile Asp Asn Lys Ala Tyr Ser Thr Gly Tyr
    450                 455                 460

Asn Leu Pro Ile Asn Gln Ala Asp Glu Met Ile Arg Tyr Ile Glu Glu
465                 470                 475                 480

Asn Gln Thr Arg Asp Glu Lys Ile Asn Ser Asn Lys Trp Trp Glu Ser
                485                 490                 495

Phe Asp Asp Lys Val Lys Asp Phe Asn Tyr Leu Phe Val Ser Ser Phe
            500                 505                 510

Phe Lys Gly Asn Phe Lys Asn Asn Leu Lys His Ile Ala Asn Arg Thr
        515                 520                 525

Gly Val Ser Gly Gly Ala Ile Asn Val Glu Asn Leu Leu Tyr Phe Ala
    530                 535                 540

Glu Glu Leu Lys Ala Gly Arg Leu Ser Tyr Val Asp Ser Phe Lys Met
545                 550                 555                 560

Tyr Asp Asn Asp Glu Ile Tyr Val Gly Asp Phe Ser Asp Tyr Ser Tyr
                565                 570                 575

Val Lys Phe Ala Ala Glu Glu Glu Gly Glu Tyr Leu Thr
            580                 585


<210> SEQ ID NO 19
<211> LENGTH: 279
<212> TYPE: PRT
<213> ORGANISM: Acinetobacter lwoffii

<400> SEQUENCE: 19

Lys Glu Thr Asn Ile Leu Leu Val Glu Gln Leu Glu Glu Thr Leu Asn
1               5                   10                  15

Arg Asn Arg Ile Leu Phe Glu Lys Asn Ser Ser Ile Ala Gln Ala Pro
            20                  25                  30

Ile Gly Glu Ile Lys Asn Tyr Arg Tyr His Leu Glu Glu Leu Leu Phe
        35                  40                  45

Glu Asn Asn Glu Lys Lys Phe Ala Glu Asn Gln Lys Asn Glu Trp Asp
    50                  55                  60

Glu Ile Leu Ala Tyr Met Asp Leu Leu Ile Ser Pro Lys Pro Ile Ser
65                  70                  75                  80

Ile Glu Ile Ala Asp Lys Glu Ile Ser Ile Pro Ser Gly Glu Arg Pro
                85                  90                  95

Ala Tyr Phe Glu Trp Val Leu Trp Arg Ala Phe Leu Ala Leu Asn His
            100                 105                 110

Leu Ile Ile Glu Pro Gln Gln Cys Arg Arg Phe Lys Val Asp Gln Asp
        115                 120                 125

Phe Lys Pro Ile His Asn Ala Pro Gly Gly Gly Ala Asp Val Ile Phe
    130                 135                 140

Glu Tyr Glu Asn Phe Lys Ile Leu Gly Glu Val Thr Leu Thr Ser Asn
145                 150                 155                 160

Ser Arg Gln Glu Ala Ala Glu Gly Glu Pro Val Arg Arg His Ile Ala
                165                 170                 175

Val Glu Thr Val Asn Thr Pro Asp Lys Asp Val Tyr Gly Leu Phe Leu
            180                 185                 190

Ala Leu Thr Ile Asp Thr Asn Thr Ala Glu Thr Phe Arg His Gly Ala
        195                 200                 205

Trp Tyr His Gln Glu Glu Leu Met Asp Val Lys Ile Leu Pro Leu Thr
    210                 215                 220
```

```
Leu Glu Ser Phe Lys Lys Tyr Leu Glu Ser Leu Arg Lys Lys Asn Gln
225                 230                 235                 240

Val Glu Thr Gly Ile Phe Asp Leu Lys Lys Met Met Asp Glu Ser Leu
                245                 250                 255

Lys Leu Arg Glu Thr Leu Thr Ala Pro Gln Trp Lys Asn Glu Ile Thr
            260                 265                 270

Asn Lys Phe Ala Arg Pro Ile
        275


<210> SEQ ID NO 20
<211> LENGTH: 201
<212> TYPE: PRT
<213> ORGANISM: Clostridium leptum

<400> SEQUENCE: 20

Lys Leu Ala Lys Ser Ser Gln Ser Glu Thr Lys Glu Lys Leu Arg Glu
1               5                   10                  15

Lys Leu Arg Asn Leu Pro His Glu Tyr Leu Ser Leu Val Asp Leu Ala
            20                  25                  30

Tyr Asp Ser Lys Gln Asn Arg Leu Phe Glu Met Lys Val Ile Glu Leu
        35                  40                  45

Leu Thr Glu Glu Cys Gly Phe Gln Gly Leu His Leu Gly Gly Ser Arg
    50                  55                  60

Arg Pro Asp Gly Val Leu Tyr Thr Ala Gly Leu Thr Asp Asn Tyr Gly
65                  70                  75                  80

Ile Ile Leu Asp Thr Lys Ala Tyr Ser Ser Gly Tyr Ser Leu Pro Ile
                85                  90                  95

Ala Gln Ala Asp Glu Met Glu Arg Tyr Val Arg Glu Asn Gln Thr Arg
            100                 105                 110

Asp Glu Leu Val Asn Pro Asn Gln Trp Trp Glu Asn Phe Glu Asn Gly
        115                 120                 125

Leu Gly Thr Phe Tyr Phe Leu Phe Val Ala Gly His Phe Asn Gly Asn
    130                 135                 140

Val Gln Ala Gln Leu Glu Arg Ile Ser Arg Asn Thr Gly Val Leu Gly
145                 150                 155                 160

Ala Ala Ala Ser Ile Ser Gln Leu Leu Leu Leu Ala Asp Ala Ile Arg
                165                 170                 175

Gly Gly Arg Met Asp Arg Glu Arg Leu Arg His Leu Met Phe Gln Asn
            180                 185                 190

Glu Glu Phe Leu Leu Glu Gln Glu Leu
        195                 200


<210> SEQ ID NO 21
<211> LENGTH: 250
<212> TYPE: PRT
<213> ORGANISM: Micrococcus lylae

<400> SEQUENCE: 21

Ile Asn Ser Lys Ile Lys Gln Leu Asp Asp Ser Ile Asn Val Glu Ser
1               5                   10                  15

Leu Lys Ile Asp Asp Ala Lys Asp Leu Leu Asn Asp Leu Glu Ile Gln
            20                  25                  30

Arg Lys Ala Lys Thr Ile Glu Asp Thr Val Asn His Leu Lys Leu Arg
        35                  40                  45

Ser Asp Ile Glu Asp Ile Leu Asp Val Phe Ala Lys Ile Lys Lys Arg
    50                  55                  60
```

```
Asp Val Pro Asp Val Pro Leu Phe Leu Glu Trp Asn Ile Trp Arg Ala
65                  70                  75                  80

Phe Ala Ala Leu Asn His Thr Gln Ala Ile Glu Gly Asn Phe Ile Val
                85                  90                  95

Asp Leu Asp Gly Met Pro Leu Asn Thr Ala Pro Gly Lys Lys Pro Asp
            100                 105                 110

Ile Glu Ile Asn Tyr Gly Ser Phe Ser Cys Ile Val Glu Val Thr Met
        115                 120                 125

Ser Ser Gly Glu Thr Gln Phe Asn Met Glu Gly Ser Ser Val Pro Arg
    130                 135                 140

His Tyr Gly Asp Leu Val Arg Lys Val Asp His Asp Ala Tyr Cys Ile
145                 150                 155                 160

Phe Ile Ala Pro Lys Val Ala Pro Gly Thr Lys Ala His Phe Phe Asn
                165                 170                 175

Leu Asn Arg Leu Ser Thr Lys His Tyr Gly Gly Lys Thr Lys Ile Ile
            180                 185                 190

Pro Met Ser Leu Asp Asp Phe Ile Cys Phe Leu Gln Val Gly Ile Thr
        195                 200                 205

His Asn Phe Gln Asp Ile Asn Lys Leu Lys Asn Trp Leu Asp Asn Leu
    210                 215                 220

Ile Asn Phe Asn Leu Glu Ser Glu Asp Glu Glu Ile Trp Phe Glu Glu
225                 230                 235                 240

Ile Ile Ser Lys Ile Ser Thr Trp Ala Ile
                245                 250


<210> SEQ ID NO 22
<211> LENGTH: 213
<212> TYPE: PRT
<213> ORGANISM: Peptoniphilus duerdenii

<400> SEQUENCE: 22

Lys Ile Ser Lys Thr Asn Val Leu Glu Leu Lys Asp Lys Val Arg Asp
1               5                   10                  15

Lys Leu Lys Tyr Val Asp His Arg Tyr Leu Ala Leu Ile Asp Leu Ala
            20                  25                  30

Tyr Asp Gly Thr Ala Asn Arg Asp Phe Glu Ile Gln Thr Ile Asp Leu
        35                  40                  45

Leu Ile Asn Glu Leu Lys Phe Lys Gly Val Arg Leu Gly Glu Ser Arg
    50                  55                  60

Lys Pro Asp Gly Ile Ile Ser Tyr Asn Ile Asn Gly Val Ile Ile Asp
65                  70                  75                  80

Asn Lys Ala Tyr Ser Thr Gly Tyr Asn Leu Pro Ile Asn Gln Ala Asp
                85                  90                  95

Glu Met Ile Arg Tyr Ile Glu Glu Asn Gln Thr Arg Asp Glu Lys Ile
            100                 105                 110

Asn Ser Asn Lys Trp Trp Glu Ser Phe Asp Asp Lys Val Lys Asp Phe
        115                 120                 125

Asn Tyr Leu Phe Val Ser Ser Phe Phe Lys Gly Asn Phe Lys Asn Asn
    130                 135                 140

Leu Lys His Ile Ala Asn Arg Thr Gly Val Ser Gly Gly Ala Ile Asn
145                 150                 155                 160

Val Glu Asn Leu Leu Tyr Phe Ala Glu Glu Leu Lys Ala Gly Arg Leu
                165                 170                 175

Ser Tyr Val Asp Ser Phe Lys Met Tyr Asp Asn Asp Glu Ile Tyr Val
```

```
            180                 185                 190

Gly Asp Phe Ser Asp Tyr Ser Tyr Val Lys Phe Ala Ala Glu Glu Glu
        195                 200                 205

Gly Glu Tyr Leu Thr
    210


<210> SEQ ID NO 23
<211> LENGTH: 163
<212> TYPE: PRT
<213> ORGANISM: Streptomyces spec. Bf-61

<400> SEQUENCE: 23

Ile Ser Val Asp Leu Pro Gly Gly Glu Glu Phe Leu Leu Ser Pro Ala
1               5                   10                  15

Gly Gln Asn Pro Leu Leu Lys Lys Met Val Glu Glu Phe Val Pro Arg
            20                  25                  30

Phe Ala Pro Arg Ser Thr Val Leu Tyr Leu Gly Asp Thr Arg Gly Lys
        35                  40                  45

His Ser Leu Phe Glu Arg Glu Ile Phe Glu Glu Val Leu Gly Leu Thr
    50                  55                  60

Phe Asp Pro His Gly Arg Met Pro Asp Leu Ile Leu His Asp Glu Val
65                  70                  75                  80

Arg Gly Trp Leu Phe Leu Met Glu Ala Val Lys Ser Lys Gly Pro Phe
                85                  90                  95

Asp Glu Glu Arg His Arg Ser Leu Gln Glu Leu Phe Val Thr Pro Ser
            100                 105                 110

Ala Gly Leu Ile Phe Val Asn Cys Phe Glu Asn Arg Glu Ser Met Arg
        115                 120                 125

Gln Trp Leu Pro Glu Leu Ala Trp Glu Thr Glu Ala Trp Val Ala Glu
    130                 135                 140

Asp Pro Asp His Leu Ile His Leu Asn Gly Ser Arg Phe Leu Gly Pro
145                 150                 155                 160

Tyr Glu Arg


<210> SEQ ID NO 24
<211> LENGTH: 163
<212> TYPE: PRT
<213> ORGANISM: Streptomyces diastaticus

<400> SEQUENCE: 24

Ile Ser Val Asp Leu Ala Asp Gly Asp Glu Phe Leu Leu Ser Pro Ala
1               5                   10                  15

Gly Gln Asn Pro Leu Leu Lys Lys Met Val Glu Glu Phe Met Pro Arg
            20                  25                  30

Phe Ala Pro Gly Ala Lys Val Leu Tyr Ile Gly Asp Trp Arg Gly Lys
        35                  40                  45

His Thr Arg Phe Glu Lys Arg Ile Phe Glu Glu Thr Leu Gly Leu Thr
    50                  55                  60

Phe Asp Pro His Gly Arg Met Pro Asp Leu Val Leu His Asp Lys Val
65                  70                  75                  80

Arg Lys Trp Leu Phe Leu Met Glu Ala Val Lys Ser Lys Gly Pro Phe
                85                  90                  95

Asp Glu Glu Arg His Arg Thr Leu Arg Glu Leu Phe Ala Thr Pro Val
            100                 105                 110

Ala Gly Leu Val Phe Val Asn Cys Phe Glu Asn Arg Glu Ala Met Arg
        115                 120                 125
```

```
Gln Trp Leu Pro Glu Leu Ala Trp Glu Thr Glu Ala Trp Val Ala Asp
    130                 135                 140

Asp Pro Asp His Leu Ile His Leu Asn Gly Ser Arg Phe Leu Gly Pro
145                 150                 155                 160

Tyr Glu Arg


<210> SEQ ID NO 25
<211> LENGTH: 208
<212> TYPE: PRT
<213> ORGANISM: Streptococcus sanguis

<400> SEQUENCE: 25

Asp Val Val Leu Glu Lys Ser Asp Ile Glu Lys Phe Lys Asn Gln Leu
1               5                   10                  15

Arg Thr Glu Leu Thr Asn Ile Asp His Ser Tyr Leu Lys Gly Ile Asp
            20                  25                  30

Ile Ala Ser Lys Lys Lys Thr Ser Asn Val Glu Asn Thr Glu Phe Glu
        35                  40                  45

Ala Ile Ser Thr Lys Ile Phe Thr Asp Glu Leu Gly Phe Ser Gly Lys
    50                  55                  60

His Leu Gly Gly Ser Asn Lys Pro Asp Gly Leu Leu Trp Asp Asp Asp
65                  70                  75                  80

Cys Ala Ile Ile Leu Asp Ser Lys Ala Tyr Ser Glu Gly Phe Pro Leu
                85                  90                  95

Thr Ala Ser His Thr Asp Ala Met Gly Arg Tyr Leu Arg Gln Phe Thr
            100                 105                 110

Glu Arg Lys Glu Glu Ile Lys Pro Thr Trp Trp Asp Ile Ala Pro Glu
        115                 120                 125

His Leu Asp Asn Thr Tyr Phe Ala Tyr Val Ser Gly Ser Phe Ser Gly
    130                 135                 140

Asn Tyr Lys Glu Gln Leu Gln Lys Phe Arg Gln Asp Thr Asn His Leu
145                 150                 155                 160

Gly Gly Ala Leu Glu Phe Val Lys Leu Leu Leu Leu Ala Asn Asn Tyr
                165                 170                 175

Lys Thr Gln Lys Met Ser Lys Lys Glu Val Lys Lys Ser Ile Leu Asp
            180                 185                 190

Tyr Asn Ile Ser Tyr Glu Glu Tyr Ala Pro Leu Leu Ala Glu Ile Glu
        195                 200                 205


<210> SEQ ID NO 26
<211> LENGTH: 196
<212> TYPE: PRT
<213> ORGANISM: Flavobacterium okeanokoites

<400> SEQUENCE: 26

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80
```

```
Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195


<210> SEQ ID NO 27
<211> LENGTH: 7903
<212> TYPE: DNA
<213> ORGANISM: Artificial sequence
<220> FEATURE:
<223> OTHER INFORMATION: pCAG-ArtTal1-AlwI

<400> SEQUENCE: 27

gacattgatt attgactagt tattaatagt aatcaattac ggggtcatta gttcatagcc      60

catatatgga gttccgcgtt acataactta cggtaaatgg cccgcctggc tgaccgccca     120

acgacccccg cccattgacg tcaataatga cgtatgttcc catagtaacg ccaataggga     180

ctttccattg acgtcaatgg gtggagtatt tacggtaaac tgcccacttg gcagtacatc     240

aagtgtatca tatgccaagt acgcccccta ttgacgtcaa tgacggtaaa tggcccgcct     300

ggcattatgc ccagtacatg accttatggg actttcctac ttggcagtac atctacgtat     360

tagtcatcgc tattaccatg gtcgaggtga gccccacgtt ctgcttcact ctccccatct     420

ccccccccctc cccaccccca attttgtatt tatttatttt ttaattattt tgtgcagcga     480

tgggggcggg gggggggggg gggcgcgcgc caggcggggc ggggcggggc gaggggcggg     540

gcggggcgag gcggagaggt gcggcggcag ccaatcagag cggcgcgctc cgaaagtttc     600

cttttatggc gaggcggcgg cggcggcggc cctataaaaa gcgaagcgcg cggcgggcgg     660

gagtcgctgc gcgctgcctt cgccccgtgc cccgctccgc cgccgcctcg cgccgcccgc     720

cccggctctg actgaccgcg ttactcccac aggtgagcgg gcgggacggc ccttctcctc     780

cgggctgtaa ttagcgcttg gtttaatgac ggcttgtttc ttttctgtgg ctgcgtgaaa     840

gccttgaggg gctccgggag ggccctttgt gcggggggga gcggctcggg gggtgcgtgc     900

gtgtgtgtgt gcgtggggag cgccgcgtgc ggctccgcgc tgcccggcgg ctgtgagcgc     960

tgcgggcgcg gcgcggggct ttgtgcgctc cgcagtgtgc gcgaggggag cgcggccggg    1020

ggcggtgccc cgcggtgcgg ggggggctgc gaggggaaca aaggctgcgt gcggggtgtg    1080

tgcgtggggg ggtgagcagg gggtgtgggc gcgtcggtcg ggctgcaacc ccccctgcac    1140

ccccctcccc gagttgctga gcacggcccg gcttcgggtg cggggctccg tacggggcgt    1200

ggcgcggggc tcgccgtgcc gggcgggggg tggcggcagg tgggggtgcc gggcggggcg    1260

gggccgcctc gggccgggga gggctcgggg gaggggcgcg gcggcccccg gagcgccggc    1320

ggctgtcgag gcgcggcgag ccgcagccat tgccttttat ggtaatcgtg cgagagggcg    1380
```

```
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
```

-continued

```
acaaagagac taatatcctc ctcgtcgagc agctggaaga gaccctcaat cgcaatcgca   3780
ttctgtttga aaagaactcc tcaatcgcac aggccccaat tggcgagatc aagaactacc   3840
ggtatcacct ggaggaactg ctcttcgaga acaatgaaaa gaaatttgca gagaaccaga   3900
aaaatgagtg ggacgaaatt ctggcctaca tggatctgct catctcaccc aagcctatca   3960
gcattgagat cgctgacaaa gaaatttcta tcccaagtgg ggagcgaccc gcatatttcg   4020
aatgggtgct gtggagggca tttctggccc tcaaccacct gatcattgag ccccagcagt   4080
gcaggagatt caaggtcgac caggacttca agcctatcca taatgctcca ggcggagggg   4140
cagatgtgat tttcgagtac gaaaacttta agatcctggg cgaggtcacc ctcacaagca   4200
attcccgaca ggaagcagct gagggagaac ccgtgcggcg ccatattgcc gtggagacag   4260
tcaacactcc tgacaaggat gtctatggac tgttcctcgc tctgaccatc gacactaata   4320
ccgccgagac atttcgacac ggggcttggt atcaccagga ggaactgatg gatgtgaaga   4380
ttctcccccct gactctcgag tccttcaaga agtatctgga atctctcaga aagaaaaatc   4440
aggtggagac aggaatcttt gacctgaaga aaatgatgga tgaaagcctg aagctccggg   4500
aaaccctgac cgcaccccag tggaaaaatg aaatcacaaa caaattcgcc agaccaatct   4560
gaacgcgtaa atgattgcag atccactagt tctagaattc cagctgagcg ccggtcgcta   4620
ccattaccag ttggtctggt gtcaaaaata ataataaccg ggcagggggg atctgcatgg   4680
atctttgtga aggaacctta cttctgtggt gtgacataat tggacaaact acctacagag   4740
atttaaagct ctaaggtaaa tataaaattt ttaagtgtat aatgtgttaa actactgatt   4800
ctaattgttt gtgtatttta gattccaacc tatggaactg atgaatggga gcagtggtgg   4860
aatgccagat ccagacatga taagatacat tgatgagttt ggacaaacca caactagaat   4920
gcagtgaaaa aaatgcttta tttgtgaaat ttgtgatgct attgctttat ttgtaaccat   4980
tataagctgc aataaacaag ttaacaacaa caattgcatt cattttatgt ttcaggttca   5040
gggggaggtg tgggaggttt tttaaagcaa gtaaaacctc tacaaatgtg gtatggctga   5100
ttatgatctg cggccgccac tggccgtcgt tttacaacgt cgtgactggg aaaaccctgg   5160
cgttacccaa cttaatcgcc ttgcagcaca tccccctttc gccagctggc gtaatagcga   5220
agaggcccgc accgatcgcc cttcccaaca gttgcgcagc ctgaatggcg aatggaacgc   5280
gccctgtagc ggcgcattaa gcgcggcggg tgtggtggtt acgcgcagcg tgaccgctac   5340
acttgccagc gccctagcgc ccgctccttt cgctttcttc ccttcctttc tcgccacgtt   5400
cgccggcttt ccccgtcaag ctctaaatcg ggggctccct ttagggttcc gatttagtgc   5460
tttacggcac ctcgacccca aaaaacttga ttagggtgat ggttcacgta gtgggccatc   5520
gccctgatag acggtttttc gccctttgac gttggagtcc acgttcttta atagtggact   5580
cttgttccaa actggaacaa cactcaaccc tatctcggtc tattcttttg atttataagg   5640
gattttgccg atttcggcct attggttaaa aaatgagctg atttaacaaa aatttaacgc   5700
gaattttaac aaaatattaa cgcttacaat ttaggtggca cttttcgggg aaatgtgcgc   5760
ggaaccccta tttgtttatt tttctaaata cattcaaata tgtatccgct catgagacaa   5820
taaccctgat aaatgcttca ataatattga aaaaggaaga gtatgagtat tcaacatttc   5880
cgtgtcgccc ttattccctt ttttgcggca ttttgccttc ctgtttttgc tcacccagaa   5940
acgctggtga aagtaaaaga tgctgaagat cagttgggtg cacgagtggg ttacatcgaa   6000
ctggatctca acagcggtaa gatccttgag agttttcgcc ccgaagaacg ttttccaatg   6060
atgagcactt ttaaagttct gctatgtggc gcggtattat cccgtattga cgccgggcaa   6120
```

```
gagcaactcg gtcgccgcat acactattct cagaatgact tggttgagta ctcaccagtc   6180

acagaaaagc atcttacgga tggcatgaca gtaagagaat tatgcagtgc tgccataacc   6240

atgagtgata acactgcggc caacttactt ctgacaacga tcggaggacc gaaggagcta   6300

accgcttttt tgcacaacat gggggatcat gtaactcgcc ttgatcgttg ggaaccggag   6360

ctgaatgaag ccataccaaa cgacgagcgt gacaccacga tgcctgtagc aatggcaaca   6420

acgttgcgca aactattaac tggcgaacta cttactctag cttcccggca acaattaata   6480

gactggatgg aggcggataa agttgcagga ccacttctgc gctcggccct tccggctggc   6540

tggtttattg ctgataaatc tggagccggt gagcgtgggt ctcgcggtat cattgcagca   6600

ctggggccag atggtaagcc ctcccgtatc gtagttatct acacgacggg gagtcaggca   6660

actatggatg aacgaaatag acagatcgct gagataggtg cctcactgat taagcattgg   6720

taactgtcag accaagttta ctcatatata ctttagattg atttaaaact tcatttttaa   6780

tttaaaagga tctaggtgaa gatccttttt gataatctca tgaccaaaat cccttaacgt   6840

gagttttcgt tccactgagc gtcagacccc gtagaaaaga tcaaaggatc ttcttgagat   6900

cctttttttc tgcgcgtaat ctgctgcttg caaacaaaaa aaccaccgct accagcggtg   6960

gtttgtttgc cggatcaaga gctaccaact ctttttccga aggtaactgg cttcagcaga   7020

gcgcagatac caaatactgt ccttctagtg tagccgtagt taggccacca cttcaagaac   7080

tctgtagcac cgcctacata cctcgctctg ctaatcctgt taccagtggc tgctgccagt   7140

ggcgataagt cgtgtcttac cgggttggac tcaagacgat agttaccgga taaggcgcag   7200

cggtcgggct gaacgggggg ttcgtgcaca cagcccagct tggagcgaac gacctacacc   7260

gaactgagat acctacagcg tgagctatga gaaagcgcca cgcttcccga agggagaaag   7320

gcggacaggt atccggtaag cggcagggtc ggaacaggag agcgcacgag ggagcttcca   7380

gggggaaacg cctggtatct ttatagtcct gtcgggtttc gccacctctg acttgagcgt   7440

cgatttttgt gatgctcgtc aggggggcgg agcctatgga aaaacgccag caacgcggcc   7500

tttttacggt tcctggcctt ttgctggcct tttgctcaca tgttctttcc tgcgttatcc   7560

cctgattctg tggataaccg tattaccgcc tttgagtgag ctgataccgc tcgccgcagc   7620

cgaacgaccg agcgcagcga gtcagtgagc gaggaagcgg aagagcgccc aatacgcaaa   7680

ccgcctctcc ccgcgcgttg gccgattcat taatgcagct ggcacgacag gtttcccgac   7740

tggaaagcgg gcagtgagcg caacgcaatt aatgtgagtt agctcactca ttaggcaccc   7800

caggctttac actttatgct tccggctcgt atgttgtgtg gaattgtgag cggataacaa   7860

tttcacacag gaaacagcta tgaccatgag gcgcgccgga ttc                     7903
```

<210> SEQ ID NO 28
<211> LENGTH: 7669
<212> TYPE: DNA
<213> ORGANISM: Artificial sequence
<220> FEATURE:
<223> OTHER INFORMATION: pCAG-ArtTal1-CLEDORF

<400> SEQUENCE: 28

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240
```

-continued

```
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtga gccccacgtt ctgcttcact ctccccatct    420
cccccccctc cccaccccca attttgtatt tatttatttt ttaattattt tgtgcagcga    480
tgggggcggg gggggggggg gggcgcgcgc caggcggggc ggggcggggc gaggggcggg    540
gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct ttgtgcgctc cgcagtgtgc gcgaggggag cgcggccggg   1020
ggcggtgccc cgcggtgcgg ggggggctgc gaggggaaca aaggctgcgt gcggggtgtg   1080
tgcgtggggg ggtgagcagg gggtgtgggc gcgtcggtcg ggctgcaacc ccccctgcac   1140
ccccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
```

-continued

```
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acaagctcgc aaagtcaagc cagtccgaaa caaaggaaaa actcagagaa aaactcagaa   3780
acctgcccca tgaatacctg tccctcgtcg acctggccta cgattcaaag cagaaccgcc   3840
tctttgagat gaaagtgatc gaactgctca cagaggaatg cgggttccag ggtctgcacc   3900
tcggcggaag caggagacca gacggcgtcc tgtacaccgc cggactcaca gacaactatg   3960
ggatcattct ggatactaag gcttacagct ccggatattc cctgcccatt gcccaggctg   4020
acgagatgga acggtacgtg cgcgagaatc agactagaga tgaactggtc aaccctaatc   4080
agtggtggga gaactttgaa aatggcctgg gaaccttcta ttttctcttc gtggctgggc   4140
atttcaacgg taatgtccag gcacagctgg agcgaatcag taggaatacc ggcgtgctgg   4200
gagccgctgc atctatcagt cagctgctcc tgctcgcaga cgccattaga gggggtcgga   4260
tggatagaga gagactgcgg cacctcatgt ttcagaacga agagtttctg ctggaacagg   4320
agctgtgaac gcgtaaatga ttgcagatcc actagttcta gaattccagc tgagcgccgg   4380
tcgctaccat taccagttgg tctggtgtca aaaataataa taaccgggca ggggggatct   4440
gcatggatct ttgtgaagga accttacttc tgtggtgtga cataattgga caaactacct   4500
acagagattt aaagctctaa ggtaaatata aaatttttaa gtgtataatg tgttaaacta   4560
ctgattctaa ttgtttgtgt attttagatt ccaacctatg gaactgatga atgggagcag   4620
tggtggaatg ccagatccag acatgataag atacattgat gagtttggac aaaccacaac   4680
tagaatgcag tgaaaaaaat gctttatttg tgaaatttgt gatgctattg ctttatttgt   4740
aaccattata agctgcaata aacaagttaa caacaacaat tgcattcatt ttatgtttca   4800
ggttcagggg gaggtgtggg aggtttttta aagcaagtaa aacctctaca aatgtggtat   4860
ggctgattat gatctgcggc cgccactggc cgtcgtttta caacgtcgtg actgggaaaa   4920
ccctggcgtt acccaactta atcgccttgc agcacatccc cctttcgcca gctggcgtaa   4980
```

```
tagcgaagag gcccgcaccg atcgcccttc ccaacagttg cgcagcctga atggcgaatg   5040
gaacgcgccc tgtagcggcg cattaagcgc ggcgggtgtg gtggttacgc gcagcgtgac   5100
cgctacactt gccagcgccc tagcgcccgc tcctttcgct ttcttccctt cctttctcgc   5160
cacgttcgcc ggctttcccc gtcaagctct aaatcggggg ctccctttag ggttccgatt   5220
tagtgcttta cggcacctcg accccaaaaa acttgattag ggtgatggtt cacgtagtgg   5280
gccatcgccc tgatagacgg tttttcgccc tttgacgttg gagtccacgt tctttaatag   5340
tggactcttg ttccaaactg gaacaacact caaccctatc tcggtctatt cttttgattt   5400
ataagggatt ttgccgattt cggcctattg gttaaaaaat gagctgattt aacaaaaatt   5460
taacgcgaat tttaacaaaa tattaacgct tacaatttag gtggcacttt tcggggaaat   5520
gtgcgcggaa cccctatttg tttatttttc taaatacatt caaatatgta tccgctcatg   5580
agacaataac cctgataaat gcttcaataa tattgaaaaa ggaagagtat gagtattcaa   5640
catttccgtg tcgcccttat tccctttttt gcggcatttt gccttcctgt ttttgctcac   5700
ccagaaacgc tggtgaaagt aaaagatgct gaagatcagt tgggtgcacg agtgggttac   5760
atcgaactgg atctcaacag cggtaagatc cttgagagtt ttcgccccga agaacgtttt   5820
ccaatgatga gcacttttaa agttctgcta tgtggcgcgg tattatcccg tattgacgcc   5880
gggcaagagc aactcggtcg ccgcatacac tattctcaga atgacttggt tgagtactca   5940
ccagtcacag aaaagcatct tacggatggc atgacagtaa gagaattatg cagtgctgcc   6000
ataaccatga gtgataacac tgcggccaac ttacttctga caacgatcgg aggaccgaag   6060
gagctaaccg cttttttgca caacatgggg gatcatgtaa ctcgccttga tcgttgggaa   6120
ccggagctga atgaagccat accaaacgac gagcgtgaca ccacgatgcc tgtagcaatg   6180
gcaacaacgt tgcgcaaact attaactggc gaactactta ctctagcttc ccggcaacaa   6240
ttaatagact ggatggaggc ggataaagtt gcaggaccac ttctgcgctc ggcccttccg   6300
gctggctggt ttattgctga taaatctgga gccggtgagc gtgggtctcg cggtatcatt   6360
gcagcactgg ggccagatgg taagccctcc cgtatcgtag ttatctacac gacggggagt   6420
caggcaacta tggatgaacg aaatagacag atcgctgaga taggtgcctc actgattaag   6480
cattggtaac tgtcagacca agtttactca tatatacttt agattgattt aaaacttcat   6540
ttttaattta aaaggatcta ggtgaagatc ctttttgata atctcatgac caaaatccct   6600
taacgtgagt tttcgttcca ctgagcgtca gaccccgtag aaaagatcaa aggatcttct   6660
tgagatcctt tttttctgcg cgtaatctgc tgcttgcaaa caaaaaaacc accgctacca   6720
gcggtggttt gtttgccgga tcaagagcta ccaactcttt ttccgaaggt aactggcttc   6780
agcagagcgc agataccaaa tactgtcctt ctagtgtagc cgtagttagg ccaccacttc   6840
aagaactctg tagcaccgcc tacatacctc gctctgctaa tcctgttacc agtggctgct   6900
gccagtggcg ataagtcgtg tcttaccggg ttggactcaa gacgatagtt accggataag   6960
gcgcagcggt cgggctgaac ggggggttcg tgcacacagc ccagcttgga gcgaacgacc   7020
tacaccgaac tgagatacct acagcgtgag ctatgagaaa gcgccacgct tcccgaaggg   7080
agaaaggcgg acaggtatcc ggtaagcggc agggtcggaa caggagagcg cacgagggag   7140
cttccagggg gaaacgcctg gtatctttat agtcctgtcg ggtttcgcca cctctgactt   7200
gagcgtcgat ttttgtgatg ctcgtcaggg gggcggagcc tatggaaaaa cgccagcaac   7260
gcggcctttt tacggttcct ggccttttgc tggccttttg ctcacatgtt ctttcctgcg   7320
ttatcccctg attctgtgga taaccgtatt accgcctttg agtgagctga taccgctcgc   7380
```

```
cgcagccgaa cgaccgagcg cagcgagtca gtgagcgagg aagcggaaga gcgcccaata   7440

cgcaaaccgc ctctccccgc gcgttggccg attcattaat gcagctggca cgacaggttt   7500

cccgactgga aagcgggcag tgagcgcaac gcaattaatg tgagttagct cactcattag   7560

gcaccccagg ctttacactt tatgcttccg gctcgtatgt tgtgtggaat tgtgagcgga   7620

taacaatttc acacaggaaa cagctatgac catgaggcgc gccggattc              7669
```

<210> SEQ ID NO 29
<211> LENGTH: 7663
<212> TYPE: DNA
<213> ORGANISM: Artificial sequence
<220> FEATURE:
<223> OTHER INFORMATION: pCAG-ArtTal1-Clo051

<400> SEQUENCE: 29

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

ccccccccctc cccaccccca attttgtatt tatttatttt ttaattattt tgtgcagcga    480

tgggggcggg gggggggggg ggcgcgcgcc aggcggggcg gggcggggcg gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

gagtcgctgc gcgctgcctt cgccccgtgc cccgctccgc cgccgcctcg cgccgccccgc    720

cccggctctg actgaccgcg ttactcccac aggtgagcgg gcgggacggc ccttctcctc    780

cgggctgtaa ttagcgcttg gtttaatgac ggcttgtttc ttttctgtgg ctgcgtgaaa    840

gccttgaggg gctccgggag ggccctttgt gcggggggga gcggctcggg gggtgcgtgc    900

gtgtgtgtgt gcgtggggag cgccgcgtgc ggctccgcgc tgcccggcgg ctgtgagcgc    960

tgcgggcgcg gcgcggggct ttgtgcgctc cgcagtgtgc gcgaggggag cgcggccggg   1020

ggcggtgccc cgcggtgcgg ggggggctgc gaggggaaca aaggctgcgt gcggggtgtg   1080

tgcgtggggg ggtgagcagg gggtgtgggc gcgtcggtcg ggctgcaacc ccccctgcac   1140

ccccctcccc gagttgctga gcacggcccg gcttcgggtg cggggctccg tacggggcgt   1200

ggcgcggggc tcgccgtgcc gggcgggggg tggcggcagg tgggggtgcc gggcggggcg   1260

gggccgcctc gggccgggga gggctcgggg gaggggcgcg gcggcccccg gagcgccggc   1320

ggctgtcgag gcgcggcgag ccgcagccat tgccttttat ggtaatcgtg cgagagggcg   1380

cagggacttc ctttgtccca aatctgtgcg gagccgaaat ctgggaggcg ccgccgcacc   1440

ccctctagcg ggcgcggggc gaagcggtgc ggcgccggca ggaaggaaat gggcggggag   1500

ggccttcgtg cgtcgccgcg ccgccgtccc cttctccctc tccagcctcg gggctgtccg   1560

cggggggacg gctgccttcg gggggggacgg ggcagggcgg ggttcggctt ctggcgtgtg   1620

accggcggct ctagagcctc tgctaaccat gttcatgcct tcttcttttt cctacagatc   1680

cttaattaat aatacgactc actatagggg ccgccaccat gggacctaag aaaaagagga   1740
```

-continued

```
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acgaaggcat caaaagcaac atctccctcc tgaaagacga actccggggg cagattagcc   3780
acattagtca cgaatacctc tccctcatcg acctggcttt cgatagcaag cagaacaggc   3840
tctttgagat gaaagtgctg gaactgctcg tcaatgagta cgggttcaag ggtcgacacc   3900
tcggcggatc taggaaacca gacggcatcg tgtatagtac cacactggaa gacaactttg   3960
ggatcattgt ggataccaag gcatactctg agggttatag tctgcccatt tcacaggccg   4020
acgagatgga acggtacgtg cgcgagaact caaatagaga tgaggaagtc aaccctaaca   4080
agtggtggga gaacttctct gaggaagtga agaaatacta cttcgtcttt atcagcgggt   4140
```

```
ccttcaaggg taaatttgag gaacagctca ggagactgag catgactacc ggcgtgaatg   4200
gcagcgccgt caacgtggtc aatctgctcc tgggcgctga aaagattcgg agcggagaga   4260
tgaccatcga agagctggag agggcaatgt ttaataatag cgagtttatc ctgaaatact   4320
gaacgcgtaa atgattgcag atccactagt tctagaattc cagctgagcg ccggtcgcta   4380
ccattaccag ttggtctggt gtcaaaaata ataataaccg ggcagggggg atctgcatgg   4440
atctttgtga aggaacctta cttctgtggt gtgacataat tggacaaact acctacagag   4500
atttaaagct ctaaggtaaa tataaaattt ttaagtgtat aatgtgttaa actactgatt   4560
ctaattgttt gtgtatttta gattccaacc tatggaactg atgaatggga gcagtggtgg   4620
aatgccagat ccagacatga taagatacat tgatgagttt ggacaaacca caactagaat   4680
gcagtgaaaa aaatgcttta tttgtgaaat ttgtgatgct attgctttat ttgtaaccat   4740
tataagctgc aataaacaag ttaacaacaa caattgcatt cattttatgt ttcaggttca   4800
gggggaggtg tgggaggttt tttaaagcaa gtaaaacctc tacaaatgtg gtatggctga   4860
ttatgatctg cggccgccac tggccgtcgt tttacaacgt cgtgactggg aaaaccctgg   4920
cgttacccaa cttaatcgcc ttgcagcaca tccccctttc gccagctggc gtaatagcga   4980
agaggcccgc accgatcgcc cttcccaaca gttgcgcagc ctgaatggcg aatggaacgc   5040
gccctgtagc ggcgcattaa gcgcggcggg tgtggtggtt acgcgcagcg tgaccgctac   5100
acttgccagc gccctagcgc ccgctccttt cgctttcttc ccttcctttc tcgccacgtt   5160
cgccggcttt ccccgtcaag ctctaaatcg ggggctccct ttagggttcc gatttagtgc   5220
tttacggcac ctcgacccca aaaaacttga ttagggtgat ggttcacgta gtgggccatc   5280
gccctgatag acggtttttc gccctttgac gttggagtcc acgttcttta atagtggact   5340
cttgttccaa actggaacaa cactcaaccc tatctcggtc tattcttttg atttataagg   5400
gattttgccg atttcggcct attggttaaa aaatgagctg atttaacaaa aatttaacgc   5460
gaattttaac aaaatattaa cgcttacaat ttaggtggca cttttcgggg aaatgtgcgc   5520
ggaaccccta tttgtttatt tttctaaata cattcaaata tgtatccgct catgagacaa   5580
taaccctgat aaatgcttca ataatattga aaaaggaaga gtatgagtat tcaacatttc   5640
cgtgtcgccc ttattccctt ttttgcggca ttttgccttc ctgtttttgc tcacccagaa   5700
acgctggtga aagtaaaaga tgctgaagat cagttgggtg cacgagtggg ttacatcgaa   5760
ctggatctca acagcggtaa gatccttgag agttttcgcc ccgaagaacg ttttccaatg   5820
atgagcactt ttaaagttct gctatgtggc gcggtattat cccgtattga cgccgggcaa   5880
gagcaactcg gtcgccgcat acactattct cagaatgact tggttgagta ctcaccagtc   5940
acagaaaagc atcttacgga tggcatgaca gtaagagaat tatgcagtgc tgccataacc   6000
atgagtgata acactgcggc caacttactt ctgacaacga tcggaggacc gaaggagcta   6060
accgcttttt tgcacaacat gggggatcat gtaactcgcc ttgatcgttg ggaaccggag   6120
ctgaatgaag ccataccaaa cgacgagcgt gacaccacga tgcctgtagc aatggcaaca   6180
acgttgcgca aactattaac tggcgaacta cttactctag cttcccggca acaattaata   6240
gactggatgg aggcggataa agttgcagga ccacttctgc gctcggccct tccggctggc   6300
tggtttattg ctgataaatc tggagccggt gagcgtgggt ctcgcggtat cattgcagca   6360
ctggggccag atggtaagcc ctcccgtatc gtagttatct acacgacggg gagtcaggca   6420
actatggatg aacgaaatag acagatcgct gagataggtg cctcactgat taagcattgg   6480
```

```
taactgtcag accaagttta ctcatatata ctttagattg atttaaaact tcatttttaa   6540

tttaaaagga tctaggtgaa gatccttttt gataatctca tgaccaaaat cccttaacgt   6600

gagttttcgt tccactgagc gtcagacccc gtagaaaaga tcaaaggatc ttcttgagat   6660

cctttttttc tgcgcgtaat ctgctgcttg caaacaaaaa aaccaccgct accagcggtg   6720

gtttgtttgc cggatcaaga gctaccaact ctttttccga aggtaactgg cttcagcaga   6780

gcgcagatac caaatactgt ccttctagtg tagccgtagt taggccacca cttcaagaac   6840

tctgtagcac cgcctacata cctcgctctg ctaatcctgt taccagtggc tgctgccagt   6900

ggcgataagt cgtgtcttac cgggttggac tcaagacgat agttaccgga taaggcgcag   6960

cggtcgggct gaacgggggg ttcgtgcaca cagcccagct tggagcgaac gacctacacc   7020

gaactgagat acctacagcg tgagctatga gaaagcgcca cgcttcccga agggagaaag   7080

gcggacaggt atccggtaag cggcagggtc ggaacaggag agcgcacgag ggagcttcca   7140

gggggaaacg cctggtatct ttatagtcct gtcgggtttc gccacctctg acttgagcgt   7200

cgatttttgt gatgctcgtc aggggggcgg agcctatgga aaaacgccag caacgcggcc   7260

tttttacggt tcctggcctt ttgctggcct tttgctcaca tgttctttcc tgcgttatcc   7320

cctgattctg tggataaccg tattaccgcc tttgagtgag ctgataccgc tcgccgcagc   7380

cgaacgaccg agcgcagcga gtcagtgagc gaggaagcgg aagagcgccc aatacgcaaa   7440

ccgcctctcc ccgcgcgttg gccgattcat taatgcagct ggcacgacag gtttcccgac   7500

tggaaagcgg gcagtgagcg caacgcaatt aatgtgagtt agctcactca ttaggcaccc   7560

caggctttac actttatgct tccggctcgt atgttgtgtg gaattgtgag cggataacaa   7620

tttcacacag gaaacagcta tgaccatgag gcgcgccgga ttc                     7663
```

<210> SEQ ID NO 30
<211> LENGTH: 7816
<212> TYPE: DNA
<213> ORGANISM: Artificial sequence
<220> FEATURE:
<223> OTHER INFORMATION: pCAG-ArtTal1-MlyI

<400> SEQUENCE: 30

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

cccccccctc cccaccccca attttgtatt tatttatttt ttaattattt tgtgcagcga    480

tgggggcggg gggggggggg ggcgcgcgcc aggcggggcg gggcggggcg gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

gagtcgctgc gcgctgcctt cgccccgtgc cccgctccgc cgccgcctcg cgccgcccgc    720

cccggctctg actgaccgcg ttactcccac aggtgagcgg gcgggacggc ccttctcctc    780

cgggctgtaa ttagcgcttg gtttaatgac ggcttgtttc ttttctgtgg ctgcgtgaaa    840

gccttgaggg gctccgggag ggccctttgt gcgggggga gcggctcggg gggtgcgtgc    900
```

```
gtgtgtgtgt gcgtggggag cgccgcgtgc ggctccgcgc tgcccggcgg ctgtgagcgc    960
tgcgggcgcg gcgcggggct ttgtgcgctc cgcagtgtgc gcgaggggag cgcggccggg   1020
ggcggtgccc cgcggtgcgg ggggggctgc gaggggaaca aaggctgcgt gcggggtgtg   1080
tgcgtggggg ggtgagcagg gggtgtgggc gcgtcggtcg ggctgcaacc ccccctgcac   1140
ccccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cgggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
```

```
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acatcaatag caagatcaag cagctggacg atagcatcaa cgtggagtcc ctgaagattg   3780
acgatgccaa agatctgctg aatgacctgg agatccagcg gaaggctaaa accattgaag   3840
atacagtgaa ccacctgaag ctgcgctccg acatcgagga tattctggac gtgttcgcca   3900
aaatcaagaa aagggatgtg cccgacgtgc ctctgttcct ggagtggaat atctggcggg   3960
cctttgccgc tctgaatcat acccaggcta tcgaagggaa ctttattgtg gacctggatg   4020
gcatgcccct gaatacagct ccaggaaaga aacccgatat cgagattaac tacggaagct   4080
tctcctgcat cgtggaagtg actatgagct ccggggagac ccagtttaac atggaaggct   4140
ctagtgtgcc taggcactac ggagacctgg tgagaaaggt ggaccatgat gcctattgta   4200
tcttcattgc ccctaaggtg gctccaggga ctaaagctca cttctttaac ctgaataggc   4260
tgtctacaaa gcattatggc ggaaagacta agatcattcc aatgagtctg gacgatttca   4320
tctgctttct gcaagtgggc attacccaca actttcagga tatcaacaag ctgaaaaatt   4380
ggctggacaa cctgattaac ttcaatctgg agtctgaaga cgaggaaatc tggtttgagg   4440
aaatcatttc taagatcagt acatgggcca tttgaacgcg taaatgattg cagatccact   4500
agttctagaa ttccagctga gcgccggtcg ctaccattac cagttggtct ggtgtcaaaa   4560
ataataataa ccgggcaggg gggatctgca tggatctttg tgaaggaacc ttacttctgt   4620
ggtgtgacat aattggacaa actacctaca gagatttaaa gctctaaggt aaatataaaa   4680
tttttaagtg tataatgtgt taaactactg attctaattg tttgtgtatt ttagattcca   4740
acctatggaa ctgatgaatg ggagcagtgg tggaatgcca gatccagaca tgataagata   4800
cattgatgag tttggacaaa ccacaactag aatgcagtga aaaaaatgct ttatttgtga   4860
aatttgtgat gctattgctt tatttgtaac cattataagc tgcaataaac aagttaacaa   4920
caacaattgc attcatttta tgtttcaggt tcagggggag gtgtgggagg ttttttaaag   4980
caagtaaaac ctctacaaat gtggtatggc tgattatgat ctgcggccgc cactggccgt   5040
cgttttacaa cgtcgtgact gggaaaaccc tggcgttacc caacttaatc gccttgcagc   5100
acatccccct ttcgccagct ggcgtaatag cgaagaggcc cgcaccgatc gcccttccca   5160
acagttgcgc agcctgaatg gcgaatggaa cgcgccctgt agcggcgcat taagcgcggc   5220
gggtgtggtg gttacgcgca gcgtgaccgc tacacttgcc agcgccctag cgcccgctcc   5280
tttcgctttc ttcccttcct ttctcgccac gttcgccggc tttccccgtc aagctctaaa   5340
tcgggggctc cctttagggt tccgatttag tgctttacgg cacctcgacc ccaaaaaact   5400
tgattagggt gatggttcac gtagtgggcc atcgccctga tagacggttt ttcgcccttt   5460
gacgttggag tccacgttct ttaatagtgg actcttgttc caaactggaa caacactcaa   5520
ccctatctcg gtctattctt ttgatttata agggattttg ccgatttcgg cctattggtt   5580
aaaaaatgag ctgatttaac aaaaatttaa cgcgaatttt aacaaaatat taacgcttac   5640
```

```
aatttaggtg gcacttttcg gggaaatgtg cgcggaaccc ctatttgttt atttttctaa   5700
atacattcaa atatgtatcc gctcatgaga caataaccct gataaatgct tcaataatat   5760
tgaaaaagga agagtatgag tattcaacat ttccgtgtcg cccttattcc cttttttgcg   5820
gcattttgcc ttcctgtttt tgctcaccca gaaacgctgg tgaaagtaaa agatgctgaa   5880
gatcagttgg gtgcacgagt gggttacatc gaactggatc tcaacagcgg taagatcctt   5940
gagagttttc gccccgaaga acgttttcca atgatgagca cttttaaagt tctgctatgt   6000
ggcgcggtat tatcccgtat tgacgccggg caagagcaac tcggtcgccg catacactat   6060
tctcagaatg acttggttga gtactcacca gtcacagaaa agcatcttac ggatggcatg   6120
acagtaagag aattatgcag tgctgccata accatgagtg ataacactgc ggccaactta   6180
cttctgacaa cgatcggagg accgaaggag ctaaccgctt ttttgcacaa catgggggat   6240
catgtaactc gccttgatcg ttgggaaccg gagctgaatg aagccatacc aaacgacgag   6300
cgtgacacca cgatgcctgt agcaatggca acaacgttgc gcaaactatt aactggcgaa   6360
ctacttactc tagcttcccg gcaacaatta atagactgga tggaggcgga taaagttgca   6420
ggaccacttc tgcgctcggc ccttccggct ggctggttta ttgctgataa atctggagcc   6480
ggtgagcgtg ggtctcgcgg tatcattgca gcactggggc cagatggtaa gccctcccgt   6540
atcgtagtta tctacacgac ggggagtcag gcaactatgg atgaacgaaa tagacagatc   6600
gctgagatag gtgcctcact gattaagcat tggtaactgt cagaccaagt ttactcatat   6660
atactttaga ttgatttaaa acttcatttt taatttaaaa ggatctaggt gaagatcctt   6720
tttgataatc tcatgaccaa aatcccttaa cgtgagtttt cgttccactg agcgtcagac   6780
cccgtagaaa agatcaaagg atcttcttga gatccttttt ttctgcgcgt aatctgctgc   6840
ttgcaaacaa aaaaaccacc gctaccagcg gtggtttgtt tgccggatca agagctacca   6900
actctttttc cgaaggtaac tggcttcagc agagcgcaga taccaaatac tgtccttcta   6960
gtgtagccgt agttaggcca ccacttcaag aactctgtag caccgcctac atacctcgct   7020
ctgctaatcc tgttaccagt ggctgctgcc agtggcgata agtcgtgtct taccgggttg   7080
gactcaagac gatagttacc ggataaggcg cagcggtcgg gctgaacggg gggttcgtgc   7140
acacagccca gcttggagcg aacgacctac accgaactga gatacctaca gcgtgagcta   7200
tgagaaagcg ccacgcttcc cgaagggaga aaggcggaca ggtatccggt aagcggcagg   7260
gtcggaacag gagagcgcac gagggagctt ccagggggaa acgcctggta tctttatagt   7320
cctgtcgggt ttcgccacct ctgacttgag cgtcgatttt tgtgatgctc gtcagggggg   7380
cggagcctat ggaaaaacgc cagcaacgcg gcctttttac ggttcctggc cttttgctgg   7440
ccttttgctc acatgttctt tcctgcgtta tcccctgatt ctgtggataa ccgtattacc   7500
gcctttgagt gagctgatac cgctcgccgc agccgaacga ccgagcgcag cgagtcagtg   7560
agcgaggaag cggaagagcg cccaatacgc aaaccgcctc tccccgcgcg ttggccgatt   7620
cattaatgca gctggcacga caggtttccc gactggaaag cgggcagtga gcgcaacgca   7680
attaatgtga gttagctcac tcattaggca ccccaggctt tacactttat gcttccggct   7740
cgtatgttgt gtggaattgt gagcggataa caatttcaca caggaaacag ctatgaccat   7800
gaggcgcgcc ggattc                                                   7816
```

<210> SEQ ID NO 31
<211> LENGTH: 7705
<212> TYPE: DNA

<213> ORGANISM: Artificial sequence
<220> FEATURE:
<223> OTHER INFORMATION: pCAG-ArtTal1-Pept071

<400> SEQUENCE: 31

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtga gccccacgtt ctgcttcact ctccccatct    420
ccccccccctc cccaccccca attttgtatt tatttatttt ttaattattt tgtgcagcga    480
tgggggcggg gggggggggg gggcgcgcgc caggcggggc ggggcggggc gaggggcggg    540
gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct ttgtgcgctc cgcagtgtgc gcgaggggag cgcggccggg   1020
ggcggtgccc cgcggtgcgg ggggggctgc gaggggaaca aaggctgcgt gcggggtgtg   1080
tgcgtggggg ggtgagcagg gggtgtgggc gcgtcggtcg ggctgcaacc ccccctgcac   1140
ccccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
```

```
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acaagatcag caaaaccaat gtgctggagc tcaaggacaa agtccgagat aagctgaaat   3780
acgtggacca caggtatctg gcactcatcg acctcgccta tgatgggacc gctaacaggg   3840
acttcgaaat ccagacaatt gatctgctca ttaatgagct gaagtttaaa ggggtcaggc   3900
tcggtgaaag tagaaagccc gacggcatca tttcatacaa catcaatgga gtgatcattg   3960
ataacaaggc ttactctact ggttataacc tgcctattaa tcaggccgac gagatgatcc   4020
ggtatattga ggaaaatcag acccgcgatg aaaaaatcaa ctccaataag tggtgggagt   4080
ctttcgacga taaggtcaaa gacttcaact acctgtttgt gagctccttc tttaagggga   4140
actttaaaaa caatctgaag catatcgcta acagaacagg tgtcagcggc ggagcaatta   4200
acgtggagaa tctgctctac ttcgcagagg aactgaaagc cggccggctc tcatatgtgg   4260
atagctttaa gatgtacgac aacgatgaga tctatgtcgg cgacttctct gattacagtt   4320
atgtgaagtt tgccgctgag gaagagggag aatacctgac ttgaacgcgt aaatgattgc   4380
agatccacta gttctagaat tccagctgag cgccggtcgc taccattacc agttggtctg   4440
gtgtcaaaaa taataataac cgggcagggg ggatctgcat ggatctttgt gaaggaacct   4500
tacttctgtg gtgtgacata attggacaaa ctacctacag agatttaaag ctctaaggta   4560
```

```
aatataaaat ttttaagtgt ataatgtgtt aaactactga ttctaattgt ttgtgtattt   4620
tagattccaa cctatggaac tgatgaatgg gagcagtggt ggaatgccag atccagacat   4680
gataagatac attgatgagt ttggacaaac cacaactaga atgcagtgaa aaaaatgctt   4740
tatttgtgaa atttgtgatg ctattgcttt atttgtaacc attataagct gcaataaaca   4800
agttaacaac aacaattgca ttcattttat gtttcaggtt cagggggagg tgtgggaggt   4860
tttttaaagc aagtaaaacc tctacaaatg tggtatggct gattatgatc tgcggccgcc   4920
actggccgtc gttttacaac gtcgtgactg ggaaaaccct ggcgttaccc aacttaatcg   4980
ccttgcagca catccccctt tcgccagctg gcgtaatagc gaagaggccc gcaccgatcg   5040
cccttcccaa cagttgcgca gcctgaatgg cgaatggaac gcgccctgta gcggcgcatt   5100
aagcgcggcg ggtgtggtgg ttacgcgcag cgtgaccgct acacttgcca gcgccctagc   5160
gcccgctcct ttcgctttct tcccttcctt tctcgccacg ttcgccggct ttccccgtca   5220
agctctaaat cgggggctcc ctttagggtt ccgatttagt gctttacggc acctcgaccc   5280
caaaaaactt gattagggtg atggttcacg tagtgggcca tcgccctgat agacggtttt   5340
tcgccctttg acgttggagt ccacgttctt taatagtgga ctcttgttcc aaactggaac   5400
aacactcaac cctatctcgg tctattcttt tgatttataa gggattttgc cgatttcggc   5460
ctattggtta aaaaatgagc tgatttaaca aaaatttaac gcgaatttta acaaaatatt   5520
aacgcttaca atttaggtgg cacttttcgg ggaaatgtgc gcggaacccc tatttgttta   5580
tttttctaaa tacattcaaa tatgtatccg ctcatgagac aataaccctg ataaatgctt   5640
caataatatt gaaaaaggaa gagtatgagt attcaacatt tccgtgtcgc ccttattccc   5700
ttttttgcgg cattttgcct tcctgttttt gctcacccag aaacgctggt gaaagtaaaa   5760
gatgctgaag atcagttggg tgcacgagtg ggttacatcg aactggatct caacagcggt   5820
aagatccttg agagttttcg ccccgaagaa cgttttccaa tgatgagcac ttttaaagtt   5880
ctgctatgtg gcgcggtatt atcccgtatt gacgccgggc aagagcaact cggtcgccgc   5940
atacactatt ctcagaatga cttggttgag tactcaccag tcacagaaaa gcatcttacg   6000
gatggcatga cagtaagaga attatgcagt gctgccataa ccatgagtga taacactgcg   6060
gccaacttac ttctgacaac gatcggagga ccgaaggagc taaccgcttt tttgcacaac   6120
atgggggatc atgtaactcg ccttgatcgt tgggaaccgg agctgaatga agccatacca   6180
aacgacgagc gtgacaccac gatgcctgta gcaatggcaa caacgttgcg caaactatta   6240
actggcgaac tacttactct agcttcccgg caacaattaa tagactggat ggaggcggat   6300
aaagttgcag gaccacttct gcgctcggcc cttccggctg gctggtttat tgctgataaa   6360
tctggagccg gtgagcgtgg gtctcgcggt atcattgcag cactggggcc agatggtaag   6420
ccctcccgta tcgtagttat ctacacgacg gggagtcagg caactatgga tgaacgaaat   6480
agacagatcg ctgagatagg tgcctcactg attaagcatt ggtaactgtc agaccaagtt   6540
tactcatata tactttagat tgatttaaaa cttcattttt aatttaaaag gatctaggtg   6600
aagatccttt ttgataatct catgaccaaa atcccttaac gtgagttttc gttccactga   6660
gcgtcagacc ccgtagaaaa gatcaaagga tcttcttgag atcctttttt tctgcgcgta   6720
atctgctgct tgcaaacaaa aaaaccaccg ctaccagcgg tggtttgttt gccggatcaa   6780
gagctaccaa ctctttttcc gaaggtaact ggcttcagca gagcgcagat accaaatact   6840
gtccttctag tgtagccgta gttaggccac cacttcaaga actctgtagc accgcctaca   6900
tacctcgctc tgctaatcct gttaccagtg gctgctgcca gtggcgataa gtcgtgtctt   6960
```

```
accgggttgg actcaagacg atagttaccg gataaggcgc agcggtcggg ctgaacgggg   7020

ggttcgtgca cacagcccag cttggagcga acgacctaca ccgaactgag atacctacag   7080

cgtgagctat gagaaagcgc cacgcttccc gaagggagaa aggcggacag gtatccggta   7140

agcggcaggg tcggaacagg agagcgcacg agggagcttc caggggggaaa cgcctggtat   7200

ctttatagtc ctgtcgggtt tcgccacctc tgacttgagc gtcgattttt gtgatgctcg   7260

tcaggggggc ggagcctatg gaaaaacgcc agcaacgcgg cctttttacg gttcctggcc   7320

ttttgctggc cttttgctca catgttcttt cctgcgttat cccctgattc tgtggataac   7380

cgtattaccg cctttgagtg agctgatacc gctcgccgca gccgaacgac cgagcgcagc   7440

gagtcagtga gcgaggaagc ggaagagcgc ccaatacgca aaccgcctct ccccgcgcgt   7500

tggccgattc attaatgcag ctggcacgac aggtttcccg actggaaagc gggcagtgag   7560

cgcaacgcaa ttaatgtgag ttagctcact cattaggcac cccaggcttt acactttatg   7620

cttccggctc gtatgttgtg tggaattgtg agcggataac aatttcacac aggaaacagc   7680

tatgaccatg aggcgcgccg gattc                                          7705
```

<210> SEQ ID NO 32
<211> LENGTH: 7555
<212> TYPE: DNA
<213> ORGANISM: Artificial sequence
<220> FEATURE:
<223> OTHER INFORMATION: pCAG-ArtTal1-SbfI

<400> SEQUENCE: 32

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

cccccccctc cccaccccca attttgtatt tatttatttt ttaattattt tgtgcagcga    480

tgggggcggg gggggggggg gggcgcgcgc caggcggggc ggggcggggc gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

gagtcgctgc gcgctgcctt cgccccgtgc cccgctccgc cgccgcctcg cgccgcccgc    720

cccggctctg actgaccgcg ttactcccac aggtgagcgg gcgggacggc ccttctcctc    780

cgggctgtaa ttagcgcttg gtttaatgac ggcttgtttc ttttctgtgg ctgcgtgaaa    840

gccttgaggg gctccgggag ggccctttgt gcggggggga gcggctcggg gggtgcgtgc    900

gtgtgtgtgt gcgtggggag cgccgcgtgc ggctccgcgc tgcccggcgg ctgtgagcgc    960

tgcgggcgcg gcgcggggct ttgtgcgctc cgcagtgtgc gcgaggggag cgcggccggg   1020

ggcggtgccc cgcggtgcgg ggggggctgc gaggggaaca aaggctgcgt gcggggtgtg   1080

tgcgtggggg ggtgagcagg gggtgtgggc gcgtcggtcg ggctgcaacc ccccctgcac   1140

ccccctcccc gagttgctga gcacggcccg gcttcgggtg cggggctccg tacggggcgt   1200

ggcgcggggc tcgccgtgcc gggcgggggg tggcggcagg tgggggtgcc gggcggggcg   1260
```

-continued

```
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg gggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
```

```
atgctcccgc actgatcaag agaaccaaca ggagaattcc tgagggatcc gatcgtttaa   3720

acatctctgt ggacctgcca ggcggagagg aattcctgct gagtccagcc ggacagaacc   3780

ccctgctgaa gaaaatggtg gaggaattcg tgccccggtt tgctcctcgc agcaccgtgc   3840

tgtacctggg ggacacaagg ggcaagcact ccctgttcga gagagaaatc tttgaggaag   3900

tgctgggcct gaccttcgat cctcacggac ggatgccaga cctgattctg catgatgagg   3960

tgagggggtg gctgttcctg atggaagccg tgaagtctaa aggccccttt gatgaggaaa   4020

ggcatagaag cctgcaggag ctgtttgtga ctccttccgc cggcctgatc ttcgtgaact   4080

gctttgagaa tagggaatct atgagacagt ggctgcccga gctggcttgg gagaccgaag   4140

cctgggtggc tgaagaccct gatcacctga ttcatctgaa tggaagtcgg tttctggggc   4200

catatgagcg ctgaacgcgt aaatgattgc agatccacta gttctagaat tccagctgag   4260

cgccggtcgc taccattacc agttggtctg gtgtcaaaaa taataataac cgggcagggg   4320

ggatctgcat ggatctttgt gaaggaacct tacttctgtg gtgtgacata attggacaaa   4380

ctacctacag agatttaaag ctctaaggta aatataaaat ttttaagtgt ataatgtgtt   4440

aaactactga ttctaattgt ttgtgtattt tagattccaa cctatggaac tgatgaatgg   4500

gagcagtggt ggaatgccag atccagacat gataagatac attgatgagt ttggacaaac   4560

cacaactaga atgcagtgaa aaaaatgctt tatttgtgaa atttgtgatg ctattgcttt   4620

atttgtaacc attataagct gcaataaaca agttaacaac aacaattgca ttcattttat   4680

gtttcaggtt cagggggagg tgtgggaggt tttttaaagc aagtaaaacc tctacaaatg   4740

tggtatggct gattatgatc tgcggccgcc actggccgtc gttttacaac gtcgtgactg   4800

ggaaaaccct ggcgttaccc aacttaatcg ccttgcagca catccccctt tcgccagctg   4860

gcgtaatagc gaagaggccc gcaccgatcg cccttcccaa cagttgcgca gcctgaatgg   4920

cgaatggaac gcgccctgta gcggcgcatt aagcgcggcg ggtgtggtgg ttacgcgcag   4980

cgtgaccgct acacttgcca gcgccctagc gcccgctcct ttcgctttct tcccttcctt   5040

tctcgccacg ttcgccggct ttccccgtca agctctaaat cgggggctcc ctttagggtt   5100

ccgatttagt gctttacggc acctcgaccc caaaaaactt gattagggtg atggttcacg   5160

tagtgggcca tcgccctgat agacggtttt tcgccctttg acgttggagt ccacgttctt   5220

taatagtgga ctcttgttcc aaactggaac aacactcaac cctatctcgg tctattcttt   5280

tgatttataa gggattttgc cgatttcggc ctattggtta aaaaatgagc tgatttaaca   5340

aaaatttaac gcgaatttta acaaaatatt aacgcttaca atttaggtgg cacttttcgg   5400

ggaaatgtgc gcggaacccc tatttgttta tttttctaaa tacattcaaa tatgtatccg   5460

ctcatgagac aataaccctg ataaatgctt caataatatt gaaaaaggaa gagtatgagt   5520

attcaacatt tccgtgtcgc ccttattccc ttttttgcgg cattttgcct tcctgttttt   5580

gctcacccag aaacgctggt gaaagtaaaa gatgctgaag atcagttggg tgcacgagtg   5640

ggttacatcg aactggatct caacagcggt aagatccttg agagttttcg ccccgaagaa   5700

cgttttccaa tgatgagcac ttttaaagtt ctgctatgtg gcgcggtatt atcccgtatt   5760

gacgccgggc aagagcaact cggtcgccgc atacactatt ctcagaatga cttggttgag   5820

tactcaccag tcacagaaaa gcatcttacg gatggcatga cagtaagaga attatgcagt   5880

gctgccataa ccatgagtga taacactgcg gccaacttac ttctgacaac gatcggagga   5940

ccgaaggagc taaccgcttt tttgcacaac atgggggatc atgtaactcg ccttgatcgt   6000
```

```
tgggaaccgg agctgaatga agccatacca aacgacgagc gtgacaccac gatgcctgta   6060
gcaatggcaa caacgttgcg caaactatta actggcgaac tacttactct agcttcccgg   6120
caacaattaa tagactggat ggaggcggat aaagttgcag gaccacttct gcgctcggcc   6180
cttccggctg gctggtttat tgctgataaa tctggagccg gtgagcgtgg gtctcgcggt   6240
atcattgcag cactggggcc agatggtaag ccctcccgta tcgtagttat ctacacgacg   6300
gggagtcagg caactatgga tgaacgaaat agacagatcg ctgagatagg tgcctcactg   6360
attaagcatt ggtaactgtc agaccaagtt tactcatata tactttagat tgatttaaaa   6420
cttcattttt aatttaaaag gatctaggtg aagatccttt ttgataatct catgaccaaa   6480
atcccttaac gtgagttttc gttccactga gcgtcagacc ccgtagaaaa gatcaaagga   6540
tcttcttgag atcctttttt tctgcgcgta atctgctgct tgcaaacaaa aaaaccaccg   6600
ctaccagcgg tggtttgttt gccggatcaa gagctaccaa ctctttttcc gaaggtaact   6660
ggcttcagca gagcgcagat accaaatact gtccttctag tgtagccgta gttaggccac   6720
cacttcaaga actctgtagc accgcctaca tacctcgctc tgctaatcct gttaccagtg   6780
gctgctgcca gtggcgataa gtcgtgtctt accgggttgg actcaagacg atagttaccg   6840
gataaggcgc agcggtcggg ctgaacgggg ggttcgtgca cacagcccag cttggagcga   6900
acgacctaca ccgaactgag atacctacag cgtgagctat gagaaagcgc cacgcttccc   6960
gaagggagaa aggcggacag gtatccggta agcggcaggg tcggaacagg agagcgcacg   7020
agggagcttc cagggggaaa cgcctggtat ctttatagtc ctgtcgggtt tcgccacctc   7080
tgacttgagc gtcgattttt gtgatgctcg tcaggggggc ggagcctatg gaaaaacgcc   7140
agcaacgcgg cctttttacg gttcctggcc ttttgctggc cttttgctca catgttcttt   7200
cctgcgttat cccctgattc tgtggataac cgtattaccg cctttgagtg agctgatacc   7260
gctcgccgca gccgaacgac cgagcgcagc gagtcagtga gcgaggaagc ggaagagcgc   7320
ccaatacgca aaccgcctct ccccgcgcgt tggccgattc attaatgcag ctggcacgac   7380
aggtttcccg actggaaagc gggcagtgag cgcaacgcaa ttaatgtgag ttagctcact   7440
cattaggcac cccaggcttt acactttatg cttccggctc gtatgttgtg tggaattgtg   7500
agcggataac aatttcacac aggaaacagc tatgaccatg aggcgcgccg gattc        7555
```

<210> SEQ ID NO 33
<211> LENGTH: 7555
<212> TYPE: DNA
<213> ORGANISM: Artificial sequence
<220> FEATURE:
<223> OTHER INFORMATION: pCAG-ArtTal1-Sda

<400> SEQUENCE: 33

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtga gccccacgtt ctgcttcact ctccccatct    420
cccccccctc cccaccccca attttgtatt tatttatttt ttaattattt tgtgcagcga    480
tgggggcggg gggggggggg gggcgcgcgc caggcggggc ggggcggggc gaggggcggg    540
```

```
gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct ttgtgcgctc cgcagtgtgc gcgaggggag cgcggccggg   1020
ggcggtgccc cgcggtgcgg gggggctgc gaggggaaca aaggctgcgt gcggggtgtg   1080
tgcgtggggg ggtgagcagg gggtgtgggc gcgtcggtcg ggctgcaacc ccccctgcac   1140
ccccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
```

-continued

```
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acattagcgt ggacctcgcc gatggagatg agttcctgct gagccccgct ggacagaatc   3780
ctctgctgaa aaagatggtg gaagaattta tgccacgatt cgcacctgga gctaaggtgc   3840
tgtacatcgg cgactggcga ggaaagcaca cacggttcga gaaacgcatt tttgaggaaa   3900
ccctggggct cacatttgat ccacacggta gaatgcccga cctggtgctc catgataagg   3960
tccggaaatg gctgttcctc atggaggccg tgaagagcaa aggccctttt gacgaggaaa   4020
ggcatagaac tctgcgggaa ctcttcgcta ccccagtcgc aggactggtg ttcgtcaact   4080
gctttgagaa tcgagaagcc atgaggcagt ggctgcccga gctcgcttgg gagaccgaag   4140
catgggtggc cgacgaccct gaccacctga tccacctcaa cgggagcaga ttcctgggac   4200
cctatgaaag atgaacgcgt aaatgattgc agatccacta gttctagaat tccagctgag   4260
cgccggtcgc taccattacc agttggtctg gtgtcaaaaa taataataac cgggcagggg   4320
ggatctgcat ggatctttgt gaaggaacct tacttctgtg gtgtgacata attggacaaa   4380
ctacctacag agatttaaag ctctaaggta aatataaaat ttttaagtgt ataatgtgtt   4440
aaactactga ttctaattgt ttgtgtattt tagattccaa cctatggaac tgatgaatgg   4500
gagcagtggt ggaatgccag atccagacat gataagatac attgatgagt ttggacaaac   4560
cacaactaga atgcagtgaa aaaaatgctt tatttgtgaa atttgtgatg ctattgcttt   4620
atttgtaacc attataagct gcaataaaca agttaacaac aacaattgca ttcattttat   4680
gtttcaggtt cagggggagg tgtgggaggt tttttaaagc aagtaaaacc tctacaaatg   4740
tggtatggct gattatgatc tgcggccgcc actggccgtc gttttacaac gtcgtgactg   4800
ggaaaaccct ggcgttaccc aacttaatcg ccttgcagca catccccctt tcgccagctg   4860
gcgtaatagc gaagaggccc gcaccgatcg cccttcccaa cagttgcgca gcctgaatgg   4920
cgaatggaac gcgccctgta gcggcgcatt aagcgcggcg ggtgtggtgg ttacgcgcag   4980
cgtgaccgct acacttgcca gcgccctagc gcccgctcct ttcgctttct tcccttcctt   5040
tctcgccacg ttcgccggct ttccccgtca agctctaaat cgggggctcc ctttagggtt   5100
ccgatttagt gctttacggc acctcgaccc caaaaaactt gattagggtg atggttcacg   5160
tagtgggcca tcgccctgat agacggtttt tcgccctttg acgttggagt ccacgttctt   5220
taatagtgga ctcttgttcc aaactggaac aacactcaac cctatctcgg tctattcttt   5280
```

```
tgatttataa gggattttgc cgatttcggc ctattggtta aaaaatgagc tgatttaaca   5340
aaaatttaac gcgaatttta acaaaatatt aacgcttaca atttaggtgg cacttttcgg   5400
ggaaatgtgc gcggaacccc tatttgttta tttttctaaa tacattcaaa tatgtatccg   5460
ctcatgagac aataaccctg ataaatgctt caataatatt gaaaaaggaa gagtatgagt   5520
attcaacatt tccgtgtcgc ccttattccc ttttttgcgg cattttgcct tcctgttttt   5580
gctcacccag aaacgctggt gaaagtaaaa gatgctgaag atcagttggg tgcacgagtg   5640
ggttacatcg aactggatct caacagcggt aagatccttg agagttttcg ccccgaagaa   5700
cgttttccaa tgatgagcac ttttaaagtt ctgctatgtg gcgcggtatt atcccgtatt   5760
gacgccgggc aagagcaact cggtcgccgc atacactatt ctcagaatga cttggttgag   5820
tactcaccag tcacagaaaa gcatcttacg gatggcatga cagtaagaga attatgcagt   5880
gctgccataa ccatgagtga taacactgcg gccaacttac ttctgacaac gatcggagga   5940
ccgaaggagc taaccgcttt tttgcacaac atgggggatc atgtaactcg ccttgatcgt   6000
tgggaaccgg agctgaatga agccatacca aacgacgagc gtgacaccac gatgcctgta   6060
gcaatggcaa caacgttgcg caaactatta actggcgaac tacttactct agcttcccgg   6120
caacaattaa tagactggat ggaggcggat aaagttgcag gaccacttct gcgctcggcc   6180
cttccggctg gctggtttat tgctgataaa tctggagccg gtgagcgtgg gtctcgcggt   6240
atcattgcag cactggggcc agatggtaag ccctcccgta tcgtagttat ctacacgacg   6300
gggagtcagg caactatgga tgaacgaaat agacagatcg ctgagatagg tgcctcactg   6360
attaagcatt ggtaactgtc agaccaagtt tactcatata tactttagat tgatttaaaa   6420
cttcattttt aatttaaaag gatctaggtg aagatccttt ttgataatct catgaccaaa   6480
atcccttaac gtgagttttc gttccactga gcgtcagacc ccgtagaaaa gatcaaagga   6540
tcttcttgag atcctttttt tctgcgcgta atctgctgct tgcaaacaaa aaaaccaccg   6600
ctaccagcgg tggtttgttt gccggatcaa gagctaccaa ctctttttcc gaaggtaact   6660
ggcttcagca gagcgcagat accaaatact gtccttctag tgtagccgta gttaggccac   6720
cacttcaaga actctgtagc accgcctaca tacctcgctc tgctaatcct gttaccagtg   6780
gctgctgcca gtggcgataa gtcgtgtctt accgggttgg actcaagacg atagttaccg   6840
gataaggcgc agcggtcggg ctgaacgggg ggttcgtgca cacagcccag cttggagcga   6900
acgacctaca ccgaactgag atacctacag cgtgagctat gagaaagcgc cacgcttccc   6960
gaagggagaa aggcggacag gtatccggta agcggcaggg tcggaacagg agagcgcacg   7020
agggagcttc cagggggaaa cgcctggtat ctttatagtc ctgtcgggtt tcgccacctc   7080
tgacttgagc gtcgattttt gtgatgctcg tcaggggggc ggagcctatg gaaaaacgcc   7140
agcaacgcgg cctttttacg gttcctggcc ttttgctggc cttttgctca catgttcttt   7200
cctgcgttat cccctgattc tgtggataac cgtattaccg cctttgagtg agctgatacc   7260
gctcgccgca gccgaacgac cgagcgcagc gagtcagtga gcgaggaagc ggaagagcgc   7320
ccaatacgca aaccgcctct ccccgcgcgt tggccgattc attaatgcag ctggcacgac   7380
aggtttcccg actggaaagc gggcagtgag cgcaacgcaa ttaatgtgag ttagctcact   7440
cattaggcac cccaggcttt acactttatg cttccggctc gtatgttgtg tggaattgtg   7500
agcggataac aatttcacac aggaaacagc tatgaccatg aggcgcgccg gattc        7555
```

<210> SEQ ID NO 34

<211> LENGTH: 7690
<212> TYPE: DNA
<213> ORGANISM: Artificial sequence
<220> FEATURE:
<223> OTHER INFORMATION: pCAG-ArtTal1-StsI

<400> SEQUENCE: 34
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtcgaggtga gccccacgtt ctgcttcact ctccccatct 420
cccccccctc cccaccccca attttgtatt tatttatttt ttaattattt tgtgcagcga 480
tgggggcggg gggggggggg ggcgcgcgc caggcggggc ggggcggggc gaggggcggg 540
gcggggcgag gcggagaggt gcggcggcag ccaatcagag cggcgcgctc cgaaagtttc 600
cttttatggc gaggcggcgg cggcggcggc cctataaaaa gcgaagcgcg cggcgggcgg 660
gagtcgctgc gcgctgcctt cgccccgtgc cccgctccgc cgccgcctcg cgccgcccgc 720
cccggctctg actgaccgcg ttactcccac aggtgagcgg gcgggacggc ccttctcctc 780
cgggctgtaa ttagcgcttg gtttaatgac ggcttgtttc ttttctgtgg ctgcgtgaaa 840
gccttgaggg gctccgggag ggccctttgt gcggggggga gcggctcggg gggtgcgtgc 900
gtgtgtgtgt gcgtggggag cgccgcgtgc ggctccgcgc tgcccggcgg ctgtgagcgc 960
tgcgggcgcg gcgcggggct ttgtgcgctc cgcagtgtgc gcgaggggag cgcggccggg 1020
ggcggtgccc cgcggtgcgg ggggggctgc gaggggaaca aaggctgcgt gcggggtgtg 1080
tgcgtggggg ggtgagcagg gggtgtgggc gcgtcggtcg ggctgcaacc ccccctgcac 1140
ccccctcccc gagttgctga gcacggcccg gcttcgggtg cggggctccg tacggggcgt 1200
ggcgcggggc tcgccgtgcc gggcgggggg tggcggcagg tgggggtgcc gggcggggcg 1260
gggccgcctc gggccgggga gggctcgggg gaggggcgcg gcggcccccg gagcgccggc 1320
ggctgtcgag gcgcggcgag ccgcagccat tgccttttat ggtaatcgtg cgagagggcg 1380
cagggacttc ctttgtccca aatctgtgcg gagccgaaat ctgggaggcg ccgccgcacc 1440
ccctctagcg ggcgcggggc gaagcggtgc ggcgccggca ggaaggaaat gggcggggag 1500
ggccttcgtg cgtcgccgcg ccgccgtccc cttctccctc tccagcctcg gggctgtccg 1560 cgggggggacg gctgccttcg gggggacgg ggcagggcgg ggttcggctt ctggcgtgtg 1620
accggcggct ctagagcctc tgctaaccat gttcatgcct tcttcttttt cctacagatc 1680
cttaattaat aatacgactc actatagggg ccgccaccat gggacctaag aaaaagagga 1740
aggtggcggc cgctgactac aaggatgacg acgataaacc aggtggcgga ggtagtggcg 1800
gaggtggggt acccgccagt ccagcagccc aggtggatct gagaaccctc ggctacagcc 1860
agcagcagca ggagaagatc aaaccaaagg tgcggtccac cgtcgctcag caccatgaag 1920
cactggtggg gcacggtttc acacacgccc atattgtggc tctgtctcag catcccgctg 1980
cactcgggac tgtggccgtc aaatatcagg acatgatcgc cgctctgcct gaggcaaccc 2040
acgaagccat tgtgggcgtc ggaaagcagt ggagcggtgc cagagcactc gaagcactcc 2100
tcaccgtcgc cggggaactg cggggtccac cactccagtc cggactggac actggacagc 2160

```
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cggggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acgatgtggt gctggagaaa agcgacatcg aaaaattcaa gaaccagctg aggaccgagc   3780
tgacaaatat tgatcactcc tacctgaagg gaatcgacat tgcctccaag aaaaagacct   3840
ctaacgtgga gaatacagag tttgaagcta tctctactaa gattttcacc gatgaactgg   3900
gcttcagcgg gaaacatctg ggcggaagca ataagccaga tggcctgctg tgggacgatg   3960
actgcgccat cattctggac agtaaggctt acagcgaggg gttccccctg acagcctccc   4020
acactgacgc tatgggcagg tatctgagac agtttactga gcggaaagag gaaatcaagc   4080
ccacctggtg ggatattgcc cctgaacatc tggacaacac ctacttcgct tatgtgagcg   4140
gctccttttc tggaaattat aaagagcagc tgcagaagtt ccgccaggat acaaaccacc   4200
tgggggggcgc cctggaattt gtgaagctgc tgctgctggc taacaattac aaaactcaga   4260
agatgtccaa aaaggaggtg aaaaagtcta tcctggacta taacattagt tacgaggaat   4320
atgcccccct gctggctgag atcgaatgaa cgcgtaaatg attgcagatc cactagttct   4380
agaattccag ctgagcgccg gtcgctacca ttaccagttg gtctggtgtc aaaaataata   4440
ataaccgggc agggggggatc tgcatggatc tttgtgaagg aaccttactt ctgtggtgtg   4500
```

-continued

```
acataattgg acaaactacc tacagagatt taaagctcta aggtaaatat aaaattttta   4560
agtgtataat gtgttaaact actgattcta attgtttgtg tattttagat tccaacctat   4620
ggaactgatg aatgggagca gtggtggaat gccagatcca gacatgataa gatacattga   4680
tgagtttgga caaaccacaa ctagaatgca gtgaaaaaaa tgctttattt gtgaaatttg   4740
tgatgctatt gctttatttg taaccattat aagctgcaat aaacaagtta acaacaacaa   4800
ttgcattcat tttatgtttc aggttcaggg ggaggtgtgg gaggtttttt aaagcaagta   4860
aaacctctac aaatgtggta tggctgatta tgatctgcgg ccgccactgg ccgtcgtttt   4920
acaacgtcgt gactgggaaa accctggcgt tacccaactt aatcgccttg cagcacatcc   4980
ccctttcgcc agctggcgta atagcgaaga ggcccgcacc gatcgccctt cccaacagtt   5040
gcgcagcctg aatggcgaat ggaacgcgcc ctgtagcggc gcattaagcg cggcgggtgt   5100
ggtggttacg cgcagcgtga ccgctacact tgccagcgcc ctagcgcccg ctcctttcgc   5160
tttcttccct tcctttctcg ccacgttcgc cggctttccc cgtcaagctc taaatcgggg   5220
gctcccttta gggttccgat ttagtgcttt acggcacctc gaccccaaaa aacttgatta   5280
gggtgatggt tcacgtagtg ggccatcgcc ctgatagacg gtttttcgcc ctttgacgtt   5340
ggagtccacg ttctttaata gtggactctt gttccaaact ggaacaacac tcaaccctat   5400
ctcggtctat tcttttgatt tataagggat tttgccgatt tcggcctatt ggttaaaaaa   5460
tgagctgatt taacaaaaat ttaacgcgaa ttttaacaaa atattaacgc ttacaattta   5520
ggtggcactt ttcggggaaa tgtgcgcgga acccctattt gtttattttt ctaaatacat   5580
tcaaatatgt atccgctcat gagacaataa ccctgataaa tgcttcaata atattgaaaa   5640
aggaagagta tgagtattca acatttccgt gtcgccctta ttcccttttt tgcggcattt   5700
tgccttcctg tttttgctca cccagaaacg ctggtgaaag taaaagatgc tgaagatcag   5760
ttgggtgcac gagtgggtta catcgaactg gatctcaaca gcggtaagat ccttgagagt   5820
tttcgccccg aagaacgttt tccaatgatg agcactttta aagttctgct atgtggcgcg   5880
gtattatccc gtattgacgc cgggcaagag caactcggtc gccgcataca ctattctcag   5940
aatgacttgg ttgagtactc accagtcaca gaaaagcatc ttacggatgg catgacagta   6000
agagaattat gcagtgctgc cataaccatg agtgataaca ctgcggccaa cttacttctg   6060
acaacgatcg gaggaccgaa ggagctaacc gcttttttgc acaacatggg ggatcatgta   6120
actcgccttg atcgttggga accggagctg aatgaagcca taccaaacga cgagcgtgac   6180
accacgatgc ctgtagcaat ggcaacaacg ttgcgcaaac tattaactgg cgaactactt   6240
actctagctt cccggcaaca attaatagac tggatggagg cggataaagt tgcaggacca   6300
cttctgcgct cggcccttcc ggctggctgg tttattgctg ataaatctgg agccggtgag   6360
cgtgggtctc gcggtatcat tgcagcactg gggccagatg gtaagccctc ccgtatcgta   6420
gttatctaca cgacggggag tcaggcaact atggatgaac gaaatagaca gatcgctgag   6480
ataggtgcct cactgattaa gcattggtaa ctgtcagacc aagtttactc atatatactt   6540
tagattgatt taaaacttca tttttaattt aaaaggatct aggtgaagat cctttttgat   6600
aatctcatga ccaaaatccc ttaacgtgag ttttcgttcc actgagcgtc agaccccgta   6660
gaaaagatca aaggatcttc ttgagatcct ttttttctgc gcgtaatctg ctgcttgcaa   6720
acaaaaaaac caccgctacc agcggtggtt tgtttgccgg atcaagagct accaactctt   6780
tttccgaagg taactggctt cagcagagcg cagataccaa atactgtcct tctagtgtag   6840
ccgtagttag gccaccactt caagaactct gtagcaccgc ctacatacct cgctctgcta   6900
```

```
atcctgttac cagtggctgc tgccagtggc gataagtcgt gtcttaccgg gttggactca   6960

agacgatagt taccggataa ggcgcagcgg tcgggctgaa cggggggttc gtgcacacag   7020

cccagcttgg agcgaacgac ctacaccgaa ctgagatacc tacagcgtga gctatgagaa   7080

agcgccacgc ttcccgaagg gagaaaggcg gacaggtatc cggtaagcgg cagggtcgga   7140

acaggagagc gcacgaggga gcttccaggg ggaaacgcct ggtatcttta tagtcctgtc   7200

gggtttcgcc acctctgact tgagcgtcga tttttgtgat gctcgtcagg ggggcggagc   7260

ctatggaaaa acgccagcaa cgcggccttt ttacggttcc tggccttttg ctggcctttt   7320

gctcacatgt tctttcctgc gttatcccct gattctgtgg ataaccgtat taccgccttt   7380

gagtgagctg ataccgctcg ccgcagccga acgaccgagc gcagcgagtc agtgagcgag   7440

gaagcggaag agcgcccaat acgcaaaccg cctctccccg cgcgttggcc gattcattaa   7500

tgcagctggc acgacaggtt tcccgactgg aaagcgggca gtgagcgcaa cgcaattaat   7560

gtgagttagc tcactcatta ggcaccccag gctttacact ttatgcttcc ggctcgtatg   7620

ttgtgtggaa ttgtgagcgg ataacaattt cacacaggaa acagctatga ccatgaggcg   7680

cgccggattc                                                          7690
```

<210> SEQ ID NO 35
<211> LENGTH: 7654
<212> TYPE: DNA
<213> ORGANISM: Artificial sequence
<220> FEATURE:
<223> OTHER INFORMATION: pCAG-ArtTal1-FokI

<400> SEQUENCE: 35

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

cccccccctc cccaccccca attttgtatt tatttatttt ttaattattt tgtgcagcga    480

tgggggcggg gggggggggg ggcgcgcgcc aggcggggcg gggcggggcg gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

gagtcgctgc gcgctgcctt cgccccgtgc cccgctccgc cgccgcctcg cgccgcccgc    720

cccggctctg actgaccgcg ttactcccac aggtgagcgg gcgggacggc ccttctcctc    780

cgggctgtaa ttagcgcttg gtttaatgac ggcttgtttc ttttctgtgg ctgcgtgaaa    840

gccttgaggg gctccgggag ggccctttgt gcggggggga gcggctcggg gggtgcgtgc    900

gtgtgtgtgt gcgtggggag cgccgcgtgc ggctccgcgc tgcccggcgg ctgtgagcgc    960

tgcgggcgcg gcgcggggct ttgtgcgctc cgcagtgtgc gcgaggggag cgcggccggg   1020

ggcggtgccc cgcggtgcgg ggggggctgc gaggggaaca aaggctgcgt gcggggtgtg   1080

tgcgtggggg ggtgagcagg gggtgtgggc gcgtcggtcg ggctgcaacc ccccctgcac   1140

ccccctcccc gagttgctga gcacggcccg gcttcgggtg cggggctccg tacggggcgt   1200
```

```
ggcgcggggc tcgccgtgcc gggcgggggg tggcggcagg tgggggtgcc gggcggggcg   1260
gggccgcctc gggccgggga gggctcgggg gaggggcgcg gcggcccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg ggggggacgg ggcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cgggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760
ccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
```

```
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
accagctcgt gaaaagcgaa ctcgaagaaa agaaaagtga actgcggcac aaactgaaat   3780
acgtcccaca tgaatacatt gagctgatcg agattgctag gaactccacc caggacagaa   3840
tcctcgagat gaaagtgatg gaattcttta tgaaagtcta cgggtatcgg ggcaagcacc   3900
tgggcggatc tcgcaaacca gatggggcaa tctacactgt gggtagtccc atcgactatg   3960
gcgtgattgt cgataccaag gcctacagtg gggttataa tctgcccatt ggacaggctg   4020
acgagatgca gcgatacgtg gaggaaaacc agacaagaaa taagcatatc aaccccaatg   4080
agtggtggaa agtgtatcct agctccgtca ctgaattcaa gtttctcttc gtgtcaggcc   4140
actttaaggg aaactacaaa gcacagctga ccaggctcaa tcatattaca aactgcaatg   4200
gcgccgtgct gagcgtcgag gaactgctca tcggcggaga gatgatcaag gccggcacac   4260
tcaccctgga ggaggtccgc cgaaaattca ataacgggga aatcaacttc tgaacgcgta   4320
aatgattgca gatccactag ttctagaatt ccagctgagc gccggtcgct accattacca   4380
gttggtctgg tgtcaaaaat aataataacc gggcaggggg gatctgcatg gatctttgtg   4440
aaggaacctt acttctgtgg tgtgacataa ttggacaaac tacctacaga gatttaaagc   4500
tctaaggtaa atataaaatt tttaagtgta taatgtgtta aactactgat tctaattgtt   4560
tgtgtatttt agattccaac ctatggaact gatgaatggg agcagtggtg gaatgccaga   4620
tccagacatg ataagataca ttgatgagtt tggacaaacc acaactagaa tgcagtgaaa   4680
aaaatgcttt atttgtgaaa tttgtgatgc tattgcttta tttgtaacca ttataagctg   4740
caataaacaa gttaacaaca acaattgcat tcattttatg tttcaggttc agggggaggt   4800
gtgggaggtt ttttaaagca agtaaaacct ctacaaatgt ggtatggctg attatgatct   4860
gcggccgcca ctggccgtcg ttttacaacg tcgtgactgg gaaaaccctg gcgttaccca   4920
acttaatcgc cttgcagcac atcccccttt cgccagctgg cgtaatagcg aagaggcccg   4980
caccgatcgc ccttcccaac agttgcgcag cctgaatggc gaatggaacg cgccctgtag   5040
cggcgcatta agcgcggcgg gtgtggtggt tacgcgcagc gtgaccgcta cacttgccag   5100
cgccctagcg cccgctcctt tcgctttctt cccttccttt ctcgccacgt tcgccggctt   5160
tccccgtcaa gctctaaatc gggggctccc tttagggttc cgatttagtg ctttacggca   5220
cctcgacccc aaaaaacttg attagggtga tggttcacgt agtgggccat cgccctgata   5280
gacggttttt cgccctttga cgttggagtc cacgttcttt aatagtggac tcttgttcca   5340
aactggaaca acactcaacc ctatctcggt ctattctttt gatttataag ggattttgcc   5400
gatttcggcc tattggttaa aaaatgagct gatttaacaa aaatttaacg cgaattttaa   5460
caaaatatta acgcttacaa tttaggtggc acttttcggg gaaatgtgcg cggaacccct   5520
atttgtttat ttttctaaat acattcaaat atgtatccgc tcatgagaca ataaccctga   5580
taaatgcttc aataatattg aaaaaggaag agtatgagta ttcaacattt ccgtgtcgcc   5640
cttattccct tttttgcggc attttgcctt cctgtttttg ctcacccaga aacgctggtg   5700
aaagtaaaag atgctgaaga tcagttgggt gcacgagtgg gttacatcga actggatctc   5760
aacagcggta agatccttga gagttttcgc cccgaagaac gttttccaat gatgagcact   5820
tttaaagttc tgctatgtgg cgcggtatta tcccgtattg acgccgggca agagcaactc   5880
ggtcgccgca tacactattc tcagaatgac ttggttgagt actcaccagt cacagaaaag   5940
```

```
catcttacgg atggcatgac agtaagagaa ttatgcagtg ctgccataac catgagtgat   6000

aacactgcgg ccaacttact tctgacaacg atcggaggac cgaaggagct aaccgctttt   6060

ttgcacaaca tgggggatca tgtaactcgc cttgatcgtt gggaaccgga gctgaatgaa   6120

gccataccaa acgacgagcg tgacaccacg atgcctgtag caatggcaac aacgttgcgc   6180

aaactattaa ctggcgaact acttactcta gcttcccggc aacaattaat agactggatg   6240

gaggcggata aagttgcagg accacttctg cgctcggccc ttccggctgg ctggtttatt   6300

gctgataaat ctggagccgg tgagcgtggg tctcgcggta tcattgcagc actggggcca   6360

gatggtaagc cctcccgtat cgtagttatc tacacgacgg ggagtcaggc aactatggat   6420

gaacgaaata gacagatcgc tgagataggt gcctcactga ttaagcattg gtaactgtca   6480

gaccaagttt actcatatat actttagatt gatttaaaac ttcattttta atttaaaagg   6540

atctaggtga agatcctttt tgataatctc atgaccaaaa tcccttaacg tgagttttcg   6600

ttccactgag cgtcagaccc cgtagaaaag atcaaaggat cttcttgaga tccttttttt   6660

ctgcgcgtaa tctgctgctt gcaaacaaaa aaaccaccgc taccagcggt ggtttgtttg   6720

ccggatcaag agctaccaac tctttttccg aaggtaactg gcttcagcag agcgcagata   6780

ccaaatactg tccttctagt gtagccgtag ttaggccacc acttcaagaa ctctgtagca   6840

ccgcctacat acctcgctct gctaatcctg ttaccagtgg ctgctgccag tggcgataag   6900

tcgtgtctta ccgggttgga ctcaagacga tagttaccgg ataaggcgca gcggtcgggc   6960

tgaacggggg gttcgtgcac acagcccagc ttggagcgaa cgacctacac cgaactgaga   7020

tacctacagc gtgagctatg agaaagcgcc acgcttcccg aagggagaaa ggcggacagg   7080

tatccggtaa gcggcagggt cggaacagga gagcgcacga gggagcttcc agggggaaac   7140

gcctggtatc tttatagtcc tgtcgggttt cgccacctct gacttgagcg tcgatttttg   7200

tgatgctcgt caggggggcg gagcctatgg aaaaacgcca gcaacgcggc ctttttacgg   7260

ttcctggcct tttgctggcc ttttgctcac atgttctttc ctgcgttatc ccctgattct   7320

gtggataacc gtattaccgc ctttgagtga gctgataccg ctcgccgcag ccgaacgacc   7380

gagcgcagcg agtcagtgag cgaggaagcg gaagagcgcc caatacgcaa accgcctctc   7440

cccgcgcgtt ggccgattca ttaatgcagc tggcacgaca ggtttcccga ctggaaagcg   7500

ggcagtgagc gcaacgcaat taatgtgagt tagctcactc attaggcacc ccaggcttta   7560

cactttatgc ttccggctcg tatgttgtgt ggaattgtga gcggataaca atttcacaca   7620

ggaaacagct atgaccatga ggcgcgccgg attc                              7654
```

<210> SEQ ID NO 36
<211> LENGTH: 947
<212> TYPE: PRT
<213> ORGANISM: Artificial sequence
<220> FEATURE:
<223> OTHER INFORMATION: ArtTal1-Alw

<400> SEQUENCE: 36

```
Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60
```

```
His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480
```

```
His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Lys Glu Thr Asn
            660                 665                 670

Ile Leu Leu Val Glu Gln Leu Glu Glu Thr Leu Asn Arg Asn Arg Ile
        675                 680                 685

Leu Phe Glu Lys Asn Ser Ser Ile Ala Gln Ala Pro Ile Gly Glu Ile
    690                 695                 700

Lys Asn Tyr Arg Tyr His Leu Glu Glu Leu Leu Phe Glu Asn Asn Glu
705                 710                 715                 720

Lys Lys Phe Ala Glu Asn Gln Lys Asn Glu Trp Asp Glu Ile Leu Ala
                725                 730                 735

Tyr Met Asp Leu Leu Ile Ser Pro Lys Pro Ile Ser Ile Glu Ile Ala
            740                 745                 750

Asp Lys Glu Ile Ser Ile Pro Ser Gly Glu Arg Pro Ala Tyr Phe Glu
        755                 760                 765

Trp Val Leu Trp Arg Ala Phe Leu Ala Leu Asn His Leu Ile Ile Glu
    770                 775                 780

Pro Gln Gln Cys Arg Arg Phe Lys Val Asp Gln Asp Phe Lys Pro Ile
785                 790                 795                 800

His Asn Ala Pro Gly Gly Gly Ala Asp Val Ile Phe Glu Tyr Glu Asn
                805                 810                 815

Phe Lys Ile Leu Gly Glu Val Thr Leu Thr Ser Asn Ser Arg Gln Glu
            820                 825                 830

Ala Ala Glu Gly Glu Pro Val Arg Arg His Ile Ala Val Glu Thr Val
        835                 840                 845

Asn Thr Pro Asp Lys Asp Val Tyr Gly Leu Phe Leu Ala Leu Thr Ile
    850                 855                 860

Asp Thr Asn Thr Ala Glu Thr Phe Arg His Gly Ala Trp Tyr His Gln
865                 870                 875                 880

Glu Glu Leu Met Asp Val Lys Ile Leu Pro Leu Thr Leu Glu Ser Phe
                885                 890                 895

Lys Lys Tyr Leu Glu Ser Leu Arg Lys Lys Asn Gln Val Glu Thr Gly
```

```
            900                 905                 910

Ile Phe Asp Leu Lys Lys Met Met Asp Glu Ser Leu Lys Leu Arg Glu
        915                 920                 925

Thr Leu Thr Ala Pro Gln Trp Lys Asn Glu Ile Thr Asn Lys Phe Ala
    930                 935                 940

Arg Pro Ile
945


<210> SEQ ID NO 37
<211> LENGTH: 869
<212> TYPE: PRT
<213> ORGANISM: Artificial sequence
<220> FEATURE:
<223> OTHER INFORMATION: ArtTal1-CLEDORF

<400> SEQUENCE: 37

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
```

```
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Lys Leu Ala Lys
            660                 665                 670

Ser Ser Gln Ser Glu Thr Lys Glu Lys Leu Arg Glu Lys Leu Arg Asn
        675                 680                 685

Leu Pro His Glu Tyr Leu Ser Leu Val Asp Leu Ala Tyr Asp Ser Lys
    690                 695                 700

Gln Asn Arg Leu Phe Glu Met Lys Val Ile Glu Leu Leu Thr Glu Glu
705                 710                 715                 720

Cys Gly Phe Gln Gly Leu His Leu Gly Gly Ser Arg Arg Pro Asp Gly
                725                 730                 735
```

```
Val Leu Tyr Thr Ala Gly Leu Thr Asp Asn Tyr Gly Ile Ile Leu Asp
            740                 745                 750

Thr Lys Ala Tyr Ser Ser Gly Tyr Ser Leu Pro Ile Ala Gln Ala Asp
        755                 760                 765

Glu Met Glu Arg Tyr Val Arg Glu Asn Gln Thr Arg Asp Glu Leu Val
    770                 775                 780

Asn Pro Asn Gln Trp Trp Glu Asn Phe Glu Asn Gly Leu Gly Thr Phe
785                 790                 795                 800

Tyr Phe Leu Phe Val Ala Gly His Phe Asn Gly Asn Val Gln Ala Gln
                805                 810                 815

Leu Glu Arg Ile Ser Arg Asn Thr Gly Val Leu Gly Ala Ala Ala Ser
            820                 825                 830

Ile Ser Gln Leu Leu Leu Leu Ala Asp Ala Ile Arg Gly Gly Arg Met
        835                 840                 845

Asp Arg Glu Arg Leu Arg His Leu Met Phe Gln Asn Glu Glu Phe Leu
    850                 855                 860

Leu Glu Gln Glu Leu
865


<210> SEQ ID NO 38
<211> LENGTH: 867
<212> TYPE: PRT
<213> ORGANISM: Artificial sequence
<220> FEATURE:
<223> OTHER INFORMATION: ArtTal1-Clo051

<400> SEQUENCE: 38

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220
```

```
Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640
```

```
Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Glu Gly Ile Lys
            660                 665                 670

Ser Asn Ile Ser Leu Leu Lys Asp Glu Leu Arg Gly Gln Ile Ser His
        675                 680                 685

Ile Ser His Glu Tyr Leu Ser Leu Ile Asp Leu Ala Phe Asp Ser Lys
    690                 695                 700

Gln Asn Arg Leu Phe Glu Met Lys Val Leu Glu Leu Leu Val Asn Glu
705                 710                 715                 720

Tyr Gly Phe Lys Gly Arg His Leu Gly Gly Ser Arg Lys Pro Asp Gly
                725                 730                 735

Ile Val Tyr Ser Thr Thr Leu Glu Asp Asn Phe Gly Ile Ile Val Asp
            740                 745                 750

Thr Lys Ala Tyr Ser Glu Gly Tyr Ser Leu Pro Ile Ser Gln Ala Asp
        755                 760                 765

Glu Met Glu Arg Tyr Val Arg Glu Asn Ser Asn Arg Asp Glu Glu Val
    770                 775                 780

Asn Pro Asn Lys Trp Trp Glu Asn Phe Ser Glu Glu Val Lys Lys Tyr
785                 790                 795                 800

Tyr Phe Val Phe Ile Ser Gly Ser Phe Lys Gly Lys Phe Glu Glu Gln
                805                 810                 815

Leu Arg Arg Leu Ser Met Thr Thr Gly Val Asn Gly Ser Ala Val Asn
            820                 825                 830

Val Val Asn Leu Leu Leu Gly Ala Glu Lys Ile Arg Ser Gly Glu Met
        835                 840                 845

Thr Ile Glu Glu Leu Glu Arg Ala Met Phe Asn Asn Ser Glu Phe Ile
    850                 855                 860

Leu Lys Tyr
865
```

<210> SEQ ID NO 39
<211> LENGTH: 918
<212> TYPE: PRT
<213> ORGANISM: Artificial sequence
<220> FEATURE:
<223> OTHER INFORMATION: ArtTal1-Mly

<400> SEQUENCE: 39

```
Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125
```

-continued

```
Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
```

```
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Asn Ser Lys
            660                 665                 670

Ile Lys Gln Leu Asp Asp Ser Ile Asn Val Glu Ser Leu Lys Ile Asp
        675                 680                 685

Asp Ala Lys Asp Leu Leu Asn Asp Leu Glu Ile Gln Arg Lys Ala Lys
    690                 695                 700

Thr Ile Glu Asp Thr Val Asn His Leu Lys Leu Arg Ser Asp Ile Glu
705                 710                 715                 720

Asp Ile Leu Asp Val Phe Ala Lys Ile Lys Lys Arg Asp Val Pro Asp
                725                 730                 735

Val Pro Leu Phe Leu Glu Trp Asn Ile Trp Arg Ala Phe Ala Ala Leu
            740                 745                 750

Asn His Thr Gln Ala Ile Glu Gly Asn Phe Ile Val Asp Leu Asp Gly
        755                 760                 765

Met Pro Leu Asn Thr Ala Pro Gly Lys Lys Pro Asp Ile Glu Ile Asn
    770                 775                 780

Tyr Gly Ser Phe Ser Cys Ile Val Glu Val Thr Met Ser Ser Gly Glu
785                 790                 795                 800

Thr Gln Phe Asn Met Glu Gly Ser Ser Val Pro Arg His Tyr Gly Asp
                805                 810                 815

Leu Val Arg Lys Val Asp His Asp Ala Tyr Cys Ile Phe Ile Ala Pro
            820                 825                 830

Lys Val Ala Pro Gly Thr Lys Ala His Phe Phe Asn Leu Asn Arg Leu
        835                 840                 845

Ser Thr Lys His Tyr Gly Gly Lys Thr Lys Ile Ile Pro Met Ser Leu
    850                 855                 860

Asp Asp Phe Ile Cys Phe Leu Gln Val Gly Ile Thr His Asn Phe Gln
865                 870                 875                 880

Asp Ile Asn Lys Leu Lys Asn Trp Leu Asp Asn Leu Ile Asn Phe Asn
                885                 890                 895

Leu Glu Ser Glu Asp Glu Glu Ile Trp Phe Glu Glu Ile Ile Ser Lys
            900                 905                 910

Ile Ser Thr Trp Ala Ile
        915
```

<210> SEQ ID NO 40
<211> LENGTH: 881
<212> TYPE: PRT
<213> ORGANISM: Artificial sequence
<220> FEATURE:
<223> OTHER INFORMATION: ArtTal1-Pept071

<400> SEQUENCE: 40

```
Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415
```

-continued

```
Pro Gln Gln Val Val Ala Ile Ala Ser Asn Asn Gly Gly Lys Gln Ala
                420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Lys Ile Ser Lys
            660                 665                 670

Thr Asn Val Leu Glu Leu Lys Asp Lys Val Arg Asp Lys Leu Lys Tyr
        675                 680                 685

Val Asp His Arg Tyr Leu Ala Leu Ile Asp Leu Ala Tyr Asp Gly Thr
    690                 695                 700

Ala Asn Arg Asp Phe Glu Ile Gln Thr Ile Asp Leu Leu Ile Asn Glu
705                 710                 715                 720

Leu Lys Phe Lys Gly Val Arg Leu Gly Glu Ser Arg Lys Pro Asp Gly
                725                 730                 735

Ile Ile Ser Tyr Asn Ile Asn Gly Val Ile Ile Asp Asn Lys Ala Tyr
            740                 745                 750

Ser Thr Gly Tyr Asn Leu Pro Ile Asn Gln Ala Asp Glu Met Ile Arg
        755                 760                 765

Tyr Ile Glu Glu Asn Gln Thr Arg Asp Glu Lys Ile Asn Ser Asn Lys
    770                 775                 780

Trp Trp Glu Ser Phe Asp Asp Lys Val Lys Asp Phe Asn Tyr Leu Phe
785                 790                 795                 800

Val Ser Ser Phe Phe Lys Gly Asn Phe Lys Asn Asn Leu Lys His Ile
                805                 810                 815

Ala Asn Arg Thr Gly Val Ser Gly Gly Ala Ile Asn Val Glu Asn Leu
            820                 825                 830
```

```
Leu Tyr Phe Ala Glu Glu Leu Lys Ala Gly Arg Leu Ser Tyr Val Asp
        835                 840                 845

Ser Phe Lys Met Tyr Asp Asn Asp Glu Ile Tyr Val Gly Asp Phe Ser
    850                 855                 860

Asp Tyr Ser Tyr Val Lys Phe Ala Ala Glu Glu Glu Gly Glu Tyr Leu
865                 870                 875                 880

Thr


<210> SEQ ID NO 41
<211> LENGTH: 831
<212> TYPE: PRT
<213> ORGANISM: Artificial sequence
<220> FEATURE:
<223> OTHER INFORMATION: ArtTal1-Sbf

<400> SEQUENCE: 41

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
```

```
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Ser Val Asp
            660                 665                 670

Leu Pro Gly Gly Glu Glu Phe Leu Leu Ser Pro Ala Gly Gln Asn Pro
        675                 680                 685

Leu Leu Lys Lys Met Val Glu Glu Phe Val Pro Arg Phe Ala Pro Arg
    690                 695                 700

Ser Thr Val Leu Tyr Leu Gly Asp Thr Arg Gly Lys His Ser Leu Phe
705                 710                 715                 720

Glu Arg Glu Ile Phe Glu Glu Val Leu Gly Leu Thr Phe Asp Pro His
                725                 730                 735
```

```
Gly Arg Met Pro Asp Leu Ile Leu His Asp Glu Val Arg Gly Trp Leu
            740                 745                 750

Phe Leu Met Glu Ala Val Lys Ser Lys Gly Pro Phe Asp Glu Glu Arg
        755                 760                 765

His Arg Ser Leu Gln Glu Leu Phe Val Thr Pro Ser Ala Gly Leu Ile
    770                 775                 780

Phe Val Asn Cys Phe Glu Asn Arg Glu Ser Met Arg Gln Trp Leu Pro
785                 790                 795                 800

Glu Leu Ala Trp Glu Thr Glu Ala Trp Val Ala Glu Asp Pro Asp His
                805                 810                 815

Leu Ile His Leu Asn Gly Ser Arg Phe Leu Gly Pro Tyr Glu Arg
            820                 825                 830


<210> SEQ ID NO 42
<211> LENGTH: 831
<212> TYPE: PRT
<213> ORGANISM: Artificial sequence
<220> FEATURE:
<223> OTHER INFORMATION: ArtTal1-SdaI

<400> SEQUENCE: 42

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270
```

```
Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Ser Val Asp
            660                 665                 670

Leu Ala Asp Gly Asp Glu Phe Leu Leu Ser Pro Ala Gly Gln Asn Pro
        675                 680                 685
```

```
Leu Leu Lys Lys Met Val Glu Glu Phe Met Pro Arg Phe Ala Pro Gly
    690                 695                 700

Ala Lys Val Leu Tyr Ile Gly Asp Trp Arg Gly Lys His Thr Arg Phe
705                 710                 715                 720

Glu Lys Arg Ile Phe Glu Glu Thr Leu Gly Leu Thr Phe Asp Pro His
                725                 730                 735

Gly Arg Met Pro Asp Leu Val Leu His Asp Lys Val Arg Lys Trp Leu
            740                 745                 750

Phe Leu Met Glu Ala Val Lys Ser Lys Gly Pro Phe Asp Glu Glu Arg
        755                 760                 765

His Arg Thr Leu Arg Glu Leu Phe Ala Thr Pro Val Ala Gly Leu Val
    770                 775                 780

Phe Val Asn Cys Phe Glu Asn Arg Glu Ala Met Arg Gln Trp Leu Pro
785                 790                 795                 800

Glu Leu Ala Trp Glu Thr Glu Ala Trp Val Ala Asp Asp Pro Asp His
                805                 810                 815

Leu Ile His Leu Asn Gly Ser Arg Phe Leu Gly Pro Tyr Glu Arg
            820                 825                 830


<210> SEQ ID NO 43
<211> LENGTH: 876
<212> TYPE: PRT
<213> ORGANISM: Artificial sequence
<220> FEATURE:
<223> OTHER INFORMATION: ArtTal1-StsI

<400> SEQUENCE: 43

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220
```

```
Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
```

```
                645                 650                 655

Asn Arg Arg Ile Pro Glu Gly Ser Asp Arg Leu Asn Asp Val Val Leu
            660                 665                 670

Glu Lys Ser Asp Ile Glu Lys Phe Lys Asn Gln Leu Arg Thr Glu Leu
        675                 680                 685

Thr Asn Ile Asp His Ser Tyr Leu Lys Gly Ile Asp Ile Ala Ser Lys
    690                 695                 700

Lys Lys Thr Ser Asn Val Glu Asn Thr Glu Phe Glu Ala Ile Ser Thr
705                 710                 715                 720

Lys Ile Phe Thr Asp Glu Leu Gly Phe Ser Gly Lys His Leu Gly Gly
                725                 730                 735

Ser Asn Lys Pro Asp Gly Leu Leu Trp Asp Asp Asp Cys Ala Ile Ile
            740                 745                 750

Leu Asp Ser Lys Ala Tyr Ser Glu Gly Phe Pro Leu Thr Ala Ser His
        755                 760                 765

Thr Asp Ala Met Gly Arg Tyr Leu Arg Gln Phe Thr Glu Arg Lys Glu
    770                 775                 780

Glu Ile Lys Pro Thr Trp Trp Asp Ile Ala Pro Glu His Leu Asp Asn
785                 790                 795                 800

Thr Tyr Phe Ala Tyr Val Ser Gly Ser Phe Ser Gly Asn Tyr Lys Glu
                805                 810                 815

Gln Leu Gln Lys Phe Arg Gln Asp Thr Asn His Leu Gly Gly Ala Leu
            820                 825                 830

Glu Phe Val Lys Leu Leu Leu Leu Ala Asn Asn Tyr Lys Thr Gln Lys
        835                 840                 845

Met Ser Lys Lys Glu Val Lys Lys Ser Ile Leu Asp Tyr Asn Ile Ser
    850                 855                 860

Tyr Glu Glu Tyr Ala Pro Leu Leu Ala Glu Ile Glu
865                 870                 875


<210> SEQ ID NO 44
<211> LENGTH: 864
<212> TYPE: PRT
<213> ORGANISM: Artificial sequence
<220> FEATURE:
<223> OTHER INFORMATION: ArtTal1-FokI

<400> SEQUENCE: 44

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
```

-continued

```
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560
```

```
Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Gln Leu Val Lys
            660                 665                 670

Ser Glu Leu Glu Glu Lys Lys Ser Glu Leu Arg His Lys Leu Lys Tyr
        675                 680                 685

Val Pro His Glu Tyr Ile Glu Leu Ile Glu Ile Ala Arg Asn Ser Thr
    690                 695                 700

Gln Asp Arg Ile Leu Glu Met Lys Val Met Glu Phe Phe Met Lys Val
705                 710                 715                 720

Tyr Gly Tyr Arg Gly Lys His Leu Gly Gly Ser Arg Lys Pro Asp Gly
                725                 730                 735

Ala Ile Tyr Thr Val Gly Ser Pro Ile Asp Tyr Gly Val Ile Val Asp
            740                 745                 750

Thr Lys Ala Tyr Ser Gly Gly Tyr Asn Leu Pro Ile Gly Gln Ala Asp
        755                 760                 765

Glu Met Gln Arg Tyr Val Glu Glu Asn Gln Thr Arg Asn Lys His Ile
    770                 775                 780

Asn Pro Asn Glu Trp Trp Lys Val Tyr Pro Ser Ser Val Thr Glu Phe
785                 790                 795                 800

Lys Phe Leu Phe Val Ser Gly His Phe Lys Gly Asn Tyr Lys Ala Gln
                805                 810                 815

Leu Thr Arg Leu Asn His Ile Thr Asn Cys Asn Gly Ala Val Leu Ser
            820                 825                 830

Val Glu Glu Leu Leu Ile Gly Gly Glu Met Ile Lys Ala Gly Thr Leu
        835                 840                 845

Thr Leu Glu Glu Val Arg Arg Lys Phe Asn Asn Gly Glu Ile Asn Phe
    850                 855                 860
```

<210> SEQ ID NO 45
<211> LENGTH: 7374
<212> TYPE: DNA
<213> ORGANISM: Artificial sequence
<220> FEATURE:
<223> OTHER INFORMATION: ArtTal1-Reporter

<400> SEQUENCE: 45

```
cgttacataa cttacggtaa atggcccgcc tggctgaccg cccaacgacc cccgcccatt      60

gacgtcaata atgacgtatg ttcccatagt aacgccaata gggactttcc attgacgtca     120

atgggtggag tatttacggt aaactgccca cttggcagta catcaagtgt atcatatgcc     180

aagtacgccc cctattgacg tcaatgacgg taaatggccc gcctggcatt atgcccagta     240

catgacctta tgggactttc ctacttggca gtacatctac gtattagtca tcgctattac     300

catggtgatg cggttttggc agtacatcaa tgggcgtgga tagcggtttg actcacgggg     360
```

```
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctcg tttagtgaac cgtcagatcg cctggagacg    540
ccatccacgc tgttttgacc tccatagaag acaccgggac cgatccagcc tccggactct    600
agaggatccg gtactcgacg acactgcaga gacctacttc actaacaacc ggtatggtcg    660
cgagtagctt ggcactggcc gtcgttttac aacgtcgtga ctgggaaaac cctggcgtta    720
cccaacttaa tcgccttgca gcacatcccc ctttcgccag ctggcgtaat agcgaagagg    780
cccgcaccga tcgcccttcc caacagttgc gcagcctgaa tggcgaatgg cgctttgcct    840
ggtttccggc accagaagcg gtgccggaaa gctggctgga gtgcgatctt cctgaggccg    900
atactgtcgt cgtcccctca aactggcaga tgcacggtta cgatgcgccc atctacacca    960
acgtgaccta tcccattacg gtcaatccgc cgtttgttcc cacggagaat ccgacgggtt   1020
gttactcgct cacatttaat gttgatgaaa gctggctata aaaccggtac agttcggcca   1080
ccatggtcgt attctgggac gttttcacac tcttctaacg tcccagaata ctcgagtagc   1140
ttggcactgg ccgtcgtttt acaacgtcgt gactgggaaa accctggcgt tacccaactt   1200
aatcgccttg cagcacatcc ccctttcgcc agctggcgta atagcgaaga ggcccgcacc   1260
gatcgccctt cccaacagtt gcgcagcctg aatggcgaat ggcgctttgc ctggtttccg   1320
gcaccagaag cggtgccgga aagctggctg gagtgcgatc ttcctgaggc cgatactgtc   1380
gtcgtcccct caaactggca gatgcacggt tacgatgcgc ccatctacac caacgtgacc   1440
tatcccatta cggtcaatcc gccgtttgtt cccacggaga atccgacggg ttgttactcg   1500
ctcacattta atgttgatga aagctggcta caggaaggcc agacgcgaat tatttttgat   1560
ggcgttaact cggcgtttca tctgtggtgc aacgggcgct gggtcggtta cggccaggac   1620
agtcgtttgc cgtctgaatt tgacctgagc gcatttttac gcgccggaga aaaccgcctc   1680
gcggtgatgg tgctgcgctg gagtgacggc agttatctgg aagatcagga tatgtggcgg   1740
atgagcggca ttttccgtga cgtctcgttg ctgcataaac cgactacaca aatcagcgat   1800
ttccatgttg ccactcgctt taatgatgat ttcagccgcg ctgtactgga ggctgaagtt   1860
cagatgtgcg gcgagttgcg tgactaccta cgggtaacag tttctttatg gcagggtgaa   1920
acgcaggtcg ccagcggcac cgcgcctttc ggcggtgaaa ttatcgatga gcgtggtggt   1980
tatgccgatc gcgtcacact acgtctgaac gtcgaaaacc cgaaactgtg gagcgccgaa   2040
atcccgaatc tctatcgtgc ggtggttgaa ctgcacaccg ccgacggcac gctgattgaa   2100
gcagaagcct gcgatgtcgg tttccgcgag gtgcggattg aaaatggtct gctgctgctg   2160
aacggcaagc cgttgctgat tcgaggcgtt aaccgtcacg agcatcatcc tctgcatggt   2220
caggtcatgg atgagcagac gatggtgcag gatatcctgc tgatgaagca gaacaacttt   2280
aacgccgtgc gctgttcgca ttatccgaac catccgctgt ggtacacgct gtgcgaccgc   2340
tacggcctgt atgtggtgga tgaagccaat attgaaaccc acggcatggt gccaatgaat   2400
cgtctgaccg atgatccgcg ctggctaccg gcgatgagcg aacgcgtaac gcgaatggtg   2460
cagcgcgatc gtaatcaccc gagtgtgatc atctggtcgc tggggaatga atcaggccac   2520
ggcgctaatc acgacgcgct gtatcgctgg atcaaatctg tcgatccttc ccgcccggtg   2580
cagtatgaag gcggcggagc cgacaccacg gccaccgata ttatttgccc gatgtacgcg   2640
cgcgtggatg aagaccagcc cttcccggct gtgccgaaat ggtccatcaa aaaatggctt   2700
```

```
tcgctacctg gagagacgcg cccgctgatc ctttgcgaat acgcccacgc gatgggtaac   2760
agtcttggcg gtttcgctaa atactggcag gcgtttcgtc agtatccccg tttacagggc   2820
ggcttcgtct gggactgggt ggatcagtcg ctgattaaat atgatgaaaa cggcaacccg   2880
tggtcggctt acggcggtga ttttggcgat acgccgaacg atcgccagtt ctgtatgaac   2940
ggtctggtct ttgccgaccg cacgccgcat ccagcgctga cggaagcaaa acaccagcag   3000
cagtttttcc agttccgttt atccgggcaa accatcgaag tgaccagcga atacctgttc   3060
cgtcatagcg ataacgagct cctgcactgg atggtggcgc tggatggtaa gccgctggca   3120
agcggtgaag tgcctctgga tgtcgctcca caaggtaaac agttgattga actgcctgaa   3180
ctaccgcagc cggagagcgc cgggcaactc tggctcacag tacgcgtagt gcaaccgaac   3240
gcgaccgcat ggtcagaagc cgggcacatc agcgcctggc agcagtggcg tctggcggaa   3300
aacctcagtg tgacgctccc cgccgcgtcc cacgccatcc cgcatctgac caccagcgaa   3360
atggattttt gcatcgagct gggtaataag cgttggcaat ttaaccgcca gtcaggcttt   3420
ctttcacaga tgtggattgg cgataaaaaa caactgctga cgccgctgcg cgatcagttc   3480
acccgtgcac cgctggataa cgacattggc gtaagtgaag cgacccgcat tgaccctaac   3540
gcctgggtcg aacgctggaa ggcggcgggc cattaccagg ccgaagcagc gttgttgcag   3600
tgcacggcag atacacttgc tgatgcggtg ctgattacga ccgctcacgc gtggcagcat   3660
caggggaaaa ccttatttat cagccggaaa acctaccgga ttgatggtag tggtcaaatg   3720
gcgattaccg ttgatgttga agtggcgagc gatacaccgc atccggcgcg gattggcctg   3780
aactgccagc tggcgcaggt agcagagcgg gtaaactggc tcggattagg gccgcaagaa   3840
aactatcccg accgccttac tgccgcctgt tttgaccgct gggatctgcc attgtcagac   3900
atgtataccc cgtacgtctt cccgagcgaa aacggtctgc gctgcgggac gcgcgaattg   3960
aattatggcc cacaccagtg gcgcggcgac ttccagttca acatcagccg ctacagtcaa   4020
cagcaactga tggaaaccag ccatcgccat ctgctgcacg cggaagaagg cacatggctg   4080
aatatcgacg gtttccatat ggggattggt ggcgacgact cctggagccc gtcagtatcg   4140
gcggaattac agctgagcgc cggtcgctac cattaccagt tggtctggtg tcaaaaataa   4200
taataaccgg gcaggccatg tctgcccgta tttcgcgtaa ggaaatccat tatgtactat   4260
ttaaaaaaca caaacttttg gatgttcggt ttattctttt tcttttactt ttttatcatg   4320
ggagcctact tcccgttttt cccgatttgg ctacatgaca tcaaccatat cagcaaaagt   4380
gatacgggta ttatttttgc cgctatttct ctgttctcgc tattattcca accgctgttt   4440
ggtctgcttt ctgacaaact cggcctcgac tctaggcggc cgcggggatc cagacatgat   4500
aagatacatt gatgagtttg gacaaaccac aactagaatg cagtgaaaaa aatgctttat   4560
ttgtgaaatt tgtgatgcta ttgctttatt tgtaaccatt ataagctgca ataaacaagt   4620
taacaacaac aattgcattc attttatgtt tcaggttcag ggggaggtgt gggaggtttt   4680
ttcggatcct ctagagtcga cctgcaggca tgcaagcttg gcgtaatcat ggtcatagct   4740
gtttcctgtg tgaaattgtt atccgctcac aattccacac aacatacgag ccggaagcat   4800
aaagtgtaaa gcctggggtg cctaatgagt gagctaactc acattaattg cgttgcgctc   4860
actgcccgct ttccagtcgg gaaacctgtc gtgccagctg cattaatgaa tcggccaacg   4920
cgcggggaga ggcggtttgc gtattgggcg ctcttccgct tcctcgctca ctgactcgct   4980
gcgctcggtc gttcggctgc ggcgagcggt atcagctcac tcaaaggcgg taatacggtt   5040
atccacagaa tcaggggata acgcaggaaa gaacatgtga gcaaaaggcc agcaaaaggc   5100
```

```
caggaaccgt aaaaaggccg cgttgctggc gtttttccat aggctccgcc cccctgacga   5160
gcatcacaaa aatcgacgct caagtcagag gtggcgaaac ccgacaggac tataaagata   5220
ccaggcgttt ccccctggaa gctccctcgt gcgctctcct gttccgaccc tgccgcttac   5280
cggatacctg tccgcctttc tcccttcggg aagcgtggcg ctttctcata gctcacgctg   5340
taggtatctc agttcggtgt aggtcgttcg ctccaagctg ggctgtgtgc acgaaccccc   5400
cgttcagccc gaccgctgcg ccttatccgg taactatcgt cttgagtcca acccggtaag   5460
acacgactta tcgccactgg cagcagccac tggtaacagg attagcagag cgaggtatgt   5520
aggcggtgct acagagttct tgaagtggtg gcctaactac ggctacacta gaaggacagt   5580
atttggtatc tgcgctctgc tgaagccagt taccttcgga aaaagagttg gtagctcttg   5640
atccggcaaa caaaccaccg ctggtagcgg tggttttttt gtttgcaagc agcagattac   5700
gcgcagaaaa aaaggatctc aagaagatcc tttgatcttt tctacggggt ctgacgctca   5760
gtggaacgaa aactcacgtt aagggatttt ggtcatgaga ttatcaaaaa ggatcttcac   5820
ctagatcctt ttaaattaaa aatgaagttt taaatcaatc taaagtatat atgagtaaac   5880
ttggtctgac agttaccaat gcttaatcag tgaggcacct atctcagcga tctgtctatt   5940
tcgttcatcc atagttgcct gactccccgt cgtgtagata actacgatac gggagggctt   6000
accatctggc cccagtgctg caatgatacc gcgagaccca cgctcaccgg ctccagattt   6060
atcagcaata aaccagccag ccggaagggc cgagcgcaga agtggtcctg caactttatc   6120
cgcctccatc cagtctatta attgttgccg ggaagctaga gtaagtagtt cgccagttaa   6180
tagtttgcgc aacgttgttg ccattgctac aggcatcgtg gtgtcacgct cgtcgtttgg   6240
tatggcttca ttcagctccg gttcccaacg atcaaggcga gttacatgat cccccatgtt   6300
gtgcaaaaaa gcggttagct ccttcggtcc tccgatcgtt gtcagaagta agttggccgc   6360
agtgttatca ctcatggtta tggcagcact gcataattct cttactgtca tgccatccgt   6420
aagatgcttt tctgtgactg gtgagtactc aaccaagtca ttctgagaat agtgtatgcg   6480
gcgaccgagt tgctcttgcc cggcgtcaat acgggataat accgcgccac atagcagaac   6540
tttaaaagtg ctcatcattg gaaaacgttc ttcggggcga aaactctcaa ggatcttacc   6600
gctgttgaga tccagttcga tgtaacccac tcgtgcaccc aactgatctt cagcatcttt   6660
tactttcacc agcgtttctg ggtgagcaaa aacaggaagg caaaatgccg caaaaaaggg   6720
aataagggcg acacggaaat gttgaatact catactcttc ctttttcaat attattgaag   6780
catttatcag ggttattgtc tcatgagcgg atacatattt gaatgtattt agaaaaataa   6840
acaaataggg gttccgcgca catttccccg aaaagtgcca cctgacgtct aagaaaccat   6900
tattatcatg acattaacct ataaaaatag gcgtatcacg aggccctttc gtctcgcgcg   6960
tttcggtgat gacggtgaaa acctctgaca catgcagctc ccggagacgg tcacagcttg   7020
tctgtaagcg gatgccggga gcagacaagc ccgtcagggc gcgtcagcgg gtgttggcgg   7080
gtgtcggggc tggcttaact atgcggcatc agagcagatt gtactgagag tgcaccatat   7140
gcggtgtgaa ataccgcaca gatgcgtaag gagaaaatac cgcatcaggc gccattcgcc   7200
attcaggctg cgcaactgtt gggaagggcg atcggtgcgg gcctcttcgc tattacgcca   7260
gctggcgaaa gggggatgtg ctgcaaggcg attaagttgg gtaacgccag ggttttccca   7320
gtcacgacgt tgtaaaacga cggccagtga attcgagctt gcatgcctgc aggt         7374
```

<210> SEQ ID NO 46

<211> LENGTH: 7374
<212> TYPE: DNA
<213> ORGANISM: Artificial sequence
<220> FEATURE:
<223> OTHER INFORMATION: TalRab1-Reporter

<400> SEQUENCE: 46
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagctcg tttagtgaac cgtcagatcg cctggagacg 540
ccatccacgc tgttttgacc tccatagaag acaccgggac cgatccagcc tccggactct 600
agaggatccg gtactcgacg acactgcaga gacctacttc actaacaacc ggtatggtcg 660
cgagtagctt ggcactggcc gtcgttttac aacgtcgtga ctgggaaaac cctggcgtta 720
cccaacttaa tcgccttgca gcacatcccc ctttcgccag ctggcgtaat agcgaagagg 780
cccgcaccga tcgcccttcc caacagttgc gcagcctgaa tggcgaatgg cgctttgcct 840
ggtttccggc accagaagcg gtgccggaaa gctggctgga gtgcgatctt cctgaggccg 900
atactgtcgt cgtcccctca aactggcaga tgcacggtta cgatgcgccc atctacacca 960
acgtgaccta tcccattacg gtcaatccgc cgtttgttcc cacggagaat ccgacgggtt 1020
gttactcgct cacatttaat gttgatgaaa gctggctata aaaccggtac agttcggcca 1080
ccatggtcgt gtgcaccaaa acttttcaca ctcttctaag ttttggtgca cacgagtagc 1140
ttggcactgg ccgtcgtttt acaacgtcgt gactgggaaa accctggcgt tacccaactt 1200
aatcgccttg cagcacatcc ccctttcgcc agctggcgta atagcgaaga ggcccgcacc 1260
gatcgccctt cccaacagtt gcgcagcctg aatggcgaat ggcgctttgc ctggtttccg 1320
gcaccagaag cggtgccgga aagctggctg gagtgcgatc ttcctgaggc cgatactgtc 1380
gtcgtcccct caaactggca gatgcacggt tacgatgcgc ccatctacac caacgtgacc 1440
tatcccatta cggtcaatcc gccgtttgtt cccacggaga atccgacggg ttgttactcg 1500
ctcacattta atgttgatga aagctggcta caggaaggcc agacgcgaat tatttttgat 1560
ggcgttaact cggcgtttca tctgtggtgc aacgggcgct gggtcggtta cggccaggac 1620
agtcgtttgc cgtctgaatt tgacctgagc gcatttttac gcgccggaga aaaccgcctc 1680
gcggtgatgg tgctgcgctg gagtgacggc agttatctgg aagatcagga tatgtggcgg 1740
atgagcggca ttttccgtga cgtctcgttg ctgcataaac cgactacaca aatcagcgat 1800
ttccatgttg ccactcgctt taatgatgat ttcagccgcg ctgtactgga ggctgaagtt 1860
cagatgtgcg gcgagttgcg tgactaccta cgggtaacag tttctttatg gcagggtgaa 1920
acgcaggtcg ccagcggcac cgcgcctttc ggcggtgaaa ttatcgatga gcgtggtggt 1980
tatgccgatc gcgtcacact acgtctgaac gtcgaaaacc cgaaactgtg gagcgccgaa 2040
atcccgaatc tctatcgtgc ggtggttgaa ctgcacaccg ccgacggcac gctgattgaa 2100
gcagaagcct gcgatgtcgg tttccgcgag gtgcggattg aaaatggtct gctgctgctg 2160

```
aacggcaagc cgttgctgat tcgaggcgtt aaccgtcacg agcatcatcc tctgcatggt   2220

caggtcatgg atgagcagac gatggtgcag gatatcctgc tgatgaagca gaacaacttt   2280

aacgccgtgc gctgttcgca ttatccgaac catccgctgt ggtacacgct gtgcgaccgc   2340

tacggcctgt atgtggtgga tgaagccaat attgaaaccc acggcatggt gccaatgaat   2400

cgtctgaccg atgatccgcg ctggctaccg gcgatgagcg aacgcgtaac gcgaatggtg   2460

cagcgcgatc gtaatcaccc gagtgtgatc atctggtcgc tggggaatga atcaggccac   2520

ggcgctaatc acgacgcgct gtatcgctgg atcaaatctg tcgatccttc ccgcccggtg   2580

cagtatgaag gcggcggagc cgacaccacg gccaccgata ttatttgccc gatgtacgcg   2640

cgcgtggatg aagaccagcc cttcccggct gtgccgaaat ggtccatcaa aaaatggctt   2700

tcgctacctg gagagacgcg cccgctgatc ctttgcgaat acgcccacgc gatgggtaac   2760

agtcttggcg gtttcgctaa atactggcag gcgtttcgtc agtatccccg tttacagggc   2820

ggcttcgtct gggactgggt ggatcagtcg ctgattaaat atgatgaaaa cggcaacccg   2880

tggtcggctt acggcggtga ttttggcgat acgccgaacg atcgccagtt ctgtatgaac   2940

ggtctggtct ttgccgaccg cacgccgcat ccagcgctga cggaagcaaa acaccagcag   3000

cagtttttcc agttccgttt atccgggcaa accatcgaag tgaccagcga atacctgttc   3060

cgtcatagcg ataacgagct cctgcactgg atggtggcgc tggatggtaa gccgctggca   3120

agcggtgaag tgcctctgga tgtcgctcca caaggtaaac agttgattga actgcctgaa   3180

ctaccgcagc cggagagcgc cgggcaactc tggctcacag tacgcgtagt gcaaccgaac   3240

gcgaccgcat ggtcagaagc cggccacatc agcgcctggc agcagtggcg tctggcggaa   3300

aacctcagtg tgacgctccc cgccgcgtcc cacgccatcc cgcatctgac caccagcgaa   3360

atggattttt gcatcgagct gggtaataag cgttggcaat ttaaccgcca gtcaggcttt   3420

ctttcacaga tgtggattgg cgataaaaaa caactgctga cgccgctgcg cgatcagttc   3480

acccgtgcac cgctggataa cgacattggc gtaagtgaag cgacccgcat tgaccctaac   3540

gcctgggtcg aacgctggaa ggcggcgggc cattaccagg ccgaagcagc gttgttgcag   3600

tgcacggcag atacacttgc tgatgcggtg ctgattacga ccgctcacgc gtggcagcat   3660

caggggaaaa ccttatttat cagccggaaa acctaccgga ttgatggtag tggtcaaatg   3720

gcgattaccg ttgatgttga agtggcgagc gatacaccgc atccggcgcg gattggcctg   3780

aactgccagc tggcgcaggt agcagagcgg gtaaactggc tcggattagg gccgcaagaa   3840

aactatcccg accgccttac tgccgcctgt tttgaccgct gggatctgcc attgtcagac   3900

atgtataccc cgtacgtctt cccgagcgaa aacggtctgc gctgcgggac gcgcgaattg   3960

aattatggcc cacaccagtg gcgcggcgac ttccagttca acatcagccg ctacagtcaa   4020

cagcaactga tggaaaccag ccatcgccat ctgctgcacg cggaagaagg cacatggctg   4080

aatatcgacg gtttccatat ggggattggt ggcgacgact cctggagccc gtcagtatcg   4140

gcggaattac agctgagcgc cggtcgctac cattaccagt tggtctggtg tcaaaaataa   4200

taataaccgg gcaggccatg tctgcccgta tttcgcgtaa ggaaatccat tatgtactat   4260

ttaaaaaaca caaacttttg gatgttcggt ttattctttt tcttttactt ttttatcatg   4320

ggagcctact tcccgttttt cccgatttgg ctacatgaca tcaaccatat cagcaaaagt   4380

gatacgggta ttatttttgc cgctatttct ctgttctcgc tattattcca accgctgttt   4440

ggtctgcttt ctgacaaact cggcctcgac tctaggcggc cgcggggatc cagacatgat   4500
```

```
aagatacatt gatgagtttg gacaaaccac aactagaatg cagtgaaaaa aatgctttat   4560
ttgtgaaatt tgtgatgcta ttgctttatt tgtaaccatt ataagctgca ataaacaagt   4620
taacaacaac aattgcattc attttatgtt tcaggttcag ggggaggtgt gggaggtttt   4680
ttcggatcct ctagagtcga cctgcaggca tgcaagcttg gcgtaatcat ggtcatagct   4740
gtttcctgtg tgaaattgtt atccgctcac aattccacac aacatacgag ccggaagcat   4800
aaagtgtaaa gcctggggtg cctaatgagt gagctaactc acattaattg cgttgcgctc   4860
actgcccgct ttccagtcgg gaaacctgtc gtgccagctg cattaatgaa tcggccaacg   4920
cgcggggaga ggcggtttgc gtattgggcg ctcttccgct tcctcgctca ctgactcgct   4980
gcgctcggtc gttcggctgc ggcgagcggt atcagctcac tcaaaggcgg taatacggtt   5040
atccacagaa tcaggggata acgcaggaaa gaacatgtga gcaaaaggcc agcaaaaggc   5100
caggaaccgt aaaaaggccg cgttgctggc gtttttccat aggctccgcc cccctgacga   5160
gcatcacaaa aatcgacgct caagtcagag gtggcgaaac ccgacaggac tataaagata   5220
ccaggcgttt ccccctggaa gctccctcgt gcgctctcct gttccgaccc tgccgcttac   5280
cggatacctg tccgcctttc tcccttcggg aagcgtggcg ctttctcata gctcacgctg   5340
taggtatctc agttcggtgt aggtcgttcg ctccaagctg ggctgtgtgc acgaaccccc   5400
cgttcagccc gaccgctgcg ccttatccgg taactatcgt cttgagtcca acccggtaag   5460
acacgactta tcgccactgg cagcagccac tggtaacagg attagcagag cgaggtatgt   5520
aggcggtgct acagagttct tgaagtggtg gcctaactac ggctacacta gaaggacagt   5580
atttggtatc tgcgctctgc tgaagccagt taccttcgga aaaagagttg gtagctcttg   5640
atccggcaaa caaaccaccg ctggtagcgg tggttttttt gtttgcaagc agcagattac   5700
gcgcagaaaa aaaggatctc aagaagatcc tttgatcttt tctacggggt ctgacgctca   5760
gtggaacgaa aactcacgtt aagggatttt ggtcatgaga ttatcaaaaa ggatcttcac   5820
ctagatcctt ttaaattaaa aatgaagttt taaatcaatc taaagtatat atgagtaaac   5880
ttggtctgac agttaccaat gcttaatcag tgaggcacct atctcagcga tctgtctatt   5940
tcgttcatcc atagttgcct gactccccgt cgtgtagata actacgatac gggagggctt   6000
accatctggc cccagtgctg caatgatacc gcgagaccca cgctcaccgg ctccagattt   6060
atcagcaata aaccagccag ccggaagggc cgagcgcaga agtggtcctg caactttatc   6120
cgcctccatc cagtctatta attgttgccg ggaagctaga gtaagtagtt cgccagttaa   6180
tagtttgcgc aacgttgttg ccattgctac aggcatcgtg gtgtcacgct cgtcgtttgg   6240
tatggcttca ttcagctccg gttcccaacg atcaaggcga gttacatgat cccccatgtt   6300
gtgcaaaaaa gcggttagct ccttcggtcc tccgatcgtt gtcagaagta agttggccgc   6360
agtgttatca ctcatggtta tggcagcact gcataattct cttactgtca tgccatccgt   6420
aagatgcttt tctgtgactg gtgagtactc aaccaagtca ttctgagaat agtgtatgcg   6480
gcgaccgagt tgctcttgcc cggcgtcaat acgggataat accgcgccac atagcagaac   6540
tttaaaagtg ctcatcattg gaaaacgttc ttcggggcga aaactctcaa ggatcttacc   6600
gctgttgaga tccagttcga tgtaacccac tcgtgcaccc aactgatctt cagcatcttt   6660
tactttcacc agcgtttctg ggtgagcaaa aacaggaagg caaaatgccg caaaaaaggg   6720
aataagggcg acacggaaat gttgaatact catactcttc ctttttcaat attattgaag   6780
catttatcag ggttattgtc tcatgagcgg atacatattt gaatgtattt agaaaaataa   6840
acaaataggg gttccgcgca catttccccg aaaagtgcca cctgacgtct aagaaaccat   6900
```

```
tattatcatg acattaacct ataaaaatag gcgtatcacg aggccctttc gtctcgcgcg   6960

tttcggtgat gacggtgaaa acctctgaca catgcagctc ccggagacgg tcacagcttg   7020

tctgtaagcg gatgccggga gcagacaagc ccgtcagggc gcgtcagcgg gtgttggcgg   7080

gtgtcggggc tggcttaact atgcggcatc agagcagatt gtactgagag tgcaccatat   7140

gcggtgtgaa ataccgcaca gatgcgtaag gagaaaatac cgcatcaggc gccattcgcc   7200

attcaggctg cgcaactgtt gggaagggcg atcggtgcgg gcctcttcgc tattacgcca   7260

gctggcgaaa gggggatgtg ctgcaaggcg attaagttgg gtaacgccag ggttttccca   7320

gtcacgacgt tgtaaaacga cggccagtga attcgagctt gcatgcctgc aggt         7374
```

```
<210> SEQ ID NO 47
<211> LENGTH: 7377
<212> TYPE: DNA
<213> ORGANISM: Artificial sequence
<220> FEATURE:
<223> OTHER INFORMATION: TalRab2-Reporter

<400> SEQUENCE: 47

cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtgatg cggttttggc agtacatcaa tgggcgtgga tagcggtttg actcacgggg    360

atttccaagt ctccacccca ttgacgtcaa tgggagtttg ttttggcacc aaaatcaacg    420

ggactttcca aaatgtcgta acaactccgc cccattgacg caaatgggcg gtaggcgtgt    480

acggtgggag gtctatataa gcagagctcg tttagtgaac cgtcagatcg cctggagacg    540

ccatccacgc tgttttgacc tccatagaag acaccgggac cgatccagcc tccggactct    600

agaggatccg gtactcgacg acactgcaga gacctacttc actaacaacc ggtatggtcg    660

cgagtagctt ggcactggcc gtcgttttac aacgtcgtga ctgggaaaac cctggcgtta    720

cccaacttaa tcgccttgca gcacatcccc ctttcgccag ctggcgtaat agcgaagagg    780

cccgcaccga tcgcccttcc caacagttgc gcagcctgaa tggcgaatgg cgctttgcct    840

ggtttccggc accagaagcg gtgccggaaa gctggctgga gtgcgatctt cctgaggccg    900

atactgtcgt cgtcccctca aactggcaga tgcacggtta cgatgcgccc atctacacca    960

acgtgaccta tcccattacg gtcaatccgc cgtttgttcc cacggagaat ccgacgggtt   1020

gttactcgct cacatttaat gttgatgaaa gctggctata aaaccggtac agttcggcca   1080

ccatggtcga tggtggcccg gtagttttca cactcttctc actaccgggc caccacgagt   1140

agcttggcac tggccgtcgt tttacaacgt cgtgactggg aaaaccctgg cgttacccaa   1200

cttaatcgcc ttgcagcaca tccccctttc gccagctggc gtaatagcga agaggcccgc   1260

accgatcgcc cttcccaaca gttgcgcagc ctgaatggcg aatggcgctt tgcctggttt   1320

ccggcaccag aagcggtgcc ggaaagctgg ctggagtgcg atcttcctga ggccgatact   1380

gtcgtcgtcc cctcaaactg gcagatgcac ggttacgatg cgcccatcta caccaacgtg   1440

acctatccca ttacggtcaa tccgccgttt gttcccacgg agaatccgac gggttgttac   1500

tcgctcacat ttaatgttga tgaaagctgg ctacaggaag gccagacgcg aattattttt   1560
```

```
gatggcgtta actcggcgtt tcatctgtgg tgcaacgggc gctgggtcgg ttacggccag   1620
gacagtcgtt tgccgtctga atttgacctg agcgcatttt tacgcgccgg agaaaaccgc   1680
ctcgcggtga tggtgctgcg ctggagtgac ggcagttatc tggaagatca ggatatgtgg   1740
cggatgagcg gcattttccg tgacgtctcg ttgctgcata aaccgactac acaaatcagc   1800
gatttccatg ttgccactcg ctttaatgat gatttcagcc gcgctgtact ggaggctgaa   1860
gttcagatgt gcggcgagtt gcgtgactac ctacgggtaa cagtttcttt atggcagggt   1920
gaaacgcagg tcgccagcgg caccgcgcct ttcggcggtg aaattatcga tgagcgtggt   1980
ggttatgccg atcgcgtcac actacgtctg aacgtcgaaa acccgaaact gtggagcgcc   2040
gaaatcccga atctctatcg tgcggtggtt gaactgcaca ccgccgacgg cacgctgatt   2100
gaagcagaag cctgcgatgt cggtttccgc gaggtgcgga ttgaaaatgg tctgctgctg   2160
ctgaacggca agccgttgct gattcgaggc gttaaccgtc acgagcatca tcctctgcat   2220
ggtcaggtca tggatgagca gacgatggtg caggatatcc tgctgatgaa gcagaacaac   2280
tttaacgccg tgcgctgttc gcattatccg aaccatccgc tgtggtacac gctgtgcgac   2340
cgctacggcc tgtatgtggt ggatgaagcc aatattgaaa cccacggcat ggtgccaatg   2400
aatcgtctga ccgatgatcc gcgctggcta ccggcgatga gcgaacgcgt aacgcgaatg   2460
gtgcagcgcg atcgtaatca cccgagtgtg atcatctggt cgctggggaa tgaatcaggc   2520
cacggcgcta atcacgacgc gctgtatcgc tggatcaaat ctgtcgatcc ttcccgcccg   2580
gtgcagtatg aaggcggcgg agccgacacc acggccaccg atattatttg cccgatgtac   2640
gcgcgcgtgg atgaagacca gcccttcccg gctgtgccga aatggtccat caaaaaatgg   2700
ctttcgctac ctggagagac gcgcccgctg atcctttgcg aatacgccca cgcgatgggt   2760
aacagtcttg gcggtttcgc taaatactgg caggcgtttc gtcagtatcc ccgtttacag   2820
ggcggcttcg tctgggactg ggtggatcag tcgctgatta aatatgatga aaacggcaac   2880
ccgtggtcgg cttacggcgg tgattttggc gatacgccga acgatcgcca gttctgtatg   2940
aacggtctgg tctttgccga ccgcacgccg catccagcgc tgacggaagc aaaacaccag   3000
cagcagtttt tccagttccg tttatccggg caaaccatcg aagtgaccag cgaatacctg   3060
ttccgtcata gcgataacga gctcctgcac tggatggtgg cgctggatgg taagccgctg   3120
gcaagcggtg aagtgcctct ggatgtcgct ccacaaggta aacagttgat tgaactgcct   3180
gaactaccgc agccggagag cgccgggcaa ctctggctca cagtacgcgt agtgcaaccg   3240
aacgcgaccg catggtcaga agccgggcac atcagcgcct ggcagcagtg gcgtctggcg   3300
gaaaacctca gtgtgacgct ccccgccgcg tcccacgcca tcccgcatct gaccaccagc   3360
gaaatggatt tttgcatcga gctgggtaat aagcgttggc aatttaaccg ccagtcaggc   3420
tttctttcac agatgtggat tggcgataaa aaacaactgc tgacgccgct gcgcgatcag   3480
ttcacccgtg caccgctgga taacgacatt ggcgtaagtg aagcgacccg cattgaccct   3540
aacgcctggg tcgaacgctg gaaggcggcg ggccattacc aggccgaagc agcgttgttg   3600
cagtgcacgg cagatacact tgctgatgcg gtgctgatta cgaccgctca cgcgtggcag   3660
catcagggga aaaccttatt tatcagccgg aaaacctacc ggattgatgg tagtggtcaa   3720
atggcgatta ccgttgatgt tgaagtggcg agcgatacac cgcatccggc gcggattggc   3780
ctgaactgcc agctggcgca ggtagcagag cgggtaaact ggctcggatt agggccgcaa   3840
gaaaactatc ccgaccgcct tactgccgcc tgttttgacc gctgggatct gccattgtca   3900
gacatgtata ccccgtacgt cttcccgagc gaaaacggtc tgcgctgcgg gacgcgcgaa   3960
```

```
ttgaattatg gcccacacca gtggcgcggc gacttccagt tcaacatcag ccgctacagt   4020
caacagcaac tgatggaaac cagccatcgc catctgctgc acgcggaaga aggcacatgg   4080
ctgaatatcg acggtttcca tatggggatt ggtggcgacg actcctggag cccgtcagta   4140
tcggcggaat tacagctgag cgccggtcgc taccattacc agttggtctg gtgtcaaaaa   4200
taataataac cgggcaggcc atgtctgccc gtatttcgcg taaggaaatc cattatgtac   4260
tatttaaaaa acacaaactt ttggatgttc ggtttattct ttttctttta ctttttttatc   4320
atgggagcct acttcccgtt tttcccgatt tggctacatg acatcaacca tatcagcaaa   4380
agtgatacgg gtattatttt tgccgctatt tctctgttct cgctattatt ccaaccgctg   4440
tttggtctgc tttctgacaa actcggcctc gactctaggc ggccgcgggg atccagacat   4500
gataagatac attgatgagt ttggacaaac cacaactaga atgcagtgaa aaaaatgctt   4560
tatttgtgaa atttgtgatg ctattgcttt atttgtaacc attataagct gcaataaaca   4620
agttaacaac aacaattgca ttcattttat gtttcaggtt cagggggagg tgtgggaggt   4680
tttttcggat cctctagagt cgacctgcag gcatgcaagc ttggcgtaat catggtcata   4740
gctgtttcct gtgtgaaatt gttatccgct cacaattcca cacaacatac gagccggaag   4800
cataaagtgt aaagcctggg gtgcctaatg agtgagctaa ctcacattaa ttgcgttgcg   4860
ctcactgccc gctttccagt cgggaaacct gtcgtgccag ctgcattaat gaatcggcca   4920
acgcgcgggg agaggcggtt tgcgtattgg gcgctcttcc gcttcctcgc tcactgactc   4980
gctgcgctcg gtcgttcggc tgcggcgagc ggtatcagct cactcaaagg cggtaatacg   5040
gttatccaca gaatcagggg ataacgcagg aaagaacatg tgagcaaaag gccagcaaaa   5100
ggccaggaac cgtaaaaagg ccgcgttgct ggcgtttttc cataggctcc gcccccctga   5160
cgagcatcac aaaaatcgac gctcaagtca gaggtggcga aacccgacag gactataaag   5220
ataccaggcg tttccccctg gaagctccct cgtgcgctct cctgttccga ccctgccgct   5280
taccggatac ctgtccgcct ttctcccttc gggaagcgtg gcgctttctc atagctcacg   5340
ctgtaggtat ctcagttcgg tgtaggtcgt tcgctccaag ctgggctgtg tgcacgaacc   5400
ccccgttcag cccgaccgct gcgccttatc cggtaactat cgtcttgagt ccaacccggt   5460
aagacacgac ttatcgccac tggcagcagc cactggtaac aggattagca gagcgaggta   5520
tgtaggcggt gctacagagt tcttgaagtg gtggcctaac tacggctaca ctagaaggac   5580
agtatttggt atctgcgctc tgctgaagcc agttaccttc ggaaaaagag ttggtagctc   5640
ttgatccggc aaacaaacca ccgctggtag cggtggtttt tttgtttgca agcagcagat   5700
tacgcgcaga aaaaaaggat ctcaagaaga tcctttgatc ttttctacgg ggtctgacgc   5760
tcagtggaac gaaaactcac gttaagggat tttggtcatg agattatcaa aaaggatctt   5820
cacctagatc cttttaaatt aaaaatgaag ttttaaatca atctaaagta tatatgagta   5880
aacttggtct gacagttacc aatgcttaat cagtgaggca cctatctcag cgatctgtct   5940
atttcgttca tccatagttg cctgactccc cgtcgtgtag ataactacga tacgggaggg   6000
cttaccatct ggccccagtg ctgcaatgat accgcgagac ccacgctcac cggctccaga   6060
tttatcagca ataaaccagc cagccggaag ggccgagcgc agaagtggtc ctgcaacttt   6120
atccgcctcc atccagtcta ttaattgttg ccgggaagct agagtaagta gttcgccagt   6180
taatagtttg cgcaacgttg ttgccattgc tacaggcatc gtggtgtcac gctcgtcgtt   6240
tggtatggct tcattcagct ccggttccca acgatcaagg cgagttacat gatcccccat   6300
```

gttgtgcaaa aaagcggtta gctccttcgg tcctccgatc gttgtcagaa gtaagttggc 6360
cgcagtgtta tcactcatgg ttatggcagc actgcataat tctcttactg tcatgccatc 6420
cgtaagatgc ttttctgtga ctggtgagta ctcaaccaag tcattctgag aatagtgtat 6480
gcggcgaccg agttgctctt gcccggcgtc aatacgggat aataccgcgc cacatagcag 6540
aactttaaaa gtgctcatca ttggaaaacg ttcttcgggg cgaaaactct caaggatctt 6600
accgctgttg agatccagtt cgatgtaacc cactcgtgca cccaactgat cttcagcatc 6660
ttttactttc accagcgttt ctgggtgagc aaaaacagga aggcaaaatg ccgcaaaaaa 6720
gggaataagg gcgacacgga aatgttgaat actcatactc ttcctttttc aatattattg 6780
aagcatttat cagggttatt gtctcatgag cggatacata tttgaatgta tttagaaaaa 6840
taaacaaata ggggttccgc gcacatttcc ccgaaaagtg ccacctgacg tctaagaaac 6900
cattattatc atgacattaa cctataaaaa taggcgtatc acgaggccct ttcgtctcgc 6960
gcgtttcggt gatgacggtg aaaacctctg acacatgcag ctcccggaga cggtcacagc 7020
ttgtctgtaa gcggatgccg ggagcagaca agcccgtcag ggcgcgtcag cgggtgttgg 7080
cgggtgtcgg ggctggctta actatgcggc atcagagcag attgtactga gagtgcacca 7140
tatgcggtgt gaaataccgc acagatgcgt aaggagaaaa taccgcatca ggcgccattc 7200
gccattcagg ctgcgcaact gttgggaagg gcgatcggtg cgggcctctt cgctattacg 7260
ccagctggcg aaagggggat gtgctgcaag gcgattaagt tgggtaacgc cagggttttc 7320
ccagtcacga cgttgtaaaa cgacggccag tgaattcgag cttgcatgcc tgcaggt 7377

<210> SEQ ID NO 48
<211> LENGTH: 7383
<212> TYPE: DNA
<213> ORGANISM: Artificial sequence
<220> FEATURE:
<223> OTHER INFORMATION: ArtTal1/TalRab2-Reporter

<400> SEQUENCE: 48
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagctcg tttagtgaac cgtcagatcg cctggagacg 540
ccatccacgc tgttttgacc tccatagaag acaccgggac cgatccagcc tccggactct 600
agaggatccg gtactcgagg acactgcaga gacctacttc actaacaacc ggtatggtcg 660
cgagtagctt ggcactggcc gtcgttttac aacgtcgtga ctgggaaaac cctggcgtta 720
cccaacttaa tcgccttgca gcacatcccc ctttcgccag ctggcgtaat agcgaagagg 780
cccgcaccga tcgcccttcc caacagttgc gcagcctgaa tggcgaatgg cgctttgcct 840
ggtttccggc accagaagcg gtgccggaaa gctggctgga gtgcgatctt cctgaggccg 900
atactgtcgt cgtcccctca aactggcaga tgcacggtta cgatgcgccc atctacacca 960
acgtgaccta tcccattacg gtcaatccgc cgtttgttcc cacggagaat ccgacgggtt 1020

```
gttactcgct cacatttaat gttgatgaaa gctggctata aaaccggtac agttcggcca   1080
ccatggtcgt attctgggac gtttttcaca ctcttctaaa ctaccgggcc accacgggtc   1140
gcgagtagct tggcactggc cgtcgtttta caacgtcgtg actgggaaaa ccctggcgtt   1200
acccaactta atcgccttgc agcacatccc cctttcgcca gctggcgtaa tagcgaagag   1260
gcccgcaccg atcgcccttc ccaacagttg cgcagcctga atggcgaatg gcgctttgcc   1320
tggtttccgg caccagaagc ggtgccggaa agctggctgg agtgcgatct tcctgaggcc   1380
gatactgtcg tcgtcccctc aaactggcag atgcacggtt acgatgcgcc catctacacc   1440
aacgtgacct atcccattac ggtcaatccg ccgtttgttc ccacggagaa tccgacgggt   1500
tgttactcgc tcacatttaa tgttgatgaa agctggctac aggaaggcca gacgcgaatt   1560
atttttgatg gcgttaactc ggcgtttcat ctgtggtgca acgggcgctg ggtcggttac   1620
ggccaggaca gtcgtttgcc gtctgaattt gacctgagcg catttttacg cgccggagaa   1680
aaccgcctcg cggtgatggt gctgcgctgg agtgacggca gttatctgga agatcaggat   1740
atgtggcgga tgagcggcat tttccgtgac gtctcgttgc tgcataaacc gactacacaa   1800
atcagcgatt tccatgttgc cactcgcttt aatgatgatt tcagccgcgc tgtactggag   1860
gctgaagttc agatgtgcgg cgagttgcgt gactacctac gggtaacagt ttctttatgg   1920
cagggtgaaa cgcaggtcgc cagcggcacc gcgcctttcg gcggtgaaat tatcgatgag   1980
cgtggtggtt atgccgatcg cgtcacacta cgtctgaacg tcgaaaaccc gaaactgtgg   2040
agcgccgaaa tcccgaatct ctatcgtgcg gtggttgaac tgcacaccgc cgacggcacg   2100
ctgattgaag cagaagcctg cgatgtcggt ttccgcgagg tgcggattga aaatggtctg   2160
ctgctgctga acggcaagcc gttgctgatt cgaggcgtta accgtcacga gcatcatcct   2220
ctgcatggtc aggtcatgga tgagcagacg atggtgcagg atatcctgct gatgaagcag   2280
aacaacttta acgccgtgcg ctgttcgcat tatccgaacc atccgctgtg gtacacgctg   2340
tgcgaccgct acggcctgta tgtggtggat gaagccaata ttgaaaccca cggcatggtg   2400
ccaatgaatc gtctgaccga tgatccgcgc tggctaccgg cgatgagcga acgcgtaacg   2460
cgaatggtgc agcgcgatcg taatcacccg agtgtgatca tctggtcgct ggggaatgaa   2520
tcaggccacg gcgctaatca cgacgcgctg tatcgctgga tcaaatctgt cgatccttcc   2580
cgcccggtgc agtatgaagg cggcggagcc gacaccacgg ccaccgatat tatttgcccg   2640
atgtacgcgc gcgtggatga agaccagccc ttcccggctg tgccgaaatg gtccatcaaa   2700
aaatggcttt cgctacctgg agagacgcgc ccgctgatcc tttgcgaata cgcccacgcg   2760
atgggtaaca gtcttggcgg tttcgctaaa tactggcagg cgtttcgtca gtatccccgt   2820
ttacagggcg gcttcgtctg ggactgggtg gatcagtcgc tgattaaata tgatgaaaac   2880
ggcaacccgt ggtcggctta cggcggtgat tttggcgata cgccgaacga tcgccagttc   2940
tgtatgaacg gtctggtctt tgccgaccgc acgccgcatc cagcgctgac ggaagcaaaa   3000
caccagcagc agtttttcca gttccgttta tccgggcaaa ccatcgaagt gaccagcgaa   3060
tacctgttcc gtcatagcga taacgagctc ctgcactgga tggtggcgct ggatggtaag   3120
ccgctggcaa gcggtgaagt gcctctggat gtcgctccac aaggtaaaca gttgattgaa   3180
ctgcctgaac taccgcagcc ggagagcgcc gggcaactct ggctcacagt acgcgtagtg   3240
caaccgaacg cgaccgcatg gtcagaagcc gggcacatca gcgcctggca gcagtggcgt   3300
ctggcggaaa acctcagtgt gacgctcccc gccgcgtccc acgccatccc gcatctgacc   3360
```

```
accagcgaaa tggatttttg catcgagctg ggtaataagc gttggcaatt taaccgccag   3420
tcaggctttc tttcacagat gtggattggc gataaaaaac aactgctgac gccgctgcgc   3480
gatcagttca cccgtgcacc gctggataac gacattggcg taagtgaagc gacccgcatt   3540
gaccctaacg cctgggtcga acgctggaag gcggcgggcc attaccaggc cgaagcagcg   3600
ttgttgcagt gcacggcaga tacacttgct gatgcggtgc tgattacgac cgctcacgcg   3660
tggcagcatc aggggaaaac cttatttatc agccggaaaa cctaccggat tgatggtagt   3720
ggtcaaatgg cgattaccgt tgatgttgaa gtggcgagcg atacaccgca tccggcgcgg   3780
attggcctga actgccagct ggcgcaggta gcagagcggg taaactggct cggattaggg   3840
ccgcaagaaa actatcccga ccgccttact gccgcctgtt ttgaccgctg ggatctgcca   3900
ttgtcagaca tgtatacccc gtacgtcttc ccgagcgaaa acggtctgcg ctgcgggacg   3960
cgcgaattga attatggccc acaccagtgg cgcggcgact tccagttcaa catcagccgc   4020
tacagtcaac agcaactgat ggaaaccagc catcgccatc tgctgcacgc ggaagaaggc   4080
acatggctga atatcgacgg tttccatatg gggattggtg gcgacgactc ctggagcccg   4140
tcagtatcgg cggaattaca gctgagcgcc ggtcgctacc attaccagtt ggtctggtgt   4200
caaaaataat aataaccggg caggccatgt ctgcccgtat ttcgcgtaag gaaatccatt   4260
atgtactatt taaaaaacac aaacttttgg atgttcggtt tattcttttt cttttacttt   4320
tttatcatgg gagcctactt cccgtttttc ccgatttggc tacatgacat caaccatatc   4380
agcaaaagtg atacgggtat tatttttgcc gctatttctc tgttctcgct attattccaa   4440
ccgctgtttg gtctgctttc tgacaaactc ggcctcgact ctaggcggcc gcggggatcc   4500
agacatgata agatacattg atgagtttgg acaaaccaca actagaatgc agtgaaaaaa   4560
atgctttatt tgtgaaattt gtgatgctat tgctttattt gtaaccatta taagctgcaa   4620
taaacaagtt aacaacaaca attgcattca ttttatgttt caggttcagg gggaggtgtg   4680
ggaggttttt tcggatcctc tagagtcgac ctgcaggcat gcaagcttgg cgtaatcatg   4740
gtcatagctg tttcctgtgt gaaattgtta tccgctcaca attccacaca acatacgagc   4800
cggaagcata aagtgtaaag cctggggtgc ctaatgagtg agctaactca cattaattgc   4860
gttgcgctca ctgcccgctt tccagtcggg aaacctgtcg tgccagctgc attaatgaat   4920
cggccaacgc gcggggagag gcggtttgcg tattgggcgc tcttccgctt cctcgctcac   4980
tgactcgctg cgctcggtcg ttcggctgcg gcgagcggta tcagctcact caaaggcggt   5040
aatacggtta tccacagaat caggggataa cgcaggaaag aacatgtgag caaaaggcca   5100
gcaaaaggcc aggaaccgta aaaaggccgc gttgctggcg tttttccata ggctccgccc   5160
ccctgacgag catcacaaaa atcgacgctc aagtcagagg tggcgaaacc cgacaggact   5220
ataaagatac caggcgtttc cccctggaag ctccctcgtg cgctctcctg ttccgaccct   5280
gccgcttacc ggatacctgt ccgcctttct cccttcggga agcgtggcgc tttctcatag   5340
ctcacgctgt aggtatctca gttcggtgta ggtcgttcgc tccaagctgg gctgtgtgca   5400
cgaacccccc gttcagcccg accgctgcgc cttatccggt aactatcgtc ttgagtccaa   5460
cccggtaaga cacgacttat cgccactggc agcagccact ggtaacagga ttagcagagc   5520
gaggtatgta ggcggtgcta cagagttctt gaagtggtgg cctaactacg gctacactag   5580
aaggacagta tttggtatct gcgctctgct gaagccagtt accttcggaa aaagagttgg   5640
tagctcttga tccggcaaac aaaccaccgc tggtagcggt ggtttttttg tttgcaagca   5700
gcagattacg cgcagaaaaa aaggatctca agaagatcct ttgatctttt ctacggggtc   5760
```

```
tgacgctcag tggaacgaaa actcacgtta agggattttg gtcatgagat tatcaaaaag   5820
gatcttcacc tagatccttt taaattaaaa atgaagtttt aaatcaatct aaagtatata   5880
tgagtaaact tggtctgaca gttaccaatg cttaatcagt gaggcaccta tctcagcgat   5940
ctgtctattt cgttcatcca tagttgcctg actccccgtc gtgtagataa ctacgatacg   6000
ggagggctta ccatctggcc ccagtgctgc aatgataccg cgagacccac gctcaccggc   6060
tccagattta tcagcaataa accagccagc cggaagggcc gagcgcagaa gtggtcctgc   6120
aactttatcc gcctccatcc agtctattaa ttgttgccgg gaagctagag taagtagttc   6180
gccagttaat agtttgcgca acgttgttgc cattgctaca ggcatcgtgg tgtcacgctc   6240
gtcgtttggt atggcttcat tcagctccgg ttcccaacga tcaaggcgag ttacatgatc   6300
ccccatgttg tgcaaaaaag cggttagctc cttcggtcct ccgatcgttg tcagaagtaa   6360
gttggccgca gtgttatcac tcatggttat ggcagcactg cataattctc ttactgtcat   6420
gccatccgta agatgctttt ctgtgactgg tgagtactca accaagtcat tctgagaata   6480
gtgtatgcgg cgaccgagtt gctcttgccc ggcgtcaata cgggataata ccgcgccaca   6540
tagcagaact ttaaaagtgc tcatcattgg aaaacgttct tcggggcgaa aactctcaag   6600
gatcttaccg ctgttgagat ccagttcgat gtaacccact cgtgcaccca actgatcttc   6660
agcatctttt actttcacca gcgtttctgg gtgagcaaaa acaggaaggc aaaatgccgc   6720
aaaaaaggga ataagggcga cacggaaatg ttgaatactc atactcttcc tttttcaata   6780
ttattgaagc atttatcagg gttattgtct catgagcgga tacatatttg aatgtattta   6840
gaaaaataaa caaatagggg ttccgcgcac atttccccga aaagtgccac ctgacgtcta   6900
agaaaccatt attatcatga cattaaccta taaaaatagg cgtatcacga ggccctttcg   6960
tctcgcgcgt ttcggtgatg acggtgaaaa cctctgacac atgcagctcc cggagacggt   7020
cacagcttgt ctgtaagcgg atgccgggag cagacaagcc cgtcagggcg cgtcagcggg   7080
tgttggcggg tgtcggggct ggcttaacta tgcggcatca gagcagattg tactgagagt   7140
gcaccatatg cggtgtgaaa taccgcacag atgcgtaagg agaaaatacc gcatcaggcg   7200
ccattcgcca ttcaggctgc gcaactgttg ggaagggcga tcggtgcggg cctcttcgct   7260
attacgccag ctggcgaaag ggggatgtgc tgcaaggcga ttaagttggg taacgccagg   7320
gttttcccag tcacgacgtt gtaaaacgac ggccagtgaa ttcgagcttg catgcctgca   7380
ggt                                                                 7383
```

<210> SEQ ID NO 49
<211> LENGTH: 5566
<212> TYPE: DNA
<213> ORGANISM: Artificial sequence
<220> FEATURE:
<223> OTHER INFORMATION: pCMV-hLuc

<400> SEQUENCE: 49

```
ggtaccgagc tcttacgcgt gctagcccgg gctcgaggag cttggcccat tgcatacgtt     60
gtatccatat cataatatgt acatttatat tggctcatgt ccaacattac cgccatgttg    120
acattgatta ttgactagtt attaatagta atcaattacg gggtcattag ttcatagccc    180
atatatggag ttccgcgtta cataacttac ggtaaatggc ccgcctggct gaccgcccaa    240
cgacccccgc ccattgacgt caataatgac gtatgttccc atagtaacgc caatagggac    300
tttccattga cgtcaatggg tggagtattt acgctaaact gcccacttgg cagtacatca    360
```

-continued

```
agtgtatcat atgccaagta cgccccctat tgacgtcaat gacggtaaat ggcccgcctg    420
gcattatgcc cagtacatga ccttatggga ctttcctact tggcagtaca tctacgtatt    480
agtcatcgct attaccatgg tgatgcggtt ttggcagtac atcaatgggc gtggatagcg    540
gtttgactca cggggatttc caagtctcca ccccattgac gtcaatggga gtttgttttg    600
gcaccaaaat caacgggact ttccaaaatg tcgtaacaac tccgccccat tgacgcaaat    660
gggcggtagg cgtgtacggt gggaggtcta tataagcaga gctcgtttag tgaaccgtca    720
gatcgcctgg agacgccatc cacgctgttt tgacctccat agaagacacc gggaccgatc    780
cagcctccgc ggccccgaat tagcttggca ttccggtact gttggtaaag ccaccatgga    840
agacgccaaa aacataaaga aaggcccggc gccattctat ccgctggaag atggaaccgc    900
tggagagcaa ctgcataagg ctatgaagag atacgccctg gttcctggaa caattgcttt    960
tacagatgca catatcgagg tggacatcac ttacgctgag tacttcgaaa tgtccgttcg   1020
gttggcagaa gctatgaaac gatatgggct gaatacaaat cacagaatcg tcgtatgcag   1080
tgaaaactct cttcaattct ttatgccggt gttgggcgcg ttatttatcg gagttgcagt   1140
tgcgcccgcg aacgacattt ataatgaacg tgaattgctc aacagtatgg gcatttcgca   1200
gcctaccgtg gtgttcgttt ccaaaaaggg gttgcaaaaa attttgaacg tgcaaaaaaa   1260
gctcccaatc atccaaaaaa ttattatcat ggattctaaa acggattacc agggatttca   1320
gtcgatgtac acgttcgtca catctcatct acctcccggt tttaatgaat acgattttgt   1380
gccagagtcc ttcgataggg acaagacaat tgcactgatc atgaactcct ctggatctac   1440
tggtctgcct aaaggtgtcg ctctgcctca tagaactgcc tgcgtgagat tctcgcatgc   1500
cagagatcct atttttggca atcaaatcat tccggatact gcgattttaa gtgttgttcc   1560
attccatcac ggttttggaa tgtttactac actcggatat ttgatatgtg gatttcgagt   1620
cgtcttaatg tatagatttg aagaagagct gtttctgagg agccttcagg attacaagat   1680
tcaaagtgcg ctgctggtgc caaccctatt ctccttcttc gccaaaagca ctctgattga   1740
caaatacgat ttatctaatt tacacgaaat tgcttctggt ggcgctcccc tctctaagga   1800
agtcggggaa gcggttgcca agaggttcca tctgccaggt atcaggcaag gatatgggct   1860
cactgagact acatcagcta ttctgattac acccgagggg gatgataaac cgggcgcggt   1920
cggtaaagtt gttccatttt ttgaagcgaa ggttgtggat ctggataccg ggaaaacgct   1980
gggcgttaat caaagaggcg aactgtgtgt gagaggtcct atgattatgt ccggttatgt   2040
aaacaatccg gaagcgacca acgccttgat tgacaaggat ggatggctac attctggaga   2100
catagcttac tgggacgaag acgaacactt cttcatcgtt gaccgcctga agtctctgat   2160
taagtacaaa ggctatcagg tggctcccgc tgaattggaa tccatcttgc tccaacaccc   2220
caacatcttc gacgcaggtg tcgcaggtct tcccgacgat gacgccggtg aacttcccgc   2280
cgccgttgtt gttttggagc acggaaagac gatgacggaa aaagagatcg tggattacgt   2340
cgccagtcaa gtaacaaccg cgaaaaagtt gcgcggagga gttgtgtttg tggacgaagt   2400
accgaaaggt cttaccggaa aactcgacgc aagaaaaatc agagagatcc tcataaaggc   2460
caagaagggc ggaaagatcg ccgtgtaatt ctagagtcgg ggcggccggc cgcttcgagc   2520
agacatgata agatacattg atgagtttgg acaaaccaca actagaatgc agtgaaaaaa   2580
atgctttatt tgtgaaattt gtgatgctat tgctttattt gtaaccatta taagctgcaa   2640
taaacaagtt aacaacaaca attgcattca ttttatgttt caggttcagg gggaggtgtg   2700
ggaggttttt taaagcaagt aaaacctcta caaatgtggt aaaatcgata aggatccgtc   2760
```

```
gaccgatgcc cttgagagcc ttcaacccag tcagctcctt ccggtgggcg cggggcatga   2820
ctatcgtcgc cgcacttatg actgtcttct ttatcatgca actcgtagga caggtgccgg   2880
cagcgctctt ccgcttcctc gctcactgac tcgctgcgct cggtcgttcg gctgcggcga   2940
gcggtatcag ctcactcaaa ggcggtaata cggttatcca cagaatcagg ggataacgca   3000
ggaaagaaca tgtgagcaaa aggccagcaa aaggccagga accgtaaaaa ggccgcgttg   3060
ctggcgtttt tccataggct ccgcccccct gacgagcatc acaaaaatcg acgctcaagt   3120
cagaggtggc gaaacccgac aggactataa agataccagg cgtttccccc tggaagctcc   3180
ctcgtgcgct ctcctgttcc gaccctgccg cttaccggat acctgtccgc ctttctccct   3240
tcgggaagcg tggcgctttc tcatagctca cgctgtaggt atctcagttc ggtgtaggtc   3300
gttcgctcca agctgggctg tgtgcacgaa ccccccgttc agcccgaccg ctgcgcctta   3360
tccggtaact atcgtcttga gtccaacccg gtaagacacg acttatcgcc actggcagca   3420
gccactggta acaggattag cagagcgagg tatgtaggcg gtgctacaga gttcttgaag   3480
tggtggccta actacggcta cactagaaga acagtatttg gtatctgcgc tctgctgaag   3540
ccagttacct tcggaaaaag agttggtagc tcttgatccg gcaaacaaac caccgctggt   3600
agcggtggtt tttttgtttg caagcagcag attacgcgca gaaaaaaagg atctcaagaa   3660
gatcctttga tcttttctac ggggtctgac gctcagtgga acgaaaactc acgttaaggg   3720
attttggtca tgagattatc aaaaaggatc ttcacctaga tccttttaaa ttaaaaatga   3780
agttttaaat caatctaaag tatatatgag taaacttggt ctgacagtta ccaatgctta   3840
atcagtgagg cacctatctc agcgatctgt ctatttcgtt catccatagt tgcctgactc   3900
cccgtcgtgt agataactac gatacgggag ggcttaccat ctggccccag tgctgcaatg   3960
ataccgcgag acccacgctc accggctcca gatttatcag caataaacca gccagccgga   4020
agggccgagc gcagaagtgg tcctgcaact ttatccgcct ccatccagtc tattaattgt   4080
tgccgggaag ctagagtaag tagttcgcca gttaatagtt tgcgcaacgt tgttgccatt   4140
gctacaggca tcgtggtgtc acgctcgtcg tttggtatgg cttcattcag ctccggttcc   4200
caacgatcaa ggcgagttac atgatccccc atgttgtgca aaaaagcggt tagctccttc   4260
ggtcctccga tcgttgtcag aagtaagttg gccgcagtgt tatcactcat ggttatggca   4320
gcactgcata attctcttac tgtcatgcca tccgtaagat gcttttctgt gactggtgag   4380
tactcaacca agtcattctg agaatagtgt atgcggcgac cgagttgctc ttgcccggcg   4440
tcaatacggg ataataccgc gccacatagc agaactttaa aagtgctcat cattggaaaa   4500
cgttcttcgg ggcgaaaact ctcaaggatc ttaccgctgt tgagatccag ttcgatgtaa   4560
cccactcgtg cacccaactg atcttcagca tcttttactt tcaccagcgt ttctgggtga   4620
gcaaaaacag gaaggcaaaa tgccgcaaaa aagggaataa gggcgacacg gaaatgttga   4680
atactcatac tcttcctttt tcaatattat tgaagcattt atcagggtta ttgtctcatg   4740
agcggataca tatttgaatg tatttagaaa aataaacaaa taggggttcc gcgcacattt   4800
ccccgaaaag tgccacctga cgcgccctgt agcggcgcat taagcgcggc gggtgtggtg   4860
gttacgcgca gcgtgaccgc tacacttgcc agcgccctag cgcccgctcc tttcgctttc   4920
ttcccttcct ttctcgccac gttcgccggc tttccccgtc aagctctaaa tcgggggctc   4980
cctttagggt tccgatttag tgctttacgg cacctcgacc ccaaaaaact tgattagggt   5040
gatggttcac gtagtgggcc atcgccctga tagacggttt ttcgcccttt gacgttggag   5100
```

```
tccacgttct ttaatagtgg actcttgttc caaactggaa caacactcaa ccctatctcg   5160

gtctattctt ttgatttata agggattttg ccgatttcgg cctattggtt aaaaaatgag   5220

ctgatttaac aaaaatttaa cgcgaatttt aacaaaatat taacgcttac aatttgccat   5280

tcgccattca ggctgcgcaa ctgttgggaa gggcgatcgg tgcgggcctc ttcgctatta   5340

cgccagccca agctaccatg ataagtaagt aatattaagg tacgggaggt acttggagcg   5400

gccgcaataa aatatcttta ttttcattac atctgtgtgt tggttttttg tgtgaatcga   5460

tagtactaac atacgctctc catcaaaaca aaacgaaaca aaacaaacta gcaaaatagg   5520

ctgtccccag tgcaagtgca ggtgccagaa catttctcta tcgata                  5566
```

<210> SEQ ID NO 50
<211> LENGTH: 2961
<212> TYPE: DNA
<213> ORGANISM: Artificial sequence
<220> FEATURE:
<223> OTHER INFORMATION: pBS

<400> SEQUENCE: 50

```
gtaaaacgac ggccagtgag cgcgcgtaat acgactcact atagggcgaa ttggagctcc     60

accgcggtgg cggccgctct agaactagtg gatcccccgg gctgcaggaa ttcgatatca    120

agcttatcga taccgtcgac ctcgaggggg ggcccggtac ccagcttttg ttccctttag    180

tgagggttaa ttgcgcgctt ggcgtaatca tggtcatagc tgtttcctgt gtgaaattgt    240

tatccgctca caattccaca caacatacga gccggaagca taaagtgtaa agcctggggt    300

gcctaatgag tgagctaact cacattaatt gcgttgcgct cactgcccgc tttccagtcg    360

ggaaacctgt cgtgccagct gcattaatga atcggccaac gcgcggggag aggcggtttg    420

cgtattgggc gctcttccgc ttcctcgctc actgactcgc tgcgctcggt cgttcggctg    480

cggcgagcgg tatcagctca ctcaaaggcg gtaatacggt tatccacaga atcaggggat    540

aacgcaggaa agaacatgtg agcaaaaggc cagcaaaagg ccaggaaccg taaaaaggcc    600

gcgttgctgg cgtttttcca taggctccgc ccccctgacg agcatcacaa aaatcgacgc    660

tcaagtcaga ggtggcgaaa cccgacagga ctataaagat accaggcgtt tccccctgga    720

agctccctcg tgcgctctcc tgttccgacc ctgccgctta ccggatacct gtccgccttt    780

ctcccttcgg gaagcgtggc gctttctcat agctcacgct gtaggtatct cagttcggtg    840

taggtcgttc gctccaagct gggctgtgtg cacgaacccc ccgttcagcc cgaccgctgc    900

gccttatccg gtaactatcg tcttgagtcc aacccggtaa gacacgactt atcgccactg    960

gcagcagcca ctggtaacag gattagcaga gcgaggtatg taggcggtgc tacagagttc   1020

ttgaagtggt ggcctaacta cggctacact agaaggacag tatttggtat ctgcgctctg   1080

ctgaagccag ttaccttcgg aaaaagagtt ggtagctctt gatccggcaa acaaaccacc   1140

gctggtagcg gtggtttttt tgtttgcaag cagcagatta cgcgcagaaa aaaaggatct   1200

caagaagatc ctttgatctt ttctacgggg tctgacgctc agtggaacga aaactcacgt   1260

taagggattt tggtcatgag attatcaaaa aggatcttca cctagatcct tttaaattaa   1320

aaatgaagtt ttaaatcaat ctaaagtata tatgagtaaa cttggtctga cagttaccaa   1380

tgcttaatca gtgaggcacc tatctcagcg atctgtctat ttcgttcatc catagttgcc   1440

tgactccccg tcgtgtagat aactacgata cgggagggct taccatctgg ccccagtgct   1500

gcaatgatac cgcgagaccc acgctcaccg gctccagatt tatcagcaat aaaccagcca   1560

gccggaaggg ccgagcgcag aagtggtcct gcaactttat ccgcctccat ccagtctatt   1620
```

```
aattgttgcc gggaagctag agtaagtagt tcgccagtta atagtttgcg caacgttgtt   1680
gccattgcta caggcatcgt ggtgtcacgc tcgtcgtttg gtatggcttc attcagctcc   1740
ggttcccaac gatcaaggcg agttacatga tcccccatgt tgtgcaaaaa agcggttagc   1800
tccttcggtc ctccgatcgt tgtcagaagt aagttggccg cagtgttatc actcatggtt   1860
atggcagcac tgcataattc tcttactgtc atgccatccg taagatgctt ttctgtgact   1920
ggtgagtact caaccaagtc attctgagaa tagtgtatgc ggcgaccgag ttgctcttgc   1980
ccggcgtcaa tacgggataa taccgcgcca catagcagaa ctttaaaagt gctcatcatt   2040
ggaaaacgtt cttcggggcg aaaactctca aggatcttac cgctgttgag atccagttcg   2100
atgtaaccca ctcgtgcacc caactgatct tcagcatctt ttactttcac cagcgtttct   2160
gggtgagcaa aaacaggaag gcaaaatgcc gcaaaaaagg gaataagggc gacacggaaa   2220
tgttgaatac tcatactctt cctttttcaa tattattgaa gcatttatca gggttattgt   2280
ctcatgagcg gatacatatt tgaatgtatt tagaaaaata aacaaatagg ggttccgcgc   2340
acatttcccc gaaaagtgcc acctaaattg taagcgttaa tattttgtta aaattcgcgt   2400
taaatttttg ttaaatcagc tcatttttta accaataggc cgaaatcggc aaaatccctt   2460
ataaatcaaa agaatagacc gagatagggt tgagtgttgt tccagtttgg aacaagagtc   2520
cactattaaa gaacgtggac tccaacgtca aagggcgaaa aaccgtctat cagggcgatg   2580
gcccactacg tgaaccatca ccctaatcaa gtttttggg gtcgaggtgc cgtaaagcac   2640
taaatcggaa ccctaaaggg agcccccgat ttagagcttg acggggaaag ccggcgaacg   2700
tggcgagaaa ggaagggaag aaagcgaaag gagcgggcgc tagggcgctg gcaagtgtag   2760
cggtcacgct gcgcgtaacc accacacccg ccgcgcttaa tgcgccgcta cagggcgcgt   2820
cccattcgcc attcaggctg cgcaactgtt gggaagggcg atcggtgcgg gcctcttcgc   2880
tattacgcca gctggcgaaa gggggatgtg ctgcaaggcg attaagttgg gtaacgccag   2940
ggttttccca gtcacgacgt t                                              2961
```

<210> SEQ ID NO 51
<211> LENGTH: 7164
<212> TYPE: DNA
<213> ORGANISM: Artificial sequence
<220> FEATURE:
<223> OTHER INFORMATION: pCMVbeta

<400> SEQUENCE: 51

```
gaattcgagc ttgcatgcct gcaggtcgtt acataactta cggtaaatgg cccgcctggc     60
tgaccgccca acgacccccg cccattgacg tcaataatga cgtatgttcc catagtaacg    120
ccaataggga ctttccattg acgtcaatgg gtggagtatt tacggtaaac tgcccacttg    180
gcagtacatc aagtgtatca tatgccaagt acgcccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tcgaggaact gaaaaaccag    660
```

```
aaagttaact ggtaagttta gtctttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat tgtacccgcg gccgcaattc ccggggatcg    840
aaagagcctg ctaaagcaaa aaagaagtca ccatgtcgtt tactttgacc aacaagaacg    900
tgattttcgt tgccggtctg ggaggcattg gtctggacac cagcaaggag ctgctcaagc    960
gcgatcccgt cgttttacaa cgtcgtgact gggaaaaccc tggcgttacc caacttaatc   1020
gccttgcagc acatccccct ttcgccagct ggcgtaatag cgaagaggcc cgcaccgatc   1080
gcccttccca acagttgcgc agcctgaatg gcgaatggcg ctttgcctgg tttccggcac   1140
cagaagcggt gccggaaagc tggctggagt gcgatcttcc tgaggccgat actgtcgtcg   1200
tcccctcaaa ctggcagatg cacggttacg atgcgcccat ctacaccaac gtaacctatc   1260
ccattacggt caatccgccg tttgttccca cggagaatcc gacgggttgt tactcgctca   1320
catttaatgt tgatgaaagc tggctacagg aaggccagac gcgaattatt tttgatggcg   1380
ttaactcggc gtttcatctg tggtgcaacg ggcgctgggt cggttacggc caggacagtc   1440
gtttgccgtc tgaatttgac ctgagcgcat ttttacgcgc cggagaaaac cgcctcgcgg   1500
tgatggtgct gcgttggagt gacggcagtt atctggaaga tcaggatatg tggcggatga   1560
gcggcatttt ccgtgacgtc tcgttgctgc ataaaccgac tacacaaatc agcgatttcc   1620
atgttgccac tcgctttaat gatgatttca gccgcgctgt actggaggct gaagttcaga   1680
tgtgcggcga gttgcgtgac tacctacggg taacagtttc tttatggcag ggtgaaacgc   1740
aggtcgccag cggcaccgcg cctttcggcg gtgaaattat cgatgagcgt ggtggttatg   1800
ccgatcgcgt cacactacgt ctgaacgtcg aaaacccgaa actgtggagc gccgaaatcc   1860
cgaatctcta tcgtgcggtg gttgaactgc acaccgccga cggcacgctg attgaagcag   1920
aagcctgcga tgtcggtttc cgcgaggtgc ggattgaaaa tggtctgctg ctgctgaacg   1980
gcaagccgtt gctgattcga ggcgttaacc gtcacgagca tcatcctctg catggtcagg   2040
tcatggatga gcagacgatg gtgcaggata tcctgctgat gaagcagaac aactttaacg   2100
ccgtgcgctg ttcgcattat ccgaaccatc cgctgtggta cacgctgtgc gaccgctacg   2160
gcctgtatgt ggtggatgaa gccaatattg aaacccacgg catggtgcca atgaatcgtc   2220
tgaccgatga tccgcgctgg ctaccggcga tgagcgaacg cgtaacgcga atggtgcagc   2280
gcgatcgtaa tcacccgagt gtgatcatct ggtcgctggg gaatgaatca ggccacggcg   2340
ctaatcacga cgcgctgtat cgctggatca aatctgtcga tccttcccgc ccggtgcagt   2400
atgaaggcgg cggagccgac accacggcca ccgatattat ttgcccgatg tacgcgcgcg   2460
tggatgaaga ccagcccttc ccggctgtgc cgaaatggtc catcaaaaaa tggctttcgc   2520
tacctggaga gacgcgcccg ctgatccttt gcgaatacgc ccacgcgatg ggtaacagtc   2580
ttggcggttt cgctaaatac tggcaggcgt ttcgtcagta tccccgttta cagggcggct   2640
tcgtctggga ctgggtggat cagtcgctga ttaaatatga tgaaaacggc aacccgtggt   2700
cggcttacgg cggtgatttt ggcgatacgc cgaacgatcg ccagttctgt atgaacggtc   2760
tggtctttgc cgaccgcacg ccgcatccag cgctgacgga agcaaaacac cagcagcagt   2820
ttttccagtt ccgtttatcc gggcaaacca tcgaagtgac cagcgaatac ctgttccgtc   2880
atagcgataa cgagctcctg cactggatgg tggcgctgga tggtaagccg ctggcaagcg   2940
gtgaagtgcc tctggatgtc gctccacaag gtaaacagtt gattgaactg cctgaactac   3000
cgcagccgga gagcgccggg caactctggc tcacagtacg cgtagtgcaa ccgaacgcga   3060
```

```
ccgcatggtc agaagccggg cacatcagcg cctggcagca gtggcgtctg gcggaaaacc   3120

tcagtgtgac gctccccgcc gcgtcccacg ccatcccgca tctgaccacc agcgaaatgg   3180

atttttgcat cgagctgggt aataagcgtt ggcaatttaa ccgccagtca ggctttcttt   3240

cacagatgtg gattggcgat aaaaaacaac tgctgacgcc gctgcgcgat cagttcaccc   3300

gtgcaccgct ggataacgac attggcgtaa gtgaagcgac ccgcattgac cctaacgcct   3360

gggtcgaacg ctggaaggcg gcgggccatt accaggccga agcagcgttg ttgcagtgca   3420

cggcagatac acttgctgat gcggtgctga ttacgaccgc tcacgcgtgg cagcatcagg   3480

ggaaaacctt atttatcagc cggaaaacct accggattga tggtagtggt caaatggcga   3540

ttaccgttga tgttgaagtg gcgagcgata caccgcatcc ggcgcggatt ggcctgaact   3600

gccagctggc gcaggtagca gagcgggtaa actggctcgg attagggccg caagaaaact   3660

atcccgaccg ccttactgcc gcctgttttg accgctggga tctgccattg tcagacatgt   3720

ataccccgta cgtcttcccg agcgaaaacg gtctgcgctg cgggacgcgc gaattgaatt   3780

atggcccaca ccagtggcgc ggcgacttcc agttcaacat cagccgctac agtcaacagc   3840

aactgatgga aaccagccat cgccatctgc tgcacgcgga agaaggcaca tggctgaata   3900

tcgacggttt ccatatgggg attggtggcg acgactcctg gagcccgtca gtatcggcgg   3960

aattacagct gagcgccggt cgctaccatt accagttggt ctggtgtcaa aaataataat   4020

aaccgggcag gccatgtctg cccgtatttc gcgtaaggaa atccattatg tactatttaa   4080

aaaacacaaa cttttggatg ttcggtttat tctttttctt ttactttttt atcatgggag   4140

cctacttccc gtttttcccg atttggctac atgacatcaa ccatatcagc aaaagtgata   4200

cgggtattat ttttgccgct atttctctgt tctcgctatt attccaaccg ctgtttggtc   4260

tgctttctga caaactcggc ctcgactcta ggcggccgcg gggatccaga catgataaga   4320

tacattgatg agtttggaca aaccacaact agaatgcagt gaaaaaaatg ctttatttgt   4380

gaaatttgtg atgctattgc tttatttgta accattataa gctgcaataa acaagttaac   4440

aacaacaatt gcattcattt tatgtttcag gttcaggggg aggtgtggga ggttttttcg   4500

gatcctctag agtcgacctg caggcatgca agcttggcgt aatcatggtc atagctgttt   4560

cctgtgtgaa attgttatcc gctcacaatt ccacacaaca tacgagccgg aagcataaag   4620

tgtaaagcct ggggtgccta atgagtgagc taactcacat taattgcgtt gcgctcactg   4680

cccgctttcc agtcgggaaa cctgtcgtgc cagctgcatt aatgaatcgg ccaacgcgcg   4740

gggagaggcg gtttgcgtat tgggcgctct tccgcttcct cgctcactga ctcgctgcgc   4800

tcggtcgttc ggctgcggcg agcggtatca gctcactcaa aggcggtaat acggttatcc   4860

acagaatcag gggataacgc aggaaagaac atgtgagcaa aaggccagca aaaggccagg   4920

aaccgtaaaa aggccgcgtt gctggcgttt ttccataggc tccgcccccc tgacgagcat   4980

cacaaaaatc gacgctcaag tcagaggtgg cgaaacccga caggactata aagataccag   5040

gcgtttcccc ctggaagctc cctcgtgcgc tctcctgttc cgaccctgcc gcttaccgga   5100

tacctgtccg cctttctccc ttcgggaagc gtggcgcttt ctcatagctc acgctgtagg   5160

tatctcagtt cggtgtaggt cgttcgctcc aagctgggct gtgtgcacga accccccgtt   5220

cagcccgacc gctgcgcctt atccggtaac tatcgtcttg agtccaaccc ggtaagacac   5280

gacttatcgc cactggcagc agccactggt aacaggatta gcagagcgag gtatgtaggc   5340

ggtgctacag agttcttgaa gtggtggcct aactacggct acactagaag gacagtattt   5400
```

```
ggtatctgcg ctctgctgaa gccagttacc ttcggaaaaa gagttggtag ctcttgatcc   5460

ggcaaacaaa ccaccgctgg tagcggtggt ttttttgttt gcaagcagca gattacgcgc   5520

agaaaaaaag gatctcaaga agatcctttg atcttttcta cggggtctga cgctcagtgg   5580

aacgaaaact cacgttaagg gattttggtc atgagattat caaaaaggat cttcacctag   5640

atccttttaa attaaaaatg aagttttaaa tcaatctaaa gtatatatga gtaaacttgg   5700

tctgacagtt accaatgctt aatcagtgag gcacctatct cagcgatctg tctatttcgt   5760

tcatccatag ttgcctgact ccccgtcgtg tagataacta cgatacggga gggcttacca   5820

tctggcccca gtgctgcaat gataccgcga gacccacgct caccggctcc agatttatca   5880

gcaataaacc agccagccgg aagggccgag cgcagaagtg gtcctgcaac tttatccgcc   5940

tccatccagt ctattaattg ttgccgggaa gctagagtaa gtagttcgcc agttaatagt   6000

ttgcgcaacg ttgttgccat tgctacaggc atcgtggtgt cacgctcgtc gtttggtatg   6060

gcttcattca gctccggttc ccaacgatca aggcgagtta catgatcccc catgttgtgc   6120

aaaaaagcgg ttagctcctt cggtcctccg atcgttgtca gaagtaagtt ggccgcagtg   6180

ttatcactca tggttatggc agcactgcat aattctctta ctgtcatgcc atccgtaaga   6240

tgcttttctg tgactggtga gtactcaacc aagtcattct gagaatagtg tatgcggcga   6300

ccgagttgct cttgcccggc gtcaatacgg gataataccg cgccacatag cagaacttta   6360

aaagtgctca tcattggaaa acgttcttcg gggcgaaaac tctcaaggat cttaccgctg   6420

ttgagatcca gttcgatgta acccactcgt gcacccaact gatcttcagc atcttttact   6480

ttcaccagcg tttctgggtg agcaaaaaca ggaaggcaaa atgccgcaaa aaagggaata   6540

agggcgacac ggaaatgttg aatactcata ctcttccttt ttcaatatta ttgaagcatt   6600

tatcagggtt attgtctcat gagcggatac atatttgaat gtatttagaa aaataaacaa   6660

ataggggttc cgcgcacatt tccccgaaaa gtgccacctg acgtctaaga aaccattatt   6720

atcatgacat taacctataa aaataggcgt atcacgaggc cctttcgtct cgcgcgtttc   6780

ggtgatgacg gtgaaaacct ctgacacatg cagctcccgg agacggtcac agcttgtctg   6840

taagcggatg ccgggagcag acaagcccgt cagggcgcgt cagcgggtgt tggcgggtgt   6900

cggggctggc ttaactatgc ggcatcagag cagattgtac tgagagtgca ccatatgcgg   6960

tgtgaaatac cgcacagatg cgtaaggaga aaataccgca tcaggcgcca ttcgccattc   7020

aggctgcgca actgttggga agggcgatcg gtgcgggcct cttcgctatt acgccagctg   7080

gcgaaagggg gatgtgctgc aaggcgatta agttgggtaa cgccagggtt ttcccagtca   7140

cgacgttgta aaacgacggc cagt                                          7164
```

<210> SEQ ID NO 52
<211> LENGTH: 7867
<212> TYPE: DNA
<213> ORGANISM: Artificial sequence
<220> FEATURE:
<223> OTHER INFORMATION: pCAG-TalRab2-Clo051

<400> SEQUENCE: 52

```
ggcgcgccgg attcgacatt gattattgac tagttattaa tagtaatcaa ttacggggtc     60

attagttcat agcccatata tggagttccg cgttacataa cttacggtaa atggcccgcc    120

tggctgaccg cccaacgacc cccgcccatt gacgtcaata atgacgtatg ttcccatagt    180

aacgccaata gggactttcc attgacgtca atgggtggag tatttacggt aaactgccca    240

cttggcagta catcaagtgt atcatatgcc aagtacgccc cctattgacg tcaatgacgg    300
```

```
taaatggccc gcctggcatt atgcccagta catgacctta tgggactttc ctacttggca    360
gtacatctac gtattagtca tcgctattac catggtcgag gtgagcccca cgttctgctt    420
cactctcccc atctcccccc cctccccacc cccaattttg tatttattta tttttttaatt    480
attttgtgca gcgatggggg cggggggggg gggggggcgc gcgccaggcg gggcggggcg    540
gggcgagggg cggggcgggg cgaggcggag aggtgcggcg gcagccaatc agagcggcgc    600
gctccgaaag tttcctttta tggcgaggcg gcggcggcgg cggccctata aaaagcgaag    660
cgcgcggcgg gcgggagtcg ctgcgcgctg ccttcgcccc gtgccccgct ccgccgccgc    720
ctcgcgccgc ccgccccggc tctgactgac cgcgttactc ccacaggtga gcgggcggga    780
cggcccttct cctccgggct gtaattagcg cttggtttaa tgacggcttg tttcttttct    840
gtggctgcgt gaaagccttg aggggctccg ggagggccct ttgtgcgggg gggagcggct    900
cgggggtgc gtgcgtgtgt gtgtgcgtgg ggagcgccgc gtgcggctcc gcgctgcccg    960
gcggctgtga gcgctgcggg cgcggcgcgg ggctttgtgc gctccgcagt gtgcgcgagg   1020
ggagcgcggc cgggggcggt gccccgcggt gcgggggggg ctgcgagggg aacaaaggct   1080
gcgtgcgggg tgtgtgcgtg ggggggtgag caggggtgt gggcgcgtcg gtcgggctgc    1140
aacccccct gcacccccct ccccgagttg ctgagcacgg cccggcttcg ggtgcggggc    1200
tccgtacggg gcgtggcgcg gggctcgccg tgccgggcgg ggggtggcgg caggtggggg   1260
tgccgggcgg ggcggggccg cctcgggccg ggagggctc ggggggagggg cgcggcggcc   1320
cccggagcgc cggcggctgt cgaggcgcgg cgagccgcag ccattgcctt ttatggtaat   1380
cgtgcgagag ggcgcaggga cttcctttgt cccaaatctg tgcggagccg aaatctggga   1440
ggcgccgccg cacccccctct agcgggcgcg ggcgaagcg gtgcggcgcc ggcaggaagg   1500
aaatgggcgg ggagggcctt cgtgcgtcgc cgcgccgccg tccccttctc cctctccagc   1560
ctcggggctg tccgcggggg gacggctgcc ttcggggggg acggggcagg gcggggttcg   1620
gcttctggcg tgtgaccggc ggctctagag cctctgctaa ccatgttcat gccttcttct   1680
ttttcctaca gatccttaat taataatacg actcactata ggggccgcca ccatgggacc   1740
taagaaaaag aggaaggtgg cggccgctga ctacaaggat gacgacgata aaccaggtgg   1800
cggaggtagt ggcggaggtg ggtacccgc cagtccagca gcccaggtgg atctgagaac    1860
cctcggctac agccagcagc agcaggagaa gatcaaacca aaggtgcggt ccaccgtcgc   1920
tcagcaccat gaagcactgg tggggcacgg tttcacacac gcccatattg tggctctgtc   1980
tcagcatccc gctgcactcg ggactgtggc cgtcaaatat caggacatga tcgccgctct   2040
gcctgaggca acccacgaag ccattgtggg cgtcggaaag cagtggagcg gtgccagagc   2100
actcgaagca ctcctcaccg tcgccgggga actgcggggt ccaccactcc agtccggact   2160
ggacactgga cagctgctga agatcgctaa acgcggcgga gtgacagctg tggaagctgt   2220
gcacgcttgg aggaatgctc tgacaggagc cccactgaat ctgacacccc agcaggtggt   2280
ggccattgct agcaacaatg gggcaagca ggctctggag acagtgcagc gcctgctgcc    2340
tgtgctgtgc caggctcacg gactgactcc acagcaggtg gtggccatcg cttccaacaa   2400
tggagggaaa caggctctgg aaacagtgca gaggctgctg cccgtgctgt gccaggctca   2460
tggactgaca cctcagcagg tcgtcgccat tgcttctaac ggcggaggga agcaggctct   2520
ggagactgtg cagagactgc tgccagtgct gtgccaggcc catggactga cccctcagca   2580
ggtcgtggct atcgctagta acaatggcgg aaaacaggct ctggaaactg tgcagcggct   2640
```

```
gctccccgtg ctgtgccagg cccacggcct cactccacag caggtcgtcg ctatcgcctc   2700
taataacggg ggcaagcagg ctctggagac agtacagcgc ctgttacccg tgctgtgcca   2760
ggcacacggc ctcacacctc agcaggtcgt ggcaatcgct tcccatgacg gagggaaaca   2820
ggctctggaa acggtccaga ggctgctccc cgtgctgtgc caagctcacg gcctcacccc   2880
tcagcaggtg gtcgctattg cttctcatga tggcggaaag caggctctgg agaccgtgca   2940
gagactgctc cctgtgctgt gccaagccca cggcctgact ccacagcagg tcgtggccat   3000
cgctagtcat gacgggggca aacaggctct ggaaacagta cagcggctgt tacccgtgct   3060
gtgccaagcc catggcctca cacctcagca agtcgtcgct atcgctagca acaatggagg   3120
gaagcaggct ctggagacgg tgcagcgcct gctcccagtg ctgtgccaag ctcatggcct   3180
cacccctcag caagtcgtcg caattgcttc caataacggc ggaaaacagg ctctggaaac   3240
cgtccagagg ctgctgcccg tgctgtgcca agcacatggc ttaactccac agcaagtggt   3300
ggccattgct tctaatgggg gcggaaagca ggccctggag acagtccaga gactgttgcc   3360
cgtgctgtgc caagcgcatg gactgacacc tgaacaggtc gtcgctatcg ctagtaatat   3420
tgggggcaaa caggccctgg aaacagtgca gcggctgctt cccgtgctgt gccaggcgca   3480
tggactcaca ccccagcagg tcgtcgcaat cgcctctaat aacggaggga agcaggccct   3540
ggaaaccgtg cagagactgt tacctgtgct gtgccaggca catggtctga caccacagca   3600
ggtggtcgca attgctagca atggcggagg gaagcaggcc ctggagactg tccagagact   3660
gctacccgtg ctgtgccaag cgcacggcct gaccccacag caggtcgtcg ctattgcttc   3720
taatggcgga gggcggcctg ctctggagag cattgtggct cagctgtcca ggcccgatcc   3780
tgccctggct agatccgcac tcactaacga tcatctggtc gctctcgctt gcctcggtgg   3840
acggcccgct ctggacgcag tcaaaaaggg tctcccccat gctcccgcac tgatcaagag   3900
aaccaacagg agaattcctg agggatccga tcgtttaaac gaaggcatca aaagcaacat   3960
ctccctcctg aaagacgaac tccgggggca gattagccac attagtcacg aatacctctc   4020
cctcatcgac ctggctttcg atagcaagca gaacaggctc tttgagatga aagtgctgga   4080
actgctcgtc aatgagtacg ggttcaaggg tcgacacctc ggcggatcta ggaaaccaga   4140
cggcatcgtg tatagtacca cactggaaga caactttggg atcattgtgg ataccaaggc   4200
atactctgag ggttatagtc tgcccatttc acaggccgac gagatggaac ggtacgtgcg   4260
cgagaactca aatagagatg aggaagtcaa ccctaacaag tggtgggaga acttctctga   4320
ggaagtgaag aaatactact tcgtctttat cagcgggtcc ttcaagggta aatttgagga   4380
acagctcagg agactgagca tgactaccgg cgtgaatggc agcgccgtca acgtggtcaa   4440
tctgctcctg ggcgctgaaa agattcggag cggagagatg accatcgaag agctggagag   4500
ggcaatgttt aataatagcg agtttatcct gaaatactga acgcgtaaat gattgcagat   4560
ccactagttc tagaattcca gctgagcgcc ggtcgctacc attaccagtt ggtctggtgt   4620
caaaaataat aataaccggg caggggggat ctgcatggat ctttgtgaag gaaccttact   4680
tctgtggtgt gacataattg gacaaactac ctacagagat ttaaagctct aaggtaaata   4740
taaaattttt aagtgtataa tgtgttaaac tactgattct aattgtttgt gtattttaga   4800
ttccaaccta tggaactgat gaatgggagc agtggtggaa tgccagatcc agacatgata   4860
agatacattg atgagtttgg acaaaccaca actagaatgc agtgaaaaaa atgctttatt   4920
tgtgaaattt gtgatgctat tgctttattt gtaaccatta taagctgcaa taaacaagtt   4980
aacaacaaca attgcattca ttttatgttt caggttcagg gggaggtgtg ggaggttttt   5040
```

```
taaagcaagt aaaacctcta caaatgtggt atggctgatt atgatctgcg gccgccactg   5100
gccgtcgttt tacaacgtcg tgactgggaa aaccctggcg ttacccaact taatcgcctt   5160
gcagcacatc ccccttttcgc cagctggcgt aatagcgaag aggcccgcac cgatcgccct   5220
tcccaacagt tgcgcagcct gaatggcgaa tggaacgcgc cctgtagcgg cgcattaagc   5280
gcggcgggtg tggtggttac gcgcagcgtg accgctacac ttgccagcgc cctagcgccc   5340
gctcctttcg ctttcttccc ttcctttctc gccacgttcg ccggctttcc ccgtcaagct   5400
ctaaatcggg ggctcccttt agggttccga tttagtgctt tacggcacct cgaccccaaa   5460
aaacttgatt agggtgatgg ttcacgtagt gggccatcgc cctgatagac ggtttttcgc   5520
cctttgacgt tggagtccac gttctttaat agtggactct tgttccaaac tggaacaaca   5580
ctcaacccta tctcggtcta ttcttttgat ttataaggga ttttgccgat ttcggcctat   5640
tggttaaaaa atgagctgat ttaacaaaaa tttaacgcga attttaacaa aatattaacg   5700
cttacaattt aggtggcact tttcggggaa atgtgcgcgg aacccctatt tgtttatttt   5760
tctaaataca ttcaaatatg tatccgctca tgagacaata accctgataa atgcttcaat   5820
aatattgaaa aaggaagagt atgagtattc aacatttccg tgtcgccctt attccctttt   5880
ttgcggcatt ttgccttcct gtttttgctc acccagaaac gctggtgaaa gtaaaagatg   5940
ctgaagatca gttgggtgca cgagtgggtt acatcgaact ggatctcaac agcggtaaga   6000
tccttgagag ttttcgcccc gaagaacgtt ttccaatgat gagcactttt aaagttctgc   6060
tatgtggcgc ggtattatcc cgtattgacg ccgggcaaga gcaactcggt cgccgcatac   6120
actattctca gaatgacttg gttgagtact caccagtcac agaaaagcat cttacggatg   6180
gcatgacagt aagagaatta tgcagtgctg ccataaccat gagtgataac actgcggcca   6240
acttacttct gacaacgatc ggaggaccga aggagctaac cgcttttttg cacaacatgg   6300
gggatcatgt aactcgcctt gatcgttggg aaccggagct gaatgaagcc ataccaaacg   6360
acgagcgtga caccacgatg cctgtagcaa tggcaacaac gttgcgcaaa ctattaactg   6420
gcgaactact tactctagct tcccggcaac aattaataga ctggatggag gcggataaag   6480
ttgcaggacc acttctgcgc tcggcccttc cggctggctg gtttattgct gataaatctg   6540
gagccggtga gcgtgggtct cgcggtatca ttgcagcact ggggccagat ggtaagccct   6600
cccgtatcgt agttatctac acgacgggga gtcaggcaac tatggatgaa cgaaatagac   6660
agatcgctga gataggtgcc tcactgatta agcattggta actgtcagac caagtttact   6720
catatatact ttagattgat ttaaaacttc atttttaatt taaaaggatc taggtgaaga   6780
tcctttttga taatctcatg accaaaatcc cttaacgtga gttttcgttc cactgagcgt   6840
cagaccccgt agaaaagatc aaaggatctt cttgagatcc tttttttctg cgcgtaatct   6900
gctgcttgca aacaaaaaaa ccaccgctac cagcggtggt ttgtttgccg gatcaagagc   6960
taccaactct ttttccgaag gtaactggct tcagcagagc gcagatacca aatactgtcc   7020
ttctagtgta gccgtagtta ggccaccact tcaagaactc tgtagcaccg cctacatacc   7080
tcgctctgct aatcctgtta ccagtggctg ctgccagtgg cgataagtcg tgtcttaccg   7140
ggttggactc aagacgatag ttaccggata aggcgcagcg gtcgggctga acggggggtt   7200
cgtgcacaca gcccagcttg gagcgaacga cctacaccga actgagatac ctacagcgtg   7260
agctatgaga aagcgccacg cttcccgaag ggagaaaggc ggacaggtat ccggtaagcg   7320
gcagggtcgg aacaggagag cgcacgaggg agcttccagg gggaaacgcc tggtatcttt   7380
```

```
atagtcctgt cgggtttcgc cacctctgac ttgagcgtcg atttttgtga tgctcgtcag   7440

gggggcggag cctatggaaa aacgccagca acgcggcctt tttacggttc ctggcctttt   7500

gctggccttt tgctcacatg ttctttcctg cgttatcccc tgattctgtg gataaccgta   7560

ttaccgcctt tgagtgagct gataccgctc gccgcagccg aacgaccgag cgcagcgagt   7620

cagtgagcga ggaagcggaa gagcgcccaa tacgcaaacc gcctctcccc gcgcgttggc   7680

cgattcatta atgcagctgg cacgacaggt ttcccgactg gaaagcgggc agtgagcgca   7740

acgcaattaa tgtgagttag ctcactcatt aggcacccca ggctttacac tttatgcttc   7800

cggctcgtat gttgtgtgga attgtgagcg gataacaatt tcacacagga aacagctatg   7860

accatga                                                             7867
```

<210> SEQ ID NO 53
<211> LENGTH: 935
<212> TYPE: PRT
<213> ORGANISM: Artificial sequence
<220> FEATURE:
<223> OTHER INFORMATION: TalRab2-Clo051

<400> SEQUENCE: 53

```
Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Gln Gln Val Val Ala Ile Ala Ser Asn Asn Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270
```

```
Leu Cys Gln Ala His Gly Leu Thr Pro Gln Gln Val Val Ala Ile Ala
        275                 280                 285

Ser Asn Asn Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
        435                 440                 445

Leu Thr Pro Gln Gln Val Val Ala Ile Ala Ser Asn Asn Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Gln Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655

Gln Val Val Ala Ile Ala Ser Asn Gly Gly Gly Arg Pro Ala Leu Glu
            660                 665                 670

Ser Ile Val Ala Gln Leu Ser Arg Pro Asp Pro Ala Leu Ala Arg Ser
        675                 680                 685

Ala Leu Thr Asn Asp His Leu Val Ala Leu Ala Cys Leu Gly Gly Arg
```

```
    690                 695                 700

Pro Ala Leu Asp Ala Val Lys Lys Gly Leu Pro His Ala Pro Ala Leu
705                 710                 715                 720

Ile Lys Arg Thr Asn Arg Arg Ile Pro Glu Gly Ser Asp Arg Leu Asn
                725                 730                 735

Glu Gly Ile Lys Ser Asn Ile Ser Leu Leu Lys Asp Glu Leu Arg Gly
            740                 745                 750

Gln Ile Ser His Ile Ser His Glu Tyr Leu Ser Leu Ile Asp Leu Ala
        755                 760                 765

Phe Asp Ser Lys Gln Asn Arg Leu Phe Glu Met Lys Val Leu Glu Leu
    770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
                805                 810                 815

Ile Ile Val Asp Thr Lys Ala Tyr Ser Glu Gly Tyr Ser Leu Pro Ile
            820                 825                 830

Ser Gln Ala Asp Glu Met Glu Arg Tyr Val Arg Glu Asn Ser Asn Arg
        835                 840                 845

Asp Glu Glu Val Asn Pro Asn Lys Trp Trp Glu Asn Phe Ser Glu Glu
    850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
                885                 890                 895

Ser Ala Val Asn Val Val Asn Leu Leu Leu Gly Ala Glu Lys Ile Arg
            900                 905                 910

Ser Gly Glu Met Thr Ile Glu Glu Leu Glu Arg Ala Met Phe Asn Asn
        915                 920                 925

Ser Glu Phe Ile Leu Lys Tyr
    930                 935
```

<210> SEQ ID NO 54
<211> LENGTH: 7867
<212> TYPE: DNA
<213> ORGANISM: Artificial sequence
<220> FEATURE:
<223> OTHER INFORMATION: pCAG-RabChtTal1-Clo051

<400> SEQUENCE: 54

```
ggcgcgccgg attcgacatt gattattgac tagttattaa tagtaatcaa ttacggggtc     60

attagttcat agcccatata tggagttccg cgttacataa cttacggtaa atggcccgcc    120

tggctgaccg cccaacgacc cccgcccatt gacgtcaata atgacgtatg ttcccatagt    180

aacgccaata gggactttcc attgacgtca atgggtggag tatttacggt aaactgccca    240

cttggcagta catcaagtgt atcatatgcc aagtacgccc cctattgacg tcaatgacgg    300

taaatggccc gcctggcatt atgcccagta catgacctta tgggactttc ctacttggca    360

gtacatctac gtattagtca tcgctattac catggtcgag gtgagcccca cgttctgctt    420

cactctcccc atctcccccc cctccccacc cccaattttg tatttattta tttttaatt     480

attttgtgca gcgatggggg cggggggggg ggggggggcgc gcgccaggcg gggcggggcg    540

gggcgagggg cggggcgggg cgaggcggag aggtgcggcg gcagccaatc agagcggcgc    600

gctccgaaag tttcctttta tggcgaggcg gcggcggcgg cggccctata aaaagcgaag    660
```

cgcgcggcgg gcgggagtcg ctgcgcgctg ccttcgcccc gtgccccgct ccgccgccgc 720
ctcgcgccgc ccgccccggc tctgactgac cgcgttactc ccacaggtga gcgggcggga 780
cggcccttct cctccgggct gtaattagcg cttggtttaa tgacggcttg tttcttttct 840
gtggctgcgt gaaagccttg aggggctccg ggagggccct ttgtgcgggg gggagcggct 900
cggggggtgc gtgcgtgtgt gtgtgcgtgg ggagcgccgc gtgcggctcc gcgctgcccg 960
gcggctgtga gcgctgcggg cgcggcgcgg ggctttgtgc gctccgcagt gtgcgcgagg 1020
ggagcgcggc cgggggcggt gccccgcggt gcgggggggg ctgcgagggg aacaaaggct 1080
gcgtgcgggg tgtgtgcgtg ggggggtgag cagggggtgt gggcgcgtcg gtcgggctgc 1140 aacccccct gcacccccct ccccgagttg ctgagcacgg cccggcttcg ggtgcggggc 1200
tccgtacggg gcgtggcgcg gggctcgccg tgccgggcgg ggggtggcgg caggtggggg 1260
tgccgggcgg ggcggggccg cctcgggccg gggagggctc gggggagggg cgcggcggcc 1320
cccggagcgc cggcggctgt cgaggcgcgg cgagccgcag ccattgcctt ttatggtaat 1380
cgtgcgagag ggcgcaggga cttcctttgt cccaaatctg tgcggagccg aaatctggga 1440
ggcgccgccg cacccctct agcgggcgcg ggcgaagcg gtgcggcgcc ggcaggaagg 1500
aaatgggcgg ggagggcctt cgtgcgtcgc cgcgccgccg tccccttctc cctctccagc 1560
ctcggggctg tccgcggggg gacggctgcc ttcggggggg acggggcagg gcggggttcg 1620
gcttctggcg tgtgaccggc ggctctagag cctctgctaa ccatgttcat gccttcttct 1680
ttttcctaca gatccttaat taataatacg actcactata ggggccgcca ccatgggacc 1740
taagaaaaag aggaaggtgg cggccgctga ctacaaggat gacgacgata aaccaggtgg 1800
cggaggtagt ggcggaggtg ggtacccgc cagtccagca gcccaggtgg atctgagaac 1860
cctcggctac agccagcagc agcaggagaa gatcaaacca aaggtgcggt ccaccgtcgc 1920
tcagcaccat gaagcactgg tggggcacgg tttcacacac gcccatattg tggctctgtc 1980
tcagcatccc gctgcactcg ggactgtggc cgtcaaatat caggacatga tcgccgctct 2040
gcctgaggca acccacgaag ccattgtggg cgtcggaaag cagtggagcg gtgccagagc 2100
actcgaagca ctcctcaccg tcgccgggga actgcggggt ccaccactcc agtccggact 2160
ggacactgga cagctgctga agatcgctaa acgcggcgga gtgacagctg tggaagctgt 2220
gcacgcttgg aggaatgctc tgacaggagc cccactgaat cttacacccg aacaggtggt 2280
ggccatcgct agtaacattg gggcaaaca ggctctggaa acagtacagc ggctgttacc 2340
tgtgctgtgc caggctcatg gcctcacacc tcagcaggtc gtcgcaatcg cctccaatgg 2400
cggagggaag caggccctgg aaacggtgca gagactgtta ccagtgctgt gccaggccca 2460
tggcctaaca ccccagcagg tggtggccat cgccagccac gacggcggca agcaggccct 2520
ggaaaccgtg cagaggctgc tgcctgtgct gtgccaggct catggcctga cacctgagca 2580
ggtcgtcgcc atcgccagca acatcggcgg caagcaggcc ctggaaaccg tgcagaggct 2640
gctgccagtg ctgtgccagg cccatggctt aacacccgaa caggtggtgg ccatcgcttc 2700
taatattggg ggcaagcagg ccctggaaac agtccagaga ctgttgcctg tgctgtgcca 2760
ggctcatggc ttgacacctc agcaggtcgt cgctatcgcc tctaataagg ggggcaagca 2820
ggctctggag acagtacagc gcctgttacc agtgctgtgc caggcccacg ggctcacacc 2880
ccagcaggtg gtggcaatcg cttcccatga cggagggaaa caggctctgg aaacggtcca 2940
gaggctgctc cctgtgctgt gccaggctca cggtctaaca ccccagcagg tggtggccat 3000
tgctagcaac aatgggggca agcaggctct ggagacagtg cagcgcctgc tgcctgtgct 3060

```
gtgccaggct catggcctca cacctcagca ggtcgtcgcc atcgccagcc acgacggcgg   3120
caagcaggcc ctggaaaccg tgcagaggct gctgccagtg ctgtgccagg cccatggcct   3180
aacaccccag caggtggtgg caatcgcctc caatggcgga gggaagcagg ccctggaaac   3240
ggtgcagaga ctgttacctg tgctgtgcca ggctcatggc ctgacacctg agcaggtcgt   3300
cgctatcgct agcaatatcg gagggaagca ggctctggaa actgtccagc gcctgctccc   3360
agtgctgtgc caggcccatg gcttaacacc ccagcaggtg gtggcaattg ctagcaatgg   3420
cggagggaag caggccctgg agactgtcca gagactgcta cctgtgctgt gccaggctca   3480
tggcttgaca cctcagcagg tcgtcgctat cgcctctaat aaggggggca agcaggctct   3540
ggagacagta cagcgcctgt taccagtgct gtgccaggcc cacgggctca caccccagca   3600
ggtggtggcc atcgccagca acggcggcgg caagcaggcc ctggaaaccg tgcagaggct   3660
gctgcctgtg ctgtgccagg ctcacggcct gaccccacag caggtcgtcg ctattgcttc   3720
taatggcgga gggcggcctg ctctggagag cattgtggct cagctgtcca ggcccgatcc   3780
tgccctggct agatccgcac tcactaacga tcatctggtc gctctcgctt gcctcggtgg   3840
acggcccgct ctggacgcag tcaaaaaggg tctcccccat gctcccgcac tgatcaagag   3900
aaccaacagg agaattcctg agggatccga tcgtttaaac gaaggcatca aaagcaacat   3960
ctccctcctg aaagacgaac tccgggggca gattagccac attagtcacg aatacctctc   4020
cctcatcgac ctggctttcg atagcaagca gaacaggctc tttgagatga aagtgctgga   4080
actgctcgtc aatgagtacg ggttcaaggg tcgacacctc ggcggatcta ggaaaccaga   4140
cggcatcgtg tatagtacca cactggaaga caactttggg atcattgtgg ataccaaggc   4200
atactctgag ggttatagtc tgcccatttc acaggccgac gagatggaac ggtacgtgcg   4260
cgagaactca aatagagatg aggaagtcaa ccctaacaag tggtgggaga acttctctga   4320
ggaagtgaag aaatactact tcgtctttat cagcgggtcc ttcaagggta aatttgagga   4380
acagctcagg agactgagca tgactaccgg cgtgaatggc agcgccgtca acgtggtcaa   4440
tctgctcctg ggcgctgaaa agattcggag cggagagatg accatcgaag agctggagag   4500
ggcaatgttt aataatagcg agtttatcct gaaatactga acgcgtaaat gattgcagat   4560
ccactagttc tagaattcca gctgagcgcc ggtcgctacc attaccagtt ggtctggtgt   4620
caaaaataat aataaccggg caggggggat ctgcatggat ctttgtgaag gaaccttact   4680
tctgtggtgt gacataattg gacaaactac ctacagagat ttaaagctct aaggtaaata   4740
taaaattttt aagtgtataa tgtgttaaac tactgattct aattgtttgt gtattttaga   4800
ttccaaccta tggaactgat gaatgggagc agtggtggaa tgccagatcc agacatgata   4860
agatacattg atgagtttgg acaaaccaca actagaatgc agtgaaaaaa atgctttatt   4920
tgtgaaattt gtgatgctat tgctttattt gtaaccatta taagctgcaa taaacaagtt   4980
aacaacaaca attgcattca ttttatgttt caggttcagg gggaggtgtg ggaggttttt   5040
taaagcaagt aaaacctcta caaatgtggt atggctgatt atgatctgcg gccgccactg   5100
gccgtcgttt tacaacgtcg tgactgggaa aaccctggcg ttacccaact taatcgcctt   5160
gcagcacatc ccccttcgc  cagctggcgt aatagcgaag aggcccgcac cgatcgccct   5220
tcccaacagt tgcgcagcct gaatggcgaa tggaacgcgc cctgtagcgg cgcattaagc   5280
gcggcgggtg tggtggttac gcgcagcgtg accgctacac ttgccagcgc cctagcgccc   5340
gctcctttcg ctttcttccc ttcctttctc gccacgttcg ccggctttcc ccgtcaagct   5400
```

ctaaatcggg ggctcccttt agggttccga tttagtgctt tacggcacct cgaccccaaa 5460
aaacttgatt agggtgatgg ttcacgtagt gggccatcgc cctgatagac ggtttttcgc 5520
cctttgacgt tggagtccac gttctttaat agtggactct tgttccaaac tggaacaaca 5580
ctcaacccta tctcggtcta ttcttttgat ttataaggga ttttgccgat ttcggcctat 5640
tggttaaaaa atgagctgat ttaacaaaaa tttaacgcga attttaacaa aatattaacg 5700
cttacaattt aggtggcact tttcggggaa atgtgcgcgg aacccctatt tgtttatttt 5760
tctaaataca ttcaaatatg tatccgctca tgagacaata accctgataa atgcttcaat 5820
aatattgaaa aaggaagagt atgagtattc aacatttccg tgtcgccctt attccctttt 5880
ttgcggcatt ttgccttcct gtttttgctc acccagaaac gctggtgaaa gtaaaagatg 5940
ctgaagatca gttgggtgca cgagtgggtt acatcgaact ggatctcaac agcggtaaga 6000
tccttgagag ttttcgcccc gaagaacgtt ttccaatgat gagcactttt aaagttctgc 6060
tatgtggcgc ggtattatcc cgtattgacg ccgggcaaga gcaactcggt cgccgcatac 6120
actattctca gaatgacttg gttgagtact caccagtcac agaaaagcat cttacggatg 6180
gcatgacagt aagagaatta tgcagtgctg ccataaccat gagtgataac actgcggcca 6240
acttacttct gacaacgatc ggaggaccga aggagctaac cgcttttttg cacaacatgg 6300
gggatcatgt aactcgcctt gatcgttggg aaccggagct gaatgaagcc ataccaaacg 6360
acgagcgtga caccacgatg cctgtagcaa tggcaacaac gttgcgcaaa ctattaactg 6420
gcgaactact tactctagct tcccggcaac aattaataga ctggatggag gcggataaag 6480
ttgcaggacc acttctgcgc tcggcccttc cggctggctg gtttattgct gataaatctg 6540
gagccggtga gcgtgggtct cgcggtatca ttgcagcact ggggccagat ggtaagccct 6600
cccgtatcgt agttatctac acgacgggga gtcaggcaac tatggatgaa cgaaatagac 6660
agatcgctga gataggtgcc tcactgatta agcattggta actgtcagac caagtttact 6720
catatatact ttagattgat ttaaaacttc atttttaatt taaaaggatc taggtgaaga 6780
tcctttttga taatctcatg accaaaatcc cttaacgtga gttttcgttc cactgagcgt 6840
cagaccccgt agaaaagatc aaaggatctt cttgagatcc tttttttctg cgcgtaatct 6900
gctgcttgca aacaaaaaaa ccaccgctac cagcggtggt ttgtttgccg gatcaagagc 6960
taccaactct ttttccgaag gtaactggct tcagcagagc gcagatacca aatactgtcc 7020
ttctagtgta gccgtagtta ggccaccact tcaagaactc tgtagcaccg cctacatacc 7080
tcgctctgct aatcctgtta ccagtggctg ctgccagtgg cgataagtcg tgtcttaccg 7140
ggttggactc aagacgatag ttaccggata aggcgcagcg gtcgggctga acggggggtt 7200
cgtgcacaca gcccagcttg gagcgaacga cctacaccga actgagatac ctacagcgtg 7260
agctatgaga aagcgccacg cttcccgaag ggagaaaggc ggacaggtat ccggtaagcg 7320
gcagggtcgg aacaggagag cgcacgaggg agcttccagg gggaaacgcc tggtatcttt 7380
atagtcctgt cgggtttcgc cacctctgac ttgagcgtcg atttttgtga tgctcgtcag 7440
gggggcggag cctatggaaa aacgccagca acgcggcctt tttacggttc ctggcctttt 7500
gctggccttt tgctcacatg ttctttcctg cgttatcccc tgattctgtg gataaccgta 7560
ttaccgcctt tgagtgagct gataccgctc gccgcagccg aacgaccgag cgcagcgagt 7620
cagtgagcga ggaagcggaa gagcgcccaa tacgcaaacc gcctctcccc gcgcgttggc 7680
cgattcatta atgcagctgg cacgacaggt ttcccgactg gaaagcgggc agtgagcgca 7740
acgcaattaa tgtgagttag ctcactcatt aggcacccca ggctttacac tttatgcttc 7800

```
cggctcgtat gttgtgtgga attgtgagcg gataacaatt tcacacagga aacagctatg   7860

accatga                                                             7867


<210> SEQ ID NO 55
<211> LENGTH: 935
<212> TYPE: PRT
<213> ORGANISM: Artificial sequence
<220> FEATURE:
<223> OTHER INFORMATION: RabChtTal1-Clo051

<400> SEQUENCE: 55

Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Ile Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Ala His Gly Leu Thr Pro Gln Gln Val
```

```
            340                 345                 350

Val Ala Ile Ala Ser Asn Lys Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Gln Gln Val Val Ala Ile Ala Ser His Asp Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Lys Gly Gly Lys Gln Ala Leu Glu Thr Val Gln Arg
        595                 600                 605

Leu Leu Pro Val Leu Cys Gln Ala His Gly Leu Thr Pro Gln Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655

Gln Val Val Ala Ile Ala Ser Asn Gly Gly Gly Arg Pro Ala Leu Glu
            660                 665                 670

Ser Ile Val Ala Gln Leu Ser Arg Pro Asp Pro Ala Leu Ala Arg Ser
        675                 680                 685

Ala Leu Thr Asn Asp His Leu Val Ala Leu Ala Cys Leu Gly Gly Arg
    690                 695                 700

Pro Ala Leu Asp Ala Val Lys Lys Gly Leu Pro His Ala Pro Ala Leu
705                 710                 715                 720

Ile Lys Arg Thr Asn Arg Arg Ile Pro Glu Gly Ser Asp Arg Leu Asn
                725                 730                 735

Glu Gly Ile Lys Ser Asn Ile Ser Leu Leu Lys Asp Glu Leu Arg Gly
            740                 745                 750

Gln Ile Ser His Ile Ser His Glu Tyr Leu Ser Leu Ile Asp Leu Ala
        755                 760                 765
```

```
Phe Asp Ser Lys Gln Asn Arg Leu Phe Glu Met Lys Val Leu Glu Leu
    770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
                805                 810                 815

Ile Ile Val Asp Thr Lys Ala Tyr Ser Glu Gly Tyr Ser Leu Pro Ile
            820                 825                 830

Ser Gln Ala Asp Glu Met Glu Arg Tyr Val Arg Glu Asn Ser Asn Arg
        835                 840                 845

Asp Glu Glu Val Asn Pro Asn Lys Trp Trp Glu Asn Phe Ser Glu Glu
    850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
                885                 890                 895

Ser Ala Val Asn Val Val Asn Leu Leu Leu Gly Ala Glu Lys Ile Arg
            900                 905                 910

Ser Gly Glu Met Thr Ile Glu Glu Leu Glu Arg Ala Met Phe Asn Asn
        915                 920                 925

Ser Glu Phe Ile Leu Lys Tyr
    930                 935
```

<210> SEQ ID NO 56
<211> LENGTH: 7867
<212> TYPE: DNA
<213> ORGANISM: Artificial sequence
<220> FEATURE:
<223> OTHER INFORMATION: pCAG-RabChtTal2-Clo051

<400> SEQUENCE: 56

```
ggcgcgccgg attcgacatt gattattgac tagttattaa tagtaatcaa ttacggggtc     60

attagttcat agcccatata tggagttccg cgttacataa cttacggtaa atggcccgcc    120

tggctgaccg cccaacgacc cccgcccatt gacgtcaata atgacgtatg ttcccatagt    180

aacgccaata gggactttcc attgacgtca atgggtggag tatttacggt aaactgccca    240

cttggcagta catcaagtgt atcatatgcc aagtacgccc cctattgacg tcaatgacgg    300

taaatggccc gcctggcatt atgcccagta catgacctta tgggactttc ctacttggca    360

gtacatctac gtattagtca tcgctattac catggtcgag gtgagcccca cgttctgctt    420

cactctcccc atctcccccc cctccccacc cccaattttg tatttattta ttttttaatt    480

attttgtgca gcgatggggg cggggggggg gggggggcgc gcgccaggcg gggcggggcg    540

gggcgagggg cggggcgggg cgaggcggag aggtgcggcg gcagccaatc agagcggcgc    600

gctccgaaag tttcctttta tggcgaggcg gcggcggcgg cggccctata aaaagcgaag    660

cgcgcggcgg gcgggagtcg ctgcgcgctg ccttcgcccc gtgccccgct ccgccgccgc    720

ctcgcgccgc ccgccccggc tctgactgac cgcgttactc ccacaggtga gcgggcggga    780

cggcccttct cctccgggct gtaattagcg cttggtttaa tgacggcttg tttcttttct    840

gtggctgcgt gaaagccttg aggggctccg ggagggccct ttgtgcgggg gggagcggct    900

cggggggtgc gtgcgtgtgt gtgtgcgtgg ggagcgccgc gtgcggctcc gcgctgcccg    960

gcggctgtga gcgctgcggg cgcggcgcgg ggctttgtgc gctccgcagt gtgcgcgagg   1020

ggagcgcggc cgggggcggt gccccgcggt gcgggggggg ctgcgagggg aacaaaggct   1080
```

```
gcgtgcgggg tgtgtgcgtg ggggggtgag caggggggtgt gggcgcgtcg gtcgggctgc   1140
aacccccccct gcacccccct ccccgagttg ctgagcacgg cccggcttcg ggtgcggggc   1200
tccgtacggg gcgtggcgcg gggctcgccg tgccgggcgg ggggtggcgg caggtggggg   1260
tgccgggcgg ggcggggccg cctcgggccg gggagggctc gggggagggg cgcggcggcc   1320
cccggagcgc cggcggctgt cgaggcgcgg cgagccgcag ccattgcctt ttatggtaat   1380
cgtgcgagag ggcgcaggga cttcctttgt cccaaatctg tgcggagccg aaatctggga   1440
ggcgccgccg cacccccctct agcgggcgcg ggcgaagcgg gtgcggcgcc ggcaggaagg   1500
aaatgggcgg ggagggcctt cgtgcgtcgc cgcgccgccg tccccttctc cctctccagc   1560
ctcggggctg tccgcggggg gacggctgcc ttcggggggg acggggcagg gcggggttcg   1620
gcttctggcg tgtgaccggc ggctctagag cctctgctaa ccatgttcat gccttcttct   1680
ttttcctaca gatccttaat taataatacg actcactata ggggccgcca ccatgggacc   1740
taagaaaaag aggaaggtgg cggccgctga ctacaaggat gacgacgata aaccaggtgg   1800
cggaggtagt ggcggaggtg ggtacccgc cagtccagca gcccaggtgg atctgagaac   1860
cctcggctac agccagcagc agcaggagaa gatcaaacca aaggtgcggt ccaccgtcgc   1920
tcagcaccat gaagcactgg tggggcacgg tttcacacac gcccatattg tggctctgtc   1980
tcagcatccc gctgcactcg ggactgtggc cgtcaaatat caggacatga tcgccgctct   2040
gcctgaggca acccacgaag ccattgtggg cgtcggaaag cagtggagcg gtgccagagc   2100
actcgaagca ctcctcaccg tcgccgggga actgcggggt ccaccactcc agtccggact   2160
ggacactgga cagctgctga agatcgctaa acgcggcgga gtgacagctg tggaagctgt   2220
gcacgcttgg aggaatgctc tgacaggagc cccactgaat cttacacccc agcaggtggt   2280
ggccattgct agcaacaatg gggcaagca ggctctggag acagtgcagc gcctgctgcc   2340
tgtgctgtgc caggctcatg gcctcacacc tcagcaggtc gtcgccattg cttctaacaa   2400
tggagggaag caggctctgg agactgtgca gagactgctg ccagtgctgt gccaggccca   2460
tggcctaaca ccccagcagg tggtggccat cgccagccac gacggcggca agcaggccct   2520
ggaaaccgtg cagaggctgc tgcctgtgct gtgccaggct catggcctga cacctcagca   2580
ggtcgtcgcc atcgccagcc acgacggcgg caagcaggcc ctggaaaccg tgcagaggct   2640
gctgccagtg ctgtgccagg cccatggctt aacaccccag caggtggtgg ccatcgctag   2700
tcatgacggg ggcaaacagg ctctggaaac agtacagcgg ctgttacctg tgctgtgcca   2760
ggctcatggc ttgacacctc agcaggtcgt cgctatcgcc tctaataagg ggggcaagca   2820
ggctctggag acagtacagc gcctgttacc agtgctgtgc caggcccacg ggctcacacc   2880
ccagcaggtg gtggcaattg cttccaataa gggcggaaaa caggctctgg aaaccgtcca   2940
gaggctgctg cctgtgctgt gccaggctca cggtctaaca ccccagcagg tggtggccat   3000
cgcttccaac ggagggggca aacaggctct ggaaacagtg cagaggctgc tgcctgtgct   3060
gtgccaggct catggcctca cacctgagca ggtcgtcgcc atcgccagca acatcggcgg   3120
caagcaggcc ctggaaaccg tgcagaggct gctgccagtg ctgtgccagg cccatggcct   3180
aacaccccag caggtggtgg caattgcttc caataagggc ggaaaacagg ctctggaaac   3240
cgtccagagg ctgctgcctg tgctgtgcca ggctcatggc ctgacacctc agcaggtcgt   3300
cgcaatcgcc tccaatggcg gagggaagca ggccctggaa acggtgcaga gactgttacc   3360
agtgctgtgc caggcccatg gcttaacacc ccagcaggtg gtggcaatcg cctctaataa   3420
```

```
gggagggaag caggccctgg aaaccgtgca gagactgtta cctgtgctgt gccaggctca   3480
tggcttgaca cctcagcagg tcgtcgctat cgctagtcat gatggcggaa aacaggctct   3540
ggaaactgtg cagcggctgc tcccagtgct gtgccaggcc cacgggctca caccccagca   3600
ggtggtggcc atcgccagca acaagggcgg caagcaggcc ctggaaaccg tgcagaggct   3660
gctgcctgtg ctgtgccagg ctcacggcct gaccccacag caggtcgtcg ctattgcttc   3720
taatggcgga gggcggcctg ctctggagag cattgtggct cagctgtcca ggcccgatcc   3780
tgccctggct agatccgcac tcactaacga tcatctggtc gctctcgctt gcctcggtgg   3840
acggcccgct ctggacgcag tcaaaaaggg tctcccccat gctcccgcac tgatcaagag   3900
aaccaacagg agaattcctg agggatccga tcgtttaaac gaaggcatca aaagcaacat   3960
ctccctcctg aaagacgaac tccgggggca gattagccac attagtcacg aatacctctc   4020
cctcatcgac ctggctttcg atagcaagca gaacaggctc tttgagatga aagtgctgga   4080
actgctcgtc aatgagtacg ggttcaaggg tcgacacctc ggcggatcta ggaaaccaga   4140
cggcatcgtg tatagtacca cactggaaga caactttggg atcattgtgg ataccaaggc   4200
atactctgag ggttatagtc tgcccatttc acaggccgac gagatggaac ggtacgtgcg   4260
cgagaactca aatagagatg aggaagtcaa ccctaacaag tggtgggaga acttctctga   4320
ggaagtgaag aaatactact tcgtctttat cagcgggtcc ttcaagggta aatttgagga   4380
acagctcagg agactgagca tgactaccgg cgtgaatggc agcgccgtca acgtggtcaa   4440
tctgctcctg ggcgctgaaa agattcggag cggagagatg accatcgaag agctggagag   4500
ggcaatgttt aataatagcg agtttatcct gaaatactga acgcgtaaat gattgcagat   4560
ccactagttc tagaattcca gctgagcgcc ggtcgctacc attaccagtt ggtctggtgt   4620
caaaaataat aataaccggg caggggggat ctgcatggat ctttgtgaag gaaccttact   4680
tctgtggtgt gacataattg gacaaactac ctacagagat ttaaagctct aaggtaaata   4740
taaaattttt aagtgtataa tgtgttaaac tactgattct aattgtttgt gtattttaga   4800
ttccaaccta tggaactgat gaatgggagc agtggtggaa tgccagatcc agacatgata   4860
agatacattg atgagtttgg acaaaccaca actagaatgc agtgaaaaaa atgctttatt   4920
tgtgaaattt gtgatgctat tgctttattt gtaaccatta taagctgcaa taaacaagtt   4980
aacaacaaca attgcattca ttttatgttt caggttcagg gggaggtgtg ggaggttttt   5040
taaagcaagt aaaacctcta caaatgtggt atggctgatt atgatctgcg gccgccactg   5100
gccgtcgttt tacaacgtcg tgactgggaa aaccctggcg ttacccaact taatcgcctt   5160
gcagcacatc ccccttttcgc cagctggcgt aatagcgaag aggcccgcac cgatcgccct   5220
tcccaacagt tgcgcagcct gaatggcgaa tggaacgcgc cctgtagcgg cgcattaagc   5280
gcggcgggtg tggtggttac gcgcagcgtg accgctacac ttgccagcgc cctagcgccc   5340
gctcctttcg ctttcttccc ttcctttctc gccacgttcg ccggctttcc ccgtcaagct   5400
ctaaatcggg ggctcccttt agggttccga tttagtgctt tacggcacct cgaccccaaa   5460
aaacttgatt agggtgatgg ttcacgtagt gggccatcgc cctgatagac ggtttttcgc   5520
cctttgacgt tggagtccac gttctttaat agtggactct tgttccaaac tggaacaaca   5580
ctcaacccta tctcggtcta ttcttttgat ttataaggga ttttgccgat ttcggcctat   5640
tggttaaaaa atgagctgat ttaacaaaaa tttaacgcga attttaacaa aatattaacg   5700
cttacaattt aggtggcact tttcggggaa atgtgcgcgg aacccctatt tgtttatttt   5760
tctaaataca ttcaaatatg tatccgctca tgagacaata accctgataa atgcttcaat   5820
```

```
aatattgaaa aaggaagagt atgagtattc aacatttccg tgtcgccctt attccctttt   5880
ttgcggcatt ttgccttcct gtttttgctc acccagaaac gctggtgaaa gtaaaagatg   5940
ctgaagatca gttgggtgca cgagtgggtt acatcgaact ggatctcaac agcggtaaga   6000
tccttgagag ttttcgcccc gaagaacgtt ttccaatgat gagcactttt aaagttctgc   6060
tatgtggcgc ggtattatcc cgtattgacg ccgggcaaga gcaactcggt cgccgcatac   6120
actattctca gaatgacttg gttgagtact caccagtcac agaaaagcat cttacggatg   6180
gcatgacagt aagagaatta tgcagtgctg ccataaccat gagtgataac actgcggcca   6240
acttacttct gacaacgatc ggaggaccga aggagctaac cgcttttttg cacaacatgg   6300
gggatcatgt aactcgcctt gatcgttggg aaccggagct gaatgaagcc ataccaaacg   6360
acgagcgtga caccacgatg cctgtagcaa tggcaacaac gttgcgcaaa ctattaactg   6420
gcgaactact tactctagct tcccggcaac aattaataga ctggatggag gcggataaag   6480
ttgcaggacc acttctgcgc tcggcccttc cggctggctg gtttattgct gataaatctg   6540
gagccggtga gcgtgggtct cgcggtatca ttgcagcact ggggccagat ggtaagccct   6600
cccgtatcgt agttatctac acgacgggga gtcaggcaac tatggatgaa cgaaatagac   6660
agatcgctga gataggtgcc tcactgatta agcattggta actgtcagac caagtttact   6720
catatatact ttagattgat ttaaaacttc atttttaatt taaaaggatc taggtgaaga   6780
tcctttttga taatctcatg accaaaatcc cttaacgtga gttttcgttc cactgagcgt   6840
cagaccccgt agaaaagatc aaaggatctt cttgagatcc tttttttctg cgcgtaatct   6900
gctgcttgca aacaaaaaaa ccaccgctac cagcggtggt ttgtttgccg gatcaagagc   6960
taccaactct ttttccgaag gtaactggct tcagcagagc gcagatacca aatactgtcc   7020
ttctagtgta gccgtagtta ggccaccact tcaagaactc tgtagcaccg cctacatacc   7080
tcgctctgct aatcctgtta ccagtggctg ctgccagtgg cgataagtcg tgtcttaccg   7140
ggttggactc aagacgatag ttaccggata aggcgcagcg gtcgggctga acggggggtt   7200
cgtgcacaca gcccagcttg gagcgaacga cctacaccga actgagatac ctacagcgtg   7260
agctatgaga aagcgccacg cttcccgaag ggagaaaggc ggacaggtat ccggtaagcg   7320
gcagggtcgg aacaggagag cgcacgaggg agcttccagg gggaaacgcc tggtatcttt   7380
atagtcctgt cgggtttcgc cacctctgac ttgagcgtcg atttttgtga tgctcgtcag   7440
gggggcggag cctatggaaa aacgccagca acgcggcctt tttacggttc ctggcctttt   7500
gctggccttt tgctcacatg ttctttcctg cgttatcccc tgattctgtg gataaccgta   7560
ttaccgcctt tgagtgagct gataccgctc gccgcagccg aacgaccgag cgcagcgagt   7620
cagtgagcga ggaagcggaa gagcgcccaa tacgcaaacc gcctctcccc gcgcgttggc   7680
cgattcatta atgcagctgg cacgacaggt ttcccgactg gaaagcgggc agtgagcgca   7740
acgcaattaa tgtgagttag ctcactcatt aggcacccca ggctttacac tttatgcttc   7800
cggctcgtat gttgtgtgga attgtgagcg gataacaatt tcacacagga aacagctatg   7860
accatga                                                             7867
```

<210> SEQ ID NO 57
<211> LENGTH: 935
<212> TYPE: PRT
<213> ORGANISM: Artificial sequence
<220> FEATURE:
<223> OTHER INFORMATION: RabChtTal2-Clo051

<400> SEQUENCE: 57

```
Met Gly Pro Lys Lys Lys Arg Lys Val Ala Ala Ala Asp Tyr Lys Asp
1               5                   10                  15

Asp Asp Asp Lys Pro Gly Gly Gly Gly Ser Gly Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Gln Gln Val Val Ala Ile Ala Ser Asn Asn Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Lys Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Lys Gly Gly Lys Gln Ala Leu Glu
385                 390                 395                 400

Thr Val Gln Arg Leu Leu Pro Val Leu Cys Gln Ala His Gly Leu Thr
                405                 410                 415
```

```
Pro Gln Gln Val Val Ala Ile Ala Ser Asn Gly Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Lys Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Lys Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Ala His Gly Leu Thr Pro Gln Gln Val
    610                 615                 620

Val Ala Ile Ala Ser Asn Lys Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655

Gln Val Val Ala Ile Ala Ser Asn Gly Gly Gly Arg Pro Ala Leu Glu
            660                 665                 670

Ser Ile Val Ala Gln Leu Ser Arg Pro Asp Pro Ala Leu Ala Arg Ser
        675                 680                 685

Ala Leu Thr Asn Asp His Leu Val Ala Leu Ala Cys Leu Gly Gly Arg
    690                 695                 700

Pro Ala Leu Asp Ala Val Lys Lys Gly Leu Pro His Ala Pro Ala Leu
705                 710                 715                 720

Ile Lys Arg Thr Asn Arg Arg Ile Pro Glu Gly Ser Asp Arg Leu Asn
                725                 730                 735

Glu Gly Ile Lys Ser Asn Ile Ser Leu Leu Lys Asp Glu Leu Arg Gly
            740                 745                 750

Gln Ile Ser His Ile Ser His Glu Tyr Leu Ser Leu Ile Asp Leu Ala
        755                 760                 765

Phe Asp Ser Lys Gln Asn Arg Leu Phe Glu Met Lys Val Leu Glu Leu
    770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
                805                 810                 815

Ile Ile Val Asp Thr Lys Ala Tyr Ser Glu Gly Tyr Ser Leu Pro Ile
            820                 825                 830
```

```
Ser Gln Ala Asp Glu Met Glu Arg Tyr Val Arg Glu Asn Ser Asn Arg
        835                 840                 845

Asp Glu Glu Val Asn Pro Asn Lys Trp Trp Glu Asn Phe Ser Glu Glu
    850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
                885                 890                 895

Ser Ala Val Asn Val Val Asn Leu Leu Leu Gly Ala Glu Lys Ile Arg
            900                 905                 910

Ser Gly Glu Met Thr Ile Glu Glu Leu Glu Arg Ala Met Phe Asn Asn
        915                 920                 925

Ser Glu Phe Ile Leu Lys Tyr
    930                 935


<210> SEQ ID NO 58
<211> LENGTH: 6607
<212> TYPE: DNA
<213> ORGANISM: Artificial sequence
<220> FEATURE:
<223> OTHER INFORMATION: pRab38-chtTAL

<400> SEQUENCE: 58

caccgcatta ccctgggcgt tgaaaccgaa gaagacctgg atttgaaata ggcgttttct      60

ttacatttct aaagtgggac tcctcacttg taaaaggaaa aataatgata cttttaagac     120

ttccaggatg actaaatggt gtgtatgaga agatttataa acatctgccg ctacttacaa     180

tgataagacc acttgtgtgt tgttcagctt ggagaattta ggataggagt ggaggctgaa     240

agaaaagtaa gcccttagca tttcctctca ggtggcctct actttaggtc attaacagtt     300

gaataggcgc taagagatag cattaccact ttatagaagc ccaggcaaaa ggagattaaa     360

gggtttgcct aaattctttc aactctaagg gccagagaag acctaagtct actgctttgc     420

tgtttctcaa ggtctcccca actttacaac actgtgtggg tggcaacagg gcttaatagc     480

ctcagaagac ctgggtattt ttcgacactc agttctctcc ccggcagaac gtggaaaaca     540

aaatccacat aagtttgtgt catggacggg aggcgagaga aaaatctctg tgaaaggagt     600

aaagcactgt gcaaatacca gcttgacagg cagtagcact ggggtcccgg gtcctttagc     660

ttccagtccc aggagttgct cttgtctcct cccactctgg agtccgcaga gtaggaagga     720

ggattaaacc cgggggagga gttccgcacc agctccctat cctgcgccag cacgcctagc     780

ctaagcgccc acatagagct ccggtctccg tcggtgccca gccccggctg tgcttcccag     840

agcaagctcc aggctccgca agacccgcgg gcctccagga tgcagacacc tcacaaggag     900

cacctgtaca agctgctggt gatcggcgac ctggtagtgg gcaagaccag cattattaaa     960

cggtacgtgc atcaaaattt ctcctctcat tatcgagcca ccattggtgt ggacttcgcg    1020

ctgaaggtgc tccactggga cccagagacg gtggtgcgct tgcagctctg ggacattgct    1080

ggtgagcgat cagagcagcg cgcaacgggt gagggtggag tgagccagtg aggagttcgg    1140

gggtgaaggt tcggggagtg gaaaatgact tttcagtcgg ttccagtccc gggacccttg    1200

agtgcaatca agcaggagat ccggatcgcc tgggcgctcc actcttggaa agtttggctt    1260

aatggcttgg aaacctgatt tcaaagaaat ggaagtgttt tcttttcttt ctttcctttt    1320

ttttttttt ttttttctt ttgctgttgt ttctgttgga gtcgtcccca ctctacctgt    1380

aacttctaga taacttcgct ggctctcact ggctgtgaga aagcgaacca ctttctcctg    1440
```

-continued

```
ggattcttgg gtgcagagaa ggctgtcgcc tggactcaca aggagattgt agtcgcattc   1500
ttgtttcatt ctagtccttt tctggacaca ggtagccgcg acttggccca gagtatctca   1560
cgtggctttc atccttcgtg tttagagggg aagcccctag gaaatttaag aaggagcagg   1620
attatcttag gaatttagtt tctttcaaat ctcactacta tcatctcctt gcttattggc   1680
ctcttcagtc agaaaaattt gagatgctaa atttgtatac atctagaacg aactatctct   1740
tctcactcca ctcccctctt ccccatctct cttccgtctc cctccatcct tggctatctc   1800
ttcttcactt tccatttcaa acaggagact gtgtatgttt tttaggaaaa cattaaaaaa   1860
aaaaccacaa aaacaaaaac aaaacggaga cagggtcccg tcatgtaact ctgctaacct   1920
atatcaagct gaccttgacc tcatagagac ccacttgcct ctgcctccct agaggcaagg   1980
gtcggggtta tggtgatgtt aatgtcgttt gctttaagat tccttgattt gatcttggtg   2040
tatttttga gaaatctaaa gtatgaaatc agagtttgac taacagcttc taccagctcc   2100
tagccacaat aaagactgag gcaggctata gttagtgctc aatactgggt cctacctggc   2160
tgcttgtaac ctgggcatgc ctagcattct agatgctaac tcaccaaagc agtagcattt   2220
taagctgcaa atggctaggc agcgacagct caagaatctt cttgctttgg agttttaaac   2280
tccaatgaga ttttccatga tccctttcaa ataaccctac ttaatctctc ttcatagccc   2340
acagtaccaa gaagcctttg ataagctctg gattgaaaag aagcagttct ttttcaaaag   2400
atgtgctcat ttgaactagt gcatttccct ggaaacactt tgccaggact tgagatgggc   2460
actaagaagg aaaattcctc aaaggacatg tacagtcttg agatgcattc gcttctgtag   2520
ccatgagctt gctggtcttg agataaggtt agttggtgta gctaggttca tggtttggag   2580
tctttggcag ttctagagaa gcatgagcta ttagagactt ggagattgca tcaagtagag   2640
ccttttgagc ttttcactgt gtacctgggc cctctgtcgc tgcacgtttt agtgtctgaa   2700
atgtctttca gctgtagcag ttttctcggg accccagttt aaaatagctt actgtttaaa   2760
agatgtagct gtagctagca ttattgaact agcataatta tagtctaaat agcattatgt   2820
cttcagcctt gttatatgtt ggtgagtttt agtttcctct tctaaacggg aagaacagaa   2880
agatgtaatg attctgagct tccagagtga gacacctcta gagagaaata ccttcttctg   2940
aagactaccg tgtgattaca gataaattct gatatctttg tttagctttt gatatctata   3000
aacagggagt gtattttatc tctccaaatg agagaagaat aaacaataat gcaaggtaaa   3060
ggcaatagtg ctacactcta ggagttacca ctctttgtac atttatttat aaatactaag   3120
caagaggaac atgccataca tacactgact aagtcctaac aagtggcagt tcttatatca   3180
cacatttatc ttgccctcaa atgccagtcc agcatcagtt tagtctcatg catttggcag   3240
cataaggcag tttgagttcc acacttgctc tcagaagcaa tttaactccc acacttggga   3300
atcctttcct aagccacagt ttcagaccaa agttttggtg aaggctataa tcacagaagt   3360
ctgcacaagt agggagtctg aaggatctga gctccattca gcagtcagag cggcatccaa   3420
ccccaaggta atgctcagct cactttgata acttcaagct caaaggccct gaactgctga   3480
gttggaggtt gaaagatgtt tgggtaaaag caaggtaatt ggcggatagg atggttgtaa   3540
cgtaattgtt tcaagttgta ttagagacct ctgggttcta aggggatatg aaatccaacc   3600
tccactctcc actgagattc aagttaggtt aagtatgcct ttgagtaccc tcaagtcaca   3660
gcatgccact ctccttttct taactctaat atgtatctat aaagaacggg tagtagtcaa   3720
ctgagtcgac ggtatcgata agcttgatcc agcttttgtt ccctttagtg agggttaatt   3780
gcgcgcttgg cgtaatcatg gtcatagctg tttcctgtgt gaaattgtta tccgctcaca   3840
```

```
attccacaca acatacgagc cggaagcata aagtgtaaag cctggggtgc ctaatgagtg   3900
agctaactca cattaattgc gttgcgctca ctgcccgctt tccagtcggg aaacctgtcg   3960
tgccagctgc attaatgaat cggccaacgc gcggggagag gcggtttgcg tattgggcgc   4020
tcttccgctt cctcgctcac tgactcgctg cgctcggtcg ttcggctgcg gcgagcggta   4080
tcagctcact caaaggcggt aatacggtta tccacagaat caggggataa cgcaggaaag   4140
aacatgtgag caaaaggcca gcaaaaggcc aggaaccgta aaaaggccgc gttgctggcg   4200
tttttccata ggctccgccc ccctgacgag catcacaaaa atcgacgctc aagtcagagg   4260
tggcgaaacc cgacaggact ataaagatac caggcgtttc cccctggaag ctccctcgtg   4320
cgctctcctg ttccgaccct gccgcttacc ggatacctgt ccgcctttct cccttcggga   4380
agcgtggcgc tttctcatag ctcacgctgt aggtatctca gttcggtgta ggtcgttcgc   4440
tccaagctgg gctgtgtgca cgaacccccc gttcagcccg accgctgcgc cttatccggt   4500
aactatcgtc ttgagtccaa cccggtaaga cacgacttat cgccactggc agcagccact   4560
ggtaacagga ttagcagagc gaggtatgta ggcggtgcta cagagttctt gaagtggtgg   4620
cctaactacg gctacactag aaggacagta tttggtatct gcgctctgct gaagccagtt   4680
accttcggaa aaagagttgg tagctcttga tccggcaaac aaaccaccgc tggtagcggt   4740
ggtttttttg tttgcaagca gcagattacg cgcagaaaaa aaggatctca agaagatcct   4800
ttgatctttt ctacggggtc tgacgctcag tggaacgaaa actcacgtta agggattttg   4860
gtcatgagat tatcaaaaag gatcttcacc tagatccttt taaattaaaa atgaagtttt   4920
aaatcaatct aaagtatata tgagtaaact tggtctgaca gttaccaatg cttaatcagt   4980
gaggcaccta tctcagcgat ctgtctattt cgttcatcca tagttgcctg actccccgtc   5040
gtgtagataa ctacgatacg ggagggctta ccatctggcc ccagtgctgc aatgataccg   5100
cgagacccac gctcaccggc tccagattta tcagcaataa accagccagc cggaagggcc   5160
gagcgcagaa gtggtcctgc aactttatcc gcctccatcc agtctattaa ttgttgccgg   5220
gaagctagag taagtagttc gccagttaat agtttgcgca acgttgttgc cattgctaca   5280
ggcatcgtgg tgtcacgctc gtcgtttggt atggcttcat tcagctccgg ttcccaacga   5340
tcaaggcgag ttacatgatc ccccatgttg tgcaaaaaag cggttagctc cttcggtcct   5400
ccgatcgttg tcagaagtaa gttggccgca gtgttatcac tcatggttat ggcagcactg   5460
cataattctc ttactgtcat gccatccgta agatgctttt ctgtgactgg tgagtactca   5520
accaagtcat tctgagaata gtgtatgcgg cgaccgagtt gctcttgccc ggcgtcaata   5580
cgggataata ccgcgccaca tagcagaact ttaaaagtgc tcatcattgg aaaacgttct   5640
tcggggcgaa aactctcaag gatcttaccg ctgttgagat ccagttcgat gtaacccact   5700
cgtgcaccca actgatcttc agcatctttt actttcacca gcgtttctgg gtgagcaaaa   5760
acaggaaggc aaaatgccgc aaaaaaggga ataagggcga cacggaaatg ttgaatactc   5820
atactcttcc tttttcaata ttattgaagc atttatcagg gttattgtct catgagcgga   5880
tacatatttg aatgtattta gaaaaataaa caaatagggg ttccgcgcac atttccccga   5940
aaagtgccac ctaaattgta agcgttaata ttttgttaaa attcgcgtta aatttttgtt   6000
aaatcagctc attttttaac caataggccg aaatcggcaa aatcccttat aaatcaaaag   6060
aatagaccga gatagggttg agtgttgttc cagtttggaa caagagtcca ctattaaaga   6120
acgtggactc caacgtcaaa gggcgaaaaa ccgtctatca gggcgatggc ccactacgtg   6180
```

```
aaccatcacc ctaatcaagt tttttggggt cgaggtgccg taaagcacta aatcggaacc   6240

ctaaagggag cccccgattt agagcttgac ggggaaagcc ggcgaacgtg gcgagaaagg   6300

aagggaagaa agcgaaagga gcgggcgcta gggcgctggc aagtgtagcg gtcacgctgc   6360

gcgtaaccac cacacccgcc gcgcttaatg cgccgctaca gggcgcgtcc cattcgccat   6420

tcaggctgcg caactgttgg gaagggcgat cggtgcgggc ctcttcgcta ttacgccagc   6480

tggcgaaagg gggatgtgct gcaaggcgat taagttgggt aacgccaggg ttttcccagt   6540

cacgacgttg taaaacgacg gccagtgagc gcgcgtaata cgactcacta tagggcgaat   6600

tggagct                                                             6607
```

<210> SEQ ID NO 59
<211> LENGTH: 202
<212> TYPE: DNA
<213> ORGANISM: Mus musculus

<400> SEQUENCE: 59

```
atgcagacac ctcacaagga gcacctgtac aagctgctgg tgatcggcga cctgggtgtg     60

ggcaagacca gcattatcaa gcgctatgtg caccaaaact tctcctcgca ctaccgggcc    120

accattggtg tggacttcgc gctgaaggtg ctccactggg acccagagac ggtggtgcgc    180

ttgcagctct gggacattgc tg                                             202
```

<210> SEQ ID NO 60
<211> LENGTH: 8218
<212> TYPE: DNA
<213> ORGANISM: Artificial sequence
<220> FEATURE:
<223> OTHER INFORMATION: pRab38-chtTAL-neo

<400> SEQUENCE: 60

```
caccgcatta ccctgggcgt tgaaaccgaa gaagacctgg atttgaaata ggcgttttct     60

ttacatttct aaagtgggac tcctcacttg taaaaggaaa aataatgata cttttaagac    120

ttccaggatg actaaatggt gtgtatgaga agatttataa acatctgccg ctacttacaa    180

tgataagacc acttgtgtgt tgttcagctt ggagaattta ggataggagt ggaggctgaa    240

agaaaagtaa gcccttagca tttcctctca ggtggcctct actttaggtc attaacagtt    300

gaataggcgc taagagatag cattaccact ttatagaagc ccaggcaaaa ggagattaaa    360

gggtttgcct aaattctttc aactctaagg gccagagaag acctaagtct actgctttgc    420

tgtttctcaa ggtctcccca actttacaac actgtgtggg tggcaacagg gcttaatagc    480

ctcagaagac ctgggtattt ttcgacactc agttctctcc ccggcagaac gtggaaaaca    540

aaatccacat aagtttgtgt catggacggg aggcgagaga aaaatctctg tgaaaggagt    600

aaagcactgt gcaaatacca gcttgacagg cagtagcact ggggtcccgg gtcctttagc    660

ttccagtccc aggagttgct cttgtctcct cccactctgg agtccgcaga gtaggaagga    720

ggattaaacc cgggggagga gttccgcacc agctccctat cctgcgccag cacgcctagc    780

ctaagcgccc acatagagct ccggtctccg tcggtgccca gccccggctg tgcttcccag    840

agcaagctcc aggctccgca agacccgcgg gcctccagga tgcagacacc tcacaaggag    900

cacctgtaca agctgctggt gatcggcgac ctggtagtgg gcaagaccag cattattaaa    960

cggtacgtgc atcaaaatac cgggtagggg aggcgctttt cccaaggcag tctggagcat   1020

gcgctttagc agccccgctg ggcacttggc gctacacaag tggcctctgg cctcgcacac   1080

attccacatc caccggtagg cgccaaccgg ctccgttctt tggtggcccc ttcgcgccac   1140
```

```
cttctactcc tcccctagtc aggaagttcc cccccgcccc gcagctcgcg tcgtgcagga   1200
cgtgacaaat ggaagtagca cgtctcacta gtctcgtgca gatggacagc accgctgagc   1260
aatggaagcg ggtaggcctt tggggcagcg gccaatagca gctttgctcc ttcgctttct   1320
gggctcagag gctgggaagg ggtgggtccg ggggcgggct caggggcggg ctcaggggcg   1380
gggcgggcgc ccgaaggtcc tccggaggcc cggcattctg cacgcttcaa aagcgcacgt   1440
ctgccgcgct gttctcctct tcctcatctc cgggcctttc gacctgcagc caatatggga   1500
tcggccattg aacaagatgg attgcacgca ggttctccgg ccgcttgggt ggagaggcta   1560
ttcggctatg actgggcaca acagacaatc ggctgctctg atgccgccgt gttccggctg   1620
tcagcgcagg ggcgcccggt tctttttgtc aagaccgacc tgtccggtgc cctgaatgaa   1680
ctgcaggacg aggcagcgcg gctatcgtgg ctggccacga cgggcgttcc ttgcgcagct   1740
gtgctcgacg ttgtcactga agcgggaagg gactggctgc tattgggcga agtgccgggg   1800
caggatctcc tgtcatctca ccttgctcct gccgagaaag tatccatcat ggctgatgca   1860
atgcggcggc tgcatacgct tgatccggct acctgcccat tcgaccacca agcgaaacat   1920
cgcatcgagc gagcacgtac tcggatggaa gccggtcttg tcgatcagga tgatctggac   1980
gaagagcatc aggggctcgc gccagccgaa ctgttcgcca ggctcaaggc gcgcatgccc   2040
gacggcgatg atctcgtcgt gacccatggc gatgcctgct tgccgaatat catggtggaa   2100
aatggccgct tttctggatt catcgactgt ggccggctgg gtgtggcgga ccgctatcag   2160
gacatagcgt tggctacccg tgatattgct gaagagcttg gcggcgaatg ggctgaccgc   2220
ttcctcgtgc tttacggtat cgccgctccc gattcgcagc gcatcgcctt ctatcgcctt   2280
cttgacgagt tcttctgagg ggatcaattc tctagagctc gctgatcagc ctcgactgtg   2340
ccttctagtt gccagccatc tgttgtttgc ccctcccccg tgccttcctt gaccctggaa   2400
ggtgccactc ccactgtcct ttcctaataa aatgaggaaa ttgcatcgca ttgtctgagt   2460
aggtgtcatt ctattctggg gggtggggtg gggcaggaca gcaaggggga ggattgggaa   2520
gacaatagca ggcatgctgg ggatgcggtg ggctctatgg cttctgaggc ggaaagaacc   2580
agctggggtt tctcctctca ttatcgagcc accattggtg tggacttcgc gctgaaggtg   2640
ctccactggg acccagagac ggtggtgcgc ttgcagctct gggacattgc tggtgagcga   2700
tcagagcagc gcgcaacggg tgagggtgga gtgagccagt gaggagttcg gggtgaagg    2760
ttcggggagt ggaaaatgac ttttcagtcg gttccagtcc cgggaccctt gagtgcaatc   2820
aagcaggaga tccggatcgc ctgggcgctc cactcttgga aagtttggct taatggcttg   2880
gaaacctgat ttcaaagaaa tggaagtgtt ttcttttctt tctttccttt tttttttttt   2940
tttttttct tttgctgttg tttctgttgg agtcgtcccc actctacctg taacttctag    3000
ataacttcgc tggctctcac tggctgtgag aaagcgaacc actttctcct gggattcttg   3060
ggtgcagaga aggctgtcgc ctggactcac aaggagattg tagtcgcatt cttgtttcat   3120
tctagtcctt ttctggacac aggtagccgc gacttggccc agagtatctc acgtggcttt   3180
catccttcgt gtttagaggg gaagccccta ggaaatttaa gaaggagcag gattatctta   3240
ggaatttagt ttctttcaaa tctcactact atcatctcct tgcttattgg cctcttcagt   3300
cagaaaaatt tgagatgcta aatttgtata catctagaac gaactatctc ttctcactcc   3360
actcccctct tccccatctc tcttccgtct ccctccatcc ttggctatct cttcttcact   3420
ttccatttca aacaggagac tgtgtatgtt ttttaggaaa acattaaaaa aaaaaccaca   3480
```

```
aaaacaaaaa caaaacggag acagggtccc gtcatgtaac tctgctaacc tatatcaagc   3540
tgaccttgac ctcatagaga cccacttgcc tctgcctccc tagaggcaag ggtcggggtt   3600
atggtgatgt taatgtcgtt tgctttaaga ttccttgatt tgatcttggt gtatttttg    3660
agaaatctaa agtatgaaat cagagtttga ctaacagctt ctaccagctc ctagccacaa   3720
taaagactga ggcaggctat agttagtgct caatactggg tcctacctgg ctgcttgtaa   3780
cctgggcatg cctagcattc tagatgctaa ctcaccaaag cagtagcatt ttaagctgca   3840
aatggctagg cagcgacagc tcaagaatct tcttgctttg gagttttaaa ctccaatgag   3900
attttccatg atccctttca aataacccta cttaatctct cttcatagcc cacagtacca   3960
agaagccttt gataagctct ggattgaaaa gaagcagttc tttttcaaaa gatgtgctca   4020
tttgaactag tgcatttccc tggaaacact ttgccaggac ttgagatggg cactaagaag   4080
gaaaattcct caaaggacat gtacagtctt gagatgcatt cgcttctgta gccatgagct   4140
tgctggtctt gagataaggt tagttggtgt agctaggttc atggtttgga gtctttggca   4200
gttctagaga agcatgagct attagagact tggagattgc atcaagtaga gccttttgag   4260
cttttcactg tgtacctggg ccctctgtcg ctgcacgttt tagtgtctga aatgtctttc   4320
agctgtagca gttttctcgg gaccccagtt taaaatagct tactgtttaa aagatgtagc   4380
tgtagctagc attattgaac tagcataatt atagtctaaa tagcattatg tcttcagcct   4440
tgttatatgt tggtgagttt tagtttcctc ttctaaacgg gaagaacaga aagatgtaat   4500
gattctgagc ttccagagtg agacacctct agagagaaat accttcttct gaagactacc   4560
gtgtgattac agataaattc tgatatcttt gtttagcttt tgatatctat aaacagggag   4620
tgtattttat ctctccaaat gagagaagaa taaacaataa tgcaaggtaa aggcaatagt   4680
gctacactct aggagttacc actctttgta catttattta taaatactaa gcaagaggaa   4740
catgccatac atacactgac taagtcctaa caagtggcag ttcttatatc acacatttat   4800
cttgccctca aatgccagtc cagcatcagt ttagtctcat gcatttggca gcataaggca   4860
gtttgagttc cacacttgct ctcagaagca atttaactcc cacacttggg aatcctttcc   4920
taagccacag tttcagacca aagttttggt gaaggctata atcacagaag tctgcacaag   4980
tagggagtct gaaggatctg agctccattc agcagtcaga gcggcatcca accccaaggt   5040
aatgctcagc tcactttgat aacttcaagc tcaaaggccc tgaactgctg agttggaggt   5100
tgaaagatgt ttgggtaaaa gcaaggtaat tggcggatag gatggttgta acgtaattgt   5160
ttcaagttgt attagagacc tctgggttct aaggggatat gaaatccaac ctccactctc   5220
cactgagatt caagttaggt taagtatgcc tttgagtacc ctcaagtcac agcatgccac   5280
tctccttttc ttaactctaa tatgtatcta taaagaacgg gtagtagtca actgagtcga   5340
cggtatcgat aagcttgatc cagcttttgt tccctttagt gagggttaat tgcgcgcttg   5400
gcgtaatcat ggtcatagct gtttcctgtg tgaaattgtt atccgctcac aattccacac   5460
aacatacgag ccggaagcat aaagtgtaaa gcctggggtg cctaatgagt gagctaactc   5520
acattaattg cgttgcgctc actgcccgct ttccagtcgg gaaacctgtc gtgccagctg   5580
cattaatgaa tcggccaacg cgcggggaga ggcggtttgc gtattgggcg ctcttccgct   5640
tcctcgctca ctgactcgct gcgctcggtc gttcggctgc ggcgagcggt atcagctcac   5700
tcaaaggcgg taatacggtt atccacagaa tcaggggata acgcaggaaa gaacatgtga   5760
gcaaaaggcc agcaaaaggc caggaaccgt aaaaaggccg cgttgctggc gtttttccat   5820
aggctccgcc cccctgacga gcatcacaaa aatcgacgct caagtcagag gtggcgaaac   5880
```

```
ccgacaggac tataaagata ccaggcgttt cccccctggaa gctccctcgt gcgctctcct   5940
gttccgaccc tgccgcttac cggatacctg tccgcctttc tcccttcggg aagcgtggcg   6000
ctttctcata gctcacgctg taggtatctc agttcggtgt aggtcgttcg ctccaagctg   6060
ggctgtgtgc acgaaccccc cgttcagccc gaccgctgcg ccttatccgg taactatcgt   6120
cttgagtcca acccggtaag acacgactta tcgccactgg cagcagccac tggtaacagg   6180
attagcagag cgaggtatgt aggcggtgct acagagttct tgaagtggtg gcctaactac   6240
ggctacacta gaaggacagt atttggtatc tgcgctctgc tgaagccagt taccttcgga   6300
aaaagagttg gtagctcttg atccggcaaa caaaccaccg ctggtagcgg tggttttttt   6360
gtttgcaagc agcagattac gcgcagaaaa aaaggatctc aagaagatcc tttgatcttt   6420
tctacggggt ctgacgctca gtggaacgaa aactcacgtt aagggatttt ggtcatgaga   6480
ttatcaaaaa ggatcttcac ctagatcctt ttaaattaaa aatgaagttt taaatcaatc   6540
taaagtatat atgagtaaac ttggtctgac agttaccaat gcttaatcag tgaggcacct   6600
atctcagcga tctgtctatt tcgttcatcc atagttgcct gactccccgt cgtgtagata   6660
actacgatac gggagggctt accatctggc cccagtgctg caatgatacc gcgagaccca   6720
cgctcaccgg ctccagattt atcagcaata aaccagccag ccggaagggc cgagcgcaga   6780
agtggtcctg caactttatc cgcctccatc cagtctatta attgttgccg ggaagctaga   6840
gtaagtagtt cgccagttaa tagtttgcgc aacgttgttg ccattgctac aggcatcgtg   6900
gtgtcacgct cgtcgtttgg tatggcttca ttcagctccg gttcccaacg atcaaggcga   6960
gttacatgat cccccatgtt gtgcaaaaaa gcggttagct ccttcggtcc tccgatcgtt   7020
gtcagaagta agttggccgc agtgttatca ctcatggtta tggcagcact gcataattct   7080
cttactgtca tgccatccgt aagatgcttt tctgtgactg gtgagtactc aaccaagtca   7140
ttctgagaat agtgtatgcg gcgaccgagt tgctcttgcc cggcgtcaat acgggataat   7200
accgcgccac atagcagaac tttaaaagtg ctcatcattg gaaaacgttc ttcggggcga   7260
aaactctcaa ggatcttacc gctgttgaga tccagttcga tgtaacccac tcgtgcaccc   7320
aactgatctt cagcatcttt tactttcacc agcgtttctg ggtgagcaaa aacaggaagg   7380
caaaatgccg caaaaaaggg aataagggcg acacggaaat gttgaatact catactcttc   7440
ctttttcaat attattgaag catttatcag ggttattgtc tcatgagcgg atacatattt   7500
gaatgtattt agaaaaataa acaaataggg gttccgcgca catttccccg aaaagtgcca   7560
cctaaattgt aagcgttaat attttgttaa aattcgcgtt aaatttttgt taaatcagct   7620
cattttttaa ccaataggcc gaaatcggca aaatccctta taaatcaaaa gaatagaccg   7680
agatagggtt gagtgttgtt ccagtttgga acaagagtcc actattaaag aacgtggact   7740
ccaacgtcaa agggcgaaaa accgtctatc agggcgatgg cccactacgt gaaccatcac   7800
cctaatcaag ttttttgggg tcgaggtgcc gtaaagcact aaatcggaac cctaaaggga   7860
gcccccgatt tagagcttga cggggaaagc cggcgaacgt ggcgagaaag gaagggaaga   7920
aagcgaaagg agcgggcgct agggcgctgg caagtgtagc ggtcacgctg cgcgtaacca   7980
ccacacccgc cgcgcttaat gcgccgctac agggcgcgtc ccattcgcca ttcaggctgc   8040
gcaactgttg ggaagggcga tcggtgcggg cctcttcgct attacgccag ctggcgaaag   8100
gggga tgtgc tgcaaggcga ttaagttggg taacgccagg gttttcccag tcacgacgtt   8160
gtaaaacgac ggccagtgag cgcgcgtaat acgactcact atagggcgaa ttggagct     8218
```

<210> SEQ ID NO 61
<211> LENGTH: 9989
<212> TYPE: DNA
<213> ORGANISM: Artificial sequence
<220> FEATURE:
<223> OTHER INFORMATION: pCMV-Rab-Reporter (hygro)

<400> SEQUENCE: 61
gaattcgagc ttgcatgcct gcaggtcgtt acataactta cggtaaatgg cccgcctggc 60
tgaccgccca acgacccccg cccattgacg tcaataatga cgtatgttcc catagtaacg 120
ccaataggga ctttccattg acgtcaatgg gtggagtatt tacggtaaac tgcccacttg 180
gcagtacatc aagtgtatca tatgccaagt acgcccccta ttgacgtcaa tgacggtaaa 240
tggcccgcct ggcattatgc ccagtacatg accttatggg actttcctac ttggcagtac 300
atctacgtat tagtcatcgc tattaccatg gtgatgcggt tttggcagta catcaatggg 360
cgtggatagc ggtttgactc acggggattt ccaagtctcc accccattga cgtcaatggg 420
agtttgtttt ggcaccaaaa tcaacgggac tttccaaaat gtcgtaacaa ctccgcccca 480
ttgacgcaaa tgggcggtag gcgtgtacgg tgggaggtct atataagcag agctcgttta 540
gtgaaccgtc agatcgcctg gagacgccat ccacgctgtt ttgacctcca tagaagacac 600
cgggaccgat ccagcctccg gactctagag gatccggtac tcgaggacac tgcagagacc 660
tacttcacta acaaccggta tggtcgccag tagcttggca ctggccgtcg ttttacaacg 720
tcgtgactgg gaaaaccctg gcgttaccca acttaatcgc cttgcagcac atcccccttt 780
cgccagctgg cgtaatagcg aagaggcccg caccgatcgc ccttcccaac agttgcgcag 840
cctgaatggc gaatggcgct ttgcctggtt tccggcacca gaagcggtgc cggaaagctg 900
gctggagtgc gatcttcctg aggccgatac tgtcgtcgtc ccctcaaact ggcagatgca 960
cggttacgat gcgcccatct acaccaacgt gacctatccc attacggtca atccgccgtt 1020
tgttcccacg gagaatccga cgggttgtta ctcgctcaca tttaatgttg atgaaagctg 1080
gctataaaac cggtacagtt cggccaccat ggtcgtatca agcgctatgt gcaccaaaac 1140
ttctcctcgc actaccgggc caccattggt cgagtagctt ggcactggcc gtcgttttac 1200
aacgtcgtga ctgggaaaac cctggcgtta cccaacttaa tcgccttgca gcacatcccc 1260
ctttcgccag ctggcgtaat agcgaagagg cccgcaccga tcgcccttcc caacagttgc 1320
gcagcctgaa tggcgaatgg cgctttgcct ggtttccggc accagaagcg gtgccggaaa 1380
gctggctgga gtgcgatctt cctgaggccg atactgtcgt cgtcccctca aactggcaga 1440
tgcacggtta cgatgcgccc atctacacca acgtgaccta tcccattacg gtcaatccgc 1500
cgtttgttcc cacggagaat ccgacgggtt gttactcgct cacatttaat gttgatgaaa 1560
gctggctaca ggaaggccag acgcgaatta tttttgatgg cgttaactcg gcgtttcatc 1620
tgtggtgcaa cgggcgctgg gtcggttacg gccaggacag tcgtttgccg tctgaatttg 1680
acctgagcgc atttttacgc gccggagaaa accgcctcgc ggtgatggtg ctgcgctgga 1740
gtgacggcag ttatctggaa gatcaggata tgtggcggat gagcggcatt ttccgtgacg 1800
tctcgttgct gcataaaccg actacacaaa tcagcgattt ccatgttgcc actcgcttta 1860
atgatgattt cagccgcgct gtactggagg ctgaagttca gatgtgcggc gagttgcgtg 1920
actacctacg ggtaacagtt tctttatggc agggtgaaac gcaggtcgcc agcggcaccg 1980
cgcctttcgg cggtgaaatt atcgatgagc gtggtggtta tgccgatcgc gtcacactac 2040
gtctgaacgt cgaaaacccg aaactgtgga gcgccgaaat cccgaatctc tatcgtgcgg 2100

```
tggttgaact gcacaccgcc gacggcacgc tgattgaagc agaagcctgc gatgtcggtt   2160
tccgcgaggt gcggattgaa aatggtctgc tgctgctgaa cggcaagccg ttgctgattc   2220
gaggcgttaa ccgtcacgag catcatcctc tgcatggtca ggtcatggat gagcagacga   2280
tggtgcagga tatcctgctg atgaagcaga acaactttaa cgccgtgcgc tgttcgcatt   2340
atccgaacca tccgctgtgg tacacgctgt gcgaccgcta cggcctgtat gtggtggatg   2400
aagccaatat tgaaacccac ggcatggtgc caatgaatcg tctgaccgat gatccgcgct   2460
ggctaccggc gatgagcgaa cgcgtaacgc gaatggtgca gcgcgatcgt aatcacccga   2520
gtgtgatcat ctggtcgctg gggaatgaat caggccacgg cgctaatcac gacgcgctgt   2580
atcgctggat caaatctgtc gatccttccc gcccggtgca gtatgaaggc ggcggagccg   2640
acaccacggc caccgatatt atttgcccga tgtacgcgcg cgtggatgaa gaccagccct   2700
tcccggctgt gccgaaatgg tccatcaaaa aatggctttc gctacctgga gagacgcgcc   2760
cgctgatcct ttgcgaatac gcccacgcga tgggtaacag tcttggcggt ttcgctaaat   2820
actggcaggc gtttcgtcag tatccccgtt tacagggcgg cttcgtctgg gactgggtgg   2880
atcagtcgct gattaaatat gatgaaaacg gcaacccgtg gtcggcttac ggcggtgatt   2940
ttggcgatac gccgaacgat cgccagttct gtatgaacgg tctggtcttt gccgaccgca   3000
cgccgcatcc agcgctgacg gaagcaaaac accagcagca gtttttccag ttccgtttat   3060
ccgggcaaac catcgaagtg accagcgaat acctgttccg tcatagcgat aacgagctcc   3120
tgcactggat ggtggcgctg gatggtaagc cgctggcaag cggtgaagtg cctctggatg   3180
tcgctccaca aggtaaacag ttgattgaac tgcctgaact accgcagccg gagagcgccg   3240
ggcaactctg gctcacagta cgcgtagtgc aaccgaacgc gaccgcatgg tcagaagccg   3300
ggcacatcag cgcctggcag cagtggcgtc tggcggaaaa cctcagtgtg acgctccccg   3360
ccgcgtccca cgccatcccg catctgacca ccagcgaaat ggatttttgc atcgagctgg   3420
gtaataagcg ttggcaattt aaccgccagt caggctttct ttcacagatg tggattggcg   3480
ataaaaaaca actgctgacg ccgctgcgcg atcagttcac ccgtgcaccg ctggataacg   3540
acattggcgt aagtgaagcg acccgcattg accctaacgc ctgggtcgaa cgctggaagg   3600
cggcgggcca ttaccaggcc gaagcagcgt tgttgcagtg cacggcagat acacttgctg   3660
atgcggtgct gattacgacc gctcacgcgt ggcagcatca ggggaaaacc ttatttatca   3720
gccggaaaac ctaccggatt gatggtagtg gtcaaatggc gattaccgtt gatgttgaag   3780
tggcgagcga tacaccgcat ccggcgcgga ttggcctgaa ctgccagctg gcgcaggtag   3840
cagagcgggt aaactggctc ggattagggc cgcaagaaaa ctatcccgac cgccttactg   3900
ccgcctgttt tgaccgctgg gatctgccat tgtcagacat gtataccccg tacgtcttcc   3960
cgagcgaaaa cggtctgcgc tgcgggacgc gcgaattgaa ttatggccca caccagtggc   4020
gcggcgactt ccagttcaac atcagccgct acagtcaaca gcaactgatg gaaaccagcc   4080
atcgccatct gctgcacgcg gaagaaggca catggctgaa tatcgacggt ttccatatgg   4140
ggattggtgg cgacgactcc tggagcccgt cagtatcggc ggaattccag ctgagcgccg   4200
gtcgctacca ttaccagttg gtctggtgtc aggggatccc ccgggctgca gccaatatgg   4260
gatcggccat tgaacaagat ggattgcacg caggttctcc ggccgcttgg gtggagaggc   4320
tattcggcta tgactgggca caacagacaa tcggctgctc tgatgccgcc gtgttccggc   4380
tgtcagcgca ggggcgcccg gttctttttg tcaagaccga cctgtccggt gccctgaatg   4440
```

-continued

```
aactgcagga cgaggcagcg cggctatcgt ggctggccac gacgggcgtt ccttgcgcag   4500
ctgtgctcga cgttgtcact gaagcgggaa gggactggct gctattgggc gaagtgccgg   4560
ggcaggatct cctgtcatct caccttgctc ctgccgagaa agtatccatc atggctgatg   4620
caatgcggcg gctgcatacg cttgatccgg ctacctgccc attcgaccac caagcgaaac   4680
atcgcatcga gcgagcacgt actcggatgg aagccggtct tgtcgatcag gatgatctgg   4740
acgaagagca tcaggggctc gcgccagccg aactgttcgc caggctcaag gcgcgcatgc   4800
ccgacggcga ggatctcgtc gtgacccatg gcgatgcctg cttgccgaat atcatggtgg   4860
aaaatggccg cttttctgga ttcatcgact gtggccggct gggtgtggcg gaccgctatc   4920
aggacatagc gttggctacc cgtgatattg ctgaagagct tggcggcgaa tgggctgacc   4980
gcttcctcgt gctttacggt atcgccgctc ccgattcgca gcgcatcgcc ttctatcgcc   5040
ttcttgacga gttcttctga ggggatcaat tctctagagc tcgctgatca gcctcgactg   5100
tgccttctag ttgccagcca tctgttgttt gcccctcccc cgtgccttcc ttgaccctgg   5160
aaggtgccac tcccactgtc ctttcctaat aaaatgagga aattgcatcg cattgtctga   5220
gtaggtgtca ttctattctg gggggtgggg tggggcagga cagcaagggg gaggattggg   5280
aagacaatag caggcatgct ggggatgcgg tgggctctat ggcttctgag acggaaagaa   5340
ccagctgggg ctcgatcctc tagagtcgac gtttgatctg atatcatcga tgaattctac   5400
cgggtagggg aggcgctttt cccaaggcag tctggagcat gcgctttagc agccccgctg   5460
ggcacttggc gctacacaag tggcctctgg cctcgcacac attccacatc caccggtagg   5520
cgccaaccgg ctccgttctt tggtggcccc ttcgcgccac cttctactcc tcccctagtc   5580
aggaagttcc cccccgcccc gcagctcgcg tcgtgcagga cgtgacaaat ggaagtagca   5640
cgtctcacta gtctcgtgca gatggacagc accgctgagc aatggaagcg ggtaggcctt   5700
tggggcagcg gccaatagca gctttgctcc ttcgctttct gggctcagag gctgggaagg   5760
ggtgggtccg gggcgggct cagggcggg ctcaggggcg gggcgggcgc ccgaaggtcc   5820
tccggaggcc cggcattctg cacgcttcaa aagcgcacgt ctgccgcgct gttctcctct   5880
tcctcatctc cgggcctttc gaccgatcca gccgccacca tgaaaaagcc tgaactcacc   5940
gcgacgtctg tcgagaagtt tctgatcgaa aagttcgaca gcgtctccga cctgatgcag   6000
ctctcggagg gcgaagaatc tcgtgctttc agcttcgatg taggagggcg tggatatgtc   6060
ctgcgggtaa atagctgcgc cgatggtttc tacaaagatc gttatgttta tcggcacttt   6120
gcatcggccg cgctcccgat tccggaagtg cttgacattg gggaattcag cgagagcctg   6180
acctattgca tctcccgccg tgcacagggt gtcacgttgc aagacctgcc tgaaaccgaa   6240
ctgcccgctg ttctgcagcc ggtcgcggag gccatggatg cgatcgctgc ggccgatctt   6300
agccagacga gcgggttcgg cccattcgga ccgcaaggaa tcggtcaata cactacatgg   6360
cgtgatttca tatgcgcgat tgctgatccc catgtgtatc actggcaaac tgtgatggac   6420
gacaccgtca gtgcgtccgt cgcgcaggct ctcgatgagc tgatgctttg ggccgaggac   6480
tgccccgaag tccggcacct cgtgcacgcg gatttcggct ccaacaatgt cctgacggac   6540
aatggccgca taacagcggt cattgactgg agcgaggcga tgttcgggga ttcccaatac   6600
gaggtcgcca acatcttctt ctggaggccg tggttggctt gtatggagca gcagacgcgc   6660
tacttcgagc ggaggcatcc ggagcttgca ggatcgccgc ggctccgggc gtatatgctc   6720
cgcattggtc ttgaccaact ctatcagagc ttggttgacg gcaatttcga tgatgcagct   6780
tgggcgcagg gtcgatgcga cgcaatcgtc cgatccggag ccgggactgt cgggcgtaca   6840
```

```
caaatcgccc gcagaagcgc ggccgtctgg accgatggct gtgtagaagt actcgccgat   6900
agtggaaacc gacgccccag cactcgtccg agggcaaagg aatagtcgag aaattgatga   6960
tctattaaac aataaagatg tccactaaaa tggaagtttt tcctgtcata ctttgttaag   7020
aagggtgaga acagagtacc tacattttga atggaaggat tggagctacg gggggtgggg   7080
tggggtggga ttagataaat gcctgctctt tactgaaggc tctttactat tgctttatga   7140
taatgtttca tagttggata tcataattta aacaagcaaa accaaattaa gggccagctc   7200
attcctccca ctcatgatct atagatcaaa catgcatgaa gttcctattc cgaagttcct   7260
attctctaga aagtatagga acttcataaa acctgcaggc atgcaagcga tcgcggccgg   7320
ccaaggcccg cggggccact agttctagag cggccagctt ggcgtaatca tggtcatagc   7380
tgtttcctgt gtgaaattgt tatccgctca caattccaca caacatacga gccggaagca   7440
taaagtgtaa agcctggggt gcctaatgag tgagctaact cacattaatt gcgttgcgct   7500
cactgcccgc tttccagtcg ggaaacctgt cgtgccagct gcattaatga atcggccaac   7560
gcgcggggag aggcggtttg cgtattgggc gctcttccgc ttcctcgctc actgactcgc   7620
tgcgctcggt cgttcggctg cggcgagcgg tatcagctca ctcaaaggcg gtaatacggt   7680
tatccacaga atcaggggat aacgcaggaa agaacatgtg agcaaaaggc cagcaaaagg   7740
ccaggaaccg taaaaaggcc gcgttgctgg cgtttttcca taggctccgc ccccctgacg   7800
agcatcacaa aaatcgacgc tcaagtcaga ggtggcgaaa cccgacagga ctataaagat   7860
accaggcgtt tccccctgga agctccctcg tgcgctctcc tgttccgacc ctgccgctta   7920
ccggatacct gtccgccttt ctcccttcgg gaagcgtggc gctttctcat agctcacgct   7980
gtaggtatct cagttcggtg taggtcgttc gctccaagct gggctgtgtg cacgaacccc   8040
ccgttcagcc cgaccgctgc gccttatccg gtaactatcg tcttgagtcc aacccggtaa   8100
gacacgactt atcgccactg gcagcagcca ctggtaacag gattagcaga gcgaggtatg   8160
taggcggtgc tacagagttc ttgaagtggt ggcctaacta cggctacact agaaggacag   8220
tatttggtat ctgcgctctg ctgaagccag ttaccttcgg aaaaagagtt ggtagctctt   8280
gatccggcaa acaaaccacc gctggtagcg gtggtttttt tgtttgcaag cagcagatta   8340
cgcgcagaaa aaaaggatct caagaagatc ctttgatctt ttctacgggg tctgacgctc   8400
agtggaacga aaactcacgt taagggattt tggtcatgag attatcaaaa aggatcttca   8460
cctagatcct tttaaattaa aaatgaagtt ttaaatcaat ctaaagtata tatgagtaaa   8520
cttggtctga cagttaccaa tgcttaatca gtgaggcacc tatctcagcg atctgtctat   8580
ttcgttcatc catagttgcc tgactccccg tcgtgtagat aactacgata cgggagggct   8640
taccatctgg ccccagtgct gcaatgatac cgcgagaccc acgctcaccg gctccagatt   8700
tatcagcaat aaaccagcca gccggaaggg ccgagcgcag aagtggtcct gcaactttat   8760
ccgcctccat ccagtctatt aattgttgcc gggaagctag agtaagtagt tcgccagtta   8820
atagtttgcg caacgttgtt gccattgcta caggcatcgt ggtgtcacgc tcgtcgtttg   8880
gtatggcttc attcagctcc ggttcccaac gatcaaggcg agttacatga tcccccatgt   8940
tgtgcaaaaa agcggttagc tccttcggtc ctccgatcgt tgtcagaagt aagttggccg   9000
cagtgttatc actcatggtt atggcagcac tgcataattc tcttactgtc atgccatccg   9060
taagatgctt ttctgtgact ggtgagtact caaccaagtc attctgagaa tagtgtatgc   9120
ggcgaccgag ttgctcttgc ccggcgtcaa tacgggataa taccgcgcca catagcagaa   9180
```

```
ctttaaaagt gctcatcatt ggaaaacgtt cttcggggcg aaaactctca aggatcttac   9240
cgctgttgag atccagttcg atgtaaccca ctcgtgcacc caactgatct tcagcatctt   9300
ttactttcac cagcgtttct gggtgagcaa aaacaggaag gcaaaatgcc gcaaaaaagg   9360
gaataagggc gacacggaaa tgttgaatac tcatactctt cctttttcaa tattattgaa   9420
gcatttatca gggttattgt ctcatgagcg gatacatatt tgaatgtatt tagaaaaata   9480
aacaaatagg ggttccgcgc acatttcccc gaaaagtgcc acctgacgtc taagaaacca   9540
ttattatcat gacattaacc tataaaaata ggcgtatcac gaggcccttt cgtctcgcgc   9600
gtttcggtga tgacggtgaa aacctctgac acatgcagct cccggagacg gtcacagctt   9660
gtctgtaagc ggatgccggg agcagacaag cccgtcaggg cgcgtcagcg ggtgttggcg   9720
ggtgtcgggg ctggcttaac tatgcggcat cagagcagat tgtactgaga gtgcaccata   9780
tgcggtgtga aataccgcac agatgcgtaa ggagaaaata ccgcatcagg cgccattcgc   9840
cattcaggct gcgcaactgt tgggaagggc gatcggtgcg ggcctcttcg ctattacgcc   9900
agctggcgaa agggggatgt gctgcaaggc gattaagttg ggtaacgcca gggttttccc   9960
agtcacgacg ttgtaaaacg acggccagt                                     9989
```

```
<210> SEQ ID NO 62
<211> LENGTH: 12
<212> TYPE: DNA
<213> ORGANISM: Artificial Sequence
<220> FEATURE:
<223> OTHER INFORMATION: DNA target sequence

<400> SEQUENCE: 62

attctgggac gt                                                         12


<210> SEQ ID NO 63
<211> LENGTH: 14
<212> TYPE: DNA
<213> ORGANISM: Mus musculus

<400> SEQUENCE: 63

ggtggcccgg tagt                                                       14


<210> SEQ ID NO 64
<211> LENGTH: 34
<212> TYPE: PRT
<213> ORGANISM: Xanthomonas campestris

<400> SEQUENCE: 64

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 65
<211> LENGTH: 34
<212> TYPE: PRT
<213> ORGANISM: Xanthomonas campestris

<400> SEQUENCE: 65

Leu Thr Pro Gln Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30
```

His Gly

<210> SEQ ID NO 66
<211> LENGTH: 34
<212> TYPE: PRT
<213> ORGANISM: Xanthomonas campestris

<400> SEQUENCE: 66

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 67
<211> LENGTH: 34
<212> TYPE: PRT
<213> ORGANISM: Xanthomonas campestris

<400> SEQUENCE: 67

Leu Thr Pro Gln Gln Val Val Ala Ile Ala Ser Asn Asn Gly Gly Lys
1               5                   10                  15

Gln Ala Leu Glu Thr Val Gln Ala Leu Leu Pro Val Leu Cys Gln Ala
            20                  25                  30

His Gly

<210> SEQ ID NO 68
<211> LENGTH: 12
<212> TYPE: DNA
<213> ORGANISM: Artificial Sequence
<220> FEATURE:
<223> OTHER INFORMATION: DNA target sequence

<400> SEQUENCE: 68
attctgggac gt                                                          12

<210> SEQ ID NO 69
<211> LENGTH: 12
<212> TYPE: DNA
<213> ORGANISM: Artificial Sequence
<220> FEATURE:
<223> OTHER INFORMATION: DNA target sequence

<400> SEQUENCE: 69
acgtcccaga at                                                          12

<210> SEQ ID NO 70
<211> LENGTH: 12
<212> TYPE: DNA
<213> ORGANISM: Artificial Sequence
<220> FEATURE:
<223> OTHER INFORMATION: DNA target sequence

<400> SEQUENCE: 70
taagaccctg ca                                                          12

<210> SEQ ID NO 71
<211> LENGTH: 12
<212> TYPE: DNA
<213> ORGANISM: Artificial Sequence
<220> FEATURE:
<223> OTHER INFORMATION: DNA target sequence

<400> SEQUENCE: 71
tgcagggtct ta 12

<210> SEQ ID NO 72
<211> LENGTH: 13
<212> TYPE: DNA
<213> ORGANISM: Artificial Sequence
<220> FEATURE:
<223> OTHER INFORMATION: DNA target sequence

<400> SEQUENCE: 72
gtgcaccaaa act 13

<210> SEQ ID NO 73
<211> LENGTH: 13
<212> TYPE: DNA
<213> ORGANISM: Artificial Sequence
<220> FEATURE:
<223> OTHER INFORMATION: DNA target sequence

<400> SEQUENCE: 73
agttttggtg cac 13

<210> SEQ ID NO 74
<211> LENGTH: 13
<212> TYPE: DNA
<213> ORGANISM: Artificial Sequence
<220> FEATURE:
<223> OTHER INFORMATION: DNA target sequence

<400> SEQUENCE: 74
cacgtggttt tga 13

<210> SEQ ID NO 75
<211> LENGTH: 13
<212> TYPE: DNA
<213> ORGANISM: Artificial Sequence
<220> FEATURE:
<223> OTHER INFORMATION: DNA target sequence

<400> SEQUENCE: 75
tcaaaaccac gtg 13

<210> SEQ ID NO 76
<211> LENGTH: 14
<212> TYPE: DNA
<213> ORGANISM: Artificial Sequence
<220> FEATURE:
<223> OTHER INFORMATION: DNA target sequence

<400> SEQUENCE: 76
actaccgggc cacc 14

<210> SEQ ID NO 77
<211> LENGTH: 14
<212> TYPE: DNA
<213> ORGANISM: Artificial Sequence
<220> FEATURE:
<223> OTHER INFORMATION: DNA target sequence

<400> SEQUENCE: 77
ccaccgggcc atca 14

<210> SEQ ID NO 78
<211> LENGTH: 14

<212> TYPE: DNA
<213> ORGANISM: Artificial Sequence
<220> FEATURE:
<223> OTHER INFORMATION: DNA target sequence

<400> SEQUENCE: 78
tgatggcccg gtgg 14

<210> SEQ ID NO 79
<211> LENGTH: 12
<212> TYPE: DNA
<213> ORGANISM: Artificial Sequence
<220> FEATURE:
<223> OTHER INFORMATION: DNA target sequence

<400> SEQUENCE: 79
attctgggac gt 12

<210> SEQ ID NO 80
<211> LENGTH: 14
<212> TYPE: DNA
<213> ORGANISM: Artificial Sequence
<220> FEATURE:
<223> OTHER INFORMATION: DNA target sequence

<400> SEQUENCE: 80
actaccgggc cacc 14

<210> SEQ ID NO 81
<211> LENGTH: 12
<212> TYPE: DNA
<213> ORGANISM: Artificial Sequence
<220> FEATURE:
<223> OTHER INFORMATION: DNA target sequence

<400> SEQUENCE: 81
taagaccctg ca 12

<210> SEQ ID NO 82
<211> LENGTH: 14
<212> TYPE: DNA
<213> ORGANISM: Artificial Sequence
<220> FEATURE:
<223> OTHER INFORMATION: DNA target sequence

<400> SEQUENCE: 82
tgatggcccg gtgg 14

<210> SEQ ID NO 83
<211> LENGTH: 69
<212> TYPE: DNA
<213> ORGANISM: Artificial Sequence
<220> FEATURE:
<223> OTHER INFORMATION: Rab38 Exon 1 partial sequence

<400> SEQUENCE: 83
tgggtgtggg caagaccagc attatcaagc gctatgtgca ccaaaacttc tcctcgcact 60
accgggcca 69

<210> SEQ ID NO 84
<211> LENGTH: 69
<212> TYPE: DNA
<213> ORGANISM: Artificial Sequence
<220> FEATURE:
<223> OTHER INFORMATION: Rab38 Exon 1 partial sequence

```
<400> SEQUENCE: 84

acccacaccc gttctggtcg taatagttcg cgatacacgt ggttttgaag aggagcgtga     60

tggcccggt                                                             69


<210> SEQ ID NO 85
<211> LENGTH: 100
<212> TYPE: DNA
<213> ORGANISM: Artificial Sequence
<220> FEATURE:
<223> OTHER INFORMATION: Rab38 Exon 1 partial sequence

<400> SEQUENCE: 85

tgatcggcga cctggtagtg ggcaagacca gcattattaa acggtacgtg catcaaaatt     60

tctcctctca ttatcgagcc accattggtg tggacttcgc                          100


<210> SEQ ID NO 86
<211> LENGTH: 100
<212> TYPE: DNA
<213> ORGANISM: Artificial Sequence
<220> FEATURE:
<223> OTHER INFORMATION: Rab38 Exon 1 partial sequence

<400> SEQUENCE: 86

actagccgct ggaccatcac ccgttctggt cgtaataatt tgccatgcac gtagttttaa     60

agaggagagt aatagctcgg tggtaaccac acctgaagcg                          100


<210> SEQ ID NO 87
<211> LENGTH: 24
<212> TYPE: PRT
<213> ORGANISM: Artificial Sequence
<220> FEATURE:
<223> OTHER INFORMATION: Rab38 Exon 1 partial sequence

<400> SEQUENCE: 87

Asp Leu Val Val Gly Lys Thr Ser Ile Ile Lys Arg Tyr Val His Gln
1               5                   10                  15

Asn Phe Ser Ser His Tyr Arg Ala
            20
```